United States Patent

Al-Awar et al.

(10) Patent No.: US 6,680,311 B1
(45) Date of Patent: *Jan. 20, 2004

(54) CRYPTOPHYCIN COMPOUNDS

(75) Inventors: Rima S Al-Awar, Indianapolis, IN (US); William J Ehlhardt, Indianapolis, IN (US); Subbaraju V Gottumukkala, Tirupati, IN (US); Michael J Martinelli, Zionsville, IN (US); Eric D Moher, Indianapolis, IN (US); Richard E Moore, Honolulu, HI (US); John E Munroe, Indianapolis, IN (US); Bryan H Norman, Indianapolis, IN (US); Vinod F Patel, Carmel, IN (US); James E Ray, Indianapolis, IN (US); Chuan Shih, Carmel, IN (US); John E Toth, Indianapolis, IN (US); Venkatraghavan Vasudevan, Indianapolis, IN (US)

(73) Assignees: Eli Lilly and Company, Indianapolis, IN (US); Wayne State University, Detroit, MI (US); University of Hawaii, Honolulu, HI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/029,190
(22) PCT Filed: Aug. 29, 1997
(86) PCT No.: PCT/US97/15240
§ 371 (c)(1),
(2), (4) Date: Feb. 25, 1998
(87) PCT Pub. No.: WO98/08505
PCT Pub. Date: Mar. 5, 1998

Related U.S. Application Data

(60) Provisional application No. 60/040,029, filed on Mar. 4, 1997, provisional application No. 60/039,530, filed on Mar. 3, 1997, provisional application No. 60/039,113, filed on Feb. 26, 1997, and provisional application No. 60/025,816, filed on Aug. 30, 1996.

(51) Int. Cl.$^7$ .................. A61K 31/33; A61K 31/40; C07D 267/22; C07D 245/00; A61P 35/00

(52) U.S. Cl. .................. 514/183; 514/340; 514/365; 514/397; 514/414; 514/422; 514/443; 514/444; 514/471; 540/454; 540/455; 540/460

(58) Field of Search .................. 514/183, 340, 514/365, 397, 414, 422, 443, 444, 471; 540/454, 455, 460

(56) References Cited

U.S. PATENT DOCUMENTS

| 4,845,085 A | 7/1989 | Sesin ............................ 31/395 |
| 4,845,086 A | 7/1989 | Sesin ............................ 31/395 |
| 4,868,208 A | 9/1989 | Sesin et al. ................. 514/475 |
| 4,946,835 A | 8/1990 | Hirsch et al. ............... 514/183 |
| 6,180,679 B1 * | 1/2001 | Shih et al. .................. 514/619 |

FOREIGN PATENT DOCUMENTS

| WO | WO 95/17093 | 12/1994 |
| WO | WO 96/40184 | 3/1996 |
| WO | WO 96/39829 | 6/1996 |
| WO | WO 97/07798 | 8/1996 |
| WO | WO 97/083334 | 8/1996 |
| WO | WO 97/23211 | 12/1996 |
| WO | WO 98/08505 | 8/1997 |

OTHER PUBLICATIONS

Balasubramanian et al., Recent Developments in Cancer Cytotoxics, Annual Reports in Medicinal Chemistry, vol. 33, pp. 151–159, 1998.*

Draetta et al., Cell Cycle Control and Cancer, Annual Reports in Medicinal Chemistry, vol. 31, pp. 241–248, 1996.*

Salmon et al., Principles of Cancer Therapy, Cecil Textbook of Medicine, 20th Edition, pp. 1036–1049, 1996.*

Russell A. Barrow, et al., Total Synthesis of Cryptophycins. Revision of the Structures of Cryptophycins A and C. *J. Am. Chem. Soc.* (1995), 117, 2479–2490.

Robert E. Schwartz, et al. Pharmaceuticals from Cultured Algae. *Journal of Industrial Microbiology*, 5 (1990) 113–123.

Motomasa Kobayashi, et al. A total synthesis of Arenastatin A, an extremely potent cyctotoxic eepsipeptide, from the Okinawan marine sponge *Dysidea Arenaria*, *Chem. Pharm. Bull.* (1994) 42 (11) ; 2394–2396.

Charles D. Smith, et al., Cryptophycin: A New Antimicrotubule Agent Active Against Drug–Resistant Cells. *Cancer Research 54*, 3779–3784, Jul. 15, 1994.

(List continued on next page.)

Primary Examiner—Brenda Coleman
(74) Attorney, Agent, or Firm—Merchant & Gould P.C.

(57) ABSTRACT

The present invention provides cryptophycin compounds of Formula I that are useful in the treatment of neoplasms.

21 Claims, No Drawings

OTHER PUBLICATIONS

Golakoti Trimurtulu, et al., Total Structures of Cryptophycins, Potent Antitumor Depsipeptides from the Blue–Green Alga Nostoc sp. Strain GSV 224. *J. Am. Chem. Soc.* 1994, 116, 4729–4737.

Kristen Kerksiek, et al., Interaction of Cryptophycin 1 with Tubulin and Microtubules. *FEBS Letters* 377 (1995) 59–61.

Motomasa Kobayashi, et al. Improved Total Synthesis and Structure–Activity Relationship of Arenastatin A, A Potent Cytotoxic Spongean Depsipeptide. *Chem. Pharm. Bull* 43 (9) 1598–1600 (1995).

F. A. Valeriote, et al. Anticancer Activity of Cryptophycin Analogs. *Proc. Amer. Assoc. Cancer Res.,* vol. 36, Mar. 1995, abstract 1802, 303.

Trimurtulu Golakoti, et al. Structure Determination, Conformational Analysis, Chemical Stability Studies, and Antitumor Evaluation of the Cryptophycins. Isolation of 18 New Analogs from Nostoc sp. Strain GSV 224. *J. Am. Chem. Soc.,* 1995, 117, 12030–12049.

Ruoli Bai, et al. characterization of the interaction of cryptophycin 1 with tubulin: binding in the vinca domain, competitive inhibition of dolastatin 10 binding, and an unusual aggregation reaction. *Cancer Research* 56, 4398–4406, Oct. 1, 1996.

Charles D. Smith, et al. Mechanism of Action of Cryptophycin. *Journal of Biological Chemistry,* vol. 271, No. 11, Mar. 15, 1996, pp. 6192–6198.

Gregorz M. Salamonczyk, et al. Total Synthesis of Cryptophycins Via a Chemoenzymatic Approach *J. Org. Chem.,* 1996, 61, 6893–6900.

Rabindra Rej, et al. total synthesis of cryptophycins and their 16–(3–phenylacryloyl) derivatives. *J. Org. Chem.* 1996, 61, 6289–6295.

Richard E. Moore, et al. The Search for New Antitumor Drugs from Blue–Green Algae. *Current Pharmaceutical Design,* 1996, 2, 317–330.

T.H. Corbett, et al. Preclinical Anticancer Activity of Cryptophycin–8. *Journal of Experimental Therapeutics and Oncology,* vol. 1, No. 2, Mar. 1996, pp. 95–108.

Dulal Panda, et al. Mechanism of Action of the Unusually Potent Microtubule Inhibitor Cryptophycin 1. *Biochemistry* 1997, 36, 12948–12953.

L. Polin, et al. Preclinical Antitumor Activity of Cryptophycin–52/55 (C–52;C–55) Against Human Tumors in Scid Mice. *Proc. Amer. Assoc. Cancer Res.,* vol. 38, Mar. 1997, abstract 1514, 225.

Kevin M. Gardinier, et al. Enantiospecific Total Synthesis of the Potent Antitumor Macrolides Cryptophycins 1 and 8. *J. Org. Chem.* 1997, 62, 7098–7099.

Syed M. Ali, et al., Formal Synthesis of Cryptophycin A and Arenastatin A. *Tetrahedron Letters,* vol. 38, No. 10, pp. 1703–1706, 1997.

Gottumukkala V. Subbaraju, et al., Three New Cryptophycins from Nostoc sp. GSV 224, *J. Nat. Prod.,* 1997, 60, 302–305.

* cited by examiner

CRYPTOPHYCIN COMPOUNDS

This application is a §371 application of PCT/US97/15240 filed on Aug. 29, 1997 which claims the benefit of U.S. Provisional Application No. 60/025,816 filed on Aug. 30, 1996, U.S. Provisional Application No. 60/039,113 filed on Feb. 26, 1997, U.S. Provisional Application No. 60/039,530 filed on Mar. 3, 1997, and U.S. Provisional Application No. 60/040,029 filed on Mar. 4, 1997.

This invention relates to the fields of pharmaceutical and organic chemistry and provides novel cryptophycin compounds useful as anti-microtubule agents.

Neoplastic diseases, characterized by the proliferation of cells not subject to the normal control of cell growth, are a major cause of death in humans and other mammals. Clinical experience in cancer chemotherapy has demonstrated that new and more effective drugs are desirable to treat these diseases.

The microtubule system of eucaryotic cells is a major component of the cytoskeleton and is a dynamic assembly and disassembly; this is heterodimers of tubulin are polymerized and form microtubule. Microtubules play a key role in the regulation of cell architecture, metabolism, and division. The dynamic state of microtubules is critical to their normal function. With respect to cell division, tubulin is polymerized into microtubules that form the mitotic spindle.

The microtubules are then depolymerized when the mitotic spindle's use has been fulfilled. Accordingly, agents which disrupt the polymerization or depolymerization of microtubules, and thereby inhibit mitosis, comprise some of the most effective cancer chemotherapeutic agents in clinical use.

Additionally, the compounds claimed herein possess fungicidal properties as well. Further, such agents having the ability to disrupt the microtubule system can be useful for research purposes.

Certain cryptophycin compounds are known in the literature; however, cryptophycin compounds having even greater solubility and stability are desired for most pharmaceutical uses. Further, a broader library of cryptophycin compounds could provide additional treatment options for the patient suffering from cancer. Applicants have now discovered novel compounds which can provide greater aqueous solubility as well as compounds having the ability to disrupt the microtubule system. Compounds of this invention can be useful for the treatment of neoplasms. Such compounds can be prepared using total synthetic methods and are therefore well suited for development as pharmaceutically useful agents.

The presently claimed invention provides novel cryptophycin compounds of Formula I Ar is selected from the group consisting of phenyl, any simple unsubstituted aromatic, simple substituted aromatic, substituted heteroaromatic group, unsubstituted heteroaromatic group, heterocyclic, $C_1$–$C_{12}$ alkyl, $C_2$–$C_{12}$ alkenyl, $C_2$–$C_{12}$ alkynyl, $NR^{51}R^{52}$, $COR^{52}$, $OR^{53}$, and Formula Ar' —$CH_2$—CH=CH-phenyl, —S-phenyl, 3-methoxyphenyl, 3,5-dimethoxyphenyl, 4-trifluoromethylphenyl, 4-TBDMSOH$_2$C—Ph, 4-t-BocHNH$_2$C—Ph, 3-t-BocHN—Ph, $_4$—HOOCH$_2$C—Ph, and 4-HOH$_2$C—Ph.

$R^{51}$ is selected from the group consisting of hydrogen and $C_1$–$C_3$ alkyl;

$R^{52}$ is selected from the group consisting of hydrogen and $C_1$–$C_3$ alkyl;

$R^{53}$ is selected from the group consisting of $C_1$–$C_{12}$ alkyl;

$R^{54}$ is selected from the group consisting of hydrogen, $C_1$–$C_6$ alkyl, $C_1$–$C_6$alkyl($R^{57'}R^{57''}R^{57'''}$), simple unsubstituted aromatic, simple substituted aromatic, heterocyclic, phenyl, halogen, 4-(tert-butyldimethylsiloxy)-benzyltriphenylphosophonium, $COOR^{57}$, $PO_3H$, $SO_3H$, $SO_2R^{58}$, $N(R^{59})R^{60}$, $NHOR^{61}$, $NHCHR^{61'}$, CN, $NO_2$, halogen, $OR^{62}$, $CH_2(O)R^{62'}$, —$CH_2OC(O)R^{95}$, $CH_2N(R^{96})R^{96'}$, $COR^{100}$, ($C_1$–$C_6$alkyl)$OR^{100}$, $SR^{63}$;

and $R^{95}$ is selected from the group consisting of —$R^{98}NH_2$;

$R^{96}$ and $R^{96'}$ are each independently selected from the group consisting of hydrogen and $C_1$–$C_6$ alkyl, —$R^{97}NH_2$, and —$R^{99}$ $NR^{99'}$ $R^{99''}$;

$R^{97}$ is selected from the group consisting of $C_1$–$C_6$ alkyl;

$R^{98}$ is selected from the group consisting of $C_1$–$C_6$ alkyl;

$R^{99}$ is $C_1$–$C_6$ alkyl;

$R^{99'}$ and $R^{99''}$ are each independently selected from the group consisting of hydrogen and $C_1$–$C_6$ alkyl;

$R^{100}$ is selected from the group consisting of hydrogen, and $Si(R^{101}R^{102}R^{103})$;

$R^{101}$ is $C_1$–$C_6$ alkyl;

$R^{102}$ is $C_1$–$C_6$ alkyl;

$R^{103}$ is $C_1$–$C_6$ alkyl;

$R^{104}$ is selected from the group consisting of $C(O)C_1$–$C_6$ alkylN($R^{106}$) ($R^{59}$)$R^{60}$, $C(O)C_1$–$C_6$ alkylN$^+$, fused bicyclic, and $NHR^{105}N(R^{106})$ ($R^{59}$)$R^{60}$;

$R^{105}$ is selected from the group consisting of $C(O)C_1$–$C_6$ alkyl, $C_1$–$C_6$ alkyl;

$R^{106}$ is selected from the group consisting of hydrogen, $C_1$–$C_6$ alkyl, $C(O)OR^{107}$;

$R^{107}$ is selected from the group consisting of hydrogen, $C_1$–$C_6$ alkyl, $CR^{108}$ $R^{109}$ $R^{110}$;

$R^{108}$ is selected from the group consisting of hydrogen and $C_1$–$C_6$ alkyl;

$R^{109}$ is selected from the group consisting of hydrogen and $C_1$–$C_6$ alkyl;

$R^{110}$ is selected from the group consisting of hydrogen and $C_1$–$C_6$ alkyl;

$R^{111}$ is selected from the group consisting of hydrogen, $C_1$–$C_6$ alkyl, and $C(O)OR^{107}$;

$R^{55}$ is selected from the group consisting of hydrogen, $C_1$–$C_6$ alkyl, $C(R^{57'}R^{57''}R^{57'''})$, simple unsubstituted aromatic, simple substituted aromatic, phenyl, $COOR^{57}$, $PO_3H$, $SO_3H$, $SO_2R^{58}$, $NR^{59}R^{60}$, $NHOR^{61}$, $NHCHR^{61'}$, CN, $NO_2$, halogen, $OR^{62}$, and $SR^{63}$;

$R^{56}$ is selected from the group consisting of hydrogen, $C_1$–$C_6$ alkyl, $C(R^{57'}R^{57''}R^{57'''})$, simple unsubstituted aromatic, simple substituted aromatic, phenyl, $COOR^{57}$, $PO_3H$, $SO_3H$, $SO_2R^{58}$, $NR^{59}R^{60}$, $NHOR^{61}$, $NHCHR^{61'}$, $(C_1$–$C_6)alkylNR^{59}R^{60}$, CN, $NO_2$, halogen, $OR^{104}$, $CR^{104'}$, $OR^{62}$, and $SR^{63}$;

$R^{57}$ is selected from the group consisting of hydrogen and $C_1$–$C_{12}$ alkyl;

$R^{57'}$ is selected from the group consisting of hydrogen, halogen, and $C_1$–$C_{12}$ alkyl;

$R^{57''}$ is selected from the group consisting of hydrogen, halogen, and $C_1$–$C_{12}$ alkyl;

$R^{57'''}$ is selected from the group consisting of hydrogen, halogen, and $C_1$–$C_{12}$ alkyl;

$R^{58}$ is selected from the group consisting of hydrogen and $C_1$–$C_{12}$ alkyl;

$R^{59}$ is selected from the group consisting of hydrogen, $(C_1$–$C_6)$ alkyl, tert-butoxycarbonyl, carbo-tert-butoxy (t-BOC) and fluorenylmethoxycarbonyl (FMOC);

$R^{60}$ is selected from the group consisting of hydrogen and $(C_1$–$C_6)$ alkyl;

$R^{61}$ is selected from the group consisting of hydrogen, $OR^{64}$, $CH_2NHR^{65}$, $NHR^{65'}$ and fluorenylmethoxycarbonyl (FMOC);

$R^{61'}$ is selected from the group consisting of hydrogen, $OR^{64}$, $CH_2NHR^{65}$, $NHR^{65'}$ and fluorenylmethoxycarbonyl (FMOC);

$R^{62}$ is selected from hydrogen, and $C_1$–$C_6$ alkyl;

$R^{62'}$ is selected from hydrogen, OH, $OR^{62}$, and $C_1$–$C_6$ alkyl;

$R^{63}$ is selected from hydrogen and $C_1$–$C_6$ alkyl;

$R^{64}$ is selected from the group consisting of hydrogen, $(C_1$–$C_6)$ alkyl, $CH_2NR^{66}R^{67}$;

$R^{65}$ is selected from the group consisting of hydrogen and $C_1$–$C_6$ alkyl, $NH_2$, and fluorenylmethoxycarbonyl (FMOC);

$R^{65'}$ is selected from the group consisting of hydrogen and $C_1$–$C_6$ alkyl, $NH_2$, and fluorenylmethoxycarbonyl (FMOC);

$R^{66}$ is selected from the group consisting of hydrogen and $C_1$–$C_6$ alkyl and fluorenylmethoxycarbonyl (FMOC);

$R^{67}$ is selected from the group consisting of hydrogen and $C_1$–$C_6$ alkyl;

$R^1$ and $R^2$ are each independently selected from the group consisting of halogen, monalkylamino, dialkylamino, trialkylammonium, alkylthio, dialkylsulfonium, sulfate, phosphate, $OR^{31}$, $SR^{31}$, $NR^{31}$, OH, SH, $NR^{92}$, $R^{93}$, $NR^{94}$, and $NH_2$;

$R^{92}$, $R^{93}$, and $R^{94}$ are each independently selected from the group consisting of $C_1$–$C_6$ alkyl;

provided that one selected from the group consisting of $R^1$ and $R^2$ is selected from the group consisting of $OR^{31}$, $SR^{31}$, $R^{31}$, OH, and SH; or $R^1$ and $R^2$ may be taken together with C-18 and C-19 to form an epoxide ring, an aziridine ring, an episulfide ring, a sulfate ring, a cyclopropyl ring or mono($C_1$–$C_6$) alkylphosphate ring; or $R^1$ and $R^2$ may be taken together to form a second bond between C-18 and C-19;

$R^3$ is a lower alkyl group;

$R^4$ is H or OH;

$R^5$ is H or OH;

$R^4$ and $R^5$ may be taken together to form a second bond between $C_{13}$ and $C_{14}$;

$R^6$ is a substituent selected from the group consisting of benzyl, hydroxybenzyl, alkoxybenzyl, halohydroxybenzyl, dihalohydroxybenzyl, haloalkoxybenzyl, or dihaloalkyoxybenzyl group, B-ring heteroaromatic, substituted heteroaromatic, B-ring $(C_1$–$C_6)$alkyl, $(C_3$–$C_8)$cycloalkyl, substituted $C_3$–$C_8$ cycloalkyl, substituted $(C_1$–$C_6)$alkyl, a group of the formula III'

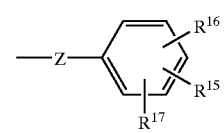

III' and a group of the formula III":

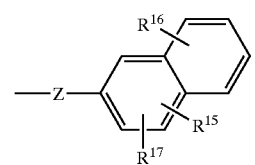

III"

$R^7$ is selected from the group consisting of $NR^{51}R^{52}$, $R^{53}NR^{51}R^{52}$, $OR^{53}$, H and a lower alkyl group; $R^{51}$ and $R^{52}$ are independently selected from the group consisting of $C_1$–$C_3$ alkyl; $R^{53}$ is $C_1$–$C_3$ alkyl;

$R^8$ is H or a lower alkyl group; or $R^7$ and $R^8$ can form a cyclopropyl ring;

$R^9$ is selected from the group consisting of H, a lower alkyl group, unsaturated lower alkyl, lower alkyl-$C_3$–$C_5$ cycloalkyl, and benzyl;

$R^{10}$ is H or a lower alkyl group;

$R^{11}$ is selected from the group consisting of hydrogen, OH, lower alkyl group, substituted phenyl, benzyl, substituted benzyl and phenyl;

$R^{14}$ is selected from the group consisting of hydrogen and lower alkyl;

$R^{15}$, $R^{16}$, and $R^{17}$ are each independently selected from the group consisting of hydrogen, $OR^{18}$, halo, $NR^{18'}R^{19'}$, $NO_2$, $OPO_3H_2$, $OR^{19}$phenyl, $SCH_2$phenyl, $CONH_2$, $CO_2H$, $PO_3H_2$, $SO_2R^{23}$, and ZZ;

$R^{18}$ is selected from the group consisting of hydrogen, aryl, $C_1$–$C_6$ alkyl, $C(O)R^{90}$ and fluorenylmethoxycarbonyl (FMOC);

$R^{18'}$ is selected from the group consisting of hydrogen, $(C_1$–$C_6)$alkyl and $C(O)R^{90'}$;

$R^{19}$ is $C_1$–$C_6$ alkyl, $C(O)R^{90''}$ and fluorenylmethoxycarbonyl (FMOC);

$R^{19'}$ is selected from the group consisting of hydrogen, $(C_1$–$C_6)$alkyl, and $C(O)R^{90'''}$;

$R^{90}$, $R^{90'}$, $R^{90''}$, and $R^{90'''}$ are each independently selected from the group consisting of hydrogen, $(C_1-C_6)$alkyl, $OR^{91}$ and aryl;

$R^{91'}$ is selected from the group consisting of $(C_1-C_6)$alkyl, aryl, and hydrogen;

$R^{23}$ is selected from the group consisting of hydrogen and $(C_1-C_3)$ alkyl;

$R^{30}$ is hydrogen or $C_1-C_6$ alkyl; or $R^{30}$ may be taken together with the N at C-11 to form a three to seven membered cyclic ring;

$R^{31}$ is selected from the group consisting of P, S, $(C_1-C_{12})$ alkyl, B, $R^{32}$ and Si;

$R^{32}$ is selected from the group consisting of amino acid, carbohydrate, amino sugar, (saccharide)$_q$, $C(O)R^{33}$, and

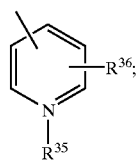

$R^{33}$ is selected from the group consisting of $R^{37}R^{38}$, $R^{38}$, $R^{37}N$ $(R^{20'})R^{38}$, $R^{37}N(R^{20'})$ $(C_1-C_6)$alkylC(O)R$^{38}$, $R^{37}N(R^{20'})$ $C(O)R^{38}$, $R^{37}O(C_1-C_6)$alkylO$(C_1-C_6)$ alkylO$(C_1-C_6)$alkylO$(C_1-C_6)$alkyl and $R^{37}(N$ $R^{18'}R^{20'})R^{38}$;

$R^{20'}$ is selected from the group consisting of hydrogen, $C_1-C_6$ alkyl, and $-CO_2R^{21'}$;

$R^{21'}$ is selected from the group consisting of hydrogen and $(C_1-C_6)$alkyl;

$R^{34}$ is $(C_1-C_4)$alkyl;

$R^{35}$ is hydrogen or $(C_1-C_3)$alkyl;

$R^{36}$ is hydrogen, OH, halo, $(C_1-C_3)$alkyl, $OR^{34}$, $NO_2$, $NH_2$ and heteroaromatic;

$R^{37}$ is $(C_1-C_6)$alkyl;

$R^{38}$ is $COOR^{39}$,

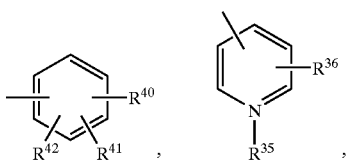

$NH_2$, (N $R^{18'}R^{20'}$), heterocyclic, heteroaromatic, OH, $(C_1-C_6)$alkyl, and amino acid;

$R^{39}$ is H or $(C_1-C_6)$alkyl;

$R^{40}$, $R^{41}$, and $R^{42}$ are each independently selected from the group consisting of hydrogen, $OR^{43}$, halo, $NH_2$, $NO_2$, $OPO(OR^{46})_2$, $-OR^{44}$phenyl, and $R^{45}$;

$R^{43}$ is $C_1-C_6$ alkyl;

$R^{44}$ is $C_1-C_6$ alkyl;

$R^{45}$ is selected from the group consisting of a unsubstituted simple aromatic group and a substituted simple aromatic group;

$R^{46}$ is selected from the group consisting of H, Na, $(C_1-C_6)$alkyl and $-C(CH_3)_3$;

$R^{50}$ is hydrogen or

n is 0, 1, or 2;

m is 0, 1, or 2;

p is 0, 1, or 2;

q is 2, 3, or 4;

X is selected from the group consisting of O, C, S, NH and alkylamino;

Y is selected from the group consisting of C, O, NH, S, SO, $SO_2$ and alkylamino;

Z is selected from the group consisting of $-(CH_2)_n-$, $-(CH_2)_p-O-(CH_2)_m-$ and $(C_3-C_5)$ cycloalkyl;

ZZ is selected from the group consisting of a simple unsubstituted aromatic group and a simple substituted aromatic group; or a pharmaceutically acceptable salt or solvate thereof;

provided that if $R^1$ is selected from the group consisting of halogen, OH, $OR^{31}$, SH, amino, monoalkylamino, dialkylamino, trialkylamino, trialkylammonium, alkylthio, dialkylsulfonium, sulfate and phosphate, and $R^2$ is selected from the group consisting of OH, $NH_2$, $NR^{31}$ and SH or $R^1$ and $R^2$ together form an epoxide ring, an aziridine ring, an episulfide ring, a sulfate ring, a cyclopropyl ring, or monoalkylphosphate ring, or $R^1$ and $R^2$ together form a second bond; $R^3$ is lower alkyl; $R^4$ and $R^5$ are H or $R^4$ and $R^5$ taken together form double bond between $C_{13}$ and $C_{14}$; $R^6$ is benzyl, hydroxybenzyl, alkoxybenzyl, halohydroxybenzyl, dihalohydroxybenzyl, halohydroxybenzyl, or dihalohydroxybenzyl; $R^7$, $R^8$, $R^9$, and $R^{10}$ are each independently H or a lower alkyl group; and X and Y are each independently O, NH or alkylamino and $R^{50}$ is

and $R^{11}$ is hydrogen; then

Ar is not selected from the group consisting of $C_1-C_{12}$alkyl, $C_1-C_{12}$alkynyl, phenyl, simple unsubstituted aromatic, substituted aromatic, unsubstituted heteroaromatic, and substituted heteroaromatic; or if Ar is selected from the group consisting of $C_1-C_{12}$alkyl, $C_1-C_{12}$alkynyl, phenyl, simple unsubstituted aromatic, substituted aromatic, unsubstituted heteroaromatic, and substituted heteroaromatic; and $R^{50}$ is

and $R^{11}$ is hydrogen; then $R^2$ is selected from the group consisting of halogen, amino, monoalkylamino, dialkylamino, trialkylammonium, alkylthio, dialkylsulfonium, sulfate, phosphate, $OR^{31}$ and $SR^{31}$; or if $R^1$ is selected from the group consisting of halogen, OH, $OR^{31}$, SH, amino, monoalkylamino, dialkylamino, trialkylamino, trialkylammonium, alkylthio, dialkylsulfonium, sulfate and phosphate, and $R^2$ is selected from the group consisting of OH, $NH_2$, $NR^{31}$ and SH or $R^1$ and $R^2$ together form an epoxide ring, an aziridine ring, an episulfide ring, a sulfate ring, a cyclopropyl ring, or monoalkylphosphate ring, or $R^1$ and $R^2$ together form a second bond and $R^3$ is lower alkyl and $R^4$ is H and $R^5$ is H and $R^{50}$ is hydrogen and $R^{11}$ is hydrogen; then Ar is not selected from the group consisting of $C_1$–$C_{12}$alkyl, $C_1$–$C_{12}$alkynyl, phenyl, simple unsubstituted aromatic, substituted aromatic, and heteroaromatic; or if $R^1$ is selected from the group consisting of halogen, OH, $OR^{31}$, SH, amino, monoalkylamino, dialkylamino, trialkylamino, trialkylammonium, alkylthio, dialkylsulfonium, sulfate and phosphate, and $R^2$ is selected from the group consisting of OH, $NH_2$, $NR^{31}$ and SH or $R^1$ and $R^2$ together form an epoxide ring, an aziridine ring, an episulfide ring, a sulfate ring, a cyclopropyl ring, or monoalkylphosphate ring, or $R^1$ and $R^2$ together form a second bond and $R^3$ is lower alkyl and $R^4$ is H and $R^5$ is H and $R^{50}$ is hydrogen and $R^{11}$ is hydrogen; or $R^{50}$ is selected from the group consisting of

and hydrogen; and $R^{11}$ is selected from the group consisting of OH, lower alkyl group, substituted phenyl, benzyl, substituted benzyl and phenyl; then Ar is not selected from the group consisting of $C_1$–$C_{12}$alkyl, $C_1$–$C_{12}$alkynyl, phenyl, simple unsubstituted aromatic, substituted aromatic, substituted heteroaromatic and unsubstituted heteroaromatic; or if $R^3$ is lower alkyl; $R^4$ and $R^5$ are H or $R^4$ and $R^5$ taken together form a double bond between $C_{13}$ and $C_{14}$; $R^6$ is benzyl, hydroxybenzyl, alkoxybenzyl, halohydroxybenzyl, dihalohydroxybenzyl, halohydroxybenzyl, or dihalohydroxybenzyl; $R^7$, $R^8$, $R^9$, and $R^{10}$ are each independently H or a lower alkyl group; and X and Y are each independently O, NH or alkylamino; and Ar is of the formula Ar′ and one of $R^{54}$, $R^{55}$, $R^{56}$ is selected from the group consisting of alkyl or halogen; and $R^1$ and $R^2$ may be taken together to form an epoxide ring, an aziridine ring, an episulfide ring, a sulfate ring, a cyclopropyl ring or monoalkylphosphate ring; or $R^1$ and $R^2$ may be taken together to form a second bond between $C_{18}$ and $C_{19}$; or $R^2$ is selected from the group consisting of OH and SH;

then at least two of $R^{54}$, $R^{55}$, and $R^{56}$ must be selected from the group consisting of $C_1$–$C_6$ alkyl, simple aromatic, phenyl, $COOR^{57}$, $PO_3H$, $SO_3H$, $SO_2R^{58}$, $NR^{59}R^{60}$, $NHOR^{61}$, $NHCHR^{61'}$, CN, $NO_2$, halogen, $OR^{62}$, and $SR^{63}$; or if $R^3$ is lower alkyl; $R^4$ and $R^5$ are H or $R^4$ and $R^5$ taken together form a double bond between $C_{13}$ and $C_{14}$; $R^6$ is B-ring heteroaromatic, substituted heteroaromatic, B-ring ($C_1$–$C_6$) alkyl, ($C_3$–$C_8$)cycloalkyl, substituted $C_3$–$C_8$ cycloalkyl, substituted ($C_1$–$C_6$)alkyl, a group of the formula III′

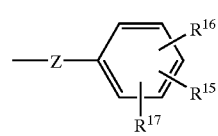

and a group of the formula III″:

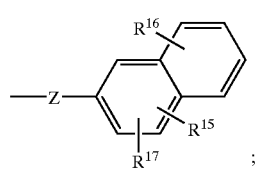

and

X and Y are each independently O, NH or alkylamino; then

Ar is not selected from the group consisting of phenyl or any simple unsubstituted or substituted aromatic or heteroaromatic group, $C_1$–$C_{12}$ alkyl, and $C_1$–$C_{12}$ alkynyl.

The present invention provides pharmaceutical formulations, a method for disrupting a microtubulin system using an effective amount of a compound of Formula I, a method for inhibiting the proliferation of mammalian cells comprising administering an effective amount of a compound of Formula I, and a method for treating neoplasia in a mammal comprising administering an effective amount of a compound of Formula I. Also, provided is a method for controlling a mycotic infection comprising administering to an animal infected with or susceptible to infection with a fungi, an antifungally effective amount of a compound of Formula I.

As used herein, the term "simple alkyl" shall refer to $C_1$–$C_7$ alkyl wherein the alkyl may be saturated, unsaturated, branched, or straight chain. Examples include, but are in no way limited to, methyl, ethyl, n-propyl, iso-propyl, n-butyl, propenyl, ethenyl, sec-butyl, n-pentyl, isobutyl, tert-butyl, sec-butyl, methylated butyl groups, pentyl, tert pentyl, sec-pentyl, methylated pentyl groups and the like. The term "alkenyl" refers to an alkyl group, as defined above, having from one to three double bonds. The term "alkynyl" refers to an alkyl group, as defined above, having at least one triple bond. It is especially preferred that alkynyl has only one triple bond. The term $C_1$–$C_{n'}$ alkyl; wherein n' is an integer from 2 to 12 means an alkyl group having from one to the indicated number of carbon atoms. The $C_1$–$C_{n'}$ alkyl can be straight or branched chain.

As used herein, the term "B-ring $C_1$–$C_6$ alkyl" refers to saturated, unsaturated, branched and straight chain alkyl wherein the B-ring $C_1$–$C_6$alkyl group may include up to three (3) non-carbon substituents. Such non-carbon substituents are most preferredly selected from the group consisting of OH, $SCH_2$phenyl, $NH_2$, CO, $CONH_2$, $CO_2H$, $PO_3H_2$, $SO_2R^{21}$ wherein $R^{21}$ is selected from hydrogen and $C_1$–$C_3$alkyl.

As used herein the term "amino acid" means an organic acid containing an amino group. The term includes both naturally occurring and synthetic amino acids, therefore, the amino group can be, but is not required to be, attached to the carbon next to the acid. The amino acid substituent is attached to the parent molecule via the organic acid functionality.

As used herein, the term "carbohydrate" refers to a class of substituents made up of carbon, hydrogen, and oxygen wherein hydrogen and oxygen are in the same proportions as in water or nearly the proportions as water. The term "carbohydrate" further refers to an aldehyde or ketone alcohol or a compound which on hydrolysis produces an aldehyde or ketone. The term "carbohydrate" is as commonly understood by the skilled artisan. For example, the term refers to, but is in no way limited to, $C_{12}H_{22}O_{11}$ and $C_6H_{10}O_5$.

As used herein, the term "amino sugar" refers to a carbohydrate group containing from one to three amino substituents at any available position on the carbohydrate molecule.

As used herein, the term "saccharide" refers to carbohydrate subunits to form disaccharides or polysaccharides. The term means for example, but in no way limited to, lactose, maltose, sucrose, fructose, starch, and the like.

As used herein, the term "substituted phenyl" shall refer to a phenyl group with from one to three non-hydrogen substituents which may be independently selected from the group consisting of simple alkyl, Cl, Br, F, and I.

As used herein, the term "substituted benzyl" shall refer to a benzyl group with from one to three non-hydrogen substituents which may be independently selected from the group consisting of simply alkyl, Cl, Br, F, and I wherein such substituents may be attached at any available carbon atom. Some preferred substituted benzyls have been described as well. As used herein, the term "alkoxybenzyl" refers to a benzyl group having an alkoxy substituent at any available position on the benzyl ring The alkoxy group is most preferably -) ($C_1$–$C_3$) alkyl. Methoxy is especially preferred. Accordingly, the term "haloalkoxybenzyl" refers to a benzyl group having a halo substituent in addition to an alkoxy substituent. Each halo or alkoxy group is substituted at any available carbon. Similarly, "halohydroxybenzyl" refers to a hydroxy substituted benzyl group that also has a halo substituent at any available carbon on the benzyl ring. Finally, the term "dihaloalkoxybenzyl" refers to an alkoxy substituted benzyl which additionally has two halo substituents each independently substituted at any available carbon on the benzyl ring.

As used herein "B-ring heteroaromatic group" refers to aromatic rings which contain one or more non-carbon substituent selected from the group consisting of oxygen, nitrogen, and sulfur. Especially preferred B-ring heterocyclic groups are selected from, but not limited to, the group consisting of:

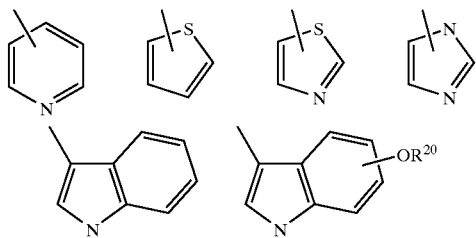

-continued

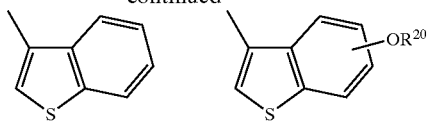

$R^{20}$ is selected from hydrogen and $C_1$–$C_6$ alkyl.

It is especially preferred that "B-ring heteroaromatic group" refers to a substituent selected from the group consisting of:

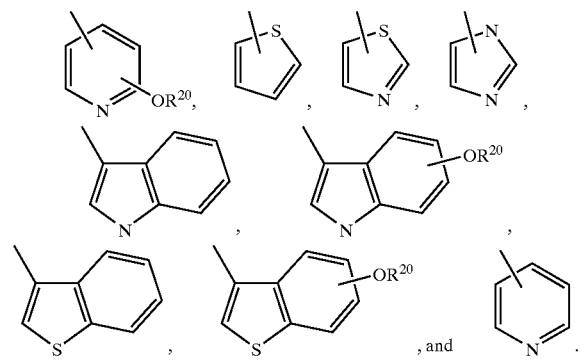

"Substituted aromatic" refers to a group substituted with from one to three substituents selected from the group consisting of simple alkyl and halo.

As used herein "cycloalkyl" refers to a saturated $C_3$–$C_8$ cycloalkyl group wherein such group may include from zero to three substituents selected from the group consisting of $C_1$–$C_3$ alkyl, halo, and $OR^{22}$ wherein $R^{22}$ is selected from hydrogen and $C_1$–$C_3$ alkyl. Such substituents may be attached at any available carbon atom. It is especially preferred that cycloalkyl refers to substituted or unsubstituted cyclohexyl.

As used herein "Lower alkoxyl group" means any alkyl group of one to five carbon atoms bonded to an oxygen atom. As used herein "lower alkyl group" means an alkyl group of one to six carbons and includes linear and non-linear hydrocarbon chains, including for example, but not limited to methyl, ethyl, propyl, isopropyl, butyl, isobutyl, tert-butyl, sec-butyl, methylated butyl groups, pentyl, tert pentyl, sec-pentyl, and methylated pentyl groups. As used herein, the term "unsaturated lower alkyl group" and "saturated lower alkyl group" shall have the meaning that the artisan commonly associates with the terms unsaturated and saturated. The term "lower alkyl" shall refer to both saturated and unsaturated lower alkyl groups. (For example a saturated group has no double or triple bonds). As used herein "allylically substituted alkene" means any alkene having from two to seven carbon atoms which contains an alkyl substitution on it.

As used herein "epoxide ring" means a three-membered ring whose backbone consists of two carbons and an oxygen atom. As used herein, "aziridine ring" means a three-membered ring whose backbone consists of two carbon atoms and a nitrogen atom. As used herein "sulfide ring" means a three-membered ring whose backbone consists of two carbon atoms and a sulfur atom. As used herein "episulfide ring" means a three-membered ring whose backbone consists of two carbon and a sulfur atom. As used herein "sulfate group" means a five membered ring consisting of a carbon-carbon-oxygen-sulfur-oxygen backbone with two additional oxygen atoms connected to the sulfur atom. As used herein, "monalkylphosphate ring" means a five membered ring consisting of a carbon-carbon-oxygen-phosphorous-oxygen backbone with two additional oxygen atoms, one of which bears a lower alkyl group, connected to the phosphorous atom.

As used herein, "simple unsubstituted aromatic group" refers to common aromatic rings having 4n+2 electrons in a moncyclic or bicyclic conjugated system, for example, but not limited to: furyl, pyrrolyl, thienyl, pyridyl, and the like, or a bicyclic conjugated system, for example, but not limited to, indolyl or naphthyl.

As used herein "simple substituted aromatic group" refers to a simple aromatic ring substituted with a single group selected from the group consisting of halogen and lower alkyl group.

As used herein, "heteroaromatic" refers to aromatic rings which contain one or more non-carbon atoms selected from the group consisting of oxygen, nitrogen, and sulfur. Most preferred heteroaromatic rings have from three to eight members in the ring. An especially preferred group of heteroaromatic rings have from three to six members. It is particularly preferred that the heteroaromatic group will have from one to three non-carbon atoms in the ring. A five member ring containing one oxygen atom is one preferred heteroaromatic group; however, the term is in no way limited to this group.

As used herein "heterocyclic" refers to cyclic rings which contain one or more non-carbon atoms selected from the group consisting of oxygen, nitrogen, and sulfur. The heterocyclic rings may be saturated or unsaturated. Further, the heterocyclic rings may be fused with one another to form a bicyclic or tricyclic system. For example, but not limited to a five membered ring having two double bonds or a five membered ring having one double bond. The heterocyclic rings may be unsubstituted or may have from one to three substituents selected from the group consisting of $C_1$–$C_6$alkyl, carbonyl, halogen, and $OR^{62}$. Most preferred heterocyclic rings have from three to eight members in the ring. An especially preferred group of heterocyclic rings have from three to six members. It is particularly preferred that the heterocyclic group will have from one to three non-carbon atoms. One preferred heterocyclic ring is a five membered ring having one nitrogen, one sulfur, one methyl substituent, and two double bonds.

A preferred heterocyclic group includes but is not limited to:

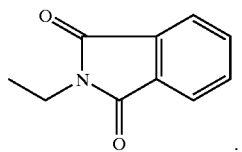

"Substituted heteroaromatic" refers to a group substituted with from one to three substituents selected from the group consisting of simple alkyl and halo.

As used herein, "halogen" or "halo" refers to those members of the group on the periodic table historically known as halogens. Methods of halogenation include, but are not limited to, the addition of hydrogen halides, substitution at high temperature, photohalogenation, etc., and such methods are known to the skilled artisan. Especially preferred halogens include, but are in no way limited to: chloro, fluoro, and bromo.

As used herein, the term "aryl" has the meaning commonly associated with the term by the artisan. Thus, the term means an organic radical derived from an aromatic hydrocarbon by the removal of one hydrogen atom. For example, but not limited to, phenyl, tolyl, salicyl, and the like.

As used herein, the term "mammal" shall refer to the Mammalia class of higher vertebrates. The term "animal" shall include, but is not limited to, mammals, reptiles, amphibians, and fish. The term "mammal" includes, but is not limited to, a human. The term "treating" as used herein includes prophylaxis of the named condition or amelioration or elimination of the condition once it has been established. The cryptophycin compounds claimed herein can be useful for veterinary health purposes as well as for the treatment of a human patient.

When the desired $R^6$ substituent in the compound contains an amine, then the amine substituent of the $R^6$ group must be protected using an amino protecting group. The artisan can readily select an appropriate amino protecting group using guidance from standard works, including, for example, "Protective Groups in Organic Chemistry", Plenum Press, (London and New York, 1973); Greene, T. W. "Protecting Groups in Organic Synthesis", Wiley (New York, 1981).

As used herein, the term "derivatizing" refers to standard chemical transformations known to the artisan which give access to desired compounds of this invention.

The presently claimed processes provide a means for preparing totally synthetic cryptophycin compounds. Conveniently, commercially available amino acids can be cyclized into the cryptophycin molecule.

Many of the known cryptophycin compounds have promising antitumor activity; however, poor aqueous solubility can present issues during intravenous administration of drug. Such issues are related to the use of solubilizing surfactants, such a Cremophor, which may possess inherent toxicity. The present invention provides new cryptophycin compounds having antitumor activity as well as greater aqueous solubility properties. Such compounds have desired solubility characteristics as well as acceptable potency.

The processes to prepare the compounds of this invention most preferably are completed in the presence of a solvent. The skilled artisan can select appropriate solvents using standard methodologies. Suitable inert organic solvents include those known to the skilled artisan, for example, but not limited to, tetrahydrofuran (THF) and dimethylformamide (DMF). DMF is especially preferred. Aqueous based solvents may be appropriate for some of the processes utilized herein. The pH of such aqueous solvent s may be adjusted as desired to facilitate the process.

Some typical compounds of this invention are provided in tabular form; however, such named compounds are not intended to limit the scope of this invention in any way.

TABLE 1

| Compound | R |
|---|---|
| 3 | acetyl (−C(O)CH₃) |
| 4 | −C(O)CH₂CH₂C(O)OH |
| 5 | −C(O)CH₂-(2-(OP(O)(O-Bu)₂)phenyl) |
| 6 | −C(O)CH₂-(2-(OP(O)(ONa)₂)phenyl) |
| 7 | nicotinoyl (pyridin-3-yl carbonyl) · HCl |
| 8 | (1-methylpyridinium-2-yl)carbonyl · OAc |
| 9 | −C(O)CH(NHCO₂t-Bu)CH₂-(3-chloro-4-methoxyphenyl) |

TABLE 1-continued
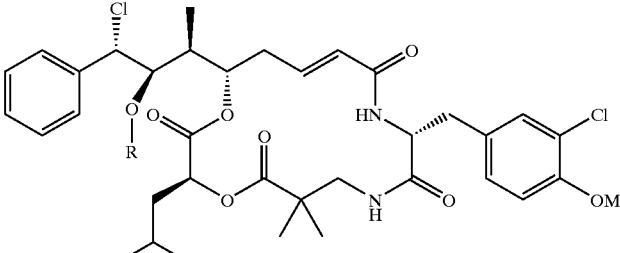
| Compound | R |
|---|---|
| 10 | 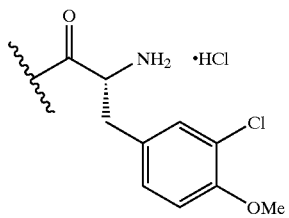 |
| 11 | 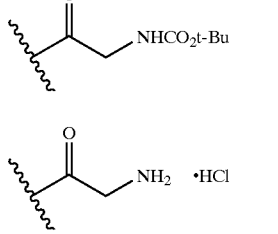 |
| 12 | 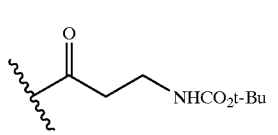 |
| 13 | 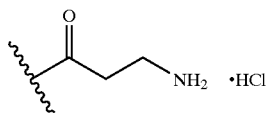 |
| 14 | 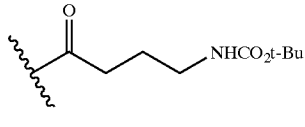 |
| 15 | 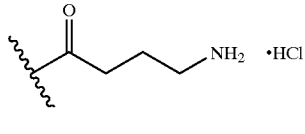 |
| 16 | 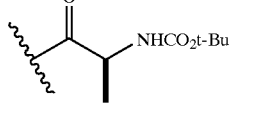 |
| 17 | 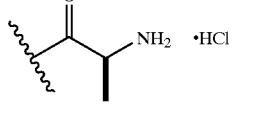 |
| 18 | |

TABLE 1-continued

| Compound | R |
|---|---|
| 19 | —C(O)—CH(CH₃)—NHCO₂t-Bu |
| 20 | —C(O)—CH(CH₃)—NH₂ ·HCl |
| 21 | —C(O)—CH(NHCO₂t-Bu)—(CH₂)₄—NHCO₂t-Bu |
| 22 | —C(O)—CH(NH₂·HCl)—(CH₂)₄—NH₂·HCl |
| 25 | tetra-O-R pyranose |
| 26 | tetra-OH pyranose |
| 27 | —C(O)—CH(NH₂·HCl)—CH₂—C₆H₅ |
| 28 | —C(O)—CH(NH₂·HCl)—CH₂CH₂—CO₂H |

TABLE 1-continued

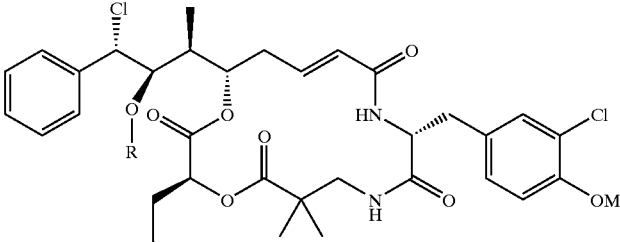

| Compound | R |
|---|---|
| 29 | 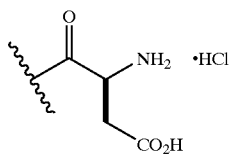 |
| 30 | 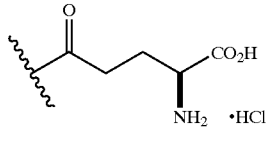 |
| 31 | 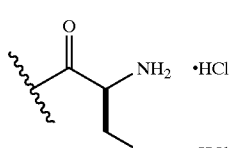 |
| 32 | |

Additional preferred compounds are, for example, but not limited to, those named above in Table I wherein the positions of the adjacent Cl and OR groups are traded. For example, the same R substituents named above wherein the base structure is as follows:

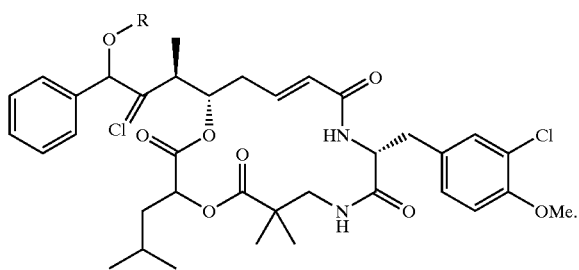

Additional compounds of interest are as named by Table I; however, Ar is Ar' instead of phenyl and $R^{54}$ is $OCH_3$ at the para position of Ar', while $R^{55}$ and $R^{56}$ are each hydrogen.

Further compounds of interest are as named by Table I; however, an NH group replaces O at the Y position of the molecule. For example, one compound in this series is:

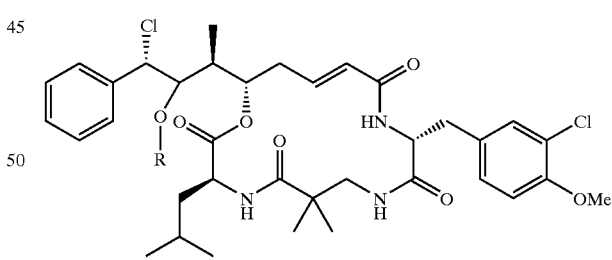

Further preferred compounds are, for example, but not limited to, those named above in Table I as well as by the compounds named by the traded positions of the adjacent Cl and OR; wherein each named compound has a single methyl group in place of the gem dimethyl group at position 6 of the cryptophycin ring. See, for example, 23 below.

Especially preferred compounds of this invention have a dimethyl group at position 6 of the cryptophycin ring.

A preferred compound of this invention is as presented in Table I wherein Ar is Ar'; only one of $R^{54}, R^{55}, R^{56}$ is $OCH_3$; $R^9$ and $R^{10}$ are each methyl.

Generally known silylating agents are employed in the processes for making compounds of this invention. See for example, Calvin, E. W., "Silicon Reagents in Organic Synthesis", Academic Press, (London, 1988). Particularly useful silylating agents include "tri-lower alkyl silyl" agents, the term of which contemplates truisopropylsilyl, trimethylsilyl and triethylsilyl, trimethylsilyl halides, silylated ureas such as bis(trimethylsilyl)urea (BSU) and silylated amides such as N,O-bis(trimethylsilyl)acetamide (BSA). Of these, BSA is preferred.

Some preferred characteristics of this invention are set forth in the following tabular form wherein the features may be independently selected to provide preferred embodiments of this invention. The invention is in no way limited to the features described below:

A) $R^8$ is ethyl, propyl, isopropyl, butyl, isobutyl or isopentyl;
B) $R^7$ is ethyl, propyl, isopropyl, butyl, isobutyl, pentyl, or isopentyl;
C) $R^7$ is H, $R^8$ is methyl, $R^3$ is methyl, and X and Y are not both O;
D) $R^3$ is ethyl, propyl, isopropyl, butyl, isobutyl, pentyl or isopentyl;
E) $R^9$ is methyl, ethyl, propyl, butyl, isobutyl, pentyl, or isopentyl;
F) $R^{10}$ is methyl, ethyl, propyl, butyl, isobutyl, pentyl, or isopentyl;
G) a cryptophycin compound wherein at least one of the groups selected from the group consisting of C-3, C-6, C-7, C-10, C-16, C-17, and C-18 has R stereochemistry (numbering as set forth in Formula I supra.);
H) a cryptophycin compound wherein at least one of the groups selected from the group consisting of C-3, C-6, C-7, C-10, C-16, C-17, and C-18 has S stereochemistry (numbering as set forth in Formula I supra.);
I) Ar' is phenyl with substituent selected from the group consisting of $NR^{59}R^{60}$, $NHOR^{61}$ and $NHCHR^{61'}$;
J) a compound wherein Y is selected from the group consisting of alkylamino, NH, and O;
K) a compound wherein Y is O, $R^7$ and $R^{10}$ are each hydrogen; $R^9$ is lower alkyl; and $R^1$ is halo;
L) $R^7$, $R^8$ are each methyl;
M) $R^7$ is hydrogen;
N) $R^2$ is a glycinate;
O) $R^2$ is an acylate;
P) $R^1$ and $R^2$ form an epoxide ring;
Q) $R^6$ is selected from the group consisting of $R^6$ is benzyl, hydroxybenzyl, alkoxybenzyl, halohydroxybenzyl, and dihalohydroxybenzyl;
R) $R^4$ and $R^5$ form a double bond;
S) n is 0; $R^6$ is substituted benzyl wherein one substituent is a halogen and one is an $OR^{12}$ group wherein $R^{12}$ is lower alkyl;
T) a compound of Formula I is used for disruption of a microtubulin system;
U) a compound of Formula I is used as a antineoplastic agent;
V) a compound of Formula I is used for the treatment of cancer in a mammal;
W) a compound of Formula Isis used as an antifungal agent;
X) $R^6$ is Formula III' and is para hydroxy substituted;

$R^6$ is selected from the group consisting

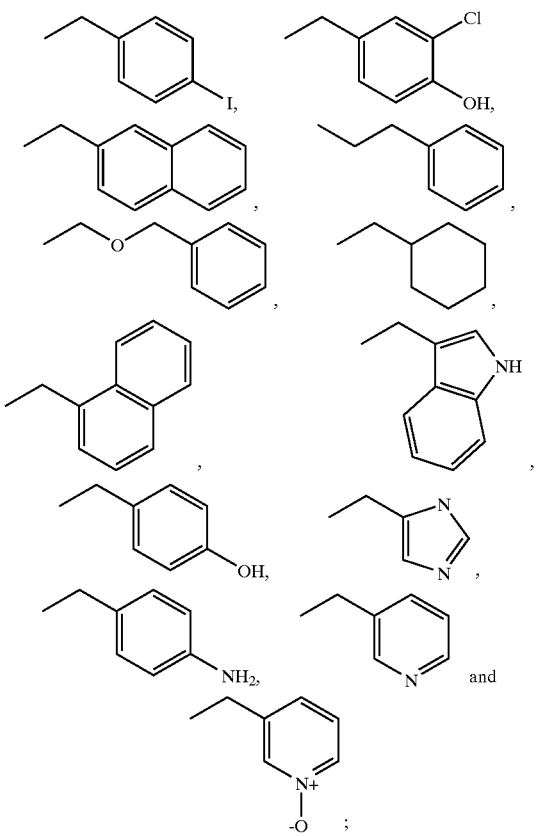

Z) Z is —$(CH_2)_n$— wherein n is 0;
AA) Z is —$(CH_2)_n$— wherein n is 2;
BB) Z is —$(CH_2)_n$— wherein n is 1;
CC) at least one of $R^{15}$, $R^{16}$, and $R^{17}$ is selected from the group consisting of $SCH_2$phenyl, $NH_2$, CO, $CONH_2$, $CO_2H$, $PO_3H_2$, and $SO_2R^{21}$; wherein $R^{21}$ is selected from hydrogen and $C_1$–$C_3$ alkyl;
DD) Ar is phenyl;
EE) Ar is phenyl substituted with one or two from the group consisting of OH, $OCH_3$, halo, and methyl;
FF) $R^2$ is selected from the group consisting of halogen, amino, monoalkylamino, dialkylamino, trialkylammonium, alkylthio, dialkylsulfonium, sulfate, phosphate, $OR^{31}R^{32}$, and $SR^{31}R^{32}$;
GG) $R^6$ has a Z wherein the first carbon of the Z group is

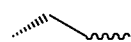

with respect to the point of attachment to the cryptophycin molecule;
a compound of Formula I is used for the treatment of fungal infection;
II) $R^{50}$ is

JJ) $R^{11}$ is hydrogen;
KK) $R^4$ and $R^5$ are each hydrogen;

LL) Ar is para ethyl substituted phenyl;
MM) Ar is para methyl substituted phenyl;
NN) Y is NH;
OO) $R^3$ is methyl;
PP) $R^6$ is selected from the group consisting of:

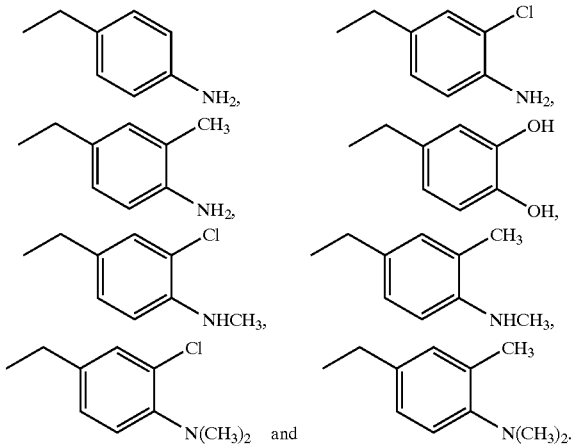

The present invention provides a method of alleviating a pathological condition caused by hyperproliferating mammalian cells comprising administering to a subject an effective amount of a pharmaceutical or veterinary composition disclosed herein to inhibit proliferation of the cells. In a preferred embodiment of this invention, the method further comprises administering to the subject at least one additional therapy directed to alleviating the pathological condition. In a preferred embodiment of the present invention, the pathological condition is characterized by the formation of neoplasms.

In a further preferred embodiment of the present invention, the neoplasms are selected from the group consisting of mammary, small-cell lung, non-small-cell lung, colorectal, leukemia, melanoma, pancreatic adenocarcinoma, central nervous system (CNS), ovarian, prostate, sarcoma of soft tissue or bone, head and neck, gastric which includes pancreatic and esophageal, stomach, myeloma, bladder, renal, neuroendocrine which includes thyroid and non-Hodgkins disease and Hodgkin's disease neoplasms.

As used herein "neoplastic" refers to a neoplasm, which is an abnormal growth, such growth occurring because of a proliferation of cells not subject to the usual limitations of growth. As used herein, "anti-neoplastic agent" is any compound, composition, admixture, co-mixture, or blend which inhibits, eliminates, retards, or reverses the neoplastic phenotype of a cell.

Anti-mitotic agents may be classified into three groups on the basis of their molecular mechanism of action.

The first group consists of agents, including colchicine and colcemid, which inhibit the formation of microtubules by sequestering tubulin. The second group consists of agents, including vinblastine and vincristine, which induce the formation of paracrystalline aggregates of tubulin. Vinblastine and vincristine are well known anticancer drugs: their action of disrupting mitotic spindle microtubules preferentially inhibits hyperproliferative cells. The third group consist of agents, including taxol, which promote the polymerization of tubuline and thus stabilizes microtubules.

The exhibition of drug resistance and multiple-drug resistance phenotype by many tumor cells and the clinically proven mode of action of antimicrotubule agents against neoplastic cells necessitates the development of antimicrotubule agents cytotoxic to non-drug resistance neoplastic cells as well as cytotoxic to neoplastic cells with a drug resistant phenotype.

Chemotherapy, surgery, radiation therapy, therapy with biological response modifiers, and immunotherapy are currently used in the treatment of cancer. Each mode of therapy has specific indications which are known to those of ordinary skill in the art, and one or all may be employed in an attempt to achieve total destruction of neoplastic cells. Moreover, combination chemotherapy, chemotherapy utilizing compounds of Formula I in combination with other neoplastic agents, is also provided by the subject invention as combination therapy is generally more effective than the use of a single anti-neoplastic agent. Thus, a further aspect of the present invention provides compositions containing a therapeutically effective amount of at least one compound of Formula I, including the non-toxic addition salts thereof, which serve to provide the above recited benefits. Such compositions can also be provided together with physiologically tolerable liquid, gel, or solid carriers, diluents, adjuvants and excipients. Such carriers, adjuvants, and excipients may be found in the *U.S. Pharmacopoeia*, Vol. XXII and *National Formulary* Vol. XVII, *U.S. Pharmacopoeia Convention, Inc.*, Rockville, Md. (1989). Additional modes of treatment are provided in *AHFS Drug Information*, 1993 e. By the American Hospital Formulary Service, pp. 522–660. Each of these references are well known and readily available to the skilled artisan.

The present invention further provides a pharmaceutical composition used to treat neoplastic disease containing at least one compound of Formula I and at least one additional anti-neoplastic agent. Anti-neoplastic agents which may be utilized in combination with Formula I compounds include those provided in the *Merck Index* 11, pp 16–17, Merck & Co., Inc. (1989). The *Merck Index* is widely recognized and readily available to the skilled artisan.

In a further embodiment of this invention, antineoplastic agents may be antimetabolite which may include but are in no way limited to those selected from the group consisting of methotrexate, 5-fluorouracil, 6-mercaptopurine, cytosine, arabinoside, hydroxyurea, and 2-chlorodeoxyadenosine. In another embodiment of the present invention, the anti-neoplastic agents contemplated are alkylating agents which may include but are in no way limited to those selected from the group consisting of cyclophosphamide, mephalan, busulfan, paraplatin, chlorambucil, and nitrogen mustard. In a further embodiment, the anti-neoplastic agents are plant alkaloids which may include but are in no way limited to those selected from the group consisting of vincristine, vinblastine, taxol, and etoposide. In a further embodiment, the anti-neoplastic agents contemplated are antibiotics which may include, but are in no way limited to those selected from the group consisting of doxorubicin, daunorubicin, mitomycin C, and bleomycin. In a further embodiment, the anti-neoplastic agents contemplated are hormone which may include, but are in no way limited to those selected from the group consisting of calusterone, diomostavolone, propionate, epitiostanol, mepitiostane, testolactone, tamoxifen, polyestradiol phosphate, megesterol acetate, flutamide, nilutamide, and trilotane.

In a further embodiment, the anti-neoplastic agents contemplated include enzymes which may include, but are in no way limited tot hose selected from the group consisting of L-Aspargenase and aminoacridine derivatives such as, but not limited to, amsacrine. Additional anti-neoplastic agents include those provided by Skeel, Roland T., "Antineoplastic Drugs and Biologic Response Modifier: Classification, Use and Toxicity of Clinically Useful Agents' *Handbook of Cancer Chemotherapy* (3$^{rd}$ ed.), Little Brown & Co. (1991).

These compounds and compositions can be administered to mammals for veterinary use. For example, domestic animals can be treated in much the same way as a human clinical patient. In general, the dosage required for therapeutic effect will vary according to the type of use, mode of administration, as well as the particularized requirements of the individual hosts. Typically, dosages will range from about 0.001 to 1000 mg/kg, and more usually 0.01 to 10 mg/kg of the host body weight. Alternatively, dosages within these ranges can be administered by constant infusion over an extended period of time, usually exceeding 24 hours, until the desired therapeutic benefits are obtained. Indeed, drug dosage, as well as route of administration, must be selected on the basis of relative effectiveness, relative toxicity, growth characteristics of tumor and effect of Formula I compound on cell cycle, drug pharmacokinetics, age, sex, physical condition of the patient and prior treatment, which can be determined by the skilled artisan.

The compound of Formula I, with or without additional anti-neoplastic agents, may be formulated into therapeutic compositions as natural or salt forms. Pharmaceutically acceptable non-toxic salts include base addition salts which may be derived from inorganic bases such as for example, sodium, potassium, ammonium, calcium, or ferric hydroxides, and such organic bases as isopropylamine, trimethylamine, 2-ethylamino ethanol, histidine, procaine, and the like. Such salts may also be formed as acid addition salts with any free cationic groups and will generally be formed with inorganic acids such as for example, hydrochloric or phosphoric acids or organic acids such as acetic, oxalic, tartaric, mandelic, and the like. Additional excipients which further the invention are provided to the skilled artisan for example in the *U.S. Pharmacopoeia*.

The suitability of particular carriers for inclusion in a given therapeutic composition depends on the preferred route of administration. For example, anti-neoplastic compositions may be formulated for oral administration. Such compositions are typically prepared as liquid solution or suspensions or in solid forms. Oral formulation usually include such additives as binders, fillers, carriers, preservatives, stabilizing agents, emulsifiers, buffers, mannitol, lactose, starch, magnesium stearate, sodium saccharin, cellulose, magnesium carbonate, and the like. These compositions may take the form of solutions, suspensions, tablets, pills, capsules, sustained release formulations, or powders, and typically contain 1% to 95% of active ingredient. More preferably, the composition contains from about 2% to about 70% active ingredient.

Compositions of the present invention may be prepared as injectables, either as liquid solutions, suspensions, or emulsions; solid forms suitable for solution in or suspension in liquid prior to injection. Such injectables may be administered subcutaneously, intravenously, intraperitoneally, intramuscularly, intrathecally, or intrapleurally. The active ingredient or ingredients are often mixed with diluents, carriers, or excipients which are physiologically tolerable and compatible with the active ingredient(s). Suitable diluents and excipients are for example, water, saline, dextrose, glycerol, or the like and combinations thereof. In addition, if desired, the compositions may contain minor amounts of auxiliary substances such as wetting or emulsifying agents, stabilizing or pH buffering agents.

The invention further provides methods for using Formula I compounds to inhibit the proliferation of mammalian cells by contacting these cells with a Formula I compound in an amount sufficient to inhibit the proliferation of the mammalian cell. A preferred embodiment is a method to inhibit the proliferation of hyperproliferative mammalian cells. For purposes of this invention "hyperproliferative mammalian cells" are mammalian cells which are not subject to the characteristic limitations of growth (programmed cell death for example). A further preferred embodiment is when the mammalian cell is human. The invention further provides contacting the mammalian cell with at least one Formula I compound and at least one anti-neoplastic agent. The types of anti-neoplastic agents contemplated are discussed supra.

The invention further provides methods for using a compound of Formula I to inhibit the proliferation of hyperproliferative cells with drug-resistant phenotypes, including those with multiple drug-resistant phenotypes, by contacting said cell with a compound of Formula I in an amount sufficient to inhibit the proliferation of a hyperproliferative mammalian cell. A preferred embodiment is when the mammalian cell is human. The invention further provides contacting a Formula I compound and at least one additional anti-neoplastic agent, discussed supra.

The invention provides a method for alleviating pathological conditions caused by hyperproliferating mammalian cells for example, neoplasia, by administering to a subject an effective amount of a pharmaceutical composition containing Formula I compound to inhibit the proliferation of the hyperproliferating cells. As used herein "pathological condition" refers to any pathology arising from the proliferation of mammalian cells that are not subject to the normal limitations of growth. Such proliferation of cells may be due to neoplasms as discussed supra.

In a further preferred embodiment the neoplastic cells are human. The present invention provides methods of alleviating such pathological conditions utilizing a compound of Formula I in combination with other therapies, as well as other anti-neoplastic agents.

The effectiveness of the claimed compound can be assessed using standard methods know to the skilled artisan. Examples of such methods are as follows:

Compounds of this invention have been found to be useful against pathogenic fungi. For example, the usefulness for treating *Cryptococcus neoformans* can be illustrated with test results against *Cryptococcus neoformans* employing yeast nitrogen base dextrose agar medium. In carrying out the assay, a compound of this invention is solubiized in dimethyl sulfoxide supplemented with Tween 20. Two fold dilutions are made with sterile distilled water/10 percent DMSO to obtain final drug concentrations in the agar dilution assay plates ranging from 0.008 µg/ml to 16.0 µg/ml against an expanded panel of 84 *Cryptococcus neoformans* strains. The minimum inhibitory concentration against the panel of 84 *Cryptococcus neoformans* isolates is determined to illustrate the desired antifungal activity.

The compounds are screened for minimum inhibitory concentrations against KB, a human nasopharyngeal carcinoma cell line, LoVo, a human colorectal adenocarcinoma cell line using The Corbett assay, see Corbett, T. H. et al. *Cytotoxic Anticancer Drugs: Models and Concepts for Drug Discovery and Development*, pp 35–87, Kluwer Academic Publishers: Norwell, 1992. See also, Valeriote, et al. *Discovery and Development of Anticancer Agents*; Kluwer Academic Publisher, Norwell, 1993 is used for the evaluation of compounds.

The most active compounds are further evaluated for cytotoxicity against four different cell types, for example a murine leukemia, a murine solid tumor, a human solid tumor, and a low malignancy fibroblast using the Corbett assay.

The compounds are further evaluated against a broad spectrum of murine and human tumors implanted in mice, including drug resistant tumors.

Tumor burden (T/C) (mean tumor burden in treated animals versus mean tumor burden in untreated animals) are used as a further assessment. T/C values that are less than 42% are considered to be active by National Cancer Institute Standards; T/C values less than 10% are considered to have excellent activity and potential clinical activity by National Cancer Institute standard.

Material

Vinblastine, cytochalasin B, tetramethylrhodamine lisothiocyanate (TRITC)-phalloidin, sulforhodamine B (SRB) and antibodies against β-tubulin and vimentin are commercially available from recognized commercial vendors. Basal Medium Eagle containing Earle's salts (BME) and Fetal Bovine Serum (FBS) are also commercially available.

Cell Lines

The Jurkat T cell leukemia line and A-10 rat aortic smooth muscle cells are obtained from the American Type Culture Collection and are cultured in BME containing 10% FBS and 50 μg/ml gentamycin sulfate. Human ovarian carcinoma cells (SKOV3) and a sub-line which has been selected for resistance to vinblastine (SKVLB1) were a generous gift from Dr. Victor Ling of the Ontario Cancer Institute. Both cell lines are maintained in BME containing 10% FBS and 50 μg/ml gentamycin sulfate. Vinblastine is added to a final concentration of 1 μg/ml to SKVLB1 cells 24 hours after passage to maintain selection pressure for P-glycoprotein-overexpressing cells.

Cell Proliferation and Cycle Arrest Assays

Cell proliferation assays are performed as described by Skehan et al. For Jurkat cells, cultures are treated with the indicated drugs as described in Skehan and total cell numbers are determined by counting the cells in a hemacytometer. The percentage of cells in mitosis are determined by staining with 0.4% Giemsa in PBS followed by rapid washes with PBS. At least 1000 cells per treatment are scored for the presence of mitotic figures and the mitotic index is calculated as the ration of the cells with mitotic figures to the total number of cells counted.

Immunofluorescence Assays

A-10 cells are grown to near-confluency on glass coverslips in BME/10% FBS. Compounds in PBS are added to the indicated final concentrations and cells are incubated for an additional 24 hours. For the staining of microtubules and intermediate filaments, the cells are fixed with cold methanol and incubated with PBS containing 10% calf serum to block nonspecific binding sites. Cells are then incubated at 37° C. for 60 min. With either monoclonal anti-β-tubulin or with monoclonal anti-vimentin at dilutions recommended by the manufacturer. Bound primary antibodies are subsequently visualized by a 45 minute incubation with fluorescein-conjugated rabbit antimouse IgG. The coverslips are mounted on microscope slides and the fluorescence patterns are examined and photographed using a Zeiss Photomicroscope III equipped with epifluorescence optics for fluorescein. For staining of microfilaments, cells are fixed with 3% paraformaldehyde, permeabilized with 0.2% Triton X-100 and chemically reduced with sodium borohydride (1 mg/ML). PBS containing 100 nM TRITC-phalloidin is then added and the mixture is allowed to incubate for 45 min. At 37° C. The cells are washed rapidly with PBS before the coverslips are mounted and immediately photographed as described above.

Effects of Cryptophycins and Vinblastine on Jurkat Cell Proliferation and Cell Cycle Dose-response curves for the effects of cryptophycin compounds and vinblastine on cell proliferation and the percentage of cells in mitosis are determined.

Effects of Cytochalasin B, Vinblastine and Cryptophycins on the Cytoskeleton

Aortic smooth muscle (A-10) cells are grown on glass coverslips and treated with PBS, 2 μM cytochalasin B, 100 nM vinblastine or 10 nM cryptophycin compounds. After 24 hours, microtubules and vimentin intermediate filaments are visualized by indirect immunofluorescence and microfilaments are stained using TRITC-phalloidin. The morphological effects of each drug is examined. Untreated cells displayed extensive microtubule networks complete with perinuclear microtubule organizing centers. Vimentin intermediate filaments were also evenly distributed throughout the cytoplasm, while bundles of microfilaments were concentrated along the major axis of the cell. Cytochalasin B caused complete depolymerization of microfilaments along with the accumulation of paracrystalline remnants. This compound did not affect the distribution of either microtubules or intermediate filaments. The cryptophycin treated microtubules and vimentin intermediates are observed for depletion of microtubules, and collapse of rimentin intermediate filaments.

Effects of Cryptophycins and Vinblastine on Taxol-stabilized Microtubules

A-10 cells are treated for 3 hours with 0 or 10 μM taxol before the addition of PBS, 100 nM vinbiastine or 10 nM cryptophycin compound. After 24 hours, microtubule organization is examined by immunofluorescence as described above. Compared with those in control cells, microtubules in taxol-treated cells were extensively bundled, especially in the cell polar regions. As before, vinblastine caused complete depolymerization of microtubules non-pretreated cells. However, pretreatment with taxol prevented microtubule depolymerization in response to vinblastine. Similarly, microtubules pretreated with taxol are observed with cryptophycin treatment.

Reversibility of Microtubule Depolymerization by Vinblastine and Cryptophycin

A-10 cells are treated with either 100 nM vinblastine or 10 nM cryptophycins for 24 hr., resulting in complete microtubule depolymerization. The cells are then washed and incubated in drug-free medium for periods of 1 hour or 24 hours. Microtubules repolymerized rapidly after the removal of vinblastine, showing significant levels of microtubules after 1 hour and complete morphological recovery by 24 hour. Cells are visualized for microtubule state after treatment with a cryptophycin compound of this invention at either 1 hour or 24 hours after removal of the cryptophycin compounds.

Effects of Combinations of Vinblastine and Cryptophycins on Cell Proliferation

SKOV3 cells are treated with combinations of cryptophycins and vinblastine for 48 hours. The percentages of surviving cells are then determined and the $IC_{50}s$ for each combination is calculated.

Toxicity of Cryptophycins, Vinblastine and Taxol Toward SKOV3 and SKVLB1 Cells

SKVLB1 cells are resistant to natural product anticancer drugs because o their over expression of P-glycoprotein. The abilities of taxol, vinblastine and cryptophycin compounds to inhibit the growth of SKOV3 and SKVLB1 cells are observed. Taxol caused dose-dependent inhibition of the proliferation of both cell lines with $IC_{50}s$ for SKOV3 and SKVLB1 cells of 1 and 8000 nM, respectively. Vinblastine also inhibited the growth of both cell lines, with $IC_{50}s$ of 0.35 and 4200 nM for SKOV3 and SKVLB1 cells, respectively. Cryptophycins compounds of this invention demonstrate activity with an $IC_{50}s$ of from about 1 to about 1000 pM for SKOV3 and SKVLB1 cells.

Thus, it can be demonstrated that the present invention provides novel cryptophycin compounds which are potent inhibitors of cell proliferation, acting by disruption of the microtubule network and inhibition of mitosis. These studies can illustrate that cryptophycin compounds disrupt microtubule organization and thus normal cellular functions, including those of mitosis.

Classic anti-microtubule agents, such as colchicine and Vinca alkaloids, arrest cell division at mitosis. It seems appropriate to compare the effect of one of these agents on cell proliferation with the cryptophycin compounds. For this purpose, the Vinca alkaloid vinblastine was selected as representative of the classic anti-microtubule agents. Accordingly, the effect of cryptophycin compounds and vinblastine on the proliferation and cell cycle progression of the Jurkat T-cell leukemia cell line is compared.

Since antimitotic effects are commonly mediated by disruption of microtubules in the mitotic spindles, the effects of cryptophycin compounds on cytoskeletal structures are characterized by fluorescence microscopy. Immunofluorescence staining of cells treated with either a cryptophycin compound or vinblastine demonstrate that both compounds cause the complete loss of microtubules. Similar studies with SKOV 3 cells can show that the anti-microtubule effects of cryptophycin compounds are not unique to the smooth muscle cell line.

GC$_3$ Human Colon Carcinoma Screen

Selected wells of a 96 well plate were seeded with GC3 human colon carcinoma cells (1×10 cells in 100 μl assay medium/well) twenty four hours prior to test compound addition. Cell free assay medium was added to other select wells of the 96 well plate. The assay medium.(RPMI-1640 was the medium used; however, any medium that will allow the cells to survive would be acceptable) was supplemented with 10% dialyzed fetal bovine serum and 25 mM HEPES buffer.

The test compound was stored in an amber bottle prior to testing. Fresh dimethylsulfoxide stock solution (200 μg/ml) was prepared immediately prior to preparation of test sample dilutions in phosphate-buffered saline (PBS). A dilution of 1:20 dimethylsulfoxide solution in PBS was prepared such that the final concentration was 10 ug/ml. Serial 1:3 dilutions using PBS (0.5 ml previous sample of 1 ml PBS) were prepared. Falcon 2054 tubes were used for the assay.

A 10 ul sample of each dilution of test compound was added in triplicate to wells of GC3 plates. The plates were incubated for 72 hours at about 37° C. A 10 μl sample of stock 3-[4,5-dimethyl-2-yl]-2,5-diphenyltetrazolium bromide salt ("MTT" 5 mg/ml in PBS) was added to each well. The plates were incubated for about an hour at 37°. The plates were centrifuged, media was decanted from the wells and 100 μl acid-isopropanol (0.04 N HCl in isopropanol) was added to each well. The plate was read within one hour using a test wavelength of 570 nm (SpectraMax reader).

Evaluation of compounds of Formula I suggest that the compounds can be useful in the treatment methods claimed herein. Further, the compounds will be useful for disrupting the microtubule system.

The preparation of the compounds of this invention can be completed using several protocols involving an activated ester followed by chromatography and acid induced deblocking where necessary.

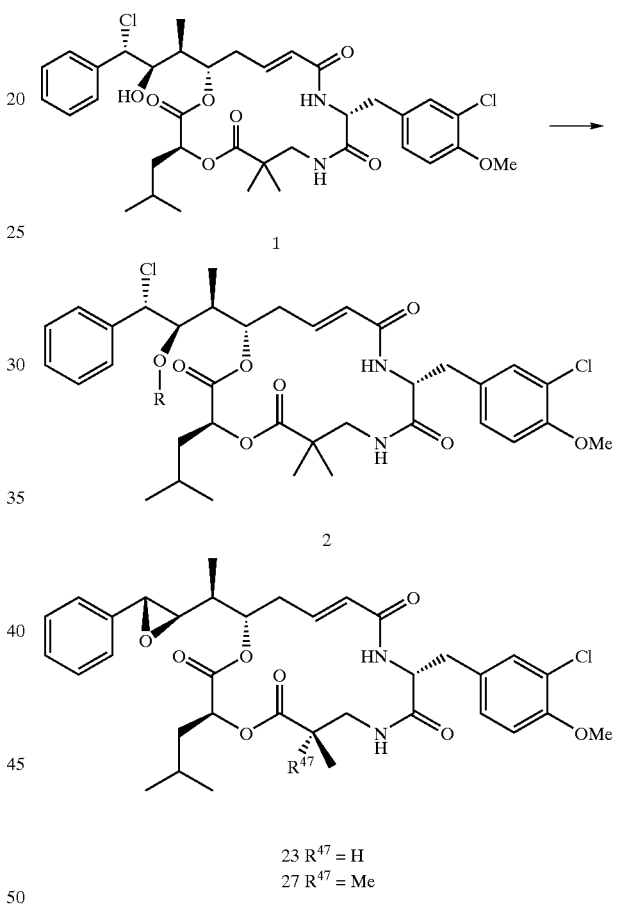

23 $R^{47}$ = H
27 $R^{47}$ = Me

For example, the treatment of 1(wherein the bolded numbers refer to the compound numbers indicated in the Example section) with acetic anhydride in the presence of triethylamine and 4-dimethylamino pyridine provides 3 in 89% yield after flash chromatography. Similarly, 4 is prepared from 1 via the agency of succinic anhydride followed by reverse phase HPLC purification. Exposure of pyridine solution of 1 to commercially available nicotinoyl chloride hydrochloride in the presence of triethylamine and 4-dimethylamino pyridine followed by chromatogrpahy and hydrogen chloride treatment gives rise to 7 in high yield. Pyridinium salt 8 is prepared in 47% yield according to the method of Nicolaou, *Angew. Chem. Int. Ed. Engl.*, 1994, 33 whereby 1 is treated with commercially available 2-fluoro-1-methylpyridinium p-toluenesulfonate followed by reverse phase HPLC purification with concomitant anion exchange (acetate for p-toluenesulfonate) and lyophilization. Esters 5, 9, 11, 13, 15, 17, 19, and 21 are all prepared in moderate to high yields from 1 and commercially available (except in the case of 5 and 9) N-t-boc protected amino acids with activation via the agency 1,3-dicyclohexylcarbodiimide in the presence of 4-dimethylamino pyridine. Hydrochloride salts 10, 12, 14, 16, 18, 20 and 22 are prepared in high yield from 9, 11, 13, 15, 17, 19, and 21 respectively upon treatment with a 4.0 M solution of hydrogen chloride in dioxane and removal of solvent in vacuo. Di-sodium salt 6 is derived from 5 following hydrochloric acid induced t-butylester cleavage and sodium hydroxide treatment. The requisite acid 24 for the preparation of 5 is synthesized in 63% yield by way of a 5 step sequence featuring the method of Johns, *Synthesis*, 1988, 142, for installing the phosphate functionality.

24

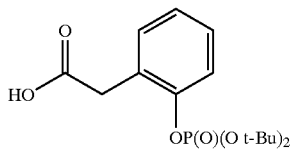

OP(O)(O t-Bu)$_2$

Several of the novel conjugates have been assayed for in vitro cytotoxicity in the GC3 tumor cell model. From the results depicted in Table 2 it is clear that good to excellent activity relative to that of cryptophycin 55 (1) is inherent to this series of compounds.

Preparation of any ester of type 2 ($R^1$ or $R^2$ derived from a carboxylic acid) includes a variety of technologies employing acid chlorides, anhydrides, and common activating reagents (e.g., carbodiimides).[2] Any solvent other than participating alcohols can be used. Any mild bases and/or catalysts (amines, carbonates) can be used to aid in esterification.

The conversion of carbamates 9, 11, 13, 15, 17, 19, and 21 to the corresponding salts could be effected with any strong acid, namely, mineral acids comprised of hydrogen halides, hydrogen sulfates, hydrogen phosphates, hydrogen nitrates, hydrogen perchlorates, or strong organic acids such as trifluoroacetic, p-toluenesulfonic, and methanesulfonic. The same acids could be used to produce salts of type 7 from the corresponding free base. A variety of counterions (cations) could comprise salts of type 6 including any of the alkali and alkaline earth' metals. A variety of counterions (anions) could comprise salts of type 8, namely, any conjugate base of an acid (organic or mineral).

Table 2. In vitro cytotoxicity data for cryptophycin derivatives using the assay described supra.

| Compound | GC3 IC$_{50}$ (nM) |
|---|---|
| 1 | 0.065 |
| 3 | 83 |
| 4 | 31 |
| 6 | 3.7 |
| 7 | 116 |
| 8 | 2.2 |
| 10 | — |
| 12 | 0.10 |
| 14 | 21 |
| 16 | 230 |
| 18 | 2.6 |
| 20 | — |
| 22 | 7.2 |
| 26 | — |

Additional compounds of this invention and the GC3 assay results are indicated:

| Structure | IC50 (uM) |
|---|---|
| CRYPTOPHYCIN-141 | 0.7950 |
| CRYPTOPHYCIN-138 | 0.0308 |

-continued
| Structure | IC50 (uM) |
|---|---|
| 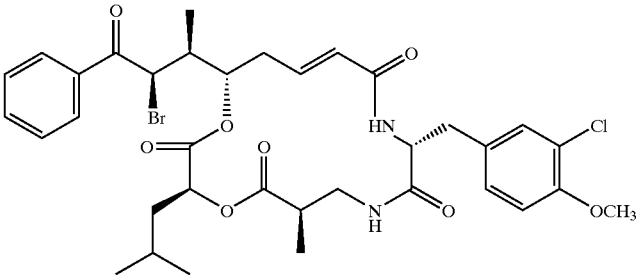 CRYPTOPHYCIN-139 | 0.0034 |
| 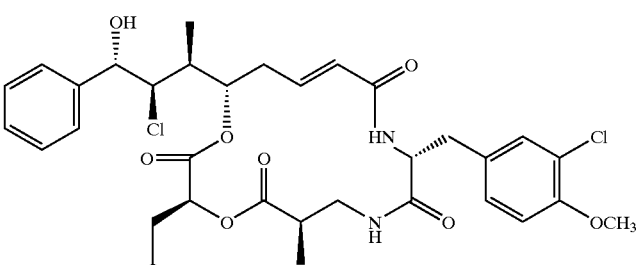 CRYPTOPHYCIN-140 | 0.863 |
| 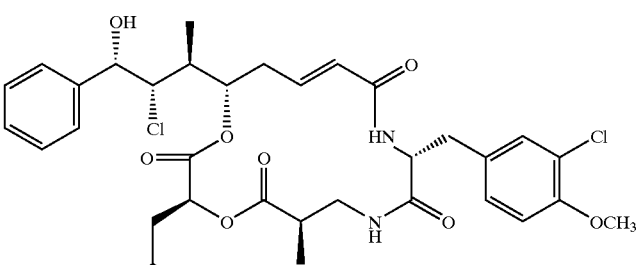 CRYPTOPHYCIN-143 | 0.8500 |
| 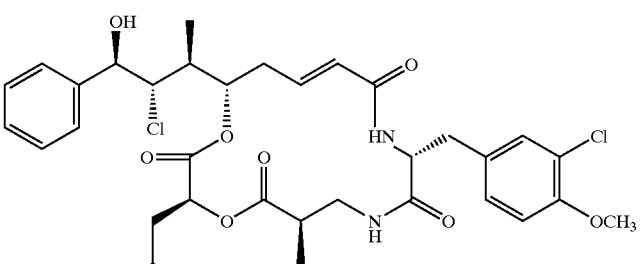 CRYPTOPHYCIN-142 | 0.0011 |
| 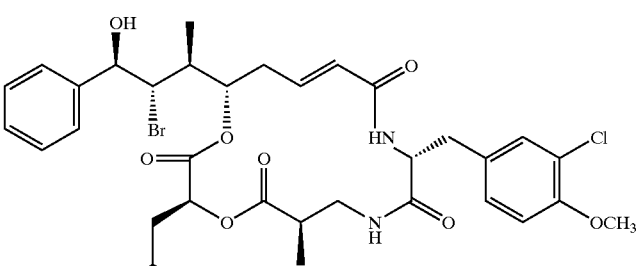 CRYPTOPHYCIN-145 | 0.000015 |

-continued

| Structure | IC50 (uM) |
|---|---|
| 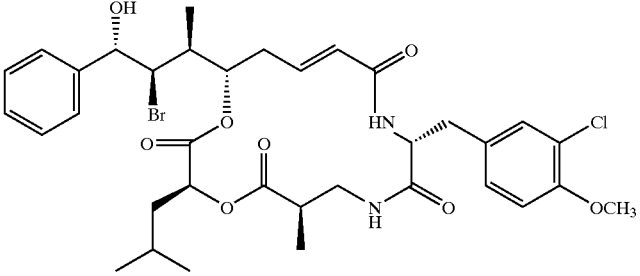<br>CRYPTOPHYCIN-129 | |

Additional compounds of this invention have been tested in the GC3 assay and had $IC_{50}$ values ranging from less than one to about 700 nM; however, the most typical values were less than 100 nM.

Results from comparative preliminary solubility studies among 27, 1, and 12 are shown in Table 3. These results indicate enhanced solubility of 12.

TABLE 3

Comparative solubilities of cryptophycin compounds 1, 12 and 27.

| | Excipient volume adjusted 0.05 M acetate buffer | % v/v | 27 (mg/ml) | 1 (mg/ml) | 12 (mg/ml) |
|---|---|---|---|---|---|
| 1 | Propylene Glycol | 15 | BQL | BQL | >2.0 |
|   | Ethanol | 10 | | | |
| 2 | Propylene Glycol | 15 | BQL | 0.0026 | >2.0 |
|   | Polyethylele Glycol 3000 | 20 | | | |
| 3 | Polysorbate 80 | 1 (w/v) | BQL | 0.3113 | 1–2 |
| 4 | Emulphor EL719 | 1 (w/v) | 0.0272 | 0.3611 | 1.5 |
| 5 | 0.05 M Acetate buffer pH 4.0 | 100 | <0.001 | <0.001 | 0.03 |

(BQL = Below quantitation limit, approximately 0.001 mg/ml)

A comparison of stability characteristics between 1 and 12 in aqueous Ph ranging from 4–8 was determined at room temperature for 6 hours. Results from these studies clearly demonstrated the superior aqueous solubility and stability profile of 12. For example, at pH 8, Cryptophycin 55 had a solubility value of 10 mg/mL at room temperature compared to a solubility of 30 mg/mL for 12 under substantially the same conditions. At a pH of 4, Cryptophycin 55 had an aqueous solubility value of about 50 mg/mL; however, the aqueous solubility of Cryptophycin 55 declined as the pH became basic, while the aqueous solubility of 12 remained substantially steady over the pH range studied.

Based on results from solubility and stability studies, appropriate parenteral vehicles were chosen to determine absolute solubility/stability characteristics of 12. Table 4 illustrates the solubility profile of 12 in these vehicles. Preliminary results indicate acceptable stability of 12 in formulation 6 for up to 3 weeks.

TABLE 4

Solubility of cryptophycin glycinate 12 in various parenteral vehicles.

| | Excipient | % v/v | 12 (mg/ml) |
|---|---|---|---|
| 1 | Ethanol | 10 | 0.11 |
|   | Propylene Glycol | 10 | |
|   | 0.05 M Citrate buffer pH 4.0 | qs | |
| 2 | Ethanol | 10 | 1.99 |
|   | Propylene Glycol | 10 | |
|   | 0.05 M Acetate buffer pH 4.0 | qs | |
| 3 | Ethanol | 10 | 1.29 |
|   | 0.05M Acetate buffer pH 4.0 | qs | |
| 4 | Propylene Glycol | 10 | 1.58 |
|   | 0.05 M Acetate buffer pH 4.0 | qs | |
| 5 | Polysorbate 80 | 0.5 (w/v) | 2.21 |
|   | 0.05 M Acetate buffer pH 4.0 | qs | |
| 6 | Ethanol | 10 | 10.27 |
|   | Propylene Glycol | 25 | |
|   | 0.05 M Acetate buffer pH 4.0 | qs | |
| 7 | Ethanol | 10 | 4.32 |
|   | Propylene Glycol | 15 | |
|   | 0.05 M Acetate buffer pH 4.0 | qs | |

Thus, it is feasible to achieve high concentrations of a compound of this invention in a vehicle containing no surfactant or an emulsifier which in turn should enable facile toxicological and clinical evaluations of these compounds. The glycinate ester (12) also affords better stability in an aqueous environment in physiological pH range over longer periods of time indicating enhanced shelf-life under normal conditions. Whereas it is necessary to prepare concentrates of 1 and 27 for storage and then diluted prior to administration, it is feasible to prepare ready to use solutions of compounds of this invention.

Compounds of Formula I can be prepared using a compound of the formula II

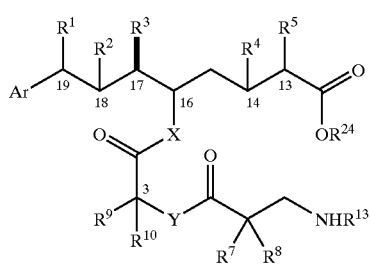

wherein

Ar, $R^1$, $R^2$, $R^3$, $R^4$, $R^5$, $R^7$, $R^8$, $R^9$, $R^{10}$ have the meanings set for supra in Formula I.

$R^{13}$ is selected from the group consisting of t-butylcarbamate (BOC);

$R^{24}$ is selected from the group consisting of

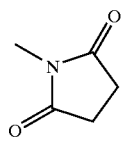

(N-hydroxysuccinimide, herein "NHS"), N-hydroxysulfosuccinimide and salts thereof, 2-nitrophenyl, 4-nitrophenyl, and 2,4-dichlorophenyl;

X is O, NH or alkylamino;

Y is O, NH, or alkylamino.

Compounds of Formula III

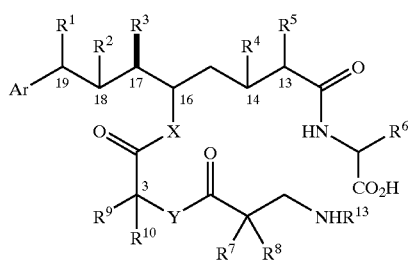

wherein the R groups and various substituents are as defined hereinbefore and throughout the specification; can be prepared by contacting a compound of the formula IV

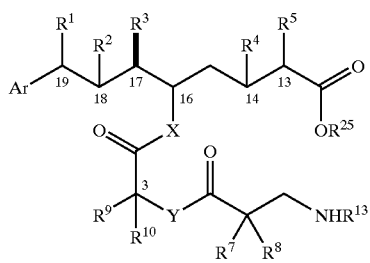

$R^{25}$ is
with an acid of the formula

$R^{27}$ is selected from the group consisting of H, $C_1$–$C_{12}$ alkyl, and aryl;

and a silylating agent. Bis N,O-trimethylsilyl acetamide (BSA) is an especially preferred silylating agent.

As used herein, the phrase "active ester substituent" refers to a substituent which makes the indicated substituent a good leaving group. Appropriate substituents can be selected with guidance from standard reference guides, for example, "Protective Groups in Organic Chemistry", Plenum Press, (London and New York, 1973); Greene, T. W. "Protecting Groups in Organic Synthesis", Wiley (New York, 1981). See especially pages 180 through 184 of Greene. An especially preferred active ester substituent group is N-hydroxysuccinimide. (NHS) Other preferred groups include, but are in no way limited to:

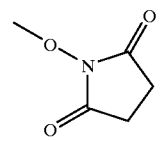

(O-N-hydroxysuccinimide), O-N-hydroxysulfosuccinimide and salts thereof, O-2-nitrophenyl, O-4-nitrophenyl, and O-2,4-dichlorophenyl, wherein the "O" refers to the oxygen group necessary to form the ester functionality.

As used herein the term "amide" refers to an amide functionality that can be cleaved using alkaline conditions. For example, the term refers to but is in no way limited to, —$NMe_2$. For additional guidance, see for example Greene, T. W. "Protecting Groups in Organic Synthesis", Wiley (New York, 1981).

As used herein the phrase "active ester substituent" refers to a substituent which makes the $OR^{24}$ substituent a good leaving group. Appropriate substituents can be selected with guidance from standard reference guides, for example, "Protective Groups in Organic Chemistry", Plenum Press, (London and New York, 1973); Greene, T. W. "Protecting Groups in Organic Synthesis", Wiley (New York, 1981). An especially preferred $R^{25}$ group is N-hydroxy-succinimide. (NHS)

The processes described herein are most preferably completed in the presence of a solvent. The artisan can select an appropriate solvent for the above described process. Inert organic solvents are particularly preferred; however, under certain conditions an aqueous solvent can be appropriate. For example, if $R^{27}$ is hydrogen and $R^{13}$ is BOC an aqueous base as solvent will be effective.

When the desired $R^6$ substituent in the compound of Formula I contains an amine, then the amine substituent of the $R^6$ group must be protected using an amino protecting group. The artisan can readily select an appropriate amino protecting group using guidance from standard works, including, for example, "Protective Groups in Organic Chemistry", Plenum Press, (London and New York, 1973); Greene, T. W. "Protecting Groups in Organic Synthesis", Wiley (New York, 1981).

$R^{27}$ should be a group that allows for the removal of the —$CO_2R^{27}$ substituent using acidic, neutral, or mild basic conditions. Preferred $R^{27}$ groups include, but are in no way limited to, hydrogen, $C_1$–$C_6$ alkyl, tricholoromethyl, trichloroethyl, and methylthiomethyl. It is especially preferred that $R^{27}$ is hydrogen.

To provide further guidance for the artisan, the following schemes are provided:

Compounds of Formula I can be prepared using a compound of the formula II

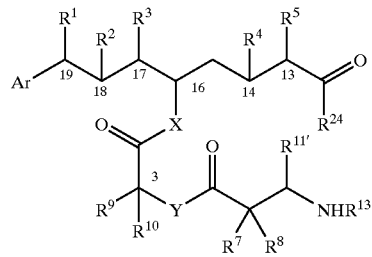

wherein

Ar $R^1$, $R^2$, $R^3$, $R^4$, $R^5$, $R^7$, $R^8$, $R^9$, $R^{10}$ have the meanings set for supra in Formula I. The term $R^{11'}$ is as defined for $R^{11}$, supra.

$R^{13}$ is a selected amino protecting group;

$R^{24}$ is selected from the group consisting of active ester substituent, amide substituent, O-2-nitrophenyl, O-4-nitrophenyl, and O-2,4-dichlorophenyl;

X is O, NH or alkylamino;

Y is C, O, NH, S, SO, $SO_2$ or alkylamino.

Compounds of Formula III

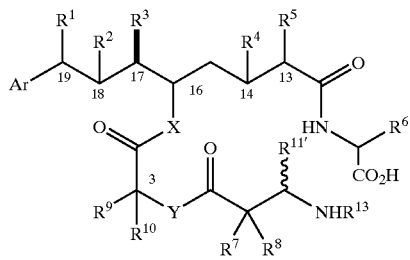

wherein the R groups and various substituents are as defined hereinbefore and throughout the specification; can be prepared by contacting a compound of the formula IV

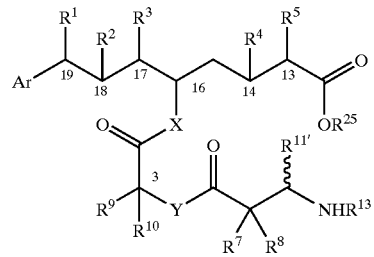

$R^{25}$ is 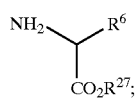
with an acid of the formula $$NH_2 - R^6$$
$$\quad\quad CO_2R^{27};$$

$R^{27}$ is selected from the group consisting of H, $C_1$–$C_{12}$ alkyl, and aryl;

and a silylating agent. Bis N,O-trimethylsilyl acetamide (BSA) is an especially preferred silylating agent.

As used with regard to $R^{25}$ the phrase "active ester substituent" refers to a substituent which makes the $OR^{24}$ substituent a good leaving group. Appropriate substituents can be selected with guidance from standard reference guides, for example, "Protective Groups in Organic Chemistry", Plenum Press, (London and New York, 1973); Greene, T. W. "Protecting Groups in Organic Synthesis", Wiley (New York, 1981). An especially preferred $R^{25}$ group is N-hydroxy-succinimide. (NHS)

The processes described herein are most preferably completed in the presence of a solvent. The artisan can select an appropriate solvent for the above described process. Inert organic solvents are particularly preferred; however, under certain conditions an aqueous solvent can be appropriate. For example, if $R^{27}$ is hydrogen and $R^{13}$ is BOC an aqueous base as solvent will be effective.

When the desired $R^6$ substituent in the compound of Formula I contains an amine, then the amine substituent of the $R^6$ group must be protected using an amino protecting group. The artisan can readily select an appropriate amino protecting group using guidance from standard works, including, for example, "Protective Groups in Organic Chemistry", Plenum Press, (London and New York, 1973); Greene, T. W. "Protecting Groups in Organic Synthesis", Wiley (New York, 1981).

$R^{27}$ should be a group that allows for the removal of the $-CO_2R^{27}$ substituent using acidic, neutral, or mild basic conditions. Preferred $R^{27}$ groups include, but are in no way limited to, hydrogen, $C_1$–$C_6$ alkyl, tricholoromethyl, trichloroethyl, and methylthiomethyl. It is especially preferred that $R^{27}$ is hydrogen.

To provide further guidance for the artisan, the following schemes are provided:

Scheme I

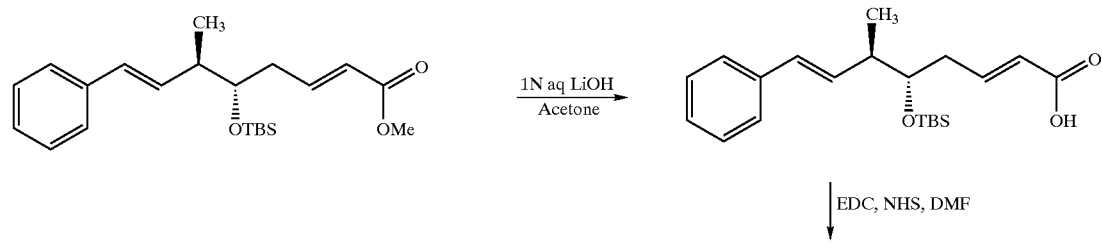

-continued

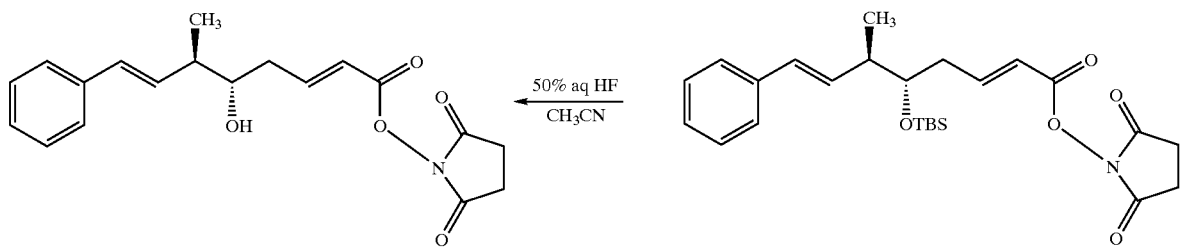

Scheme I'

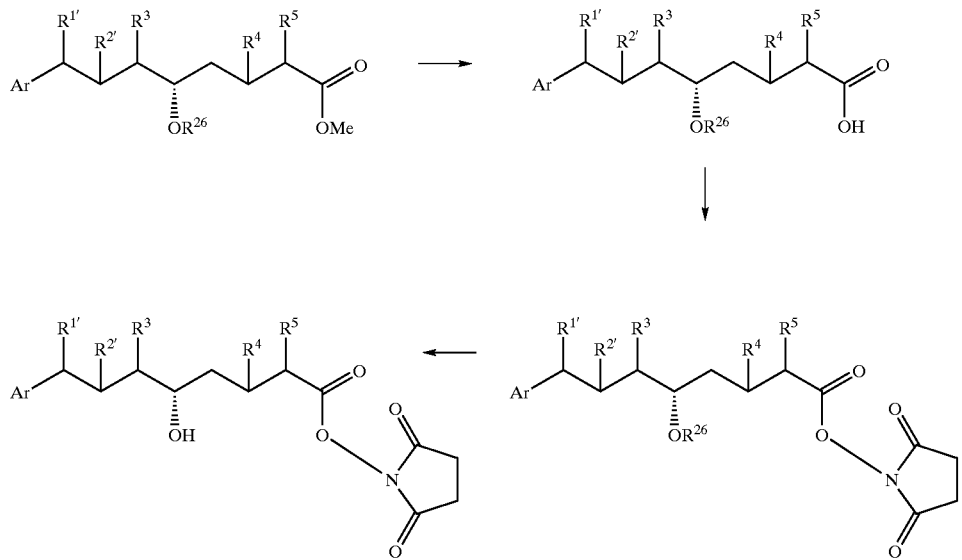

As used in Scheme I' and throughout the specification, $R^{1'}$ is halogen, SH, amino, monoalkylamino, dialkylamino, trialkylammonium, alkylthio, dialkylsulfonium, sulfate, phosphate or a. protected OH or protected SH group; $R^2$ is OH or SH; $R^{26}$ is an alcohol protecting group introduced during a portion of the synthetic process to protect an alcohol group which might otherwise react in the course of chemical manipulations, and is then removed at a later stage of the synthesis. Numerous reactions for the formation and removal of such a protecting groups are described in a number of standard works, including, for example, "Protective Groups in Organic Chemistry", Plenum Press, (London and New York, 1973); Greene, T. W. "Protecting Groups in Organic Synthesis", Wiley (New York, 1981). The skilled artisan can select an appropriate alcohol protecting group particularly with guidance provided from such works. One particularly useful alcohol protecting group is tert-butyldimethylsilyl (TBS). The products of such schemes can be derivatized using standard methods to provide other cryptophycin compounds.

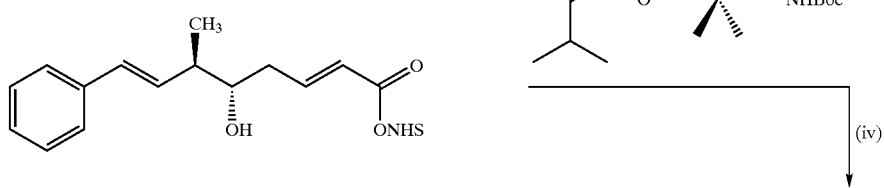

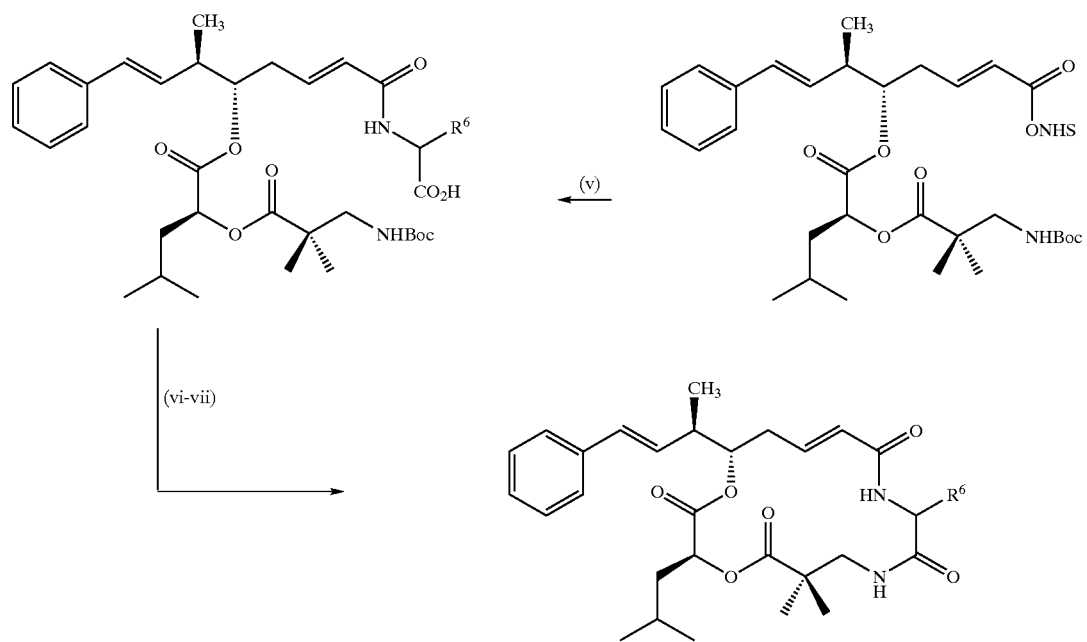
In general terms processes of this invention are as illustrated below:
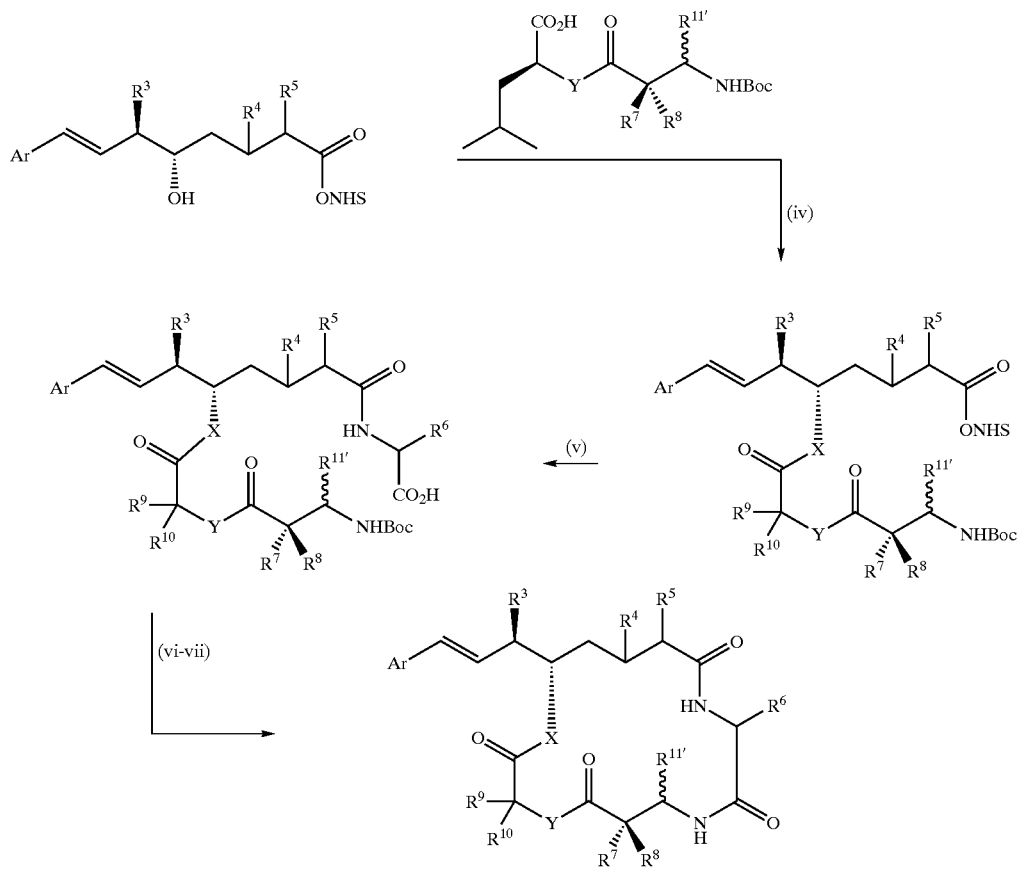

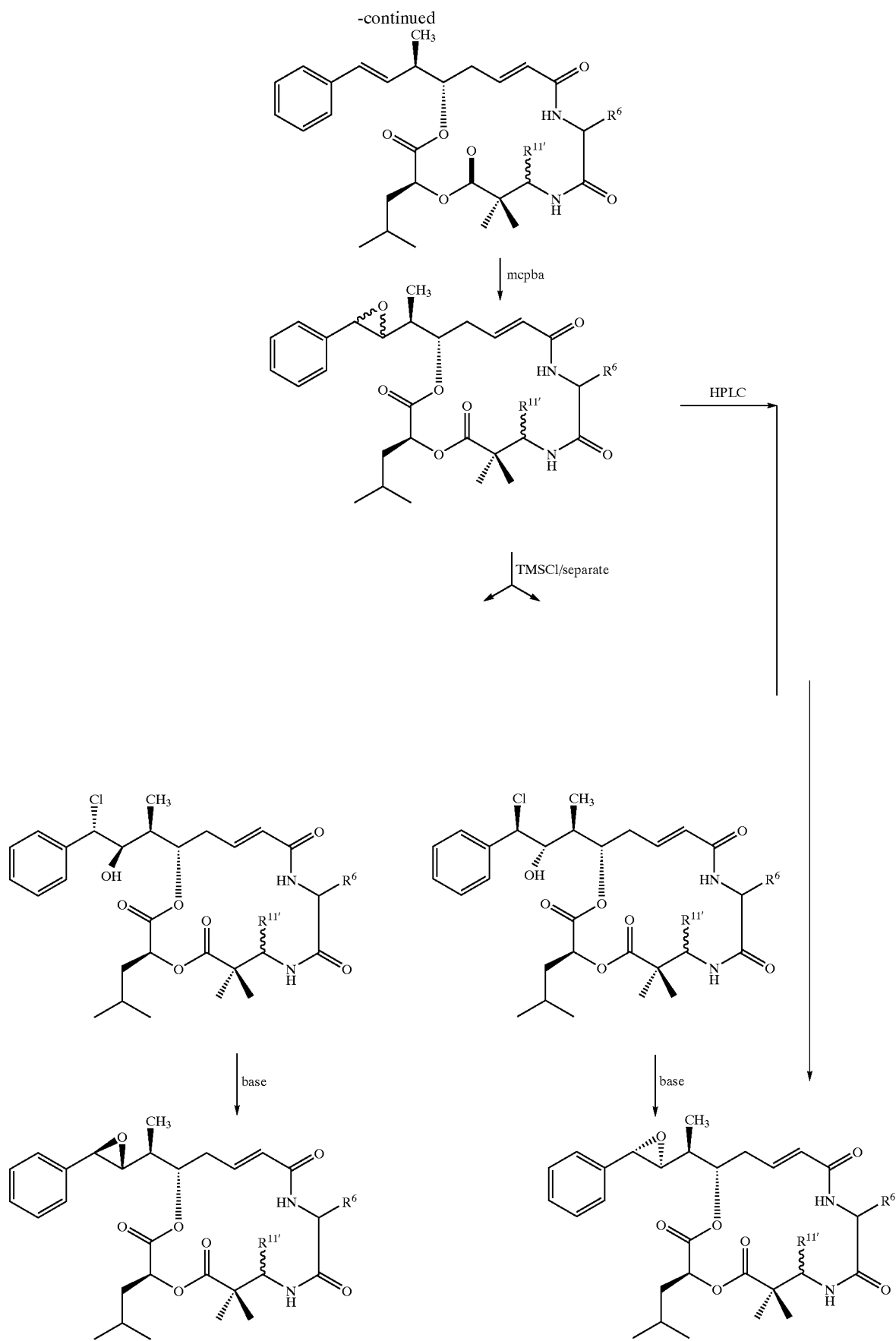

$R^6$ and $R^{11'}$ is as defined herein throughout the specification.

The product of the schemes provided herein can be further derivatized using standard methods to provide further cryptophycin compounds.

The artisan can utilize appropriate starting materials and reagents to prepare desired compounds using the guidance of the previous schemes and following examples.

The ester starting material can be prepared, for example, as follows:

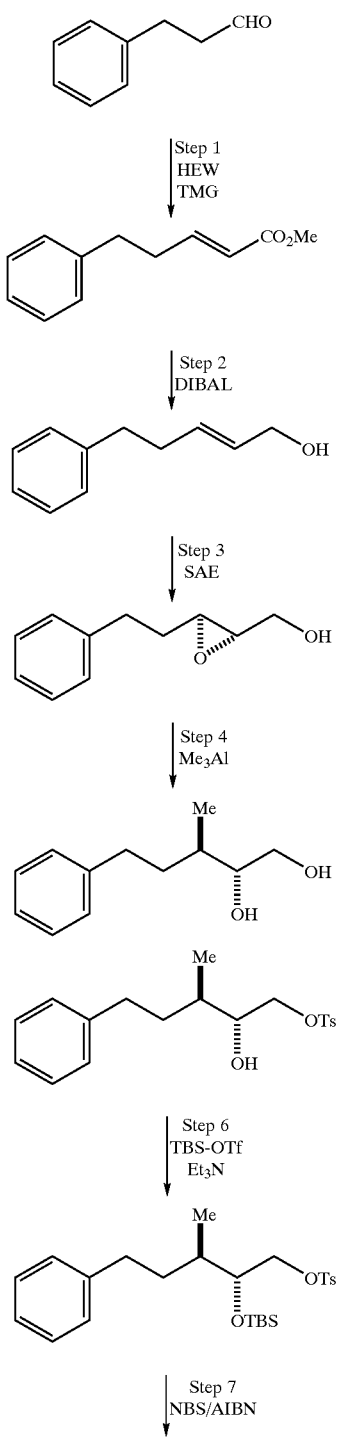

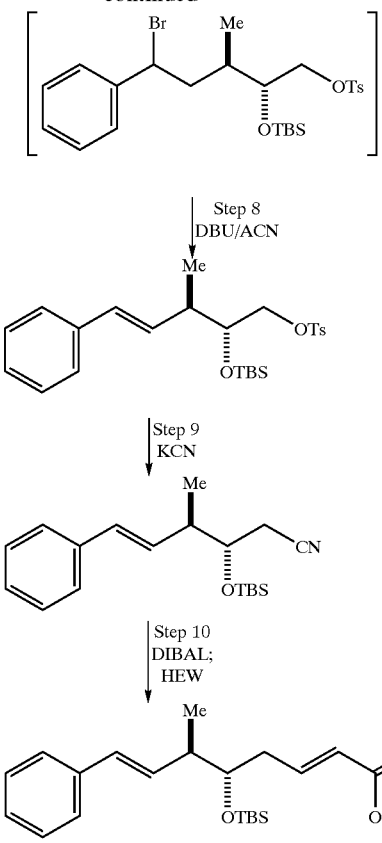

$R^6$ has the meaning defined supra.

To provide further guidance, the following schemes are provided. Certain abbreviations are used in the Schemes, Preparations and Examples which are generally known in the art. For convenience, these abbreviations include:

DMAP 4-dimethylaminopyridine
BOC tert-butoxycarbonyl
mcpba m-chloroperbenzoic acid
TMSCl chlorotrimethylsilane
HEW Horner-Emmons-Wadsworth reaction (standard reaction for olefination of an aldehyde using a phosphonate and a base)
TMG 1,1,3,3-tetramethylguanidine (standard base used for the HEW reaction)
DIBAL diisobutylaluminum hydride (standard reagent for the reduction of an unsaturated ester to an allylic alcohol)
SAE Sharpless Asymmetric Epoxidation (established reaction for the enantioselective epoxidation of allylic alcohols)
TBS tert-butyldimethylsilyl
TBS-Otf TBS trifluoromethanesulfonate (standard reagent for the t-butyldimethylsilylation of alcohols)
AIBN 2,2'-azobis(isobutyronitrile) (standard radical initiator)
ACN acetonitrile
DBU 1,8-diazabicyclo[5.4.0]undec-7-ene (standard amine base)
EDCI 1-ethyl-3-(3-dimethylaminopropyl)carbodiimide The scheme for preparing the ester is further explained by the Preparation Section herein which provides one specific application of the scheme for the convenience of the skilled artisan.

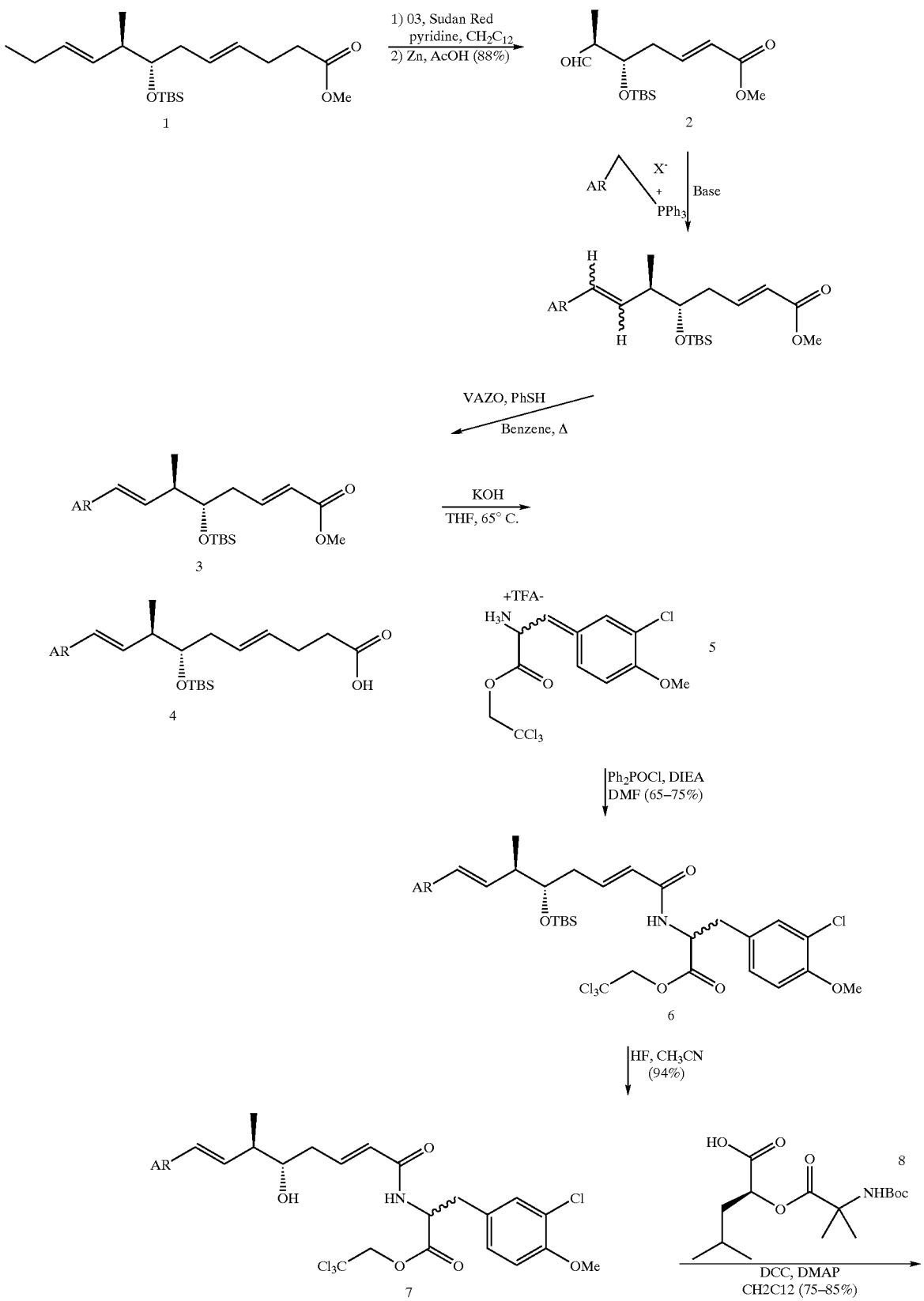

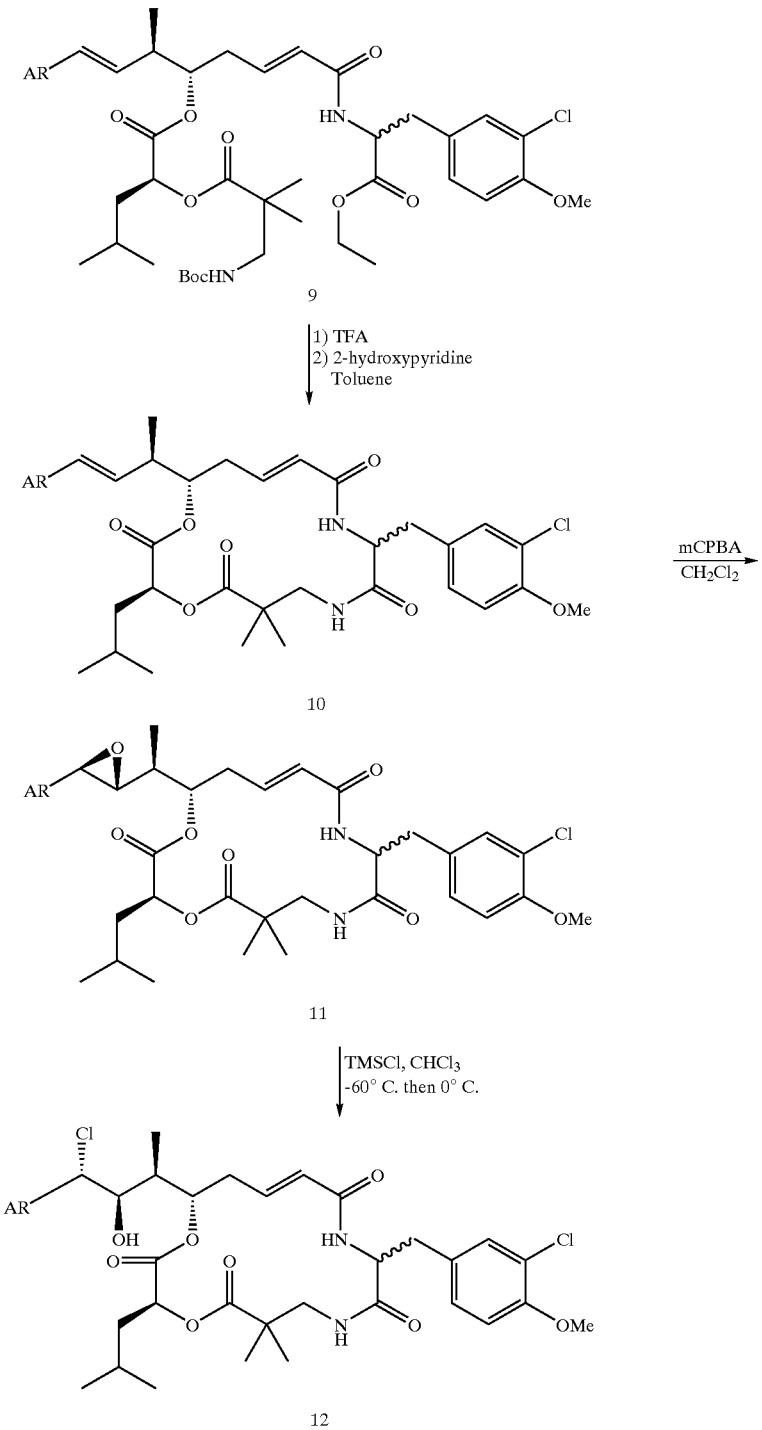

the Ar substituents claimed herein. The scheme illustration is not intended to limited the synthesis scheme only to the phenyl ring illustrated. Rather, the artisan can broadly apply this process to provide desired starting materials for the compounds claimed herein.

The necessary reaction time is related to the starting materials and operating temperature. The optimum reaction time for a given process is, as always, a compromise which is determined by considering the competing goals of throughput, which is favored by short reaction times, and maximum yield, which is favored by long reaction times.

Certain compounds of this invention can be prepared using a biosynthetic route. For example, a solution of cryptophycin 3 (about 0.24 mmol) in DME-$H_2O$ (2:1, 15.0 mL) at about 0 C is treated with bromosuccinimide (about 65 mg) and allowed to warm to room temperature. After about 24 hours the solvent is removed and the residue dissolved in a solvent such as $CH_3CN$ and subject to reverse phase HPLC (65:35 $CH_3CN/H_2O$, 6 mL/min is preferred) to give a mixture of cryptophycins. The mixture is rechromatographed by normal phase HPLC (1:1 hexane/ethyl acetate, 3 mL/min preferred) to give the desired cryptophycins.

Likewise, cryptophycin 3 (about 40 mg, 0.063 mmol) is put into 2:1 DME/$H_2O$ (about 6 mL) and N-chlorosuccinimide (0.075 mmol) is added and is heated at about 60–70 C for about 24 hours. A further quantity of NCS (8 mg) is added and continue heating for about another 24 hours. The solvent is removed and the residue subject to HPLC (35% $H_2O/CH_3CN$ 6 mL/min) to give the desired cryptophycin compounds. The resulting mixture is further purified by HPLC using methanol/water (about 4:1) to obtain the desired purified cryptophycin compounds.

To further illustrate the invention the following examples are provided. The scope of the invention is in no way to be construed as limited to or by the following examples.

Preparation 1

Step 1. Methyl 5-Phenylpent-2(E)-enoate. A solution of trimethyl phosphonoacetate (376 g, 417 mL, 2.07 mol) in THF (750 mL) was stirred at 0° C. in a 3 L 3-neck round bottom flask equipped with a mechanical stirrer and $N_2$ inlet. To the chilled solution, neat tetramethyl guanidine (239 g, 260 mL, 2.07 mol) was added dropwise via an addition funnel. The chilled clear pale yellow solution was stirred for 25 minutes at 0° C. A solution of hydrocinnamaldehyde (90%, 253 g, 248 mL, 1.9 mol) in THF (125 mL) was added dropwise to the reaction solution slowly. Upon completion of addition, the reaction was stirred for 10 h rising to room temperature. GC indicated a 95:5 ratio of product to starting material. 500 ml of water was added to the reaction vessel and the reaction stirred overnight separating into two layers. The organic layer was isolated and the aqueous layer was extracted with t-BuOMe. The organic layers were combined and dried over $MgSO_4$, then concentrated in vacuo to yield an orange oil. The crude product was distilled at 129° C./0.3 mm Hg yielding 360.5 g, 91.7% yield, of a clear slightly yellow oil.

EIMS m/z 190 (13; M+), 159 (410, 158 (39), 131(90), 130(62), 117 (22), 104 (12), 95 (57), 91 (100), 77 (21), 65 (59); HREIMS m/z 190.0998 ($C_{12}H_{14}O_2$ D –0.4 mnu); UV lmax (e) 210 (8400), 260 (230) nm; IR nmax 3027, 2949, 1723, 1658, 1454, 1319, 1203, 978, 700 cm$^{-1}$; $^1$H NMR d (CDCl$_3$) 7.15–7.3 (Ph-H5; bm), 7.00 (3-H; dt, 15.6/6.6), 5.84 (2-H; dt, 15.6/1.2), 3.70 (OMe; s), 2.76 (5-H2; t, 7.2), 2.51 (4-H2; bdt, 6.6/7.2); $^{13}$C NMR d (CDCl$_3$) 166.9 (1), 148.3 (3), 140.6 (Ph-1'$^1$), 128.4/128.2 (Ph2'/3'/5'6'), 126.1 (Ph 4:), 121.4 (2). 51.3 (OMe), 34.2/33.8 (4/5).

Step 2. 5-phenyl-pent-2-en-1-ol. To a 12 L 4-neck round bottom flask equipped with a thermocouple, mechanical stirrer and $N_2$ inlet, a solution of enoate ester (310.5 g, 1.5 mol) in THF (1.5 L) was charged and chilled to –71 ° C. via a i-PrOH/$CO_2$ bath. To the reaction vessel, was added dropwise DIBAL (2.5 L, 1.5 M in toluene, 3.75 mol) at a rate to maintain the reaction temperature<–50° C. Upon complete addition, the reaction was stirred overnight with the reaction temperature<–50° C. TLC (3:1 Hexanes:EtOAc, SiO$_2$) indicated absence of starting material after 16 h. The reaction temperature was allowed to raise to –15° C. The reaction was quenched slowly with 1N HCl (150 mL). At this point the reaction setup into a gelatinous solid. A spatula was employed to breakup the semi-solid and 1N HCl (200 mL) was added making the mixture more fluid. Concentrated HCl (625 mL) was charged to form a two phase system. The layers were separated and the product extracted with t-BuOMe. The organic layer was dried over MgSO4 and concentrated in vacuo to yield a clear pale yellow oil, 247.8 g. The crude product was distilled at 145° C./0.25 mm Hg yielding 209.7 g, 86.2%.

EIMS m/z 162 (1: M+) 144 (16), 129 (7), 117 (9) 108 (6), 92 (17), 91 (100), 75 (5), 65 (12), HREIMS m/z 162, 1049 ($C_{11}H_{14}O$, D –0.4 mmu); UV lmax (e) 206 (9900), 260 (360); IR nmax 3356, 2924, 1603, 1496, 1454, 970, 746, 700 cm$^{-1}$; $^1$H NMR d 7.15–7.3 (Ph-H5; m), 5.70 (3-H; dt, 15.6/6.0), 5.61 (2-H; dt, 15.6/4.8), 4.02 (1-H2; d 4.8), 2.68 (5-H2; t, 7.2), 2.40 (OH; bs), 2.36 (4-H2; dt, 6.0/7.2); $^{13}$C NMR d141.6 (Ph 1'), 131.8 (3), 129.5 (2), 128.3/128.2 (Ph 2'/3'/5'/6'), 125.7 (Ph 4'), 63.3 (1), 35.4/33.8 (4/5).

Step 3. (2S,3S)-2,3-Epoxy-5-phenyl-1-pentanol. To a 1 L 3 neck round bottom flask equipped with a mechanical stirrer, thermocouple and nitrogen inlet was added CH$_2$Cl$_2$ (350 mL), dried 4 Amolecular sieves (30 g) and L-(+)-diethyl tartrate (7.62 g, 0.037 mol). The resulting mixture was cooled to –20° C. and treated with Ti(O-i-Pr)$_4$ (9.2 mL, 0.031 mol), followed by the addition of t-butylhydroperoxide (4.0 M in CH$_2$Cl$_2$, 182 mL, 0.78 mol) at a rate to maintain the temperature $^2$ –20° C. Upon complete addition, the reaction mixture was stirred for another 30 min, and then treated with a solution of the allylic alcohol (50 g, 0.31 mol) in CH$_2$Cl$_2$ (30 mL) at a rate to maintain the temperature $^2$ –20° C. The reaction was stirred at the same temperature for 5 h, then filtered into a solution of ferrous sulfate heptahydrate (132 g) and tartaric acid (40 g) in water (400 mL) at 0° C. The mixture was stirred for 20 min, then transferred to a separatory funnel and extracted with t-BuOMe (2×200 mL). The combined organic phase was stirred with 30% NaOH solution containing NaCl, for 1 h at 0° C. The layers were again separated, and the aqueous phase extracted with t-BuOMe. The combined organic phase was washed with brine, dried over MgSO4 and concentrated to yield 52.8 g as an amber oil.

Step 4. (2R, 3R)-2-hydroxy-3-methyl-5-phenylpentan-1-ol. To a 5 L 3 neck round bottom flask equipped with a mechanical stirrer, thermocouple and nitrogen inlet was added hexanes (1 L) and cooled to 0° C. A 2.0M solution of Me$_3$Al in hexanes (800 mL, 1.6 mol) was added, followed by a solution of the epoxide (120 g, 0.677 mol) in hexanes (250 mL)/CH$_2$Cl$_2$ (50 mL) maintaining the temperature below 20° C. Upon complete addition, the cloudy reaction mixture was stirred at 5° C. for 35 min, whereupon a solution of 10% HCl (300 mL) was added dropwise, followed by the addition of concd HCl (350 mL). The layers were separated, and the organic phase was washed with brine and dried over MgSO$_4$. After removal of the volatiles in vacuo, 122.1 gram of an oil was obtained.

Step 5. (2R, 3R)-2-hydroxy-3-methyl-5-phenylpent-1-yl Tosylate. To a 2 L 3 neck round bottom flask equipped with a mechanical stirrer and nitrogen inlet was added the diol (58 g, 0.30 mol), dibutyltin oxide (1.5 g, 0.006 mol, 2 mol %), toluenesulfonyl chloride (57.5 g, 0.30 mol), CH$_2$Cl$_2$. (580 mL) and triethylamine (42.0 mL, 0.30 mol). The resulting mixture was stirred at room temperature for 2 h (although the reaction was complete within 1 h), filtered, washed with water and dried over MgSO$_4$. Concentration of the volatiles in vacuo afforded 104.1 gram of a slightly amber oil.

Step 6. (2R, 3R)-2-[ (tert-Butyldimethylsilyl)oxy]-3-methyl-5-phenylpent-1-yl Tosylate. A solution of the tosylate (100 g, 0.29 mol) and triethylamine (81.0 mL, 0.58 mol) in CH$_2$Cl$_2$ (1200 mL) was treated with neat TBS-OTf (99 mL, 0.43 mol) dropwise with continued stirring for another 20 min. The reaction was washed twice with brine, dried over MgSO$_4$ and concentrated to dryness. The oil was dissolved in a minimal amount of hexanes and filtered over a silica pad, eluting with hexanes:EtOAc (9:1) to yield a slightly amber oil, 134 g.

Step 7. (2R,3R,5RS)-2-[(tert-Butyldimethylsilyl)oxy]-3-methyl-5-bromo-5-phenylpent-1-yl Tosylate. To a 5 L 3 neck round bottom flask equipped with a mechanical stirrer, reflux condenser and nitrogen inlet was added CCl₄ (1680 mL), TBS Ts (140 g, 0.30 mol), NBS (65 g, 0.365 mol) and AIBN (16.5 g, 0.10 mol). The mixture was degassed by evacuation under full vacuum with stirring, and backfilling with nitrogen (3×). The reaction mixture was then heated to reflux, whereupon the color became dark brown. After 15 min at vigorous reflux, the reaction mixture became light yellow, and chromatographic analysis indicated the reaction was complete. After cooling to room temperature, the reaction was filtered and the filtrate concentrated to dryness. The residue was redissolved in hexanes and filtered again, and concentrated to dryness to afford 170.3 gram as an amber oil.

Step 8. (2R, 3R)-2-[(tert-Butyldimethylsilyl)oxy]-3-methyl-5-phenylpent-4(E)-en-1-yl Tosylate. To a 2 L 3 neck round bottom flask equipped with a mechanical stirrer, reflux condenser and nitrogen inlet was added a solution of the bromide (100 g, 0.186 mol) in acetonitrile (700 mL). DBU (83.6 mL, 0.557 mol) was added and the resulting dark brown solution was stirred at reflux for 15 min. After cooling to room temperature, the solvent was removed in vacuo, and the residue digested in CH₂Cl₂ (200 mL) and filtered through a silica pad. The volatiles were again evaporated, and the residue dissolved in EtOAc and washed with water, brine and dried over MgSO₄ and concentrated to dryness. Preparative mplc (Prep 500) chromatography afforded the desired unsaturated compound (50.3 g, 60% yield over 4 steps).

Step 9. (3S, 4R)-3-[(tert-Butyldimethylsilyl)oxy]-4-methyl-6-phenylhex-5(E)-en-1-nitrile. The tosylate (50 g, 0.11 mol) was dissolved in DMSO (1 L) and treated with KCN (14.2 g, 0.22 mol) and water (25 mL), and the resulting mixture was stirred at 60° C. under nitrogen for 18 h. After cooling to room temperature, the reaction mixture was partitioned between EtOAc (1 L) and water (1 L). The aqueous phase was extracted with EtOAc (500 mL), and the combined organic phase was washed with brine and dried over Na₂SO₄. Flash chromatography over silica with CH2Cl2 afforded the desired nitrile in 92% yield.

Step 10. Methyl (5S, 6R)-5-[(tert-Butyldimethylsilyl)oxy]-6-methyl-8-phenylocta-2 (E),7 (E) -dienoate. The nitrile (14.67 g, 46.5 mmol) was dissolved in toluene (200 mL) and cooled to −78° C. under nitrogen. A 1.5M solution of DIBAL in toluene (37.2 mL, 55.8 mmol) was added dropwise with vigorous stirring. Upon complete addition, the cooling bath was removed and the reaction was stirred at room temperature for 1 h. The reaction mixture was carefully poured into 1N HCl and the mixture stirred at room temperature for 30 min. The layers were separated, and the organic phase was washed with a saturated aqueous solution of sodium potassium tartrate (2×), brine and dried over Na₂SO₄. The volatiles were removed in vacuo, and the crude pale yellow oil was used directly in the subsequent condensation.

The crude aldehyde from above was dissolved in THF (90 mL) and treated with trimethyl phosphonoacetate (9.03 mL, 55.8 mmol) and tetramethylguanidine (7.0 mL, 55.8 mmol) at room temperature under nitrogen. The reaction mixture was stirred for 16 h, then partitioned between EtOAc (200 mL) and water (100 mL). The aqueous phase was back extracted with EtOAc (100 mL), and the combined organic phase was washed with water, brine and dried over Na2SO₄. The volatiles were removed in vacuo, and the crude yellow oil (17.0 g) was chromatographed over silica gel with CH₂Cl₂: cyclohexane (1:1 to 2:1) to afford 13.67 grams of the desired ester, 78.5%.

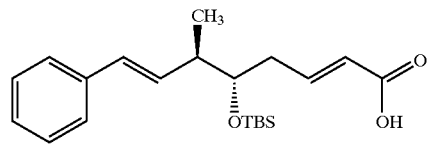

Preparation 2

Methyl ester (2.673 mmol) was dissolved in acetone and then 1N aqueous LiOH (26 mL) added at room temperature. The cloudy mixture was further diluted with acetone (20 mL) and the resulting yellow mixture stirred at room temperature for 23.5 h. The reaction was diluted with diethyl-ether (400 mL) and the organics washed with 1N HCl (120 mL), brine (200 mL) and H₂O (160 mL). The organics were dried and concentrated in vacuo to leave a yellow oil which was purified by column chromatography (gradient: 5% AcOH +20%–40% EtOAc/Hexanes) to give carboxylic acid as a yellow oil (960 mg, 100%). ¹H NMR (CDCl₃) d 7.38–7.19 (m, PhH₅), 7.09 (ddd, J=15.2, 7.6 and 7.9 Hz, 3-H), 6.38 (d, J=16 Hz, 8-H), 6.16 (dd, J=16 and 8 Hz, 7-H), 5.85 (d, J=15.8 Hz, 2-H), 3.81–3.75 (m, 5-H), 2.49–2.37 (m, 6-H, 4-CH₂), 1.12 (d, J=6.7 Hz, 6-Me), 0.91 (s, SiCMe₃), 0.065 (s, SiMe), 0.068 (s, SiMe) ppm; IR u (CHCl₃) 2957, 2930, 2858, 1697, 1258, 1098, 838 cm⁻¹; MS (FD) 360.2 (M⁺, 100); [a]$_D$ +87.6° (c 10.5, CHCl₃); Anal. calcd. for C₂₁H₃₂O₃ requires: C, 69.95; H, 8.95%. Found: C, 69.19; H, 8.39%.

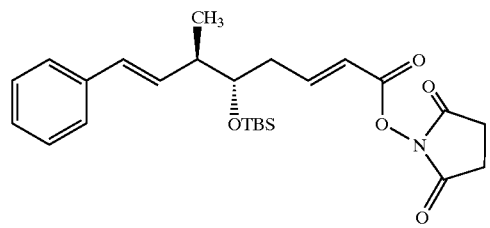

Preparation 3

To a stirred solution of carboxylic acid (2 mmol) in dry dimethylformamide (5.50 mL) was added 1-ethyl-3-(3-dimethyaminopropyl)carbodiimide (2.4 mmol) and N-hydroxysuccinimide (2.6 mmol) at room temperature. The mixture was stirred for 28 h and then diluted with EtOAc (100 mL) and washed with 1N aqueous HCl (2×50 mL), H₂O (75 mL), dried and concentrated in vacuo to leave an oil. Crude product was purified by column chromatography (gradient: 5–30% EtOAc/Hexanes) to give active ester as a pale yellow oil (724 mg, 80%)

¹H NMR (CDCl₃) d 7.36–7.20 (m, PhH₅, 3-H), 6.38 (d, J=16 Hz, 8-H), 6.14 (dd, J=16.1 and 8.0 Hz, 7-H). 6.03 (d, J=16 Hz, 2-H), 3.79 (q, J=4.3 Hz, 5-H), 2.94 (brs, CH₂CH₂), 2.58–2.42 (m, 6-H, 4-CH₂), 1.10 (d, J=6.8 Hz, 6-Me), 0.90 (s, SiCMe₃), 0.05 (s, SiMe₂) ppm; IR u (CHCl₃); 2957, 2931, 2858, 1772, 1741, 1648, 1364, 1254, 1092, 1069, 838 cm⁻¹; MS (FD) 457 (M⁺, 100); [a]$_D$ +71.3° (c 10.1, CHCl₃); Anal. calcd. for C₂₅H₃₅NO₅ requires: C, 65.61; H, 7.71; N, 3.06%. Found: C, 65.51; H, 7.56; N, 3.02%.

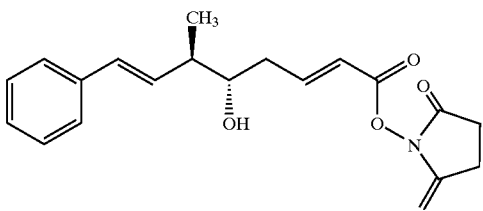

Preparation 4

To a stirred solution of silyl ether (2.50 g, 5.47 mmol) in CH₃CN (130 mL) was added 48% aqueous HF (15 mL) at 0 C. The solution was stirred at 0 C for 0.75 h and then at room temperature for 4 h. The reaction was diluted with diethylether (300 mL) and washed with H₂O until the wash was ~pH7. Organics were dried (MgSO₄) and concentrated in vacuo to give a yellow residue which was recrystallized from Et2O to give alcohol as white crystals (1.46 g, 78%). $^1$H NMR (CDCl₃) d 7.41–7.20 (m, PhH₅, 3-H), 6.48 (d, J=16 Hz, 8-H), 6.15–6.07 (m, 7-H, 2-H), 3.71–3.65 (m, 5-H), 2.83 (brs, CH₂CH₂), 2.60–2.33 (m, 6-H, 4-CH₂), 1.95 (brs, 5-OH), 1.14 (d, J=6.8 Hz, 6-Me) ppm; IR u (KBr) 3457, 1804, 1773, 1735, 1724, 1209, 1099, 1067, 1049, 975, 744, 694 cm⁻¹; UV (EtOH) $1_{max}$ 250 (e=20535) nm; MS (FD) 343.2 (M⁺, 100); [a]$_D$ –57.8° (c 10.56, CHCl₃); Anal. calcd. for C₁₉H₂₁NO₅S requires: C, 66.46; H, 6.16; N, 4.08%. Found: C, 66.49; H, 6.16; N, 4.07%.

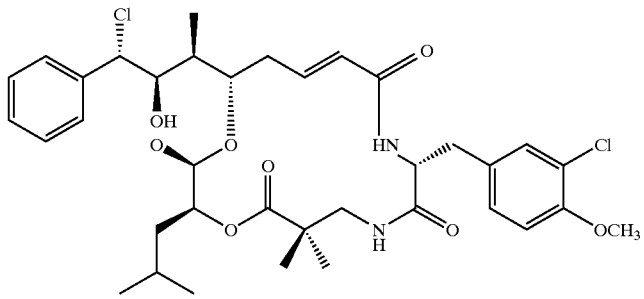

CRYPTOPHYCIN-55

EXAMPLE 1

Preparation of Cryptophycin 55 Acetate (3)

To a solution of 1 (93 mg, 0.13 mmol) in 659 ml of methylene chloride at 0° C. was added triethylamine (55 ml, 0.40 mmol), 4-dimethylamino pyridine (1.6 mg, 0.013 mmol), and acetic anhydride (19 ml, 0.20 mmol). After stirring at 0° C. for 1 h the reaction was quenched with 19 ml of methanol, concentrated to 0.5 volume, and applied directly to a flash chromatography column (19 g of flash silica gel). Elution with ethyl acetate-hexanes (3:1) provided 88 mg (89%) of the title compound as a white foam: 500 MHz $^1$H NMR (CDCl₃) d 7.38–7.31 (m, 5H), 7.24 (d, 1H, J=2.1 Hz), 7.22–7.18 (m, 1H), 7.10 (dd, 1H, J=8.5, 2.1 Hz), 6.88 (d, 1H, J=8.5 Hz), 6.75 (ddd, 1H, J=15, 13, 4.6 Hz), 5.78 (dd, 1H, J=15, 1.0 Hz), 5.55 (d, 1H, J=7.9 Hz), 5.46 (dd, 1H, J=9.8, 1.2 Hz), 4.95 (dd, 1H, J=11, 2.9 Hz), 4.89 (ddd, 1H, J=9.9, 9.9, 1.7 Hz), 4.81 (d, 1H, J=9.8 Hz), 4.79–4.74 (m, 1H), 3.91 (s, 3H), 3.39 (dd, 1H, J=13, 8.1 Hz), 3.22 (dd, 1H, J=13, 4.1 Hz), 3.16 (dd, 1H, J=14, 5.1 Hz), 3.07 (dd, 1H, J=14, 7.6 Hz), 2.65–2.55 (m, 2H), 2.47–2.39 (m, 1H), 1.95 (ddd, 1H, J=14, 13, 4.6 Hz), 1.86–1.77 (m, 1H), 1.73–1.66 (m, 1H), 1.68 (s, 3H), 1.27 (s, 3H), 1.19 (s, 3H), 1.09 (d, 3H, J=7.1 Hz), 1.03 (d, 3H, J=6.7 Hz), 0.97 (d, 3H, J=6.6 Hz).

EXAMPLE 2

Preparation of Cryptophycin 55 Succinate (4)

To a solution of 1 (27 mg, 0.038 mmol) and succinic anhydride (5.7 mg, 0.057 mmol) in 383 ml of methylene chloride at room temperature was added triethylamine (16 ml, 0.115 mmol) and 4-dimethylamino pyridine (4.7 mg, 0.038 mmol). After stirring for 19 h, another 5.7 mg (0.057 mmol) of succinic anhydride and 4.7 mg (0.038 mmol) of 4-dimethylamino pyridine were added followed by stirring an additional 29 h. The reaction was treated with 0.5 ml of 1 N aqueous hydrochloric acid and washed with methylene chloride (3×0.5 ml). The combined organic extracts were dried (Na₂SO₄), filtered, and concentrated in vacuo to white foam. Reverse phase HPLC[7] purification provided 10 mg (32%) of the title compound as a white foam: 500 MHz $^1$H NMR (CDCl₃) d 7.36–7.31 (m, 6H), 7.22 (br s, 1H), 7.08 (d, 1H, J=8.4 Hz), 7.02 (br s, 1H), 6.87 (d, 1H, J=8.4 Hz), 6.61 (m, 1H), 5.94–5.87 (m, 2H), 5.51 (d, 1H, J=9.8 Hz), 4.95 (dd, 1H, J=10, 2.8 Hz), 4.87–4.76 (m, 3H), 3.90 (s, 3H), 3.39 (dd, 1H, J=16, 5.6 Hz), 3.28 (dd, 1H, J=16, 8.2 Hz), 3.17 (dd, 1H, J=16, 5.6 Hz), 3.05 (dd, 1H, J=16, 8.2 Hz), 2.68–2.62 (m, 1H), 2.60–2.46 (m, 2H), 2.45–2.28 (m, 3H), 2.01–1.93 (m, 2H), 1.88–1.70 (m, 2H), 1.26 (s, 3H), 1.18 (s, 3H), 1.12 (d, 3H, J=7.0 Hz), 1.04 (d, 3H, J=6.6 Hz), 1.00 (d, 3H, J=6.5 Hz).

EXAMPLE 3

Preparation of Cryptophycin 55 (2'-di-t-Butylphosphatyl)phenylacetate (5)

To a solution of 1 (0.102 mmol), 24 (46 mg, 0.134 mmol), and 4-dimethylamino pyridine (12 mg, 0.102 mmol) in 250 ml of anhydrous methylene chloride at room temperature was added a solution of 1,3-dicyclohexylcarbodiimide (27 mg, 0.134 mmol) in 50 ml of methylene chloride. After stirring at room temperature for 6 h the reaction was diluted with 1 ml of ethyl acetate-hexanes (3:1) and filtered through a plug of celite, washing with ethyl acetate-hexanes (3:1). The filtrate and washings were concentrated in vacuo to a purple foam. Chromatography (15 g of flash silica gel), eluting with ethyl acetate-hexanes (4:1) provided 86 mg (82%) of the title compound as a white foam: 500 MHz $^1$H NMR (CDCl₃) d 7.35 (d, 1H, J=8.3 Hz), 7.30–7.19 (m, 8H), 7.11 (dd, 1H, J=8.4, 2.0 Hz), 7.02 (t, 1H, J=7.5 Hz), 6.87 (d, 1H, J=8.4 Hz), 6.84 (d, 1H, J=7.5 Hz), 6.73 (ddd, 1H, J=15, 13, 4.7 Hz), 5.92 (d, 1H, J=7.9 Hz), 5.79 (dd, 1H, J=15, 1.0

Hz), 5.43 (dd, 1H, J=9.4, 1.8 Hz), 4.98 (dd, 1H, J=12, 3.1 Hz), 4.81 (ddd, 1H, J=9.9, 9.9, 1.8 Hz), 4.75 (d, 1H, J=9.4 Hz), 4.73–4.67 (m, 1H), 3.90 (s, 3H), 3.49 (d, 1H, J=16 Hz), 3.44–3.38 (m, 1H), 3.38 (d, 1H, J=16 Hz), 3.27–3.17 (m, 2H), 3.10 (dd, 1H, J=14, 8.2 Hz), 2.55–2.46 (m, 2H), 2.37–2.27 (m, 1H), 1.95 (ddd, 1H, J=14, 12, 4.5 Hz), 1.83–1.70 (m, 2H), 1.49 (s, 18H), 1.27 (s, 3H), 1.20 (s, 3H), 1.03 (d, 3H, J=6.5 Hz), 0.97 (d, 3H, J=6.4 Hz), 0.92 (d, 3H, J=7.0 Hz).

EXAMPLE 4

Preparation of Cryptophycin 55 (2'-Phosphatyl) phenylacetate di-Sodium Salt (6)

To a solution of 5 (84 mg, 0.081 imol) in 400 ml of methylene chloride at room temperature was added a 4.0 M solution of hydrogen chloride in 1,4-dioxane (81 ml, 0.33 mmol). The faint yellow solution was allowed to stir at room temperature for 2 h. After concentration in vacuo to an off-waite foam, the crude dihydrogen phosphate was dissolved in 614 ml of tetrahydrofuran and treated with a 5.00 N aqueous solution of sodium hydroxide (33 ml, 0.163 mmol). After stirring for 10 min the mixture was concentrated in vacuo to a tan foam. The crude salt was taken up in 1 ml of hot acetonitrile and 0.1 ml of hot water. The insolubles were filtered off and the filtrate was concentrated in vacuo to provide 69 mg (87%) of the title compound as a white solid: 500 MHz $^1$H NMR (MeOH-d$_4$) d 7.58 (d, 1H, J=8.2 Hz), 7.38–7.32 (m, 2H), 7.32–7.28 (m, 3H), 7.28 (d, 1H, J=2.1 Hz), 7.17 (dd, 1H, J=8.5, 2.1 Hz), 7.09 (ddd, 1H, J=7.8, 7.8, 1.7 Hz), 6.98 (d, 1H, J=8.5 Hz), 6.79–6.70 (m, 2H), 6.67 (d, 1H, J=7.4 Hz), 5.91 (dd, 1H, J=15, 1.7 Hz), 5.45 (dd, 1H, J=9.4, 1.6 Hz), 5.06 (dd, 1H, J=10, 2.7 Hz), 5.01 (d, 1H, J=9.4 Hz), 4.89–4.80 (m, 1H), 4.47 (dd, 1H, J=11, 3.8 Hz), 3.84 (s, 3H), 3.67 (d, 1H, J=16 Hz), 3.45 (d, 1H, J=14 Hz), 3.42 (d, 1H, J=16 Hz), 3.18 (dd, 1H, J=14, 3.8 Hz), 3.12 (d, 1H, J=14 Hz), 2.77 (dd, 1H, J=14, 11 Hz), 2.67–2.60 (m, 1H), 2.56–2.48 (m, 1H), 2.31–2.22 (m, 1H), 1.96–1.88 (m, 1H), 1.85–1.77 (m, 2H), 1.22 (s, 3H), 1.20 (s, 3H), 1.03 (d, 3H, J=6.2 Hz), 0.98 (d, 3H, J=6.1 Hz), 0.93 (d, 3H, J=7.1 Hz).

EXAMPLE 5

Preparation of Cryptophycin 55 Nicotinoate Hydrochloride Salt (7)

To a solution of 1 (50 mg, 0.071 mmol) in 354 ml of pyridine at room temperature was added nicotinoyl chloride hydrochloride (15 mg, 0.085 mmol) followed by triethylamine (23 ml, 0.170 mmol). After stirring for 1.5 h, 4-dimethylamino pyridine (8.6 mg, 0.071 mmol) was added. After stirring 5 h, additional triethylamine (23 ml, 0.170 mmol), 4-dimethylamino pyridine (8.6 mg, 0.071 mmol), and nicotinoyl chloride hydrochloride (15 mg, 0.085 mmol) was added along with a 50 ml pyridine rinse. After stirring 18 h the reaction was treated with 0.5 ml of saturated aqueous sodium bicarbonate and washed with methylene chloride (4×1 ml). The combined organic extracts were dried (Na$_2$SO$_4$), filtered, and concentrated in vacuo to a light brown oil. Chromatography (14 g of flash silica gel), eluting with ethyl acetate-hexanes (10:1) provided 49 mg (85%) of the free base as a white foam. The nicotinoate was dissolved in 1 ml of methylene chloride and treated with a 1.0 M solution of hydrogen chloride in diethyl ether (90 ml, 0.090 mmol). The clear, colorless solution was allowed to stand at room temperature for 5 min. Removal of the solvent in vacuo produced 51 mg of the title compound as a white foam: 500 MHz $^1$H NMR (CDCl$_3$) d 8.94 (s, 1H), 8.78 (br s, 1H), 8.29 (d, 1H, J=7.0 Hz), 7.57 (br s, 1H), 7.38 (d, 2H, J=7.1 Hz), 7.30–7.16 (m, 5H), 7.10 (dd, 1H, J=8.4, 1.7 Hz), 6.88 (d, 1H, J=8.4 Hz), 6.71 (m, 1H), 5.80 (d, 1H, J=15 Hz), 5.74 (d, 1H, J=9.6 Hz), 5.56 (br s, 1H), 5.00 (d, 1H, J=9.6 Hz), 4.95 (t, 1H, J=8.9 Hz), 4.84 (d, 1H, J=9.8 Hz), 4.77–4.72 (m, 1H), 3.91 (s, 3H), 3.39 (dd, 1H, J=13, 8.2 Hz), 3.23–3.14 (m, 2H), 3.06 (dd, 1H, J=14, 7.6 Hz), 2.81–2.74 (m, 1H), 2.62–2.45 (m, 2H), 1.93 (ddd, 1H, J=14, 12, 4.8 Hz), 1.78–1.70 (m, 1H), 1.66–1.59 (m, 1H), 1.25 (s, 3H), 1.20 (d, 3H, J=7.0 Hz), 1.19 (s, 3H), 0.98 (d, 3H, J=6.7 Hz), 0.84 (d, 3H, J=6.5 Hz)

EXAMPLE 6

Preparation of Cryptophycin 55 N-Methylpyridinium Acetate Salt (8)

To a solution of 1 (53 mg, 0.075 mmol) in 751 ml of methylene chloride at 0° C. was added triethylamine (13 ml, 0.090 mmol) followed by 2-fluoro-1-methylpyridinium p-toluenesulfonate (23 mg, 0.083 mmol). The heterogeneous reaction mixture was warmed to room temperature and stirred for 3.5 h at which time another 11 mg (0.039 mmol) of 2-fluoro-1-methylpyridinium p-toluenesulfonate was added. After stirring for 14.5 h another 11 mg (0.039 mmol) of 2-fluoro-1-methylpyridinium p-toluenesulfonate was added followed by another 11 mg (0.039) of 2-fluoro-1-methylpyridinium p-toluenesulfonate and 13 ml (0.090) of triethylamine after 2.5 h. After stirring an additional 1 h the reaction was concentrated in vacuo to an orange foam. Purification by reverse phase HPLC[8] with concomitant anion exchange (acetate for p-toluenesulfonate) followed by lyophilization yielded 30 mg (47%) of the title compound as a white solid: 500 MHz $^1$H NMR (DMSO-d$_6$) d 8.65–8.58 (m, 2H), 8.36 (t, 1H, J=7.8 Hz), 7.68 (d, 1H, J=8.9 Hz), 7.60 (d, 1H, J=6.6 Hz), 7.48 (t, 1H, J=6.6 Hz), 7.35–7.21 (m, 6H), 7.19 (dd, 1H, J=8.5, 1.9 Hz), 7.05 (d, 1H, J=8.5 Hz), 6.49 (ddd, 1H, J=16, 13, 4.0 Hz), 5.91 (d, 1H, J=16 Hz), 5.72 (d, 1H, J=8.0 Hz), 5.66 (dd, 1H, J=8.0, 1.9 Hz), 5.32–5.27 (m, 1H), 4.73 (dd, 1H, J=9.7, 4.3 Hz), 4.24 (ddd, 1H, J=11, 9.8, 3.7 Hz), 3.93 (s, 3H), 3.81 (s, 3H), 3.32 (dd, 1H, J=13, 9.3 Hz), 3.05–2.97 (m, 2H), 2.77–2.57 (m, 3H), 2.54–2.47 (m, 1H), 1.76 (s, 3H), 1.68–1.62 (m, 1H), 1.55–1.46 (m, 1H), 1.37–1.30 (m, 1H), 1.15 (d, 3H, J=7.0 Hz), 1.13 (s, 3H), 1.00 (s, 3H), 0.88 (d, 3H, J=6.7 Hz), 0.73 (d, 3H, J=6.5 Hz).

EXAMPLE 7

Preparation of Cryptophycin 55 N-t-Boc-3-(3-Chloro-4-methoxyphenyl)-(D)-alaninate (9)

To a solution of 1 (23 mg, 0.033 mmol), N-t-Boc-3-(3-chloro-4-methoxyphenyl)-(D)-alanine (16 mg, 0.049 mol), and 4-dimethylamino pyridine (few crystals) in 143 ml of anhydrous methylene chloride at room temperature was added a solution of 1,3-dicyclohexylcarbodiimide (10 mg, 0.049 mmol) in 20 ml of methylene chloride. After stirring for 2 h, the cloudy white reaction mixture was diluted with ethyl acetate-hexanes (2:1, 1 ml), stirred for 10 min, and filtered through a plug of celite, washing with ethyl acetate-:hexanes (2:1). The filtrate and washings were concentrated in vacuo to a colorless oil. Chromatography (14 g of flash silica gel, 2:1 ethyl acetate-hexanes) afforded 29 mg (88%) of the title compound as a white foam: 500 MHz $^1$H NMR (CDCl$_3$) d 7.42–7.27 (m, 5H), 7.24 (d, 1H, J=2.0 Hz), 7.25–7.18 (m, 1H), 7.09 (dd, 1H, J=8.4, 1.9 Hz), 6.91–6.86 (m, 2H), 6.84–6.70 (m, 3H), 5.75 (d, 1H, J=15 Hz), 5.53 (d, 1H, J=9.6 Hz), 5.47 (d, 1H, J=7.6 Hz), 5.00 (dd, 1H, J=10, 2.9 Hz), 4.90–4.80 (m, 2H), 4.78–4.71 (m, 1H), 4.63 (d, 1H, J=8.3 Hz), 4.19–4.12 (m, 1H), 3.91 (s, 3H), 3.88 (s, 3H), 3.40 (dd, 1H, J=13, 8.1 Hz), 3.25–3.12 (m, 2H), 3.07 (dd, 1H, J=14, 7.6 Hz), 2.67–2.57 (m, 2H), 2.39–2.27 (m, 2H), 2.15 (dd, 1H, J=14, 8.0 Hz), 2.01 (ddd, 1H, J=14, 12, 4.2 Hz), 1.87–1.76 (m, 2H), 1.39 (s, 9H), 1.27 (s, 3H), 1.20 (s, 3H), 1.09–1.04 (m, 6H), 1.01 (d, 3H, J=6.3 Hz).

EXAMPLE 8

Preparation of Cryptophycin 55 3-(3-Chloro-4-methoxyphenyl)-(D)-alaninate Hydrochloride Salt (10)

To a solution of 9 (27 mg, 0.027 mmol) in 265 ml of methylene chloride at room temperature was added a 4.0 M solution of hydrogen chloride in 1,4-dioxane (33 ml, 0.133 mmol). After stirring for 3 h, the clear, colorless reaction mixture was concentrated in vacuo to provide 26 mg (96%, corrected for 5 wt% dioxane) of the title compound as a white foam: 500 MHz $^1$H NMR (MeOH-$d_4$) d 7.79 (d, 1H, J=7.3 Hz), 7.49–7.45 (m, 2H), 7.43–7.48 (m, 3H), 7.31 (d, 1H, J=2.0 Hz), 7.20 (dd, 1H, J=8.4, 2.1 Hz), 7.13 (d, 1H, J=2.2 Hz), 7.07–6.95 (m, 3H), 6.71 (ddd, 1H, 15, 13, 3.8 Hz), 5.98 (dd, 1H, J=15, 1.8 Hz), 5.69 (d, 1H, J=10 Hz), 5.22 (d, 1H, J=10 Hz), 5.18 (dd, 1H, J=10, 2.5 Hz), 4.89–4.80 (m, 1H), 4.53 (dd, 1H, J=11, 3.7 Hz), 4.16 (dd, 1H, J=10, 4.4 Hz), 3.88 (s, 3H), 3.87 (s, 3H), 3.51 .(dd, 1H, J=13, 9.9 Hz), 3.20 (dd, 1H, J=14, 3.7 Hz), 3.14 (dd, 1H, J=13, 2.3 Hz), 2.82–2.75 (m, 3H), 2.45 (dd, 1H, J=15, 4.5 Hz), 2.42–2.34 (m, 1H), 2.08–2.00 (m, 1H), 1.97–1.86 (m, 3H), 1.27 (s, 3H), 1.21 (s, 3H), 1.16 (d, 3H, J=7.1 Hz), 1.10 (d, 3H, J=6.1 Hz), 1.06 (d, 3H, J=6.0 Hz).

EXAMPLE 9

Preparation of Cryptophycin 55 N-t-boc-Glycinate (11)

To a solution of 1 ( 118 mg, 0.167 mmol), N-t-Boc-glycine (44 mg, 0.251 mmol), and 4-dimethylamino pyridine (2.0 mg, 0.0167 mmol) in 490 ml of anhydrous methylene chloride at room temperature was added a solution of 1,3-dicyclohexylcarbodiimide (52 mg, 0.251 mmol) in 67 ml of methylene chloride. After stirring for 50 min, the cloudy white reaction mixture was diluted with ethyl acetate-hexanes (3:1, 1 ml), stirred for 10 min, and filtered through a plug of celite, washing with ethyl acetate-hexanes (3:1). The filtrate and washings were concentrated in vacuo to a colorless oil. Chromatography (19 g of flash silica gel, 3:1/ethyl acetate-hexanes) afforded 138 mg (96%) of the title compound as a white foam: 500 MHz $^1$H NMR (CDCl$_3$) d 7.34 (s, 5H), 7.24 (d, 1H, J=2.0 Hz), 7.23–7.19 (m, 1H), 7.10 (dd, 1H, J=8.4, 2.0 Hz), 6.88 (d, 1H, J=8.4 Hz), 6.79–6.70 (m, 1H), 5.77 (d, 1H, J=13 Hz), 5.50 (d, lH, J=8.0 Hz), 5.47 (d, 1H, J=9.8 Hz), 4.9.7 (dd, 1H, J=11, 2.7 Hz), 4.89 (t, 1H, J=10 Hz), 4.83 (d, 1H, J=9.8 Hz), 4.79–4.72 (m, 1H), 4.68 (br s, 1H), 3.91 (s, 3H), 3.66 (dd, 1H, J=18, 5.3 Hz), 3.42–3.35 (m, 2H), 3.21 (dd, 1H, J=13, 4.0 Hz), 3.17 (dd, 1H, J=15, 5.1 Hz), 3.08 (dd, 1H, J=15, 7.6 Hz), 2.66–2.57 (m, 2H), 2.47–2.38 (m, 1H), 1.95 (ddd, 1H, J=14, 12, 4.7 Hz), 1.85–1.77 (m, 1H), 1.75–1.67 (m, 1H), 1.43 (s, 9H), 1.27 (s, 3H), 1.20 (s, 3H), 1.08 (d, 3H, J=7.0 Hz), 1.03 (d, 3H, J=6.7 Hz)., 0.98 (d, 3H, J=6.5 Hz).

EXAMPLE 9

Preparation of Cryptophycin 55 Glycinate Hydrochloride Salt (12)

To a solution of 11 (122 mg, 0.141 mmol) in 471 ml of methylene chloride at room temperature was added a 4.0 M solution of hydrogen chloride in 1,4-dioxane (178 ml, 0.707 mmol). After stirring for 1 h 20 min, the clear, colorless reaction mixture was concentrated in vacuo to provide 120 mg (99%, corrected for 7 wt% dioxane) of the title compound as a white foam: 500 MHz $^1$H NMR (MeOH-$d_4$) d 7.81 (dd, 1H, J=8.5, 2.2 Hz), 7.46–7.41 (m, 2H), 7.40–7.36 (m, 3H), 7.31 (d, 1H, J=2.1 Hz), 7.20 (dd, 1H, J=8.4, 2.1 Hz.), 7.01 (d, 1H, J=8.4 Hz), 6.70 (ddd, 1H, J=15, 13, 3.7 Hz), 5.97 (dd, 1H, J=15, 1.7 Hz), 5.55 (d, 1H, J=9.9 Hz), 5.18 (d, 1H, J=9.9 Hz), 5.14 (dd, 1H, J=10, 2.8 Hz), 4.84 (t, 1H, J=10 Hz), 4.52 (dd, 1H, J=11, 3.7 Hz), 3.87 (s, 3H), 3.78 (d, 1H, J=18 Hz), 3.50 (dd, 1H, J=13, 9.8 Hz), 3.23 (d, 1H, J=18 Hz), 3.20 (dd, 1H, J=14, 3.6 Hz), 3.13 (dd, 1H, J=13, 2.4 Hz), 2.80–2.69 (m, 3H), 2.41–2.32 (m, 1H), 1.99–1.92 (m, 1H), 1.91–1.81 (m, 2H), 1.25 (s, 3H), 1.20 (s, 3H), 1.12 (d, 3H, J=7.0 Hz), 1.06 (d, 3H, J=6.2 Hz), 1.04 (d, 3H, 6.2 Hz).

EXAMPLE 10

Preparation of Cryptophycin 55 N-t-boc-b-Alaninate (13)

To a solution of 1 (102 mg, 0.145 mmol), N-t-Boc-b-alanine (41 mg, 0.217 mmol), and 4-dimethylamino pyridine (18 mg, 0.145 mmol) in 400 ml of anhydrous methylene chloride at room temperature was added a solution of 1,3-dicyclohexylcarbodiimide (45 mg, 0.217 mmol) in 82 ml of methylene chloride. After stirring for 3.5 h, the cloudy white reaction mixture was diluted with ethyl acetate-hexanes (3:1, 1 ml), stirred for 10 min, and filtered through a plug of celite, washing with ethylacetate-hexanes (3:1). The filtrate and washings were concentrated in vacuo to a colorless oil. Chromatography (21 g of flash silica gel, 2:1 then 4:1/ethyl acetate-hexanes) afforded 121 mg (95%) of the title compound as a white foam: 500 MHz $^1$H NMR (CDCl$_3$) d 7.44–7.39 (m, 2H), 7.37–7.31 (m, 3H), 7.32 (d, 1H, J=2.1 Hz), 7.20 (dd, 1H, J=8.4, 2.1 Hz), 7.01 (d, 1H, J=8.4 Hz), 6.72 (ddd, 1H, J=15, 13, 3.7 Hz), 5.96 (dd, 1H, J=15, 1.6 Hz), 5.51 (d, 1H, J=9.8 Hz), 5.11–5.06 (m, 1H), 5.08 (d, 1H, J=9.8 Hz), 4.90–4.83 (m, 1H), 4.50 (dd, 1H, J=11, 3.6 Hz), 3.86 (s, 3H), 3.52–3.46 (m, 1H), 3.20 (dd, 1H, J=14, 3.6 Hz), 3.13 (br d, 1H, J=14 Hz), 3.05–2.92 (m, 2H), 2.79–2.63 (m, 3H), 2.45–2.37 (m, 1H), 2.24 (dt, 1H, J=16, 7.0 Hz), 2.08–1.99 (m, 1H), 1.96–1.79 (m, 3H), 1.43 (s, 9H), 1.25 (s, 3H), 1.21 (s, 3H), 1.12 (d, 3H, J=7.0 Hz), 1.06 (d, 3H, J=6.2 Hz), 1.02 (d, 3H, J=6.1 Hz).

EXAMPLE 11

Preparation of Cryptophycin 55 b-Alaninate Hydrochloride Salt (14)

To a solution of 13 (119 mg, 0.136 mmol) in 452 ml of methylene chloride at room temperature was added a 4.0 M solution of hydrogen chloride in 1,4-dioxane (170 ml, 0.679 mmol). After stirring for 2 h 15 min, the cloudy, white reaction mixture was concentrated in vacuo to provide 110 mg (96%, corrected for 4 wt % dioxane) of the title compound as a white foam: 500 MHz $^1$H NMR (MeOH-$d_4$) d 7.80 (dd, 1H, J=9.7, 2.3 Hz), 7.45–7.40 (m, 2H), 7.39–7.32 (m, 3H), 7.20 (dd, 1H, J=8.4, 2.1 Hz), 7.01 (d, 1H, J=8.4 Hz), 6.68 (ddd, 1H, J=15, 13, 3.8 Hz), 5.98 (dd, 1H, J.=15, 1.7 Hz), 5.48 (dd, 1H, J=9.4 1.0 Hz), 5.15–5.11 (m, 1H), 5.13 (d, 1H, J=9.4 Hz), 4.82 (t, 1H, J=10 Hz), 4.51 (dd, 1H, J=11, 3.7 Hz), 3.90 (s, 3H), 3.50 (dd, 1H, J=14, 9.8 Hz), 3.20 (dd, 1H, J=14, 3.7 Hz), 3.14 (dd, 1H, J=14, 2.4 Hz), 2.85 (t, 2H, J=7.0 Hz), 2.80–2.65 (m, 5H), 2.54 (dt, 1H, J=17, 7.4 Hz), 2.42–2.33 (m, 1H), 2.22 (dt, 1H, J=17, 6.7 Hz), 1.90–1.81 (m, 3H), 1.25 (s, 3H), 1.20 (s, 3H), 1.13 (d, 3H, J=7.1 Hz), 1.08 (d, 3H, J=6.3 Hz), 1.04 (d, 3H, J=6.2 Hz.

EXAMPLE 12

Preparation of Cryptophycin 55 N-t-boc-g-Aminobutyrate (15)

To a solution of 1 (48 mg, 0.068 mmol), N-t-Boc-4-aminobutyric acid (18 mg, 0.088 mmol), and 4-dimethylamino pyridine (8 mg, 0.068 mmol) in 150 ml of anhydrous methylene chloride at room temperature was added a solution of 1,3-dicyclohexylcarbodiimide (18 mg, 0.088 mmol) in 50 ml of methylene chloride. After stirring for 45 min, the cloudy white reaction mixture was diluted with ethyl acetate-hexanes (3:1, 0.5 ml), stirred for 5 min, and filtered through a plug of celite, washing with ethyl acetate-hexanes (3:1). The filtrate and washings were concentrated in vacuo to a colorless oil. Chromatography (15 g of flash silica gel, 3:1/ethyl acetate-hexanes) afforded 55 mg (90%) of the title compound as a white foam: 500 MHz $^1$H NMR (CDCl$_3$) d 7.38–7.32 (m, 5H), 7.24 (d, 1H, J=1.9 Hz), 7.22–7.19 (m, 1H), 7.10 (dd, 1H, J=8.4, 1.9 Hz), 6.88 (d, 1H, J=8.4 Hz), 6.75 (ddd, 1H, J=15, 13, 3.9 Hz), 5.78 (d, 1H, J=15 Hz), 5.60–5.55 (m, 1H), 5.49 (dd, 1H, J=9.8, 1.4 Hz), 4.96 (dd, 1H, J=11, 3.0 Hz), 4.89 (t, 1H, J=9.2 Hz), 4.81 (d, 1H, J=9.8 Hz), 4.78–4.70 (m, 1H), 4.44 (br s, 1H), 3.91 (s, 3H), 3.40 (dd, 1H, J=14, 8.1 Hz), 3.22 (dd, 1H, J=14, 4.1 Hz), 3.22–3.15 (m, 1H), 3.08 (dd, 1H, J=14, 7.8 Hz), 2.89–2.82 (m, 2H), 2.67–2.56 (m, 2H), 2.47–2.38 (m, 1H), 2.11–2.04 (m, 1H), 2.00–1.77 (m, 3H), 1.75–1.67 (m, 1H), 1.45 (s, 9H), 1.50–1.40 (m, 2H), 1.27 (s, 3H), 1.20 (s, 3H), 1.09 (d, 3H, J=7.0 Hz), 1.04 (d, 3H, J=6.6 Hz), 0.98 (d, 3H, J=6.6 Hz).

EXAMPLE 13

Preparation of Cryptophycin 55 g-Aminobutyrate Hydrochloride Salt (16)

To a solution of 15 (53 mg, 0.059 mmol) in 297 ml of methylene chloride at room temperature was added a 1.0 M solution of hydrogen chloride in diethyl ether (297 ml, 0.297 mmol). The starting material precipitated as a white paste which was redissolved with an additional 150 ml of methylene chloride. After stirring for 4 h, another 59 ml (0.059 mmol) of hydrogen chloride solution was added. Stirring was continued for another 14 h and the reaction mixture was concentrated in vacuo to provide 49 mg (100%) of the title compound as a white foam: 500 MHz $^1$H NMR (DMSO-d$_6$) d 8.49 (d, 1H, J=8.0 Hz), 7.72 (br s, 3H), 7.44–7.33 (m, 5H), 7.32 (d, 1H, J=1.9 Hz), 7.29 (dd, 1H, J=9.4, 2.6 Hz), 7.20 (dd, 1H, J=8.5, 1.9 Hz), 7.06 (d, 1H, J=8.5 Hz), 6.48 (ddd, 1H, J=15, 13, 3.9 Hz), 5.87 (d, 1H, J=15 Hz), 5.37 (d, 1H, J=9.7 Hz), 5.33 (d, 1H, J=9.7 Hz), 5.04–5.01 (m, 1H), 4.73 (t, 1H, J=11 Hz), 4.25 (ddd, 1H, J=12, 9.8, 3.5 Hz), 3.82 (s, 3H), 3.40–3.30 (m, 1H), 3.07–3.01 (m, 2H), 2.72 (dd, 1H, J=14, 12 Hz), 2.65–2.47 (m, 4H), 2.38–2.28 (m, 1H), 2.21 (dt, 1H, J=17, 7.5 Hz), 1.97 (dt, 1H, J=17, 7.5 Hz), 1.80–1.70 (m, 3H), 1.54–1.46 (m, 2H), 1.17 (s, 3H), 1.03 (s, 3H), 1.01 (d, 3H, J=7.0 Hz), 0.99 (d, 3H, J=5.8 Hz), 0.95 (d, 3H, J=5.8 Hz).

EXAMPLE 14

Preparation of Cryptophycin 55 N-t-boc-(L)-Alaninate (17)

To a solution of 1 (103 mg, 0.146 mmol), N-t-Boc-(L)-alanine (41 mg, 0.219 mmol), and 4-dimethylamino pyridine (18 mg, 0.146 mmol) in 400 ml of anhydrous methylene chloride at room temperature was added a solution of 1,3-dicyclohexylcarbodiimide (45 mg, 0.219 mmol) in 87 ml of methylene chloride. After stirring for 5 h 50 min, the cloudy white reaction mixture was treated with another 5.5 mg (0.029 mmol) of N-t-Boc-(L)-alanine, 6.0 mg (0.029 mmol) of 1,3-dicyclohexylcarbodiimide, and a few crystals of 4-dimethylamino pyridine. After stirring an additional 1 h, the reaction was diluted with ethyl acetate-hexanes (3:1, 1 ml), stirred for 10 min, and filtered through a plug of celite, washing with ethyl acetate:hexanes (3:1). The filtrate and washings were concentrated in vacuo to a colorless oil. Chromatography (22 g of flash silica gel, 1.5:1 then 2:1 then 4:1/ethyl acetate-hexanes) afforded 96 mg (75%) of the title compound as a white foam: 500 MHz $^1$H NMR (CDCl$_3$) d 7.35–7.30 (m, 5H), 7.26–7.21 (m, 2H), 7.10 (dd, 1H, J=8.4, 1.9 Hz), 6.88 (d, 1H, J=8.4 Hz), 6.76 (ddd, 1H, J=15, 13, 4.2 Hz), 5.77 (d, 1H, J=15 Hz), 5.52 (d, 1H, 7.6 Hz), 5.44 (d, 1H, J=9.7 Hz), 4.98 (dd, 1H, J=11, 2.5 Hz), 4.85–4.81 (m, 2H), 4.75 (q, 1H, J=6.8 Hz), 4.56 (d, 1H, J=7.8 Hz), 4.01–3.96 (m, 1H), 3.91 (s, 3H), 3.41 (dd, 1H, J=13, 8.3 Hz), 3.20 (dd, 1H, J=13, 4.0 Hz), 3.16 (dd, 1H, J=15, 5.9 Hz), 3.08 (dd, 1H, J=15, 7.6 Hz), 2.65–2.57 (m, 2H), 2.40–2.31 (m, 1H), 2.02–1.96 (m, 1H), 1.87–1.73 (m, 2H), 1.43 (s, 9H), 1.27 (s, 3H), 1.20 (s, 3H), 1.11–1.02 (m, 9H), 0.99 (d, 3H, J=6.3 Hz).

EXAMPLE 15

Preparation of Cryptophycin 55 (L)-Alaninate Hydrochloride Salt (18)

To a solution of 17 (95 mg, 0.108 mmol) in 361 ml of methylene chloride at room temperature was added a 4.0 M solution of hydrogen chloride in 1,4-dioxane (135 ml, 0.542 mmol). After stirring for 2.5 h, the cloudy, white reaction mixture was concentrated in vacuo to provide 90 mg (96%, corrected for 6 wt % dioxane) of the title compound as a white foam: 500 MHz $^1$H NMR (MeOH-d$_4$) d 8.54 (d, 1H, 7.6 Hz), 7.81 (br d, 1H, J=9.7 Hz), 7.46–7.44 (m, 2H), 7.39–7.37 (m, 3H), 7.32 (d, 1H, J=2.0 Hz), 7.20 (dd, 1H, J=8.4, 2.0 Hz), 7.01 (d, 1H, J=2.0 Hz), 6.69 (ddd, 1H, J=15, 11, 3.7 Hz), 5.99 (d, 1H, 15 Hz), 5.55 (d, 1H, J=9.8 Hz), 5.20 (d, 1H, J=9.8 Hz), 5.15 (dd, 1H, J=11, 2.7 Hz), 4.78 (t, 1H, J=11 Hz), 4.53–4.50 (m, 1H), 3.87 (s, 3H), 3.65 (q, 1H, J=7.3 Hz), 3.50 (dd, 1H, J=13, 9.8 Hz), 3.20 (dd, 1H, J=14, 3.5 Hz), 3.14 (br d, 1H, J=13 Hz), 2.81–2.71 (m, 3H), 2.41–2.34 (m, 1H), 1.98–1.93 (m, 1H), 1.88–1.82 (m, 2H), 1.41 (d, 3H, J=7.3 Hz), 1.25 (s, 3H), 1.20 (s, 3H), 1.13 (d, 3H, J=7.0 Hz), 1.06 (d, 3H, J=6.2 Hz), 1.04 (d, 3H, 6.0 Hz).

EXAMPLE 16

Preparation of Cryptophycin 55 N-t-boc-(D)-Alaninate (19)

To a solution of 1 (25 mg, 0.035 mmol), N-t-Boc-(D)-alanine (10 mg, 0.053 mmol), and 4-dimethylamino pyridine (0.4 mg, 0.0035 mmol) in 130 ml of anhydrous methylene chloride at room temperature was added a solution of 1,3-dicyclohexylcarbodiimide (11 mg, 0.053 mmol) in 47 ml of methylene chloride. After stirring for 5.5 h, the cloudy white reaction mixture was diluted with ethyl acetate-hexanes (3:1, 0.5 ml), stirred for 10 min, and filtered through a plug of celite, washing with ethyl acetate:hexanes (3:1). The filtrate and washings were concentrated in vacuo to a colorless oil. Chromatography (15 g of flash silica gel, 2:1/ethyl acetate-hexanes) afforded 26 mg (83%) of the title compound as a white foam: 500 MHz $^1$H NMR (CDCl$_3$) d 7.49–7.29 (m, 5H), 7.24 (d, 1H, J=2.0 Hz), 7.22–7.18 (m, 1H), 7.09 (dd, 1H, 8.4, 2.0 Hz), 6.87 (d, 1H, J=8.4 Hz), 6.76 (ddd, 1H, J=15, 13, 4.4, Hz), 5.77 (d, 1H, 15 Hz), 5.56 (d, 1H, J=9.9 Hz), 5.48 (d, 1H, J=7.7 Hz), 5.01 (dd, 1H, J=10, 2.6 Hz), 4.91 (t, 1H, J=9.4 Hz), 4.84 (d, 1H, J=9.9 Hz), 4.81–4.73 (m, 2H), 3.99–3.93 (m, 1H), 3.91 (s, 3H), 3.39

(dd, 1H, J=13, 8.0 Hz), 3.22 (dd, 1H, J=13, 3.6 Hz), 3.17 (dd, 1H, J=14, 5.0 Hz), 3.08 (dd, 1H, J=14 Hz), 2.68–2.58 (m, 2H), 2.42–2.35 (m, 1H), 2.04–1.94 (m, 1H), 1.87–1.50 (m, 2H), 1.42 (s, 9H), 1.27 (s, 3H), 1.20 (s, 3H), 1.09 (d, 3H, J=7.1 Hz), 1.04 (d, 3H, J=6.4 Hz), 0.99 (d, 3H, J=6.3 Hz), 0.65 (d, 3H, J=6.8 Hz).

EXAMPLE 17

Preparation of Cryptophycin 55 (D)-Alaninate Hydrochloride Salt (20)

To a solution of 18 (24 mg, 0.027 mmol) in 274 ml of methylene chloride at room temperature was added a 4.0 M solution of hydrogen chloride in 1,4-dioxane (34 ml, 0.137 mmol). After stirring for 3.5 h, the clear, colorless reaction mixture was concentrated in vacuo to provide 24 mg (100%, corrected for 8 wt % dioxane) of the title compound as a white foam: 500 MHz $^1$H NMR (MeOH-d4) d 7.79 (d, 1H, J=9.5 Hz), 7.47–7.40 (m, 2H), 7.40–7.36 (m, 3H), 7.31 (d, 1H, J=2.0 Hz), 7.20 (dd, 1H, J=8.4, 2.0 Hz), 7.01 (d, 1H, J=8.4 Hz), 6.71 (ddd, 1H, J=15, 13, 3.7 Hz), 5.98 (dd, 1H, J=15, 1.6 Hz), 5.65 (d, 1H, J=10 Hz), 5.20 (d, 1H, J=10 Hz), 5.17 (dd, 1H, J=11, 2.5 Hz), 4.88–4.78 (m, 1H), 4.53 (dd, 1H, J=11, 3.7 Hz), 3.95 (q, 1H, J=7.2 Hz), 3.87 (s, 3H), 3.51 (dd, 1H, J=13, 9.8 Hz), 3.20 (dd, 1H, J=14, 3.6 Hz), 3.14 (dd, 1H, J=13, 2.3 Hz), 2.81–2.74 (m, 3H), 2.41–2.34 (m, 1H), 2.07–1.99 (m, 1H), 1.96–1.84 (m 2H), 1.26 (s, 3H), 1.21 (s, 3H), 1.15 (d, 3H, J=7.1 Hz), 1.09 (d, 3H, J=6.0 Hz), 1.05 (d, 3H, J=6.0 Hz), 0.80 (d, 3H, J=7.4 Hz).

EXAMPLE 18

Preparation of Cryptophycin 55 Na—Ne-di-t-boc-(L)-Lysinate (21)

To a solution of 1 (105 mg, 0.149 mmol), Na-Ne-di-t-Boc-(L)-lysine (67 mg, 0.193 mmol), and 4-dimethylamino pyridine (18 mg, 0.149 mmol) in 400 ml of anhydrous methylene chloride at room temperature was added a solution of 1,3-dicyclohexylcarbodiimide (40 mg, 0.193 mmol) in 96 ml of methylene chloride. After stirring for 4 h, the cloudy white reaction mixture was treated with another 10 mg (0.030 mmol) of Na-Ne-di-t-Boc-(L)-lysine and 6.1 mg (0.030 mmol) of 1,3-dicyclohexylcarbodiimide as a soln in 100 ml of methylene chloride. After stirring an additional 1 h, the cloudy white reaction mixture was diluted with ethyl acetate-hexanes (3:1, 1 ml), stirred for 10 min, and filtered through a plug of celite, washing with ethyl acetate:hexanes (3:1). The filtrate and washings were concentrated in vacuo to a white foam which was resubmitted to the above conditions using 34 mg (0.097 mmol) of Na—Ne-di-t-Boc-(L)-lysine, 20 mg (0.097 mmol) of 1,3-dicyclohexylcarbodiimide, and 9.1 mg (0.075 mmol) of 4-dimethylamino pyridine. After stirring for 1.5 h, the reaction was processed as above to provide a crude white foam. Chromatography (21 g of flash silica gel, 1:1 then 4:1/ethyl acetate-hexanes) afforded 112 mg (73%) of the title compound as a white foam: 500 MHz 1H NMR (MeOH -d$_4$) d 7.42–7.37 (m, 2H), 7.36–7.29 (m, 3H), 7.27 (br s, 1H), 7.16 (br d, 1H, J=8.5 Hz), 6.97 (d, 1H, J=8.5 Hz), 6.72 (ddd, 1H, J=15, 13, 3.5 Hz), 5.92 (d, 1H, J=15 Hz), 5.50 (d, 1H, J=11 Hz), 5.11–5.04 (m, 2H), 4.84 (t, 1H, J=10 Hz), 4.48 (dd, 1H, J=11, 3.6 Hz), 3.84 (s, 3H), 3.75 (br s, 1H), 3.50–3.43 (m, 1H), 3.17 (dd, 1H, J=14, 3.6 Hz), 3.11 (d, 1H, J=14 Hz), 2.97–2.91 (m, 2H), 2.76–2.58 (m, 3H), 2.36–2.27 (m, 1H), 1.98–1.80 (m, 3H), 1.48–1.38 (m, 2H), 1.43 (s, 9H), 1.40 (s, 9H), 1.35–1.25 (m, 2H), 1.23 (s, 3H), 1.20 (s, 3H), 1.15–1.09 (m, 2H), 1.07 (d, 3H, J=6.8 Hz), 1.06 (d, 3H, J=6.0 Hz), 1.01 (d, 3H, J=6.1 Hz).

EXAMPLE 19

Preparation of Cryptophycin 55 (L)-Lysinate di-Hydrochloride Salt (22)

To a solution of 21 (107 mg, 0.103 mmol) in 345 ml of methylene chloride at room temperature was added a 4.0 M solution of hydrogen chloride in 1,4-dioxane (155 ml, 0.621 mmol). After stirring for 4 h, the cloudy white reaction mixture was filtered. The collected white solid was washed with methylene chloride (2×1 ml) and dried in vacuo at room temperature to provide 87 mg (93%) of the title compound: 500 MHz $^1$H NMR (MeOH-d$_4$) d 8.61 (d, 1H, J=7.7 Hz), 7.81 (d, 1H, J=7.7 Hz), 7.47–7.44 (m, 2H), 7.40–7.38 (m, 3H), 7.31 (d, 1H, J=2.2 Hz), 7.20 (dd, 1H, J=8.4, 2.2 Hz), 7.00 (d, 1H, J=8.4 Hz), 6.63 (ddd, 1H, J=15, 13, 4.0 Hz), 6.00 (dd, 1H, J=15, 1.6 Hz), 5.55 (d, 1H, J=9.8 Hz), 5.20 (d, 1H, J=9.8 Hz), 5.15 (dd, 1H, J=10, 2.9 Hz), 4.68 (t, 1H, J=11 Hz), 4.55–4.49 (m, 1H), 3.87 (s, 3H), 3.79 (t, 1H, J=5.6 Hz), 3.52 (dd, 1H, J=14, 9.9 Hz), 3.20 (dd, 1H, J=14, 3.6 Hz), 3.13 (dd, 1H, J=13, 2.4 Hz), 3.06–2.98 (m, 1H), 2.94–2.87 (m, 1H), 2.85–2.74 (m, 3H), 2.45–2.38 (m, 1H), 1.98–1.76 (m, 5H), 1.71–1.64 (m, 2H), 1.39–1.30 (m, 2H), 1.25 (s, 3H), 1.18 (d, 3H, J=8.2 Hz), 1.17 (s, 3H), 1.08 (d, 3H, J=6.2 Hz), 1.05 (d, 3H, J=6.1 Hz).

EXAMPLE 20

Preparation of 2'-(di-t-Butylphosphatyl)phenylacetic Acid (24)

To a solution of 2'-hydroxyphenethyl alcohol (1.05 g, 7.60 mmol) in 15.2 ml of N,N-dimethylformamide at 0° C. was added imidazole (621 mg, 9.11 mmol) and tert-butyldimethylsilyl chloride (1.26 g, 8.34 mmol). After stirring at 0° C. for 40 min and at room temperature for 45 min, another 155 mg (2.28 mmol) of imidazole and 229 mg (1.52 mmol) of tert-butyldimethylsilyl chloride were added. The reaction was allowed to stir for an additional 15 min at which time 150 ml of tert-butyl methy ether was added. The mixture was washed with cold 1N aqueous hydrochloric acid (1×15 ml) followed by water (1×15 ml). The organic layer was dried (Na$_2$SO$_4$), filtered, and concentrated in vacuo to a yellow oil. Chromatography (70 g of flash silica gel), eluting with hexanes-ethyl acetate (5:1) provided 1.81 g (94%) of the 1° silyl ether as a faintly off-white oil. To a solution of the silyl ether (506 mg, 2.00 mmol) and di-tert-butyl diethylphosphoramidite (600 ml of 93%, 2.00 mmol) in 2 ml of tetrahydrofuran at room temperature was added 1-H-tetrazole (421 mg, 6.01 mmol). After stirring for 45 min the reaction mixture was cooled to −10° C. and rapidly treated with a solution of m-chloroperbenzoic acid (450 mg of 99%, 2.61 mmol) in 3.6 ml of methylene chloride. The cloudy white reaction was allowed to warm to room temperature and stir for 15 min. The reaction was quenched with 4 ml of 10% aqueous sodium bisulfite, stirred vigorously for 10 min, diluted with 15 ml of tert-butyl methy ether, and washed with 10% aqueous sodium bisulfite (2×10 ml) followed by 0.5 N aqueous sodium hydroxide (2×10 ml). The organic layer was dried (Na$_2$SO$_4$), filtered, and concentrated in vacuo to a colorless oil (941 mg) which was used directly in the next step. The crude phosphate was dissolved in 10 ml of tetrahydrofuran, cooled to 0° C., and treated with a 1 M solution of tetra-n-butylammonium fluoride in tetrahydrofuran (2.4 ml, 2.4 mmol). After stirring at 0° C. for 20 min and at room temperature for 1.5 h, the reaction was diluted 60 ml of tert-butyl methy ether and washed with water (1×10 ml) followed by brine (1×10 ml). The organic layer was dried (Na$_2$SO$_4$), filtered, and concentrated in vacuo to a yellow oil. Chromatography (50 g of flash silica gel), eluting with ethyl acetate-hexanes (3:1) provided 525 mg (79%) of the 1° alcohol as an off-white oil. To a solution of the alcohol (123 mg, 0.372 mmol) in acetonitrile-carbon tetrachloride (1:1, 1.49 ml) at room temperature was added water (1.1 ml) followed by sodium periodate (239 mg, 1.12 mmol) and ruthenium(III)chloride hydrate (1.8 mg, 0.0082 mmol). The brown mixture was allowed to stir rapidly at room temperature for 55 min. Upon concentration in vacuo and chromatography (8 g of flash silica gel, eluting with 10% methanol-ethyl acetate) 109 mg (85%) of the title compound was obtained as a purple oil: 500 MHz $^1$H NMR (CDCl$_3$) d 7.49 (d, 1H, J=7.53 Hz), 7.30–7.15 (m, 3H), 3.77 (s, 2H), 1.51 (s, 18H).

EXAMPLE 21

The compound of Examples 21–26 were prepared using the methods substantially as hereinbefore described.

Spectral Properties of Cryptophycin-129

EIMS m/z (rel intensity) 654/656 (2.1/0.8, M-HBr), 412/414 (9.7/3.6), 280/282 (10.3/3.5), 227 (15.2), 195/197 (50.1/16.3), 105 (100), 91 (100); high resolution EIMS m/z 654.2687 (C$_{35}$H$_{43}$ClN$_2$O$_8$, D 2.1 mmu). $^1$H NMR (CDCl$_3$) amino or hydroxy acid unit d (carbon position, multiplicity; J in Hz) 7-bromo-5,8-dihydroxy-6-methyl-8-phenyl-2-octenoic acid (A) 5.76 (2,d; 15.3), 6.68 (3, ddd; 15.3,9.9 and 5.6, 2.29 (4, ddd; 14.2, 10.6 and 10.4), 2.67 (4, dd; 14.2 and 5.4), 4.95 (5, ddd; 10.3, 10.3 and 1.8), 2.47 (6, m), 1.15 (6-Me, d; 6.5), 4.29 (7, dd; 9.1 and 2.1), 4.84 (8, d; 9.0, 7.34–7.39 (10/11/12/13/14, m); 3-chloro-4-methoxyphenylalanine (B) 4.80 (2, m), 5.73 (2-NH, d; 8.8), 3.01 (3, dd; 14.6 and 7.6), 3.16 (3, dd; 14.3 and 5.6), 7.23 (5, d; 2.0), 3.87 (7-OMe, s), 6.84 (8, d; 8.4), 7.09 (9, dd; 8.4 and 2.0); 3-amino-2-methylpropionic acid (C) 2.73 (2, m), 1.23 (2-Me, d; 7.2), 3.25 (3, ddd; 13.5, 6.5 and 6.5), 3.53 (3, ddd; 13.4, 5.4 and 3.9), 6.93 (3-NH, brt; 6.1); leucic acid (D) 4.91 (2, dd; 10.5 and 2.8, 1.49 (3, m), 1.80 (3, m), 1.73 (4, m). 0.92 (4-Me, d; 6.5), 0.89 (5, d; 6.5). $^{13}$C NMR (CDCl$_3$) unit d (carbon position) A 165.4(1), 125.2 (2), 141.3 (3), 36.6 (4), 75.7 (5), 37.9 (6), 11.8 (6-Me), 60.3 (7), 76.7 (8), 141.6 (9), 126.8 (10/14), 128.7 (11/13), 128.8 (12); B 171.0 (1), 53.6 (2), 35.0 (3), 130.0 (4), 131.0 (5), 122.4 (6), 153.9 (7), 56.1 (7-OMe), 112.3 (8), 128.4 (9); C 175.4 (1), 38.4 (2), 14.0 (2-Me), 41.3 (3), D 170.2 (1), 71.3 (2), 39.6 (3), 24.8 (4), 23.2 (4-Me), 21.4 (5).

EXAMPLE 22

Spectral Properties of Cryptophycin-138

EIMS m/z (rel intensity) 734/736 (0.3/0.1), 654/656 (0.6/0.2), 412/414 (12.6/4.7), 313/315 (20.4/12.5) 280 (7.6), 227 (3.5), 195/197 (44.7/15.6), 155/157 (35.4/13.6), 105 (33.6), 91 (34.2), 80/82 (100/100); high resolution EIMS m/z 734.1985 (C$_{35}$H$_{44}$ClBrN$_2$O$_8$, D-1.6 mmu), 654.2722 (C$_{35}$H$_{43}$ClN$_2$O$_8$, D-1.4 mmu). $^1$H NMR (CDCl$_3$) amino or hydroxy acid unit d (carbon position, multiplicity; J in Hz) 7-bromo-5,8-dihydroxy-6-methyl-8-phenyl-2-octenoic acid (A) 5.78 (2, d; 15.5), 6.69 (3, ddd; 15.1, 9.8 and 5.3), 2.33 (4, m), 2.71 (4, m), 4.97 (5, ddd; 10.4, 10.4 and 1.6), 2.45 (6, m), 1.17 (6-Me, d; 6.3), 4.40 (7, dd; 10.1 and 2.2), 5.06 (8, d; 10.1), 7.36–7.42 (10/11/12/13/14, m); 3-chloro-4-methoxyphenylalanine (B) 4.82 (2, m), 5.69 (2-NH, d; 8.7), 3.02 (3, dd; 14.5 and 7.5), 3.17 (3, dd; 14.5 and 5.4), 7.23 (5, d; 2.1), 3.88 (7-OMe, s), 6.85 (8, d; 8.4), 7.09 (9, dd; 8.4 and 1.9); 3-amino-2-methylpropionic acid (C) 2.73 (2, m), 1.23 (2-Me, d; 7.3), 3.25 (3, ddd; 13.4, 6.5 and 6.5), 3.54 (3, m), 6.92 (3-NH, brt; 5.7); leucic acid (D) 4.91 (2, dd; 10.6 and 2.7), 1.43 (3, m), 1.82 (3, m), 1.75 (4, m), 0.93 (4-Me, d; 6.6), 0.90 (5, d; 6.6). $^{13}$C NMR (CDCl$_3$) unit d (carbon position) A 165.4 (1), 125.2 (2), 141.2 (3), 36.6 (4), 76.5 (5), 38.2 (6), 11.7 (6-Me), 55.3 (7), 87.4 (8), 137.4 (9), 128.0 (10/14), 128.7 (11/13), 129.3 (12); B 171.0 (1), 53.6 (2), 35.0 (3), 129.9 (4), 131.0 (5), 122.4 (6), 153.9 (7), 56.1 (7-OMe), 112.2 (8), 128.4 (9); C 175.5 (1), 38.4 (2), 14.0 (2-Me), 41.2 (3), D 170.2 (1), 71.2 (2), 39.6 (3), 24.8 (4), 23.2 (4-Me), 21.4 (5).

EXAMPLE 23

Spectral Properties of Cryptophycin-139

EIMS m/z (rel intensity) 732/734 (0.3/0.3), 652/654 (0.9/0.5), 533 (13.6), 445(5.7), 195/197 (9.2/11.4), 105 (96.2), 80/82 (100/100); high resolution EIMS m/z 732.1783 (C$_{35}$H$_{42}$ClBrN$_2$O$_8$, E 3.0 mmu), 652.2573 (C$_{35}$H$_{41}$ClN$_2$O$_8$, E -2.1 mmu). $^1$H NMR (CDCl$_3$) amino or hydroxy acid unit d (carbon position, multiplicity; J in Hz) 7-bromo-8-oxo-5-hydroxy-6-mnethyl-8-phenyl-2-octenoic acid (A) 5.75 (2, d; 15.4), 6.68 (3, ddd; 15.2, 10.1 and 5.0), 2.31 (4, ddd; 14.2, 10.7 and 10.7), 2.63 (4, dd; 14.4 and 5.1), 5.09 (5, ddd; 9.7, 9.7 and 1.5), 2.46 (6, m), 1.18 (6-Me, d; 6.6), 5.41 (7, d; 3.5), 7.94 (10/14, brd; 8.6), 7.50 (11/13, t; 7.8), 7.63 (12, brt; 7.5); 3-chloro-4-methoxyphenylalanine (B) 4.80 (2, m), 5.64 (2-NH, d; 8.3), 3.04 (3, dd; 14.6 and 7.2), 3.14 (3, dd; 14.4 and 5.5), 7.22 (5, d; 2.0), 3.87 (7-OMe, s), 6.84 (8, d; 8.3), 7.08 (9, dd; 8.3 and 2.3); 3-amino-2-methylpropionic acid (C) 2.76 (2, m), 1.26 (2-Me, d; 7.1), 3.31 (3, ddd; 13.7, 6.8 and 6.6), 3.53 (3 m), 6.95 (3-NH, brt; 5.9); leucic acid (D) 4.93 (2, dd; 10.6 and 3.0), 1.51 (3, m), 1.95 (3, m), 1.80 (4, m), 0.97 (4-Me, d; 6.8), 0.91 (5, d, 6.6), 13C NMR (CD13) unit d (carbon position) A 165.2 (1), 125.3 (2), 141.0 (3), 36.2 (4), 76.0 (5), 39.3 (6), 13.8 (6-Me), 51.8 (7), 192.3 (8), 134.2 (9), 128.7 (10/14), 129.0 (11/13), 134.0 (12); B 170.9(1), 53.7 (2), 35.0 (3), 129.8 (4), 131.0 (5), 122.4 (6), * (7, not observed), 56.2 (7-OMe), 112.3 (8), 128.4 (9); C 175.6 (1), 38.3 (2), 14.2 (2-Me), 41.1 (3), D 170.2 (1), 71.1 (2), 39.8 (3), 24.7, 23.2 (4-Me), 21.3 (5).

EXAMPLE 24

Spectral Properties of Cryptophycin-145

EIMS m/z (rel intensity) 734/736/738 (0.5/0.6/0.2), 654, 656 (1.5/1.1), 412/414 (2.2/1.0), 313/315 (19.5/12.9), 227 (4.1), 195/197 (11.5/3.7), 105 (14.6), 91 (25.2), 80/82 (100/100); high resolution EIMS m/z 736.1980 (C$_{35}$H$_{44}$ClBrN$_2$O$_8$, æ -3.1 mmu), 654.2714 (C$_{35}$H$_{43}$ClN$_2$O$_8$, æ -0.6 mmu). $^1$H NMR (CDCl$_3$) amino or hydro amino or hydroxy acid unit d (carbon position, multiplicity; J in Hz) 7-bromo-5,8-dihydroxy-6-methyl-8-phenyl-2-octenoic acid (A) 5.81 (2, d; 15.7), 6.72 (3, m), 2.31 (4, m), 2.77 (4, m), 5.62 (5, m), 2.42 (6, m), 1.22 (6-Me, d; 7.0), 4.23 (7, dd; 8.0 and 3.2), 4.94 (8, d; 7.9), 7.32–7.28 (10/11/12/13/14, m); 3-chloro-4-methoxyphenylalanine (B) 4.82 (2, m), 5.72 (2-NH, brs), 3.05 (3, m), 3.15 (3, m), 7.23 (5, brs), 3.88 (7-OMe, s), 6.84 (8, brd; 7), 7.09 (9, m); 3-amino-2-methylpropionic acid (C) 2.75 (2, m), 1.25 (2-Me, d; 7.0), 3.30 (3, m), 3.53 (3, m), 6.97 (3-N, brs); leucic acid (D) 4.90 (2, dd; 9.7 and 3.6), 1.58 (3, m), 1.82 (3, m), 1.70 (4, m). 0.95 (4-Me, d; 6.6), 0.89 (5, d; 6.6). $^{13}$C NMR (CDCl3) unit d (carbon position) A 165.14 (1), 125.2 (2), 141.3 (3), 35.8 (4), 75.8 (5), 41.2 (6), 13.4 (6-Me), 60.7 (7), 76.5 (8), 141.6 (9), 126.8 (10/14), 128.5 (11/13), 128.6 (12); B 170.5 (1), 53.7 (2), 35.0 (3), 129.9 (4), 131.0 (5), 122.4 (6), 154.0 (7), 56.2 (7.OMe), 112.3 (8), 128.5 (9); C 175.4 (1), 38.4 (2), 14.1 (2-Me), 41.2 (3), D 170.5 (1), 71.3 (2), 39.7 (3), 24.6 (4), 22.9 (4-e), 21.5 (5).

EXAMPLE 25

Spectral Properties of Cryptophycin-140

EIMS m/z (rel intensity) 690/692 (2.3/1.8), 654/656 (3.8/2.2), 412/414 (5.4/2.1), 280/282 (5.4/2.2), 227 (10.2), 195/197 (27.8/10/4), 155/157 (53.7/16/4), 105 (81.0), 91 (100); high resolution EIMS m/z 690.2427 (C35H44Cl2N2O8, æ 4.8 mmu), 654.2760 (C35H43ClN2O8, æ -5.2 mmu). 1H NMR (CDCl3) amino or hydroxy acid unit d (carbon position, multiplicity; J in Hz) 7-chloro-5,8-dihydroxy-6-methyl-8-phenyl-2-octenoic acid (A) 5.77 (2, d; 15.4), 6.68 (3, ddd; 15.3, 9.8 and 5.6), 2.29 (4, m), 2.67 (4, m), 4.98 (5, ddd; 10.3, 10.3 and 1.7), 2.64 (6, m), 1.15 (6-Me, d; 6.6), 4.19 (7, dd; 9.2 and 2.1), 4.72 (8, d; 9.2), 7.33–7.39 (10/11/12/13/14, m); 3-chloro-4-methoxyphenylalanine (B) 4.81 (2, m), 5.69 (2-NH, d; 8/8), 3.01 (3, dd; 14.5 and 7.5), 3.16 (3, dd; 14.5 and 5.5), 7.23 (5, d; 2.1), 3.87 (7-OMe, s), 6.84 (8, d; 8.3), 7.09 (9, dd; 8.4 and 2.0); 3-amino-2-methylpropionic acid (C) 2.73 (2, m), 1.22 (2-Me, d; 7.3), 3.24 (3, ddd; 13.5, 6.8 and 6.8), 3.53 (3, m), 6.91 (3-NH, brt; 6.0); leucic acid (D) 4.89 (2, dd; 10.4 and 2.9), 1.39 (3, m), 1.69–1.80 (3/4, m). 0.90 (4-Me, d; 6.4), 0.87 (5, d; 6.6). 13 C NMR (CDCl$_3$) unit d (carbon position) A 165.4 (1), 125.2, 141.4 (3), 36.7 (4), 75.5 (5), 38.1 (6), 10.4 (6-Me), 65.0 (7), 75.8 (8), 141.4 (9), 126.8 (10/14), 128.7 (11/13), 128.8 (12); B 171.0 (1), 53.6 (2), 35.0 (3), 129.9 (4), 131.0 (5), 122.4 (6), 153.9 (7), 56.1 (7-OMe), 112.2 (8), 128.4 (9); C 175.5 (1), 38.4 (2), 14.1 (2-Me), 41.3 (3), D 170.3 (1), 71.3 (2), 39.5 (c), 24.7 (4), 23.2 (4-Me), 21.4 (5).

EXAMPLE 26

Spectral Properties of Cryptophycin-141

EIMS m/z (rel intensity) 654/656 (1.8/0.8, M-HCl), 412/414 (7.6/3.1), 280/282 (3.2/2.0), 227 (8.4), 195/197 (35.6/11.9), 155/157 (100/37.2), 105 (68.1), 91 (88.4); high resolution EIMS m/z 690.2468 ($C_{35}H44Cl2N_{2O8}$, æ 0.6 mmu), 654.2706 ($C_{35}H_{43}ClN_2O_8$, æ –0.2 mmu). $^1$H NMR (CDCl$_3$) amino or hydroxy acid unit d (carbon position, multiplicity; J in Hz) 7-chloro-5,8-dihydroxy-6-methyl-8-phenyl-2-octenoic acid (A) 5.69 (2, d; 15.4), 6.62 (3, ddd;

15.1, 9.9 and 5.2), 2.07 (4, m), 2.49 (4, dd, 14.4 and 5.4), 4.96 (5, ddd; 10.5, 10.5 and 1.8), 1.88 (6, m), 1.07 (6-Me, d; 6.8, 4.24 (7, dd; 8.9 and 1.9), 4.73 (8, d; 8.8), 2.80 (8-OH, broad Peak), 7.32 (10/14, dd; 7.6 and 1.9), 7.36–7.42 (11/12/13, m); 3-chloro-4-methoxyphenylalanine (B) 4.78 (2, m), 5.65 (2-NH, d; 8.6), 3.00 (3, dd; 14.4 and 7.2), 3.13 (3, dd; 14.4 and 5.6), 7.20 (5, d; 2.3), 3.86 (7-OMe, s), 6.82 (8, d; 8.3), 7.06 (9, dd; 8.3 and 2.2); 3-amino-2-methylpropionic acid (C) 2.73 (2, ), 1.23 (2-Me, d; 7.2) 3.27 (3, ddd; 13.5, 6.8 and 6.8), 3.51 (3, ddd; 13.5, 5.0 and 3.8), 6.91 (3-NH, brt; 6.0); leucic acid (D) 4.83 (2, dd; 10.4 and 2.9), 1.48 (3, m), 1.70 (3, m), 1.76 (4, m). 0.99 (4-Me, d; 6.5), 0.95 (5, d; 6.5). $^{13}$C NMR (CDCl$_3$) unit d (carbon position) A 165.3 (1), 125.2 (s), 141.0 (3), 36.2 (4), 75.5 (5), 39.3 (6), 10.8 (6-Me), 70.0 (7), 76.2 (8), 138.9 (9), 126.7 (10/14), 129.0 (11/13), 129.0 (12); B 170.9 (1), 53.6 (2), 35.0 (3), 129.8 (4), 131.0 (5), 122.4 (6), 153.9 (7), 56.1 (7-)Me), 112.2 (8), 128.4 (9); C 175.5 (1), 38.2 (2), 14.1 (2-Me), 41.1 (3), D 170.2 (1), 71.2 (2), 39.6 (3), 24.8 (4), 23.2 (4-Me), 21.4 (5).

EXAMPLE 27

Scheme 1

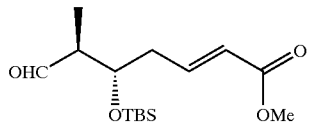

Experimentals

To a solution of alkene 1 (1.15 g, 3.52 mmol) in 50 mL of CH$_2$Cl$_2$ at –78° C., was added pyridine (0.3 mL, 3.9 mmol) and 0.98 mL of a 0.1% solution of Sudan Red 7B in CH$_2$Cl$_2$. Ozone was slowly bubbled in until the red color changed to a yellow. The reaction progress was monitored by TLC. Upon completion, zinc dust (1.63 g, 24.9 mmol) and 3.4 mL of glacial acetic acid were added. The cold bath was removed and the mixture was allowed to warm up slowly to room temperature and was stirred an additional 2 h. The reaction mixture was filtered through Celite and washed with CuSO$_4$ (3×30 mL), followed by water (3×20 mL) and finally saturated aqueous NaHCO$_3$ (2×20 mL). The organic layer was dried over MgSO$_4$, filtered and concentrated in vacuo to give 0.937 g (88%) of the desired aldehyde which was used in the next step without further purification: $^1$H NMR (300 MHz, CDCl$_3$) d 9.74–9.73 (d, 1H, J=1.97 Hz), 7.0–6.82 (m, 1H), 5.91–5.86 (d, 1H, J=15.4 Hz), 4.1–4.0 (m, 1H), 3.73 (s, 3H), 2.55–2.4 (m, 3H), 1.09–1.07 (d, 3H, J=6.8 Hz), 0.87 (s, 9H), 0.08 (s, 3H), 0.06 (s, 3H).

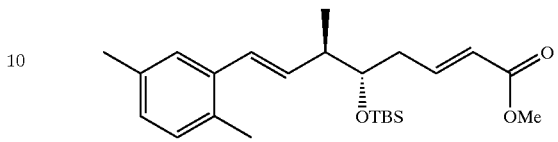

Methyllithium (9.6 mL, 14.4 mmol), as a 1.5 M solution in diethyl ether complexed with lithium bromide, was added dropwise to a –78° C. solution of 2,5-dimethylbenzyl triphenylphosphonium chloride in 120 mL of THF. The solution was allowed to warm up slowly to 0° C. and was cooled back down to –78° C. Aldehyde 2 in 40 mL of THF, was added dropwise to the ylide at –78° C. The mixture was stirred at –78° C. for 15 min and then was warmed up slowly to room temperature. Following 1 h at rt, sat. NH$_4$Cl (50 mL) was added and the solution was extracted with ether. The ether layer was washed with water (2×50 mL) then brine, dried over MgSO$_4$, filtered and concentrated in vacuo. The crude styrene as a mixture of E:Z isomers was purified on silica gel using 2% EtOAc/hexanes to yield 2.32 g (58%) of a clear oil.

The E:Z mixture was refluxed for 8 h in 120 mL of benzene in the presence of thiophenol (0.3 mL) and 1,1'-azobis(cyclohexanecarbonitrile) (VAZO) (0.16 g). The solution was then cooled to ambient temperature, concentrated under vacuum and purified by column chromatography (silica gel, 2–5% EtOAc/hexanes) to yield 2.2 g (95%) of the pure E isomer as a clear oil: [a]$^{20}{}_D$ +34.6° (c1.0, MeOH); $^1$H NMR (300 MHz, CDCl$_3$) d 7.3–7.0 (m, 4H), 6.62–6.57 (d, 1H, J=15.8 Hz), 6.11–6.03 (dd, 1H, J=15.8, 8.1 Hz), 5.93–5.88 (d, 1H, J=15.5 Hz), 3.82–3.78 (m, 1H), 3.78 (s, 3H), 2.6–2.34 (m, 3H), 2.37 (s, 3H), 2.34 (s, 3H), 1.18–1.16 (d, 3H, J=6.8 Hz), 0.96 (s, 9H), 0.13 (s, 3H), 0.11 (s, 3H); $^{13}$C NMR (75 MHz, CDCl$_3$) d 167.2, 146.9, 136.9, 135.7, 133.3, 132.4, 130.5, 128.8, 128.1, 126.5, 123.2, 75.5, 51.8, 43.4, 37.9, 26.2, 21.4, 19.7, 18.5, 16.7, –4.0, –4.2; IR (CHCl$_3$) 2955, 2930, 2858, 1718, 1658, 1603, 1496, 1472, 1438, 1362, 1325, 1280, 1258, 1097, 1040 cm$^{-1}$; Anal. Calcd for C$_{24}$H$_{38}$O$_3$Si: C, 71.59; H, 9.51. Found: C, 71.38; H, 9.30.

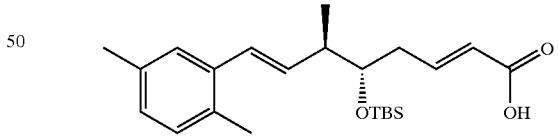

To a solution of ester 3 (2.2 g, 5.46 mmol) in 10 mL of THF was added 11 mL of a 2 M KOH solution. While being stirred vigorously, the resulting mixture was heated at 65° C. for 24 h. Upon cooling to ambient temperature, 11 mL of a 2 M solution of HCl was added and the resulting mixture was stirred vigorously for an additional 30 min. Ethyl acetate (50 mL) was added to the mixture and the layers separated.

The aqueous layer was further extracted with ethyl acetate (2×30 mL). The combined organic layers were washed with 50% brine (3×30 mL), dried over Na$_2$SO$_4$, filtered and concentrated in vacuo to yield 2.12 g (100%) of the desired acid as a thick yellow oil: 1H NMR (300 MHz, CDCl$_3$) d 7.26–6.95 (m, 4H), 6.62–6.57 (d, 1H, J=15.8 Hz), 6.1–6.02 (dd, 1H, J=15.8, 8.0 Hz), 5.92–5.87 (d, 1H, J=15.7 Hz), 3.9–3.8 (m, 1H), 2.6–2.2 (m, 3H), 2.36 (s, 3H), 2.34 (s, 3H), 1.18–1.15 (d, 3H, J=6.8 Hz), 0.94 (s, 9H), 0.12 (s, 3H), 0.11 (s, 3H).

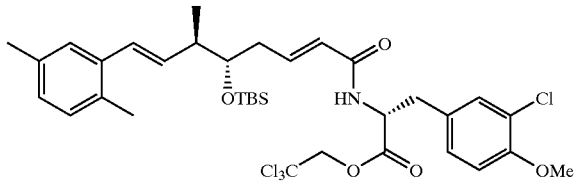

To a 0° C. solution of acid 4 (2.12 g, 5.46 mmol) and diisopropylethylamine (2.9 mL, 16.4 mmol) in 7 mL of DMF was added diphenylphosphinic chloride (1.1 mL, 6.01 mmol) dropwise. Following 5 min of stirring at 0° C. and 30 min at room temperature, the TFA salt of 3-(3-chloro-4-methoxyphenyl)-D-alanine-2,2,2-trichloroethyl ester 5 in 7 mL of DMF was added dropwise. The resulting mixture was stirred at room temperature for 2 h, poured into 100 mL of water and washed with diethyl ether (3×50 mL). The combined organic layers were washed with brine, dried over MgSO$_4$, filtered through Celite and concentrated in vacuo. Purification by column chromatography (silica gel, 10–30% EtOAc/hexanes) gave 2.86 g (72%) of amide 6 as a white foam: [a]$^{20}_D$ +44.8° (c1.0, MeOH); $^1$H NMR (300 MHz, CDCl$_3$) d 7.25 (s, 1H), 7.22 (s, 1H), 7.1–6.83 (m, 5H), 6.6–6.55 (d, 1H, J=15.7 Hz), 6.11–6.03 (dd, 1H, J=15.6, 8.1 Hz), 5.9–5.8 (m, 2H), 5.18–5.05 (m, 1H), 4.83–4.75 (q, 2H, J=12.0 Hz), 3.9 (s, 3H), 3.83–3.68 (m, 1H), 3.3–3.1 (m, 2H), 2.6–2.36 (m, 3H), 2.36 (s, 3H), 2.32 (s, 3H), 1.16–1.14 (d, 3H, J=6.7 Hz), 0.95 (s, 9H), 0.11 (s, 3H), 0.05 (s, 3H); $^{13}$C NMR (75 MHz, CDCl$_3$) d 170.0, 165.1, 154.2, 143.1, 136.4, 135.3, 133.0, 132.0, 131.0, 130.9, 130.0, 128.4, 128.3, 127.7, 126.1, 124.6, 112.3, 112.1, 94.2, 75.0, 74.7, 56.0, 52.9, 42.8, 37.5, 36.5, 25.8, 20.9, 19.3, 18.0, 16.4, −4.3, −4.7; IR (CHCl$_3$) 3428, 2957, 2930, 2857, 1759, 1676, 1645, 1606, 1503, 1464, 1442, 1380, 1349, 1281, 1259, 1173, 1067 cm$^{-1}$.

EXAMPLE 27

Scheme 1

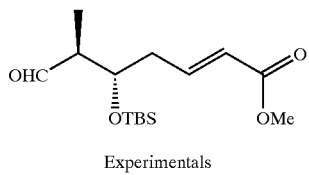

Experimentals

To a solution of alkene 1 (1.15 g, 3.52 mmol) in 50 mL of CH$_2$Cl$_2$ at −78° C., was added pyridine (0.3 mL, 3.9 mmol) and 0.98 mL of a 0.1% solution of Sudan Red 7B in CH$_2$Cl$_2$. Ozone was slowly bubbled in until the red color changed to a yellow. The reaction progress was monitored by TLC. Upon completion, zinc dust (1.63 g, 24.9 mmol) and 3.4 mL of glacial acetic acid were added. The cold bath was removed and the mixture was allowed to warm up slowly to room temperature and was stirred an additional 2 h. The reaction mixture was filtered through Celite and washed with CUSO$_4$ (3×30 mL), followed by water (3×20 mL) and finally saturated aqueous NaHCO3 (2×20 mL). The organic layer was dried over MgSO$_4$, filtered and concentrated in vacuo to give 0.937 g (88%) of the desired aldehyde which was used in the next step without further purification:

$^1$H NMR (300 MHz, CDCl$_3$) d 9.74–9.73 (d, 1H, J=1.97 Hz), 7.0–6.82 (m, 1H), 5.91–5.86 (d, 1H, J=15.4 Hz), 4.1–4.0 (m, 1H), 3.73 (s, 3H), 2.55–2.4 (m, 3H), 1.09–1.07 (d, 3H, J=6.8 Hz), 0.87 (s, 9H), 0.08 (s, 3H), 0.06 (s, 3H).

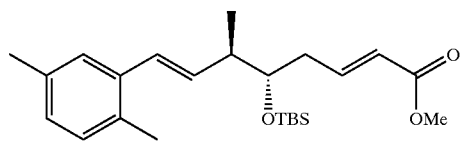

Methyllithium (9.6 mL, 14.4 mmol), as a 1.5 M solution in diethyl ether complexed with lithium bromide, was added dropwise to a −78° C. solution of 2,5-dimethylbenzyl triphenylphosphonium chloride in 120 mL of THF. The solution was allowed to warm up slowly to 0° C. and was cooled back down to −78° C. Aldehyde 2 in 40 mL of THF, was added dropwise to the ylide at −78° C. The mixture was stirred at −78° C. for 15 min and then was warmed up slowly to room temperature. Following 1 h at rt, sat. NH$_4$Cl (50 mL) was added and the solution was extracted with ether. The ether layer was washed with water (2×50 mL) then brine, dried over MgSO$_4$, filtered and concentrated in vacuo. The crude styrene as a mixture of E:Z isomers was purified on silica gel using 2% EtOAc/hexanes to yield 2.32 g (58%) of a clear oil.

The E:Z mixture was refluxed for 8 h in 120 mL of benzene in the presence of thiophenol (0.3 mL) and 1,1'-azobis(cyclohexanecarbonitrile) (VAZO) (0.16 g). The solution was then cooled to ambient temperature, concentrated under vacuum and purified by column chromatography (silica gel, 2–5% EtOAc/hexanes) to yield 2.2 g (95%) of the pure E isomer as a clear oil: [a]$^{20}_D$ +34.6° (c1.0, MeOH); $^1$H NMR (300 MHz, CDCl$_3$) d 7.3–7.0 (m, 4H), 6.62–6.57 (d, 1H, J=15.8 Hz), 6.11–6.03 (dd, 1H, J=15.8, 8.1 Hz), 5.93–5.88 (d, 1H, J=15.5 Hz), 3.82–3.78 (m, 1H), 3.78 (s, 3H), 2.6–2.34 (m, 3H), 2.37 (s, 3H), 2.34 (s, 3H), 1.18–1.16 (d, 3H, J=6.8 Hz), 0.96 (s, 9H), 0.13 (s, 3H), 0.11 (s, 3H); $^{13}$C NMR (75 MHz, CDCl$_3$) d 167.2, 146.9, 136.9, 135.7, 133.3, 132.4, 130.5, 128.8, 128.1, 126.5, 123.2, 75.5, 51.8, 43.4, 37.9, 26.2, 21.4, 19.7, 18.5, 16.7, −4.0, −4.2; IR (CHCl$_3$) 2955, 2930, 2858, 1718, 1658, 1603, 1496, 1472, 1438, 1362, 1325, 1280, 1258, 1097, 1040 cm$^{-1}$; Anal. Calcd for C$_{24}$H$_{38}$O$_3$Si: C, 71.59; H, 9.51. Found: C, 71.38; H, 9.30.

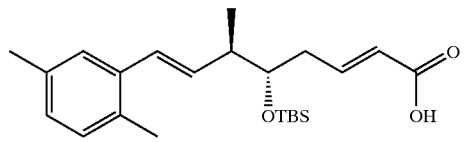

To a solution of ester 3 (2.2 g, 5.46 mmol) in 10 mL of THF was added 11 mL of a 2 M KOH solution. While being stirred vigorously, the resulting mixture was heated at 65° C. for 24 h. Upon cooling to ambient temperature, 11 mL of a 2 M solution of HCl was added and the resulting mixture was stirred vigorously for an additional 30 min. Ethyl acetate (50 mL) was added to the mixture and the layers separated. The aqueous layer was further extracted with ethyl acetate (2×30 mL). The combined organic layers were washed with 50% brine (3×30 mL), dried over Na2SO$_4$, filtered and concentrated in vacuo to yield 2.12 g (100%) of the desired acid as a thick yellow oil: $^1$H NMR (300 MHz, CDCl$_3$) d 7.26–6.95 (m, 4H), 6.62–6.57 (d, 1H, J=15.8 Hz), 6.1–6.02 (dd, 1H, J=15.8, 8.0 Hz), 5.92–5.87 (d, 1H, J=15.7 Hz), 3.9–3.8 (m, 1H), 2.6–2.2 (m, 3H), 2.36 (s, 3H), 2.34 (s, 3H), 1.18–1.15 (d, 3H, J=6.8 Hz), 0.94 (s, 9H), 0.12 (s, 3H), 0.11 (s, 3H).

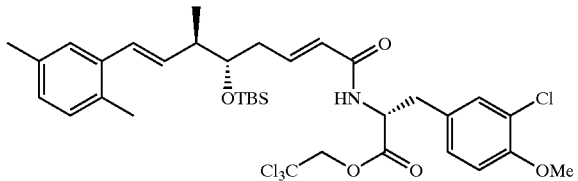

To a 0° C. solution of acid 4 (2.12 g, 5.46 mmol) and diisopropylethylamine (2.9 mL, 16.4 mmol) in 7 mL of DMF was added diphenylphosphinic chloride (1.1 mL, 6.01 mmol) dropwise. Following 5 min of stirring at 0° C. and 30 min at room temperature, the TFA salt of 3-(3-chloro-4-methoxyphenyl)-D-alanine-2,2,2-trichloroethyl ester 5 in 7 mL of DMF was added dropwise. The resulting mixture was stirred at room temperature for 2 h, poured into 100 mL of water and washed with diethyl ether (3×50 mL). The combined organic layers were washed with brine, dried over MgSO$_4$, filtered through Celite and concentrated in vacuo. Purification by column chromatography (silica gel, 10–30% EtOAc/hexanes) gave 2.86 g (72%) of amide 6 as a white foam:

[a]$^{20}$$_D$ +44.80 (c1.0, MeOH); $^1$H NMR (300 MHz, CDCl$_3$) d 7.25 (s, 1H), 7.22 (s, 1H), 7.1–6.83 (m, 5H), 6.6–6.55 (d, 1H, J=15.7 Hz), 6.11–6.03 (dd, 1H, J=15.6, 8.1 Hz), 5.9–5.8 (m, 2H), 5.18–5.05 (m, 1H), 4.83–4.75 (q, 2H, J=12.0 Hz), 3.9 (s, 3H), 3.83–3.68 (m, 1H), 3.3–3.1 (m, 2H), 2.6–2.36 (m, 3H), 2.36 (s, 3H), 2.32 (s, 3H), 1.16–1.14 (d, 3H, J=6.7 Hz), 0.95 (s, 9H), 0.11 (s, 3H), 0.05 (s, 3H); $^{13}$C NMR (75 MHz, CDCl$_3$) d 170.0, 165.1, 154.2, 143.1, 136.4, 135.3, 133.0, 132.0, 131.0, 130.9, 130.0, 128.4, 128.3, 127.7, 126.1, 124.6, 112.3, 112.1, 94.2, 75.0, 74.7, 56.0, 52.9, 42.8, 37.5, 36.5, 25.8, 20.9, 19.3, 18.0, 16.4, −4.3, −4.7; IR (CHCl$_3$) 3428, 2957, 2930, 2857, 1759, 1676, 1645, 1606, 1503, 1464, 1442, 1380, 1349, 1281, 1259, 1173, 1067 cm$^{-1}$.

EXAMPLE 29

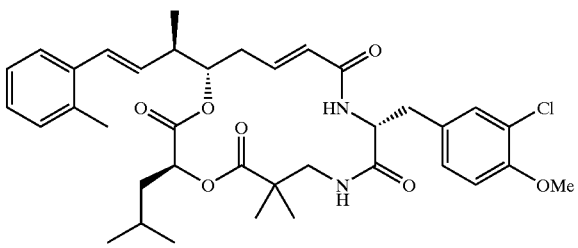

The ester (2.1 g) was prepared from 2.5 g of aldehyde 2 and 5.0 g of 3-methylbenzyl triphenylphosphonium chloride in 65% yield using the procedure described above: [a]$^{20}$$_D$ +45.55° (c 1.0, MeOH); $^1$H NMR (300 MHz, CDCl$_3$) d 7.22–6.88 (m, 5H), 6.37–6.31 (d, 1H, J=16.0 Hz), 6.18–6.10 (dd, 1H, J=16.0, 8.0 Hz), 5.86–5.81 (d, 1H, J=15.5 Hz), 3.8–3.7 (m, 4H), 2.5–2.3 (m, 6H), 1.11–1.08 (d, 3H, J=6.9 Hz), 0.91 (s, 9H), 0.061 (s, 3H), 0.052 (s, 3H); $^{13}$C NMR (75 MHz, CDCl$_3$) d 166.7, 146.4, 137.5, 135.9, 131.6, 130.4, 128.3, 127.7, 126.7, 123.1, 122.8, 75.0, 51.3, 42.7, 37.4, 33.8, 25.8, 21.9, 21.3, 18.0, 16.0, −4.5, −4.6; IR (CHCl$_3$) 2953, 2931, 2859, 1718, 1658, 1604, 1472, 1454, 1438, 1258 cm$^{-1}$.

The acid (1.93 g) was prepared from 2.0 g of ester in 100% yield using the procedure described above: $^1$H NMR (300 MHz, CDCl$_3$) d 7.22–7.0 (m, 5H), 6.38–6.33 (d, 1H, J=16.0 Hz), 6.18–6.10 (dd, 1H, J=16.0, 8.0 Hz), 5.87–5.82 (d, 1H, J=15.7 Hz), 3.8–3.7 (m, 1H), 2.5–2.35 (m, 3H), 2.34 (s, 3H), 1.12–1.09 (d, 3H, J=6.8 Hz), 0.9 (s, 9H), 0.068 (s, 3H), 0.061 (s, 3H).

The amide (2.9 g) was prepared from 1.93 g of acid in 72% yield using the procedure described above: $^1$H NMR (300 MHz, CDCl$_3$) d 7.22–7.1 (m, 4H), 7.1–7.0 (m, 2H), 6.9–6.8 (m, 2H), 6.36–6.30 (d, 1H, J=16.0 Hz), 6.19–6.11 (dd, 1H, J=16.0, 8.0 Hz), 5.82–5.77 (m, 2H), 5.1–5.0 (m, 1H), 4.78–4.71 (q, 2H, J=12.0 Hz), 3.86 (s, 3H), 3.8–3.7 (m, 1H), 3.25–3.15 (m, 2H), 2.5–2.3 (m, 6H), 1.1–1.08 (d, 3H, J=6.8 Hz), 0.88 (s, 9H), 0.056 (s, 3H), 0.044 (s, 3H).

The alcohol (2.0 g) was prepared from 2.4 g of the starting amide in 100% yield using the procedure described above: $^1$H NMR (300 MHz, CDCl$_3$) d 7.25–6.8 (m, 8H), 6.46–6.41 (d, 1H, J=15.9 Hz), 6.16–6.07 (dd, 1H, J=16.0, 8.8 Hz), 5.95–5.8 (m, 2H), 5.1–5.0 (m, 1H), 4.81–4.7 (q, 2H, J=12.0 Hz), 3.87 (s, 3H), 3.7–3.6 (m, 1H), 3.22–3.05 (m, 2H), 2.5–2.34 (m, 3H), 2.34 (s, 3H), 1.8–1.7 (bs, 1H), 1.15–1.13 (d, 3H, J=6.8 Hz).

The substrate (2.3 g) was prepared from 2.0 g of the starting alcohol in 76% yield using the procedure described above: [a]$^{20}$$_D$ +31.6° (c 1.08, MeOH); $^1$H NMR (300 MHz, CDCl$_3$) d 7.2–7.0 (m, 6H), 6.84–6.81 (d, 1H, J=8.4 Hz), 6.80–6.73 (m, 1H), 6.53–6.50 (bd, 1H, J=7.3 Hz), 6.4–6.35 (d, 1H, J=15.8 Hz), 6.03–5.95 (dd, 1H, J=15.8, 8.5 Hz), 5.9–5.85 (d, 1H, J=15.7 Hz), 5.42–5.35 (bt, 1H, J=6.38 Hz), 5.1–4.82 (m, 3H), 4.8–4.67 (q, 2H, J=12.0 Hz), 3.85 (s, 3H), 3.28–3.26 (d, 2H, J=6.46 Hz), 3.23–3.16 (dd, 1H, J=14.3, 5.8 Hz), 3.1–3.03 (dd, 1H, J=14.2, 6.7 Hz), 2.7–2.4 (m, 3H), 2.33 (s, 3H), 1.8–1.5 (m, 3H), 1.43 (s, 9H), 1.2 (s, 3H), 1.15 (s, 3H), 1.12–1.1 (d, 3H, J=6.7 Hz), 0.88–0.86 (d, 3H, J=6.2 Hz), 0.84–0.82 (d, 3H, J=6.4 Hz); $^{13}$C NMR (75 MHz, CDCl$_3$) d 170.6, 170.0, 165.2, 154.0, 139.2, 138.0, 136.7, 135.8, 131.8, 131.1, 129.7, 128.8, 128.4, 128.2, 126.8, 125.3, 123.3, 122.23, 112.1, 94.2, 78.9, 74.5, 71.3, 56.0, 53.1, 48.6, 43.9, 41.0, 39.4, 36.5, 33.3, 28.3, 24.7, 22.9, 22.7, 22.3, 21.3, 21.2, 16.5; IR (CHCl$_3$) 3426, 3383, 2967, 2935, 2874, 2841, 1727, 1710, 1680, 1646, 1605, 1504, 1368, 1280, 1259, 1169, 1151 cm$^{-1}$.

The styrene (0.86 g) was prepared from 2.2 g of the starting carbamate in 54% yield using the procedure described above: [a]$^{20}$$_D$ +33.1° (c 1.03, MeOH); $^1$H NMR (300 MHz, CDCl$_3$) d 7.24–7.0 (m, 7H), 6.85–6.82 (d, 1H, J=8.4 Hz), 6.82–6.70 (m, 1H), 6.39–6.34 (d, 1H, J=15.8 Hz), 6.03–5.95 (dd, 1H, J=15.8, 8.7 Hz), 5.78–5.73 (d, 1H, J=15.2 Hz), 5.67–5.64 (d, 1H, J=7.8 Hz), 5.1–5.0 (m, 1H), 4.87–4.83 (dd, 1H, J=10.2, 3.5 Hz), 4.8–4.7 (m, 1H), 3.9 (s, 3H), 3.45–3.38 (dd, 1H, J=13.4, 8.6 Hz), 3.2–3.0 (m, 3H), 2.6–2.3 (m, 3H), 2.32 (s, 3H), 1.75–1.25 (m, 3H), 1.22 (s, 3H), 1.15 (s, 3H), 1.13–1.11 (d, 3H, J=6.8 Hz), 0.75–0.72 (t, 6H, J=5.7 Hz); $^{13}$C NMR (75 MHz, CDCl$_3$) d 177.9, 170.5, 170.3, 165.1, 154.0, 142.1, 138.0, 136.6, 135.6, 131.8, 130.8, 129.9, 129.6, 128.4, 128.22, 128.17, 126.7, 124.5, 123.3, 122.5, 112.3, 71.4, 56.1, 54.3, 46.4, 42.7, 42.2, 39.4, 36.5, 35.3, 24.5, 22.8, 22.6, 22.5, 21.2, 21.1, 17.2; IR (CHCl$_3$) 3424, 3021, 3017, 2965, 1747, 1711, 1680, 1652, 1528, 1503, 1485, 1259, 1151, 1067 cm$^{-1}$; Anal. Calcd for C$_{37}$H$_{47}$ClN$_2$O$_7$: C, 66.60; H, 7.10; N, 4.20. Found: C, 66.79; H, 7.03; N, 4.25.

EXAMPLE 30

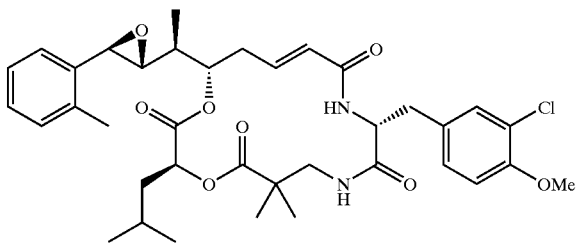

The b epoxide, title compound (0.20 g) was prepared from 0.667 g of the starting styrene in 29% yield using the procedure described above: $^1$H NMR (300 MHz, CDCl$_3$) d 7.3–7.0 (m, 7H), 6.90–6.87 (d, 1H, J=8.4 Hz), 6.87–6.75 (m, 1H), 5.79–5.74 (d, 1H, J=14.8 Hz), 5.54–5.51 (d, 1H, J=7.8 Hz), 5.28–5.22 (m, 1H), 4.89–4.85 (dd, 1H, J=10.4, 3.5 Hz), 4.82–4.75 (m, 1H), 3.92 (s, 3H), 3.69–3.68 (d, 1H, J=1.63), 3.51–3.44 (dd, 1H, J=13.4, 8.6 Hz), 3.2–3.1 (m, 2H), 2.98–2.95 (dd, 1H, J=7.6, 1.6 Hz), 2.65–2.32 (m, 3H), 2.32 (s, 3H), 1.85–1.6 (m, 3H), 1.4–1.25 (m, 1H), 1.27 (s, 3H), 1.21 (s, 3H), 1.21–1.18 (d, 3H, J=7.5 Hz), 0.90–0.86 (t, 6H, J=6.13 Hz).

EXAMPLE 31

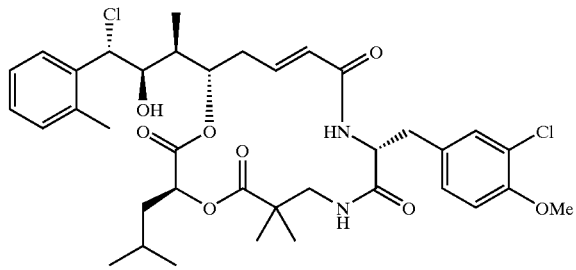

To a solution of the b epoxide (0.1 g, 0.147 mmol) in 5.0 mL of CHCl$_3$ at −60° C., was added chlorotrimethyl silane (0.093 mL, 0.74 mmol). The solution was stirred at −60° C. for 30 min and at room temperature for 1.5 h before being concentrated under vacuum. The resulting residue, containing a 50:50 mixture of the syn and anti chlorohydrins, was purified via reverse phase HPLC to yield 0.028 g (27%) of the desired trans isomer: $^1$H NMR (300 MHz, CDCl$_3$) d 7.28–7.2 (m, 5H), 7.13–7.1 (dd, 1H, J=8.32, 1.95 Hz), 6.91–6.88 (d, 1H, J=8.5 Hz), 6.88–6.78 (m, 1H), 5.86–5.81 (d, 1H, J=15.0 Hz), 5.73–5.71 (d, 1H, J=7.8 Hz), 5.24–5.17 (t, 1H, J=9.4 Hz), 5.0–4.96 (dd, 1H, J=9.58, 2.93 Hz), 4.81–4.74 (m, 1H), 4.67–4.64 (d, 1H, J=9.73 Hz), 4.06–4.03 (dd, 1H, J=9.6, 1.1 Hz), 3.92 (s, 3H), 3.47–3.39 (dd, 1H, J=13.2, 8.3 Hz), 3.24–3.0 (m, 3H), 2.8–2.4 (m, 2H), 2.4 (s, 3H), 1.9–1.4 (m, 4H), 1.28 (s, 3H), 1.22 (s, 3H), 1.09–1.07 (d, 3H, J=6.95 Hz), 0.98–0.96 (d, 6H, J=6.4 Hz).

EXAMPLE 32

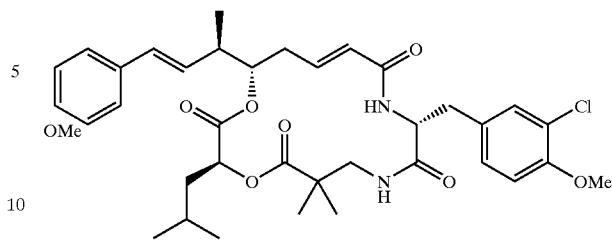

The ester (2.75 g) was prepared from 3.39 g of aldehyde 2 and 7.7 g of 4-methoxybenzyl triphenylphosphonium chloride in 54% yield using the procedure described above.: $[a]^{20}_D$ +71.85° (c 1.03, MeOH): $^1$H NMR (300 MHz, CDCl$_3$) d 7.25–7.21 (m, 2H, J=9.0 Hz), 7.0–6.85 (m, 1H), 6.81–6.78 (d, 2H, J=8.5 Hz), 6.30–6.23 (d, 1H, J=16.3 Hz), 6.0–5.9 (dd, 1H, J=16.3, 8.2 Hz), 5.81–5.75 (d, 1H, J=14.26 Hz), 3.75 (s, 3H), 3.67 (s, 4H), 2.42–2.22 (m, 3H), 1.05–1.02 (d, 3H, J=6.8 Hz), 0.86 (s, 9H), 0.005 (s, 3H), −0.001 (s, 3H); $^{13}$C NMR (75 MHz, CDCl$_3$) d 166.7, 158.8, 146.4, 130.4, 129.7, 129.7, 127.0, 122.7, 113.8, 75.0, 55.2, 51.3, 42.7, 37.4, 25.8, 18.0, 16.1, −4.5, −4.6; IR (CHCl$_3$) 3010, 2955, 2930, 2898, 2857, 1718, 1658, 1607, 1511 cm$^{-1}$.

The acid (1.58 g) was prepared from 1.7 g of ester in 96% yield using the procedure described above: $^1$H NMR (300 MHz, CDCl$_3$) d 7.3–7.27 (d, 2H, J=8.7 Hz), 7.13–7.03 (m, 1H), 6.86–6.83 (d, 2H, J=8.6 Hz), 6.35–6.29 (d, 1H, J=16.0 Hz), 6.04–5.96 (dd, 1H, J=15.9, 8.0 Hz), 5.87–5.81 (d, 1H, J=15.8 Hz), 3.8 (s, 3H), 3.79–3.7 (m, 1H), 2.5–2.33 (m, 3H), 1.1–1.08 (d, 3H, J=6.8 Hz), 0.9 (s, 9H), 0.058 (s, 3H), 0.055 (s, 3H).

The amide (2.09 g) was prepared from 1.58 g of acid in 70% yield using the procedure described above: $[a]^{20}_D$ +2.0° (c 1.0, CHCl$_3$); $^1$H NMR (300 MHz, CDCl$_3$) d 7.28–7.26 (d, 2H, J=7.33 Hz), 7.18–7.17 (d, 1H, J=1.8 Hz), 7.04–7.0 (dd, 1H, J=8.5, 1.8 Hz), 6.90–6.79 (m, 3H), 6.32–6.27 (d, 1H, J=16.0 Hz), 6.05–5.97 (dd, 1H, J=16.0, 8.1 Hz), 5.83–5.76 (m, 3H), 5.09–5.05 (m, 1H), 4.82–4.7 (q, 2H, J=11.9 Hz), 3.86 (s, 3H), 3.8 (s, 3H), 3.77–3.7 (m, 1H), 3.24–3.17 (dd, 1H, J=14.2, 5.7 Hz), 3.13–3.07 (dd, 1H, J=14.2, 5.94 Hz), 2.5–2.3 (m, 3H), 1.09–1.06 (d, 3H, J=6.8 Hz), 0.89 (s, 9H), 0.048 (s, 3H), 0.038 (s, 3H); $^{13}$C NMR (75 MHz, CDCl$_3$) d 169.9, 165.1, 158.7, 154.2, 143.0, 135.5, 131.0, 130.4, 129.6, 128.4, 127.0, 124.6, 122.5, 113.8, 112.1, 94.2, 75.0, 74.7, 56.0, 55.2, 52.9, 42.5, 37.4, 36.4, 25.8, 18.0, 16.4, −4.4, −4.7; IR (CHCl$_3$) 2957, 2931, 2857, 1757, 1676, 1644, 1607, 1511, 1503 cm$^{-1}$.

The alcohol (1.35 g) was prepared from 1.63 g of the starting amide in 98% yield using the procedure described above: $[a]^{20}_D$ +55.7° (c 1.0, MeOH); $^1$H NMR (300 MHz, CDCl$_3$) d 7.31–7.29 (d, 2H, J=7.9 Hz), 7.18 (s, 1H), 7.05–7.02 (d, 1H, J=8.3 Hz), 7.0–6.87 (m, 1H), 6.86–6.83 (d, 3H, J=8.2 Hz), 6.44–6.38 (d, 1H, J=15.8 Hz), 6.0–5.82 (m, 3H), 5.10–5.0 (m, 1H), 4.81–4.7 (q, 2H, J=11.8 Hz), 3.87 (s, 3H), 3.81 (s, 3H), 3.67–3.6 (m, 1H), 3.24–3.19 (dd, 1H, J=14.1, 6.1 Hz), 3.12–3.07 (dd, 1H, J=14.4, 5.9 Hz), 2.5–2.25 (m, 3H), 1.8–1.6 (bs, 1H), 1.14–1.12 (d, 3H, J=6.6 Hz); $^{13}$C NMR (75 MHz, CDCl$_3$) d 170.1, 165.2, 159.0, 154.2, 142.5, 131.2, 131.0, 129.8, 128.7, 128.4, 127.2, 125.0, 122.4, 113.9, 112.2, 94.2, 74.7, 73.8, 56.05, 55.2, 53.0, 43.2, 37.1, 36.4, 16.8; IR( CHCl₃) 3428, 2964, 2936, 2912, 2874, 2840, 1758, 1677, 1645, 1607, 1512, 1503, 1258, 1175 cm$^{-1}$.

The substrate (1.69 g) was prepared from 1.26 g of the starting alcohol in 89% yield using the procedure described above: $[a]^{20}_D$ +35.2° (c 1.02, MeOH); $^1$H NMR (300 MHz, CDCl₃) d 7.26–7.23 (d, 21H, J=8.0 Hz), 7.18–7.17 (d, 1H, J=1.7), 7.07–7.03 (dd, 1H, J=8.4, 1.6), 6.85–6.7 (m, 4H), 6.53–6.5 (d, 1H, J=7.9 Hz), 6.36–6.31 (d, 1H, J=15.8 Hz), 5.9–5.81 (m, 2H), 5.42–5.35 (t, 1H), 5.1–4.95 (m, 2H), 4.94–4.90 (dd, 1H, J=9.6, 3.4 Hz), 4.81–4.67 (q, 2H, J=11.9 Hz), 3.85 (s, 3H), 3.79 (s, 3H), 3.28–3.26 (d, 2H, J=6.5 Hz), 3.23–3.16 (dd, 1H, J=14.3, 5.8 Hz), 3.09–3.02 (dd, 1H, J=14.1, 6.7 Hz), 2.61–2.4 (m, 3 H), 1.8–1.5 (m, 3H), 1.43 (s, 9H), 1.20 (s, 3H), 1.15 (s, 3H), 1.11–1.09 (d, 3H, J=6.7 Hz), 0.87–0.85 (d, 3H, J=6.4 Hz), 0.84–0.82 (d, 3H, J=6.5 Hz); $^{13}$C NMR (75 MHz, CDCl₃) d 174.9, 170.6, 169.9, 165.3, 159.0, 154.0, 139.3, 135.4, 131.1, 131.0, 129.6, 128.8, 128.4, 127.8, 127.2, 125.2, 122.2, 113.9, 112.2, 94.3, 74.5, 71.3, 56.0, 55.2, 53.1, 48.6, 43.9, 41.0, 39.4, 36.5, 28.3, 24.7, 22.9, 22.7, 22.3, 21.4, 16.6; IR (CHCl₃) 3426, 3383, 2965, 2936, 2874, 2840, 1728, 1711, 1680, 1646, 1607, 1512, 1465, 1367, 1254, 1175, 1067 cm$^{-1}$.

The styrene product (0.676 g) was prepared from 1.43 g of the starting carbamate in 65% yield using the procedure described above: $^1$H NMR (300 MHz, CDCl₃) 7.26–7.23 (d, 3H, J=8.4 Hz), 7.20–7.19 (d, 1H, J=1.8 Hz), 7.07–7.03 (dd, 1H, J=8.4, 1.9 Hz), 6.84–6.81 (d, 3H, J=8.5 Hz), 6.8–6.7 (m, 1H), 6.36–6.31 (d, 1H, J=15.8 Hz), 5.89–5.81 (dd, 1H, J=15.8, 8.8 Hz), 5.78–5.73 (d, 1H, J=13.7 Hz), 5.68–5.66 (d, 1H, J=7.9 Hz), 5.05–4.99 (ddd, 1H, J=10.6, 6.6, 1.6 Hz), 4.87–4.82 (dd, 1H, J=9.7, 3.1 Hz), 4.78–4.7 (m, 1H), 3.86 (s, 3H), 3.79 (s, 3H), 3.45–3.37 (dd, 1H, J=13.4, 8.6 Hz) 3.15–3.0 (m, 3H), 2.6–2.25 (m, 3H), 1.7–1.3 (m, 3H), 1.22 (s, 3H), 1.15 (s, 3H), 1.12–1.1 (d, 3H, J=6.8 Hz), 0.76–0.75 (d, 3H, J=2.9 Hz), 0.74–0.73 (d, 3H, J=2.8 Hz).

EXAMPLE 33

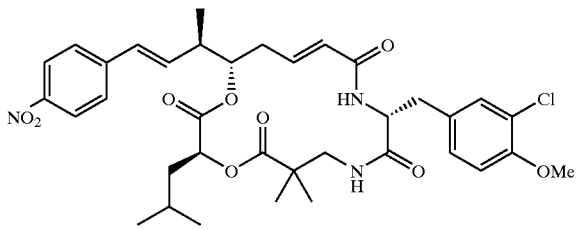

To a 0° C. solution of potassium tert-butoxide (1.17 g, 10.5 mmol) in 120 mL of THF was added p-nitro-benzyl triphenylphosphonium bromide (5.0 g, 10.5 mmol), in small portions over a period of 30 min. The mixture was stirred at 0° C. for 1 h. Aldehyde 2 in 20 mL of THF, was added dropwise to the preformed ylide. The mixture was stirred at 0° C. for 15 min, then warmed up slowly to room temperature and stirred overnight. Saturated aqueous NH₄Cl (50 mL) was added and the solution extracted with ethyl acetate. The organic layer was washed with brine, dried over MgSO₄, filtered and concentrated in vacuo. The crude styrene as a mixture of E:Z isomers was purified on silica gel using 2% EtOAc/hexanes to yield 0.5 g of the Z isomer and 1.1 g of the E isomer (42%) as a yellow oil: $[a]^{20}_D$ +63.81° (c 1.05, MeOH); $^1$H NMR (300 MHz, CDCl₃) d 8.18–8.15 (d, 2H, J=8.6 Hz), 7.47–7.44 (d, 2H, J=8.7 Hz), 7.0–6.85 (m, 1H), 6.5–6.3 (m, 2H), 5.87–5.82 (d, 1H, J=15.6 Hz), 3.8–3.73 (m, 1H), 3.73 (s, 3H), 2.55–2.35 (m, 3H), 1.13–1.11 (d, 3H, J=6.9 Hz), 0.90 (s, 9H), 0.059 (s, 3H), 0.047 (s, 3H); $^{13}$C NMR (75 MHz, CDCl₃) 166.5, 145.5, 143.9, 137.3, 128.7, 126.4, 123.9, 123.1, 74.6, 51.3, 42.8, 37.8, 33.8, 25.7, 24.3, 21.9, 18.0, 16.3, −4.4, −4.7; IR (CHCl₃) 2953, 2931, 2859, 1719, 1658, 1596, 1518, 1472, 1438, 1345, 1259, 1110 cm$^{-1}$.

The amide (3.06 g) was prepared from 2.55 g of acid in 65% yield using the procedure described above: $[a]^{20}_D$ +70.67° (c 1.05, MeOH); $^1$H NMR (300 MHz, CDCl₃) d 8.15–8.12 (d, 2H, J=8.7 Hz), 7.45–7.42 (d, 2H, J=8.7 Hz), 7.17–7.16 (d, 1H, J=2.0 Hz), 7.04–7.01 (dd, 1H, J=8.45, 1.9 Hz), 6.88–6.82 (m, 2H), 6.43–6.3 (m, 2H), 5.93–5.91 (d, 1H, J=7.5 Hz), 5.84–5.79 (d, 1H, J=15.3 Hz), 5.1–5.0 (m, 1H), 4.82–4.69 (q, 2H, J=11.9 Hz), 3.85 (s, 3H), 3.8–3.7 (m, 1H), 3.24–3.18 (dd, 1H, J=14.3, 5.7 Hz), 3.13–3.06 (dd, 1H, J=14.2, 6.05 Hz), 2.52–2.3 (m, 3H), 1.11–1.09 (d, 3H, J=6.8 Hz), 0.88 (s, 9H), 0.041 (s, 3H), 0.032 (s, 3H); $^{13}$C NMR (75 MHz, CDCl₃) d 170.0, 165.0, 154.2, 146.5, 144.0, 142.2, 137.4, 136.0, 131.0, 128.7, 128.4, 126.4, 124.9, 123.9, 122.5, 112.1, 94.1, 74.72, 74.67. 56.0, 52.9, 42.7, 37.8, 36.4, 25.7, 18.0, 16.5, −4.7, −4.3; IR (CHCl₃) 3429, 2957, 2931, 2858, 1757, 1677, 1645, 1597, 1517, 1503, 1345, 1259, 1180, 1110, 1067, 1026 cm$^{-1}$.

The substrate (3.3 g) was prepared from 2.54 g of the starting alcohol in 87% yield using the procedure described above: $[a]^{20}_D$ +38.2° (c 1.07, MeOH); $^1$H NMR (300 MHz, CDCl₃) d 8.23–8.2 (d, 2H, J=8.7 Hz), 7.52–7.49 (d, 2H, J=8.7 Hz), 7.21 (s, 1H), 7.12–7.08 (dd, 1H, J=8.2, 1.8 Hz), 6.89–6.86 (d, 1H, J=8.4 Hz), 6.86–6.75 (m, 1H), 6.6–6.58 (d, 1H, J=8.0 Hz), 6.55–6.5 (d, 1H, J=15.9 Hz), 6.31–6.23 (dd, 1H, J=15.8, 8.5 Hz), 5.97–5.92 (d, 1H, J=15.5 Hz), 5.4–5.3 (bt, 1H), 5.2–5.0 (m, 2H), 4.98–4.94 (dd, 1H, J=9.5, 3.6 Hz), 4.86–4.72 (q, 2H, J=12 Hz), 3.9 (s, 3H), 3.33–3.3 (d, 1H, J=6.6 Hz), 3.27–3.22 (dd, 1H, J=14.1, 5.7 Hz), 3.14–3.07 (dd, 2H, J=14.0, 6.7 Hz), 2.8–2.5 (m, 3H), 2.9–1.47 (m, 3H), 1.47 (s, 9H), 1.3–1.2 (m, 9H), 0.91–0.89 (d, 3H, J=6.4 Hz), 0.87–0.85 (d, 3H, J=6.4 Hz); $^{13}$C NMR (75 MHz, CDCl₃) d 176.8, 170.6, 169.9, 165.1, 156.2, 154.0, 146.8, 143.2, 138.8, 135.8, 135.4, 131.1, 129.7, 128.7, 128.4, 126.7, 126.6, 125.5, 123.9, 122.2, 112.1, 94.2, 79.0, 76.2, 74.5, 71.2, 56.0, 53.1, 48.5, 43.9, 41.2, 39.4, 36.5, 33.3, 28.3, 24.7, 22.9, 22.7, 22.3, 21.4, 16.3; IR (CHCl₃) 3426, 3385, 2967, 2936, 2874, 2841, 1712, 1681, 1646, 1597, 1519, 1500, 1345, 1280, 1259, 1170, 1150, 1067, 1024 cm$^{-1}$.

The styrene product (0.55 g) was prepared from 1.77 g of the starting carbamate in 42% yield using the procedure described above: $^1$H NMR (300 MHz, CDCl₃) 8.23–8.21 (d, 2H, J=8.7 Hz), 7.52–7.49 (d, 2H, J=8.7 Hz), 7.24–7.2 (m, 2H), 7.11–7.08 (dd, 1H, J=8.5, 1.92 Hz), 6.89–6.87 (d, 1H, J=8.4 Hz), 6.86–6.72 (m, 1H), 6.56–6.51 (d, 1H, J=15.9 Hz), 6.33–6.25 (dd, 1H, J=15.9, 8.7 Hz), 5.94–5.91 (d, 1H, J=7.8 Hz), 5.83–5.78 (d, 1H, J=15.2 Hz), 5.17–5.12 (m, 1H), 4.92–4.88 (dd, 1H, J=9.7, 3.6 Hz), 4.8–4.75 (m, 1H), 3.92 (s, 3H), 3.5–3.43 (dd, 1H, J=13.5, 8.73 Hz), 3.2–3.1 (m, 3H), 2.7–2.35 (m, 3H), 1.8–1.6 (m, 2H), 1.4–1.19 (m, 1H), 1.2 (s, 3H), 1.16–1.14 (d, 6H), 0.82–0.81 (d, 3H, J=3.73 Hz), 0.80–79 (d, 3H, J=3.87 Hz).

EXAMPLE 34
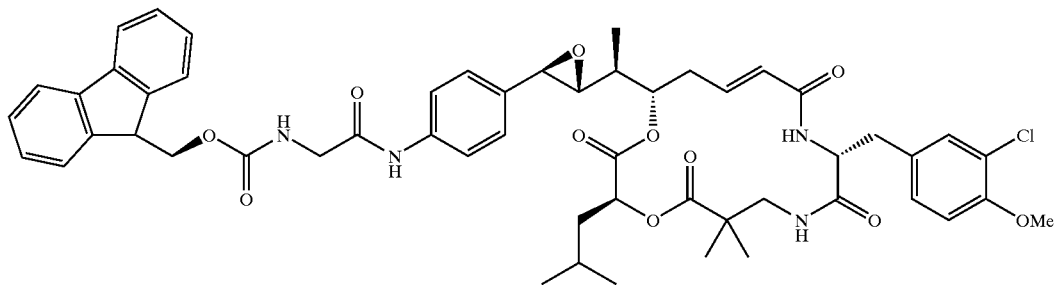
¹H NMR (300 MHz, CDCl₃) 8.5 (s, 1H), 7.76–7.74 (d, 2H, J=7.4 Hz), 7.58–7.56 (d, 2H, J=7.4 Hz), 7.5–7.1 (m, 8H), 7.03–7.0 (d, 1H, J=8.2 Hz), 6.81–6.78 (d, 1H, J=8.5 Hz), 6.78–6.65 (m, 1H), 6.37–6.34 (d, 1H, J=7.3 Hz), 5.84–5.81 (t, 1H, J=5.2 Hz), 5.69–5.64 (d, 1H, J=15.0 Hz), 5.18–5.15 (bd, 1H, J=9.0 Hz), 4.83–4.6 (m, 2H), 4.45–4.43 (d, 2H, J=6.7 Hz), 4.24–4.19 (t, 1H, J=6.6 Hz), 3.99 (bs, 2H), 3.81 (s, 3H), 3.61 (s, 1H), 3.46–3.39 (dd, 1H, J=13.4, 8.8 Hz), 3.2–2.8 (m, 5H), 2.6–2.3 (m, 3H), 1.8–1.3 (m, 3H), 1.2 (s, 3H), 1.14 (s, 3H), 1.12–1.1 (d, 3H, J=6.8 Hz), 0.86–0.81 (t, 6H, J=7.3 Hz).
EXAMPLE 35
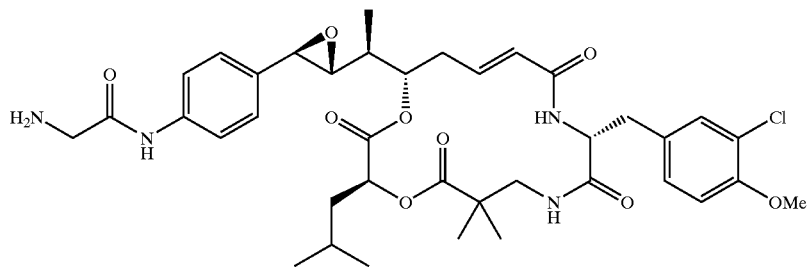
¹H NMR (300 MHz, CDCl₃) d 9.5 (bs, 2H), 7.6–7.57 (d, 2H, J=8.1 Hz), 7.24–7.18 (m, 5H), 7.05–7.03 (d, 1H, J=8.3 Hz), 6.84–6.82 (d, 1H, J=8.4 Hz), 6.82–6.65 (m, 1H), 6.02–6.0 (d, 1H, J=7.6 Hz), 5.72–5.67 (d, 1H, J=15.3 Hz), 5.19–5.16 (bd, 1H, J=10.5 Hz), 4.9–4.6 (m, 2H), 3.85 (s, 3H), 3.64 (s, 1H), 3.55–3.4 (m, 3H), 3.2–2.95 (m, 3H), 2.90–2.88 (d, 1H, 7.11 Hz), 2.6–2.3 (m, 3H), 2.0–1.3 (m, 3H), 1.2 (s, 3H), 1.15 (s, 3H), 1.13–1.11 (d, 3H, J=6.9 Hz), 0.90–0.84 (t, 6H, J=7.2 Hz).
Scheme 2
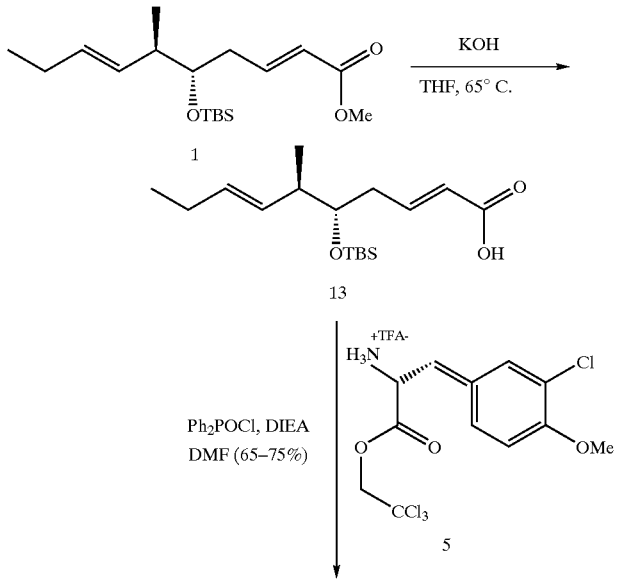

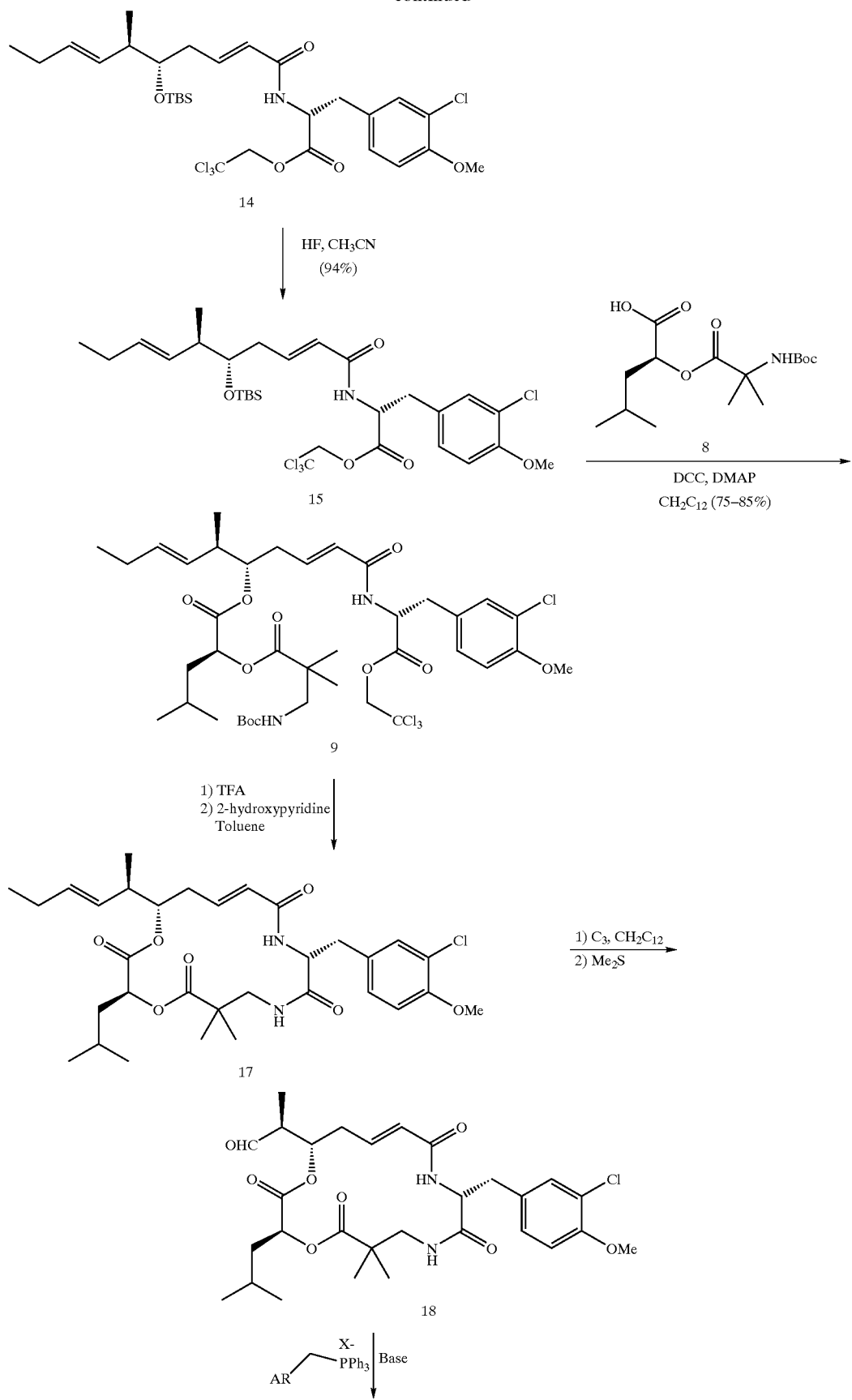

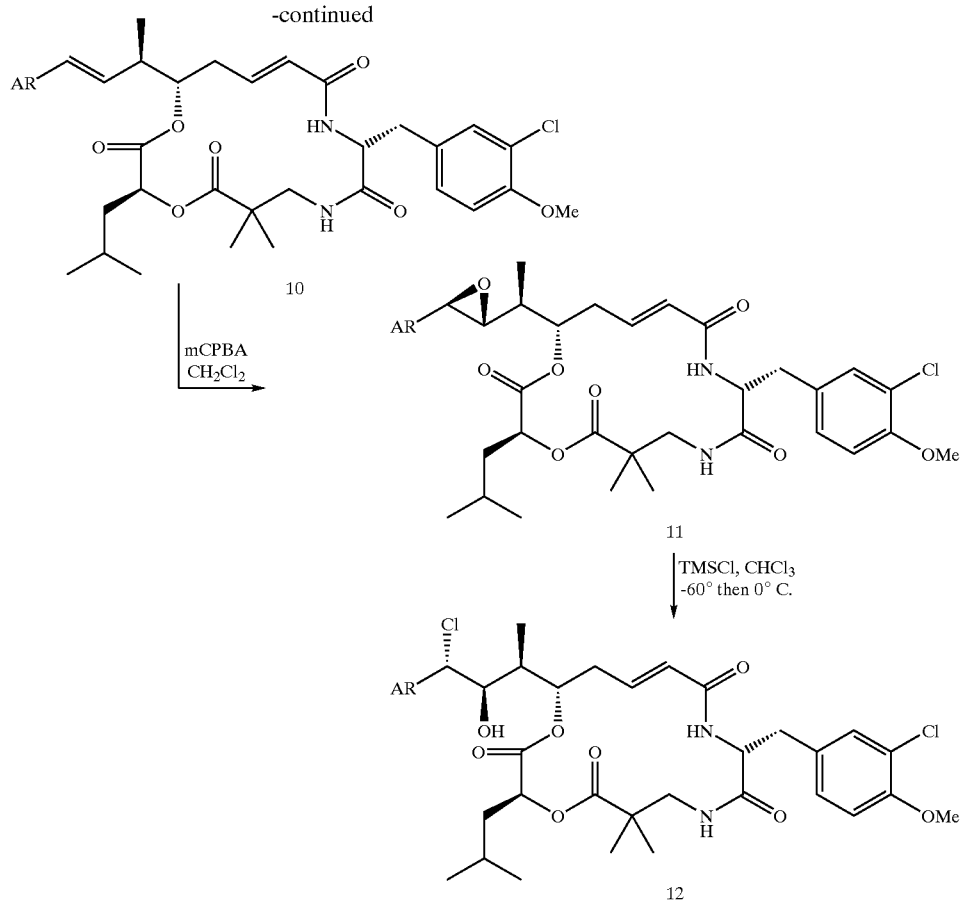

EXAMPLE 36

Via Scheme 2

To alkene 17 (0.3 g, 0.50 mmol) at −78° C. in a 9.0 mL $CH_2Cl_2$/1.0 mL MeOH was added 2-picoline (0.07 mL, 0.074 mmol). This solution was subjected to 1.2 equivalence of ozone and the resulting ozonide was quenched with dimethyl sulfide (1.1 mL, 2.2 mmol). The mixture was slowly warmed up to room temperature and stirred overnight. The solution was washed with water (2×20 mL), dried over $Na_2SO_4$, filtered and concentrated in vacuo to yield 0.251 g (87%) of aldehyde 18: $^1$H NMR (300 MHz, $CDCl_3$) d 9.64–9.63 (d, 1H, J=1.05 Hz), 7.25–7.2 (m, 2H), 7.08–7.05 (d, 1H, J=8.2 Hz), 6.86–6.83 (d, 1H, J=8.4 Hz), 6.83–6.7 (m, 1H), 5.81–5.76 (d, 1H, J=15.1 Hz), 5.75–5.65 (bs, 1H), 5.38–5.3 (m, 1H), 4.85–4.81 (dd, 1H, J=10.2, 3.2 Hz), 4.80–4.7 (m, 1H), 3.87 (s, 3H), 3.46–3.39 (dd, 1H, J=13.5, 8.7 Hz), 3.2–3.0 (m, 3H), 2.7–2.4 (m, 3H), 1.8–1.6 (m, 2H), 1.4–1.3 (m, 1H), 1.23 (s, 3H), 1.18–1.16 (d, 6H), 0.94–0.92 (d, 3H, J=6.5 Hz), 0.88–0.86 (d, 3H, J=6.4 Hz).

Scheme 3

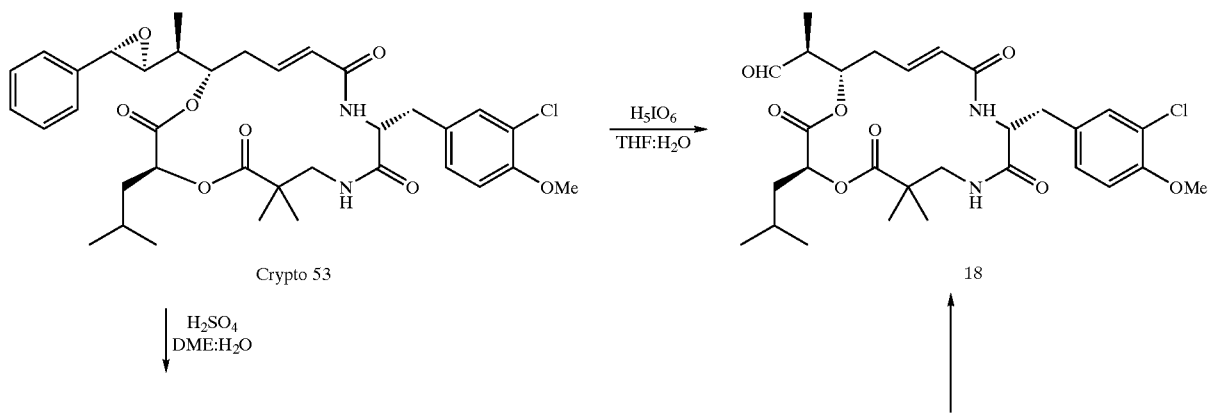

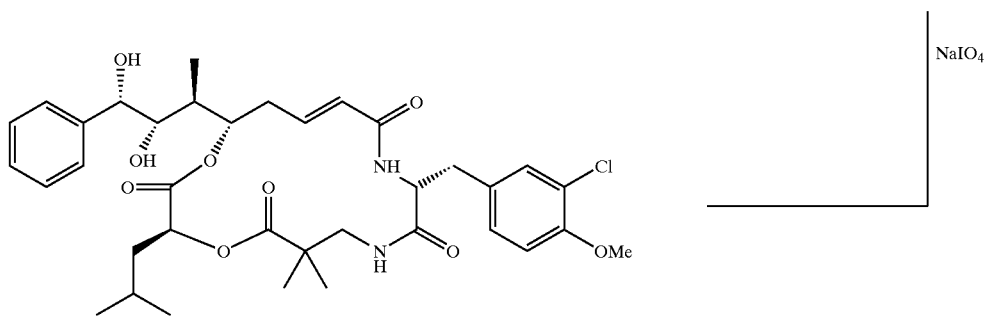
Scheme 4
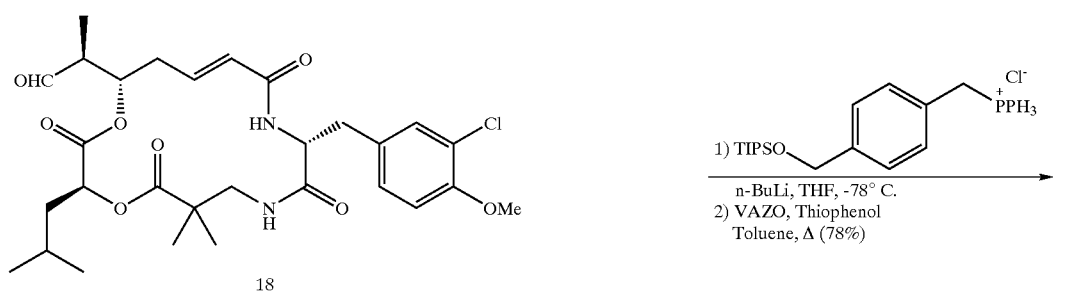
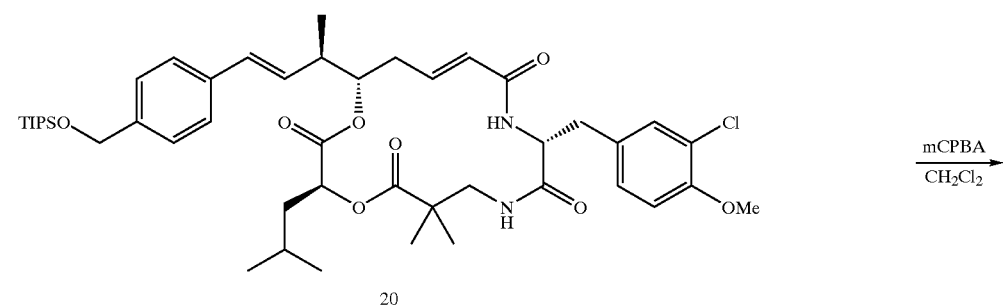
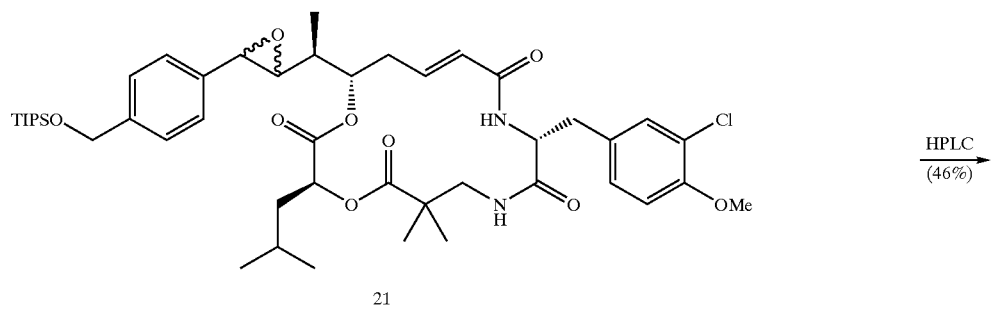
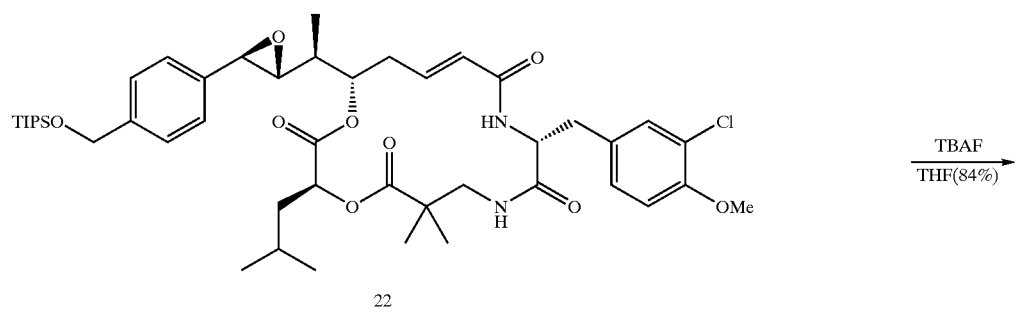

-continued
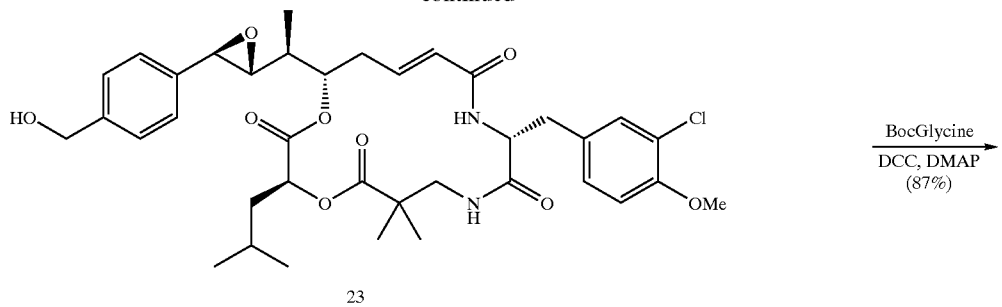
23
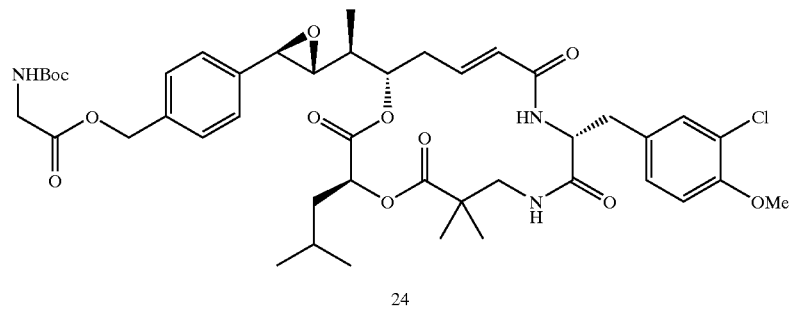
24
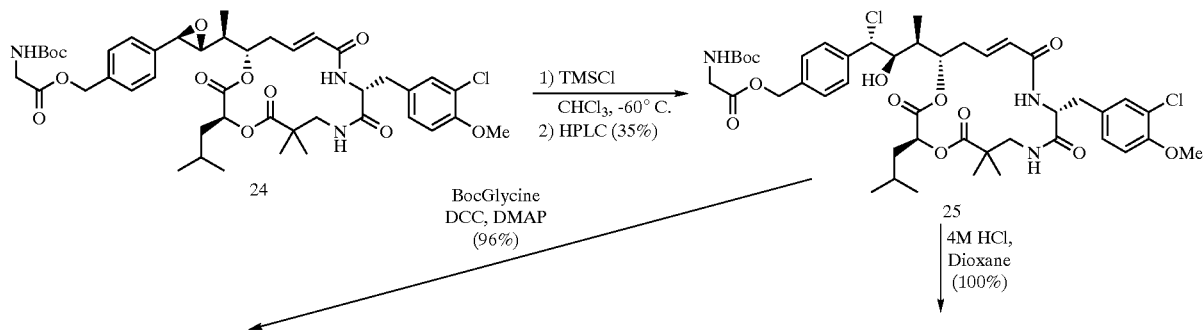
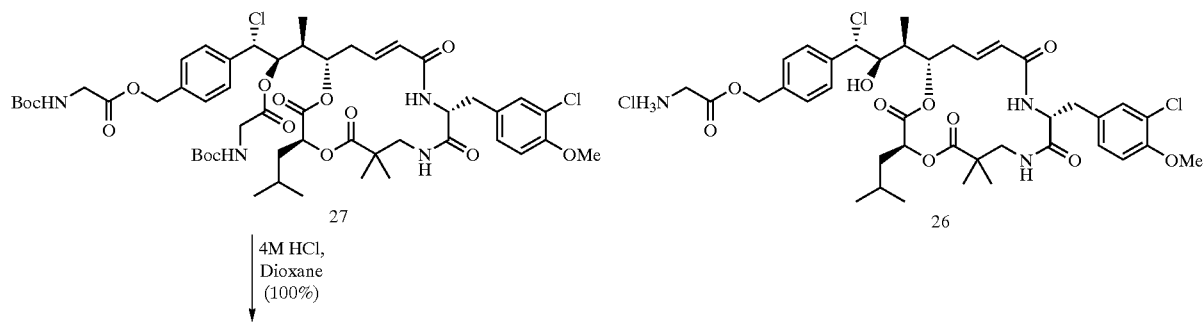
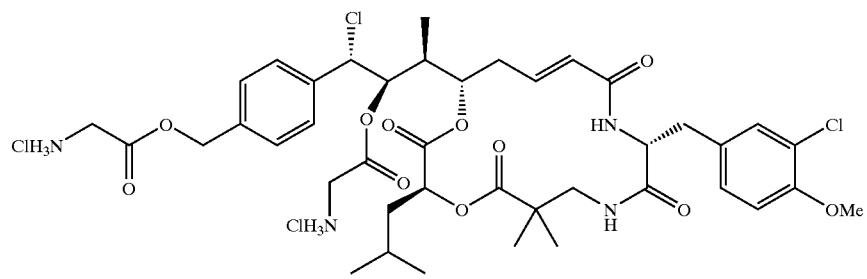
28

Scheme 5
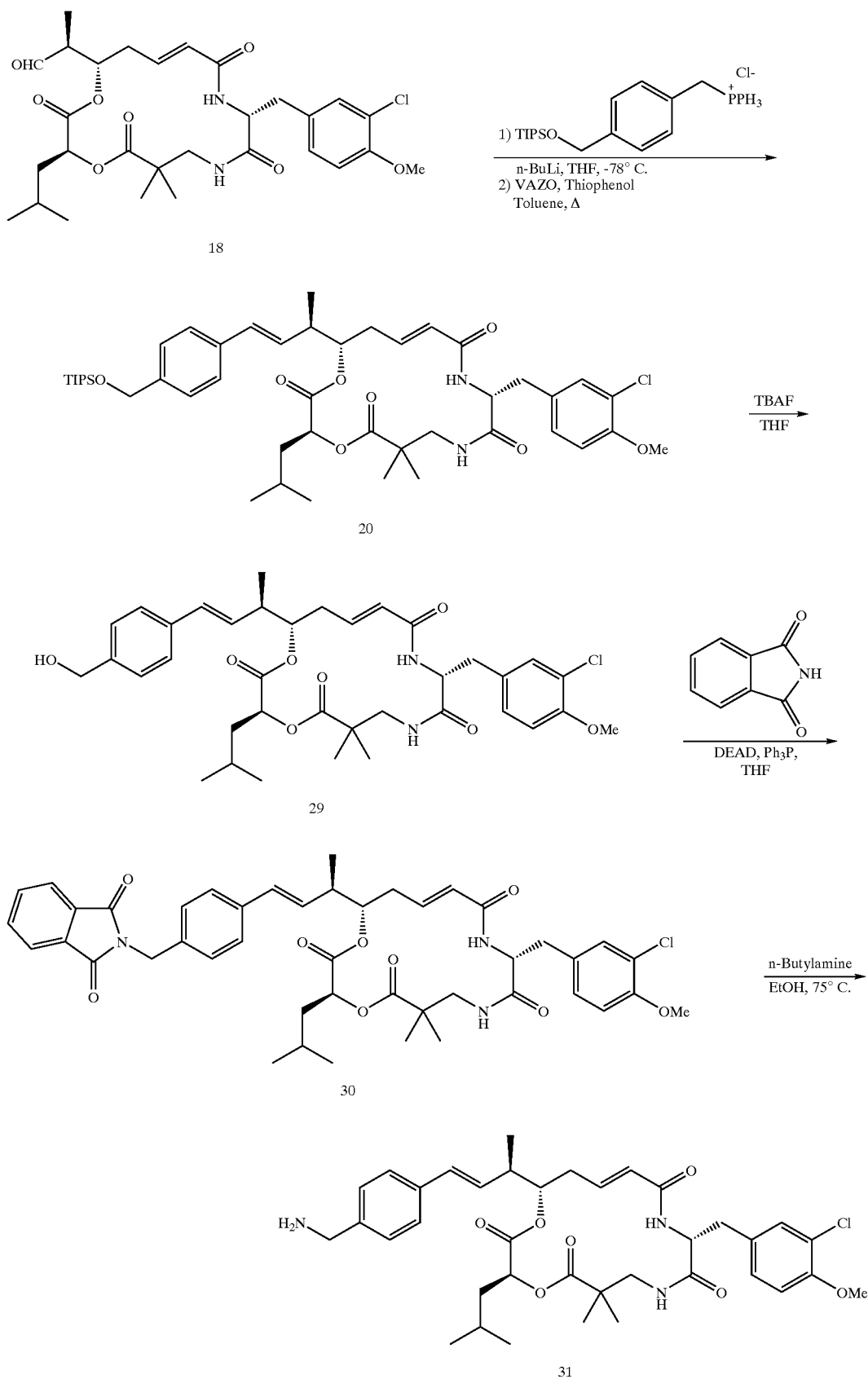

-continued
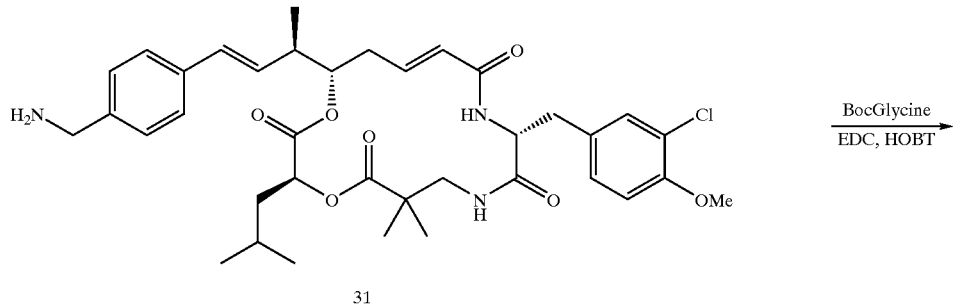
31
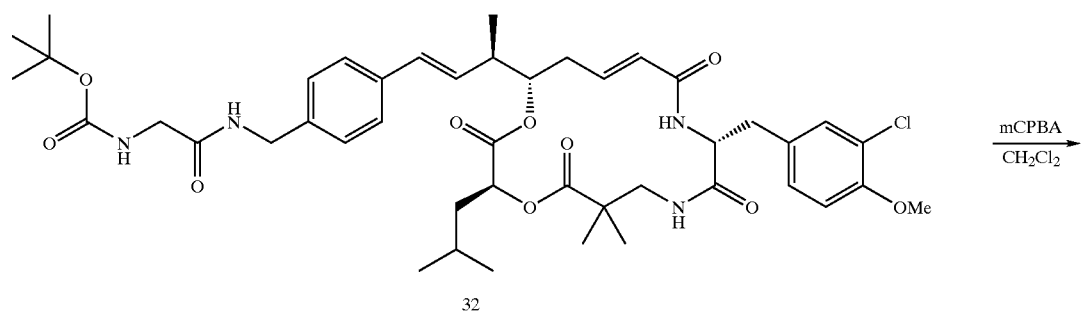
32
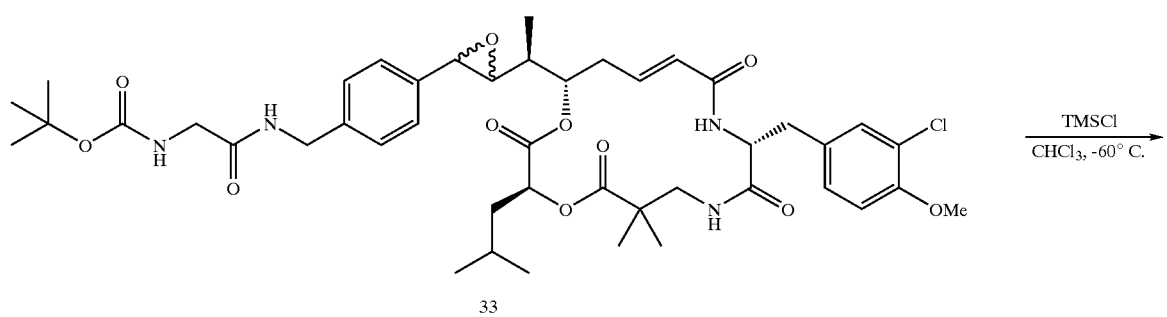
33
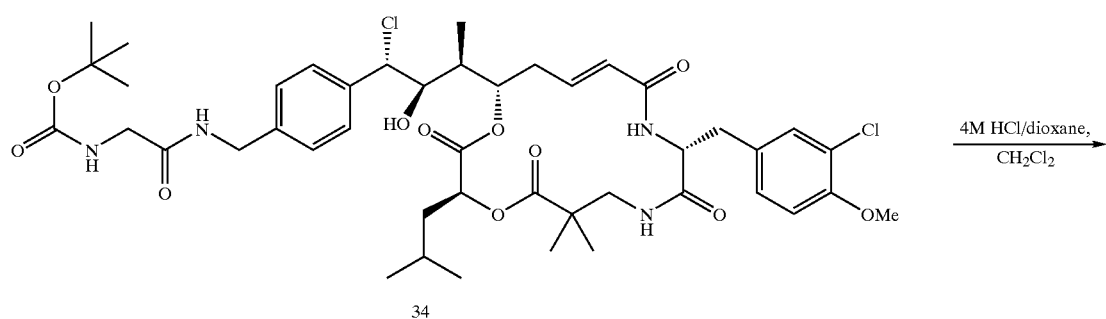
34
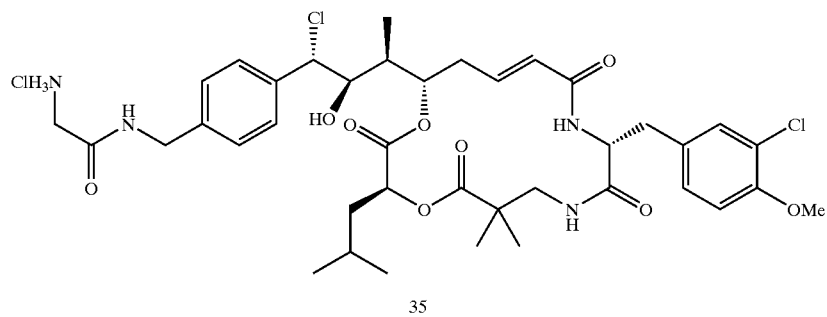
35

Scheme 6
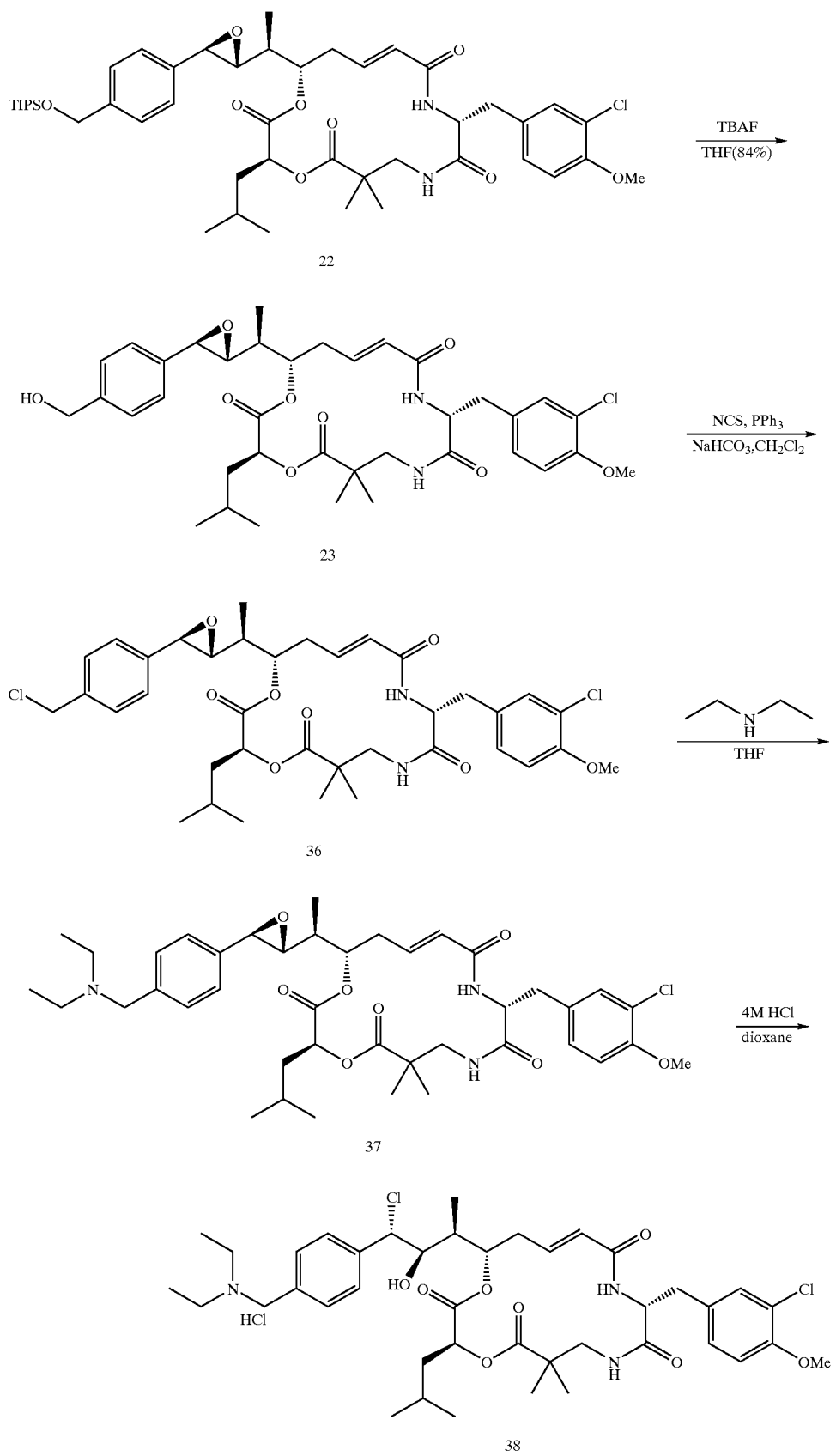

Scheme 7
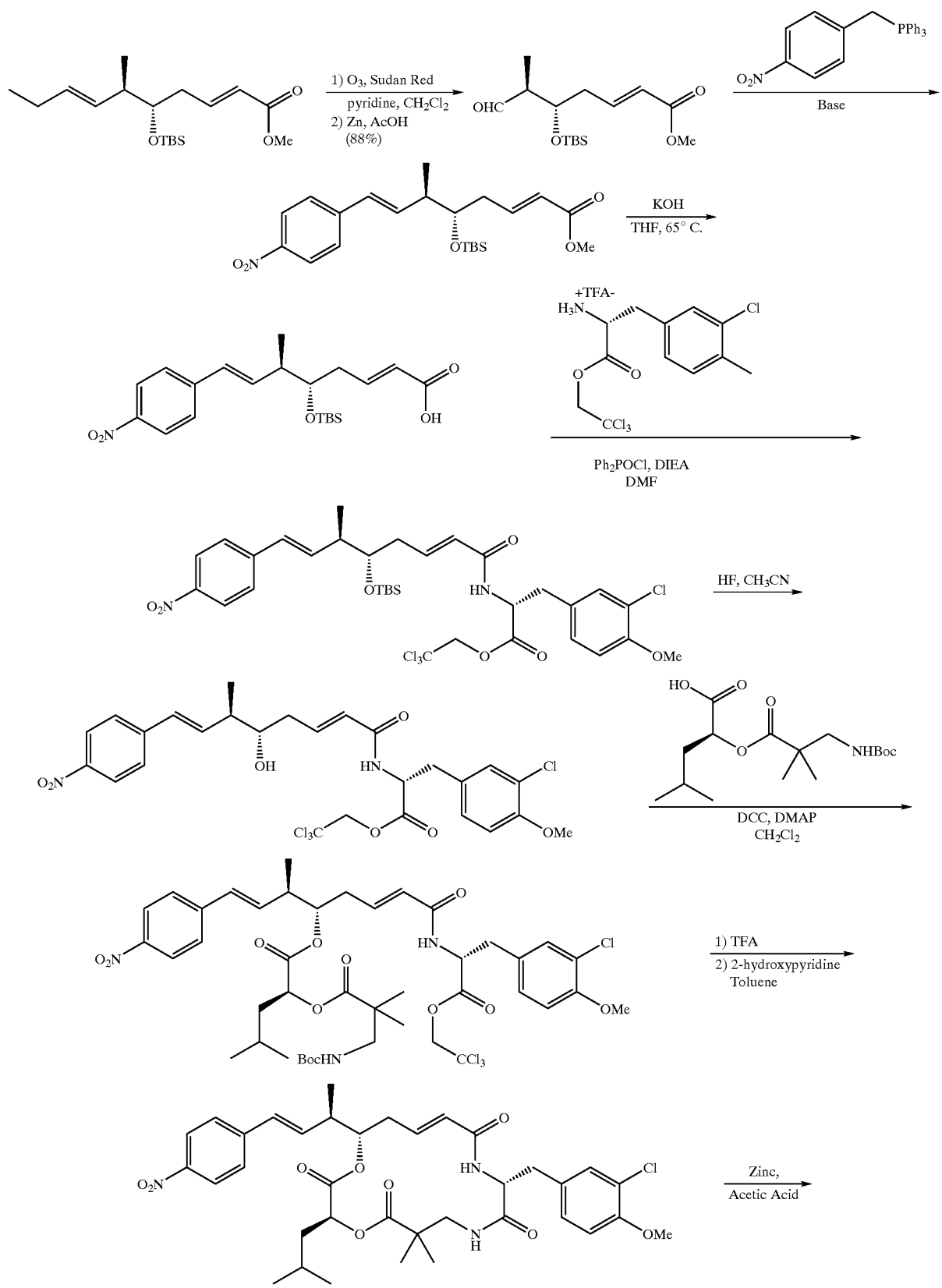

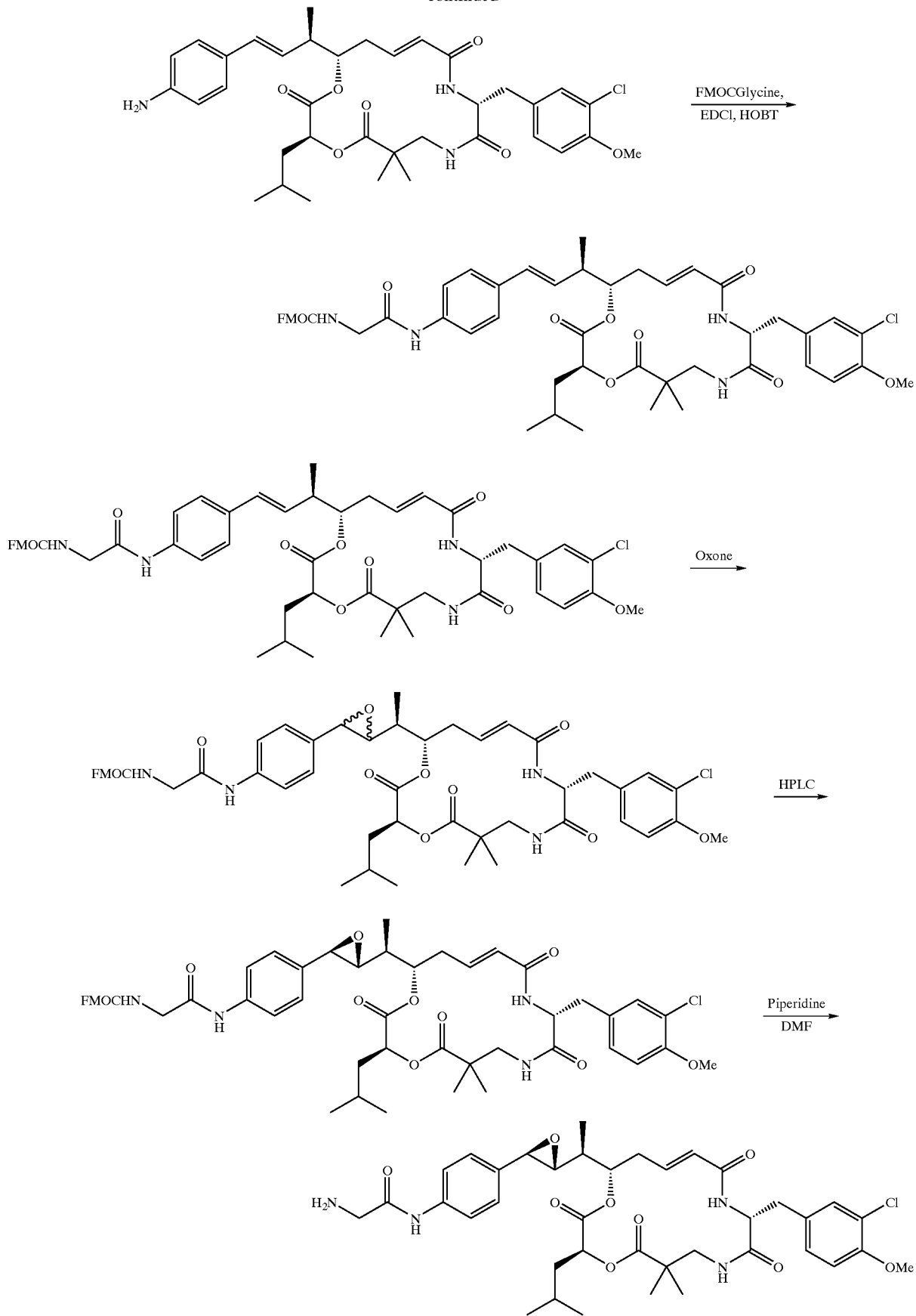

EXAMPLE 37

Via Scheme 3

To a solution of Cryptophycin 53 (0.15 g, 0.23 mmol) in 3 mL of DME and 2.0 mL of H₂O, was added 5 drops of concentrated H₂SO₄. The mixture was stirred overnight and an additional drops of H₂SO₄ were added and stirring continued for another 24 h. Saturated NaHCO₃ was added slowly until all reactivity subsided and the mixture was extracted with CH₂Cl₂. The organic layer was washed with brine, dried over Na₂SO₄, filtered and concentrated. The resulting residue was purified by column chromatography (silica gel, 2% MeOH/CH₂Cl₂) to yield 0.13 g of the diols. To the mixture of diols in 4.0 mL of THF and 2.0 mL of H2O was added NaIO₄ (0.144 g, 0.675 mmol). The resulting mixture was stirred overnight at room temperature. The mixture was concentrated in vacuo and 5 mL of H₂O were added and extracted with CH₂Cl₂. The combined organic layers were dried over Na₂SO₄, filtered and concentrated in vacuo to give 0.10 g (77%) of aldehyde 18.

To the TIPS protected 4-hydroxymethylbenzyl triphenylphosphonium chloride (0.23 g, 0.4 mmol) in 3.0 mL of THF at −78° C. was added dropwise0.25 mL of a 1.6 M solution of n-butyllithium. The mixture was warmed slowly to 0° C. and stirred for an additional 10 min. To aldehyde 18 in 4.0 mL of THF and at −78° C. was added dropwise 2.5 mL of the 0.13 M orange ylide solution. The resulting mixture was stirred at −78° C. for 2 h and at room temperature for 30 min. Saturated NH₄Cl (20 mL) was added along with ethyl acetate (10 mL), the layers separated and the organic one was washed with water (3×10 mL) and brine. Finally upon drying it over MgSO₄, the organic phase was filtered, concentrated in vacuo and the resulting residue was purified using column chromatography (silica gel, 70% EtOAc/hexanes) to give 0.09 g (62%) of the desired styrene.

EXAMPLE 38

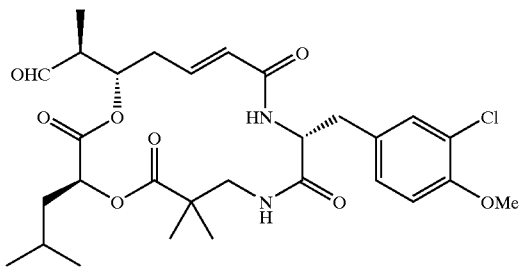

To a solution of Cryptophycin 53 (2.0 g, 2.99 mmol) in 30 mL of DME, was added a 2 M aqueous perchloric acid solution (15 mL, 30 mmol) and the resulting mixture was stirred for 6 hours. Upon careful neutralization with saturated NaHCO₃ (50 mL) the mixture was extracted with CH₂Cl₂ (4×100 mL) and the combined organic layers were dried over Na₂SO₄, filtered and concentrated in vacuo. Purification by column chromatography (silica gel, 5% MeOH/CH₂Cl₂) gave diols 19 (1.5 g) in 72% yield as a 3:1 anti/syn mixture.

To a solution of the diols (1.0 g, 1.46 mmol), in 20 mL of THF and 15 mL of water, was added NaIO₄ (1.9 g, 8.9 mmol) and the mixture was stirred under nitrogen overnight. Upon removing the bulk of the THF under reduced pressure, the residue was diluted with water (100 mL) and extracted with CH₂Cl₂ (4×50 mL). The combined organic extracts were washed with brine (1×25 mL), dried over Na₂SO₄, filtered and concentrated under vacuum. Residual benzaldehyde was removed by dissolving the solid in 100 mL of toluene and subsequently removing the toluene at 40° C. on a rotary evaporator. Two additional evaporations from toluene gave aldehyde 18 as a yellow foam (0.828 g) in 98% yield. The resulting aldehyde was used without further purification and was stored at −23° C. for stability reasons: $[\alpha]^{20}_D$ +23.0° (c 0.565, CHCl₃); ¹H NMR (300 MHz, CDCl₃) δ 9.64–9.63 (d, 1H, J=1.4 Hz), 7.28–7.26 (m, 1H), 7.21–7.20 (d, 1H, J=1.9 Hz), 7.08–7.05 (dd, 1H, J=7.1, 1.7 Hz), 6.87–6.84 (d, 1H, J=8.5 Hz), 6.82–6.72 (m, 1H), 5.80–5.75 (d, 1H, J=15.0 Hz), 5.54–5.51 (d, 1H, J=7.7 Hz), 5.40–5.33 (m, 1H), 4.85–4.81 (dd, 1H, J=9.7, 3.2 Hz), 4.78–4.71 (m, 1H), 3.88 (s, 3H), 3.46–3.39 (dd, 1H, J=13.5, 8.6 Hz), 3.15–3.03 (m, 3H), 2.68–2.35 (m, 3H), 1.82–1.63 (m, 2H), 1.45–1.37 (m, 1H), 1.24 (s, 3H), 1.19–1.16 (d, 3H, J=7.1 Hz), 1.18 (s, 3H), 0.94–0.92 (d, 3H, J=6.5 Hz), 0.89–0.87(d, 3H, J=6.5 Hz); ¹³C NMR (63 MHz, CDCl₃) δ 200.7, 177.8, 170.6, 170.1, 165.1, 153.9, 141.1, 130.7, 129.8, 128.1, 124.9, 122.3, 112.3, 73.4, 71.1, 56.0, 54.6, 49.9, 46.4, 42.7, 39.2, 36.1, 35.2, 24.7, 22.8, 22.7, 21.3, 10.7; IR (CHCl₃) 3422, 2964, 2936, 1755, 1730, 1718, 1678, 1529, 1504, 1487, 1474, 1464, 1442, 1320, 1303, 1281, 1259, 1244, 1185, 1151, 1127, 1067 cm⁻¹; Anal. (C₂₉H₃₉ClN₂O₆) C, H, N.

EXAMPLE 39

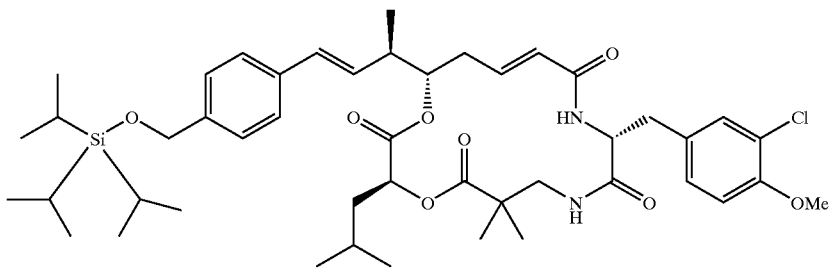

To 4-(triisopropylsiloxymethyl)benzyl triphenylphosphonium bromide (7.6 g, 12.2 mmol) in 100 mL of THF at −50° C. was added dropwise 8.0 mL of a 1.5 M solution of n-butyllithium (8.1 mL, 12.2 mmol). The mixture was warmed slowly to room temperature and stirred for an additional 30 min. To aldehyde 18 (2.95 g, 5.1 mmol), in 100 mL of THF and at −78° C., was added dropwise the red ylide solution via a double tipped needle. The resulting mixture was stirred at −78° C. for 3 h and at room temperature for 45 min. Saturated NH$_4$Cl (100 mL) was added along with ethyl acetate (100 mL), the layers separated and the aqueous one extracted with ethyl acetate (2×50 mL). The combined organic layers were washed with water (3×40 mL) and brine, dried over MgSO$_4$, filtered and concentrated in vacuo. The resulting yellow residue was purified using column chromatography (silica gel, 10–20–50% EtOAc/hexanes) to give 3.6 g (84%) of the desired styrene as a white solid and as a mixture of E:Z isomers.

The mixture of isomers (7.3 g, 8.7 mmol) was dissolved in 240 mL of benzene and heated to reflux in the presence of 1,1'-azobis(cyclohexanecarbonitrile) (VAZO) (0.32 g, 0.87 mmol) and thiophenol (3.7 mL, 4.0 mmol). Following 5 h of reflux, the solution was concentrated and the residue purified by column chromatography (silica gel, 5–50% EtOAc/hexanes) to give 6.7 g (92%) of the E isomer 20 as a white solid: $[\alpha]^{20}_D$ +31.9° (c1.0, CHCl$_3$); $^1$H NMR (300 MHz, CDCl$_3$) δ 7.3–7.22 (m, 5H), 7.20–7.19 (d, 1H, J=1.95 Hz), 7.07–7.04 (dd, 1H, J=8.4, 2.0 Hz), 6.85–6.82 (d, 1H, J=8.5 Hz), 6.8–6.7 (m, 1H), 6.4–6.38 (d, 1H, J=15.8 Hz), 6.02–5.94 (dd, 1H, J=15.8, 8.8 Hz), 5.77–5.72 (d, 1H, J=14.9 Hz), 5.56–5.54 (d, 1H, J=7.9 Hz), 5.1–4.7 (m, 5H), 3.9 (s, 3H), 3.45–3.37 (dd, 1H, J=13.5, 8.5 Hz), 3.2–3.0 (m, 3H), 2.6–2.3 (m, 3H), 1.7–1.5 (m, 2H), 1.4–1.0 (m, 31H), 0.75–0.71 (t, 6H, J=6.1 Hz); $^{13}$C NMR (63 MHz, CDCl$_3$) δ 177.8, 170.5, 170.4, 165.2, 153.9, 142.1, 141.1, 135.2, 131.5, 130.8, 129.7, 129.6, 128.1, 125.9, 124.5, 122.4, 112.2, 77.0, 71.4, 64.7, 56.0, 54.4, 46.4, 42.7, 42.2, 39.4, 36.5, 35.3. 24.5, 22.8, 22.6, 22.5, 21.2, 17.9, 17.2, 11.9; IR (CHCl$_3$) 3423, 2962, 2945, 2867, 1746, 1712, 1681, 1652, 1528, 1503, 1485, 1473, 1464, 1303, 1259 cm$^{-1}$; Anal. (C$_{46}$H$_{67}$ClN$_2$O$_8$Si): C, H, N.

EXAMPLE 40

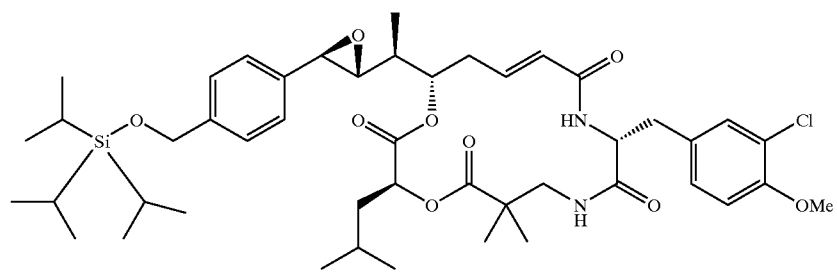

3-Chloroperoxybenzoic acid (0.27 g, 1.59 mmol) was added to a 0° C. solution of styrene 20 (1.25 9 , 1.49 mmol) in 20 mL of CH$_2$Cl$_2$. The solution was stirred for 1 h at 0° C. and overnight at room temperature. It was concentrated in vacuo and the resulting epoxides separated by reverse phase HPLC to yield 0.67 g of the β epoxide 22 (57%) as a white solid: $[\alpha]^{20}_D$ +20.9° (c 0.765, CHCl$_3$); $^1$H NMR (300 MHz, CDCl$_3$) δ 7.35–7.33 (d, 2H, J=7.8 Hz), 7.26–7.2 (m, 4H), 7.05–7.02 (bd, 1H, J=8.2 Hz), 6.84–6.81 (d, 1H, J=8.4 Hz), 6.81–6.65 (m, 1H), 5.8–5.65 (m, 2H), 5.25–5.15 (m, 1H), 4.9–4.7 (m, 4H), 3.9 (s, 3H), 3.7 (s, 1H), 3.46–3.42 (dd, 1H, J=13.4, 8.8 Hz), 3.15–3.0 (m, 3H), 2.93–2.9 (m, 1H, J=7.3 Hz), 2.6–2.4 (m, 2H), 1.8–1.6 (m, 3H), 1.4–1.0 (m, 31H), 0.83–0.79 (t, 6H, J=5.3 Hz); $^{13}$C NMR (63 MHz, CDCl$_3$) δ 177.7, 170.5, 170.4, 165.1, 153.9, 142.1, 141.6, 136.7, 135.1, 130.7, 129.8, 128.1, 125.9, 125.5, 124.6, 122.3, 112.2, 75.9, 71.0, 64.6, 63.0, 58.9, 56.0, 54.6, 46.3, 42.7, 40.5, 39.2, 36.8, 35.2. 24.2, 22.8, 22.7, 22.6, 18.0, 13.4, 11.9; IR (CHCl$_3$) 3424, 2962, 2945, 2867, 1751, 1712, 1682, 1528, 1503, 1485, 1473, 1464, cm$^{-1}$; Anal. (C$_{46}$H$_{67}$ClN$_2$O$_9$Si): C, H, N.

EXAMPLE 41

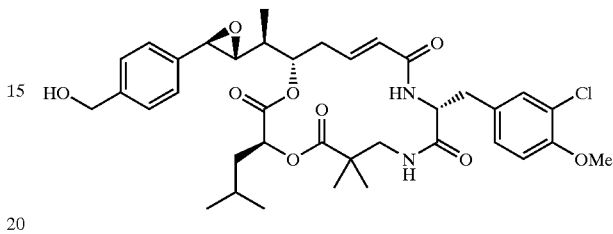

Tetrabutylammonium fluoride (0.14 mL, 0.14 mmol), as a 1.0 M solution in THF, was added dropwise to a 0° C. solution of the β epoxide 22 ( 0.1 g, 0.117 mmol) in 3.5 mL of THF. The solution was allowed to warm up to room temperature and stirring was continued for another 20 min, followed by the addition of water (10 mL) and ethyl acetate (20 mL). The layers were separated and the aqueous one was extracted with CH$_2$Cl$_2$ (3×20 mL). The combined organic layers were dried over anhydrous Na$_2$SO$_4$, filtered and concentrated in vacuo to yield the free alcohol. Purification by column chromatography (silica gel, 70–100% EtOAc-hexanes) yielded 0.068 g (84%) of the pure alcohol 23 as a white solid:

$[\alpha]^{20}_D$ +26.2° (c0.435, CHCl$_3$); $^1$H NMR (300 MHz, CDCl$_3$) δ 7.39–7.36 (d, 2H, J=7.8 Hz), 7.26–7.23 (d, 3H, J=9.1 Hz), 7.18 (s, 1H), 7.05–7.02 (d, 1H, J=8.5 Hz), 6.85–6.82 (d, 1H, J=8.2 Hz), 6.82–6.7 (m, 1H), 5.72–5.67 (d, 1H, J=15.1 Hz), 5.55–5.52 (d, 1H, J=7.8 Hz), 5.22–5.17 (m, 1H), 4.85–4.7 (m, 4H), 3.9 (s, 3H), 3.7 (s, 1H), 3.45–3.38 (dd, 1H, J=13.4, 9.3 Hz), 3.2–3.0 (m, 3H), 2.92–2.89 (d, 1H, J=7.6 Hz), 2.65–2.4 (m, 2H), 1.8–1.6 (m, 4H), 1.4–1.2 (m, 1H), 1.22 (s, 3H), 1.16 (s, 3H), 1.16–1.13 (d, 3H, J=7.2 Hz), 0.86–0.82 (t, 6H, J=6.5 Hz); $^{13}$C NMR (63 MHz, CDCl$_3$) δ 177.8, 171.0, 170.4, 165.5, 153.8, 141.5, 141.4, 135.7, 133.5, 130.6, 130.0, 128.0, 127.1, 125.6, 124.6, 122.2, 112.3, 77.2, 76.5, 76.0, 71.0, 64.2, 63.1, 58.8, 56.0, 54.7, 46.3, 42.7, 40.5, 39.3, 36.9, 35.1, 24.5, 22.7, 22.5, 22.1, 13.4; IR (CHCl$_3$) 3422, 2992, 2963, 2936, 2874, 1751, 1713, 1682, 1651, 1504, 1486, 1303, 1259, 1186, 1165, 1151, 1067 cm$^{-1}$; FAB HRMS [M+H] cacld for (C$_{37}$H$_{48}$ClN$_2$O$_9$) 699.3048, found 699.3054.

EXAMPLE 42

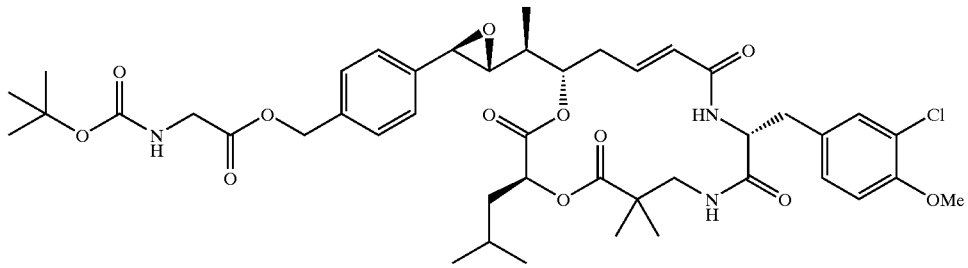

To a 0° C. solution of alcohol 23 (0.08 g, 0.114 mmol), N-(tert-butoxycarbonyl)glycine (0.034 g, 0.194 mmol) and 4-dimethylaminopyridine (DMAP) (0.004 g, 0.034 mmol) in 2.0 mL $CH_2Cl_2$ was added 1,3-dicyclohexylcarbodiimide (DCC) (0.040 g, 0.194 mmol). The mixture was stirred at 0° C. for 10 min and at room temperature for 45 min, filtered and concentrated in vacuo. The resulting residue was purified using column chromatography (silica gel, 70–80% EtOAc/hexanes) to give 0.07 g (72%) of the ester as a white solid: $[\alpha]^{20}_D$ +18.5° (c 0.65, $CHCl_3$); $^1H$ NMR (300 MHz, $CDCl_3$) δ 7.4–7.2 (m, 6H), 7.11–7.08 (dd, 1H, J=8.4, 1.8 Hz), 6.9–6.87 (d, 1H, J=8.4 Hz), 6.86–6.7 (m, 1H), 5.78–5.73 (d, 1H, J=15.2 Hz), 5.64–5.62 (d, 1H, J=7.4 Hz), 5.3–5.22 (m, 1H), 5.22 (s, 2H), 5.1–5.0 (bs, 1H), 4.9–4.7 (m, 2H), 4.0–3.99 (d, 2H, J=5.4 Hz), 3.9 (s, 3H), 3.73–3.72 (d, 1H, J=1.0 Hz), 3.5–3.43 (dd, 1H, J=13.4, 8.6 Hz), 3.2–3.0 (m, 3H), 2.95–2.92 (d, 1H, J=6.4 Hz), 2.65–2.4 (m, 2H), 1.8–1.6 (m, 3H), 1.5 (s, 9H), 1.45–1.3 (m, 1H), 1.26 (s, 3H), 1.2 (s, 3H), 1.2–1.17 (d, 3H, J=8.7 Hz), 0.9–0.86 (t, 6H, J=6.3 Hz); $^{13}C$ NMR (63 MHz, $CDCl_3$) δ 177.7, 170.6, 170.3, 170.2, 165.1, 155.6, 153.8, 141.4, 137.1, 135.6, 130.6, 129.9, 128.6, 128.0, 125.7, 124.7, 122.2, 112.2, 79.9, 75.8, 70.9, 66.4, 63.1, 58.5, 56.0, 54.7, 48.9, 46.3, 42.7, 42.4, 40.5, 39.3, 36.8, 35.2, 28.2, 24.5, 22.8, 22.7, 22.6, 21.2, 13.5; Anal. ($C_{44}H_{58}ClN_3O_{12}$): C, H, N.

EXAMPLE 43

Trimethylsilyl chloride (0.09 mL, 0.75 mmol) was added to a −60° C. solution of b epoxide 24 (0.16 g, 0.187 mmol) in 5.0 mL of $CHCl_3$. Following 2 h of stirring between −60° C. to −40° C. an additional 0.09 mL of TMSCl was added and stirring continued for 3 h. The solution was allowed to warm up to room temperature, concentrated and purified by reverse phase preparative HPLC (55:45) $CH_3CN:H_2O$ to separate the two resulting chlorohydrins. This purification gave 0.058 g (35%) of the desired chlorohydrin 25: $[\alpha]^{20}_D$ +50.5° (c 1.075, $CHCl_3$); $^1H$ NMR (300 MHz, $CDCl_3$) δ 7.42–7.2 (m, 6H), 7.13–7.09 (dd, 1H, J=8.4, 1.8 Hz), 6.9–6.87 (d, 1H, J=8.4 Hz), 6.85–6.7 (m, 1H), 5.9–5.8 (m, 2H), 5.2 (s, 3H), 5.15–5.05 (m, 1H), 5.0–4.9 (m, 1H), 4.8–4.72 (m, 1H), 4.71–4.68 (d, 1H, J=9.7 Hz), 4.07–4.03 (d, 1H, J=9.3 Hz), 3.99–3.97 (d, 2H, J=5.5 Hz), 3.9 (s, 3H), 3.44–3.37 (dd, 1H, J=13.6, 8.3 Hz), 3.23–3.14 (m, 2H), 3.08–3.0 (dd, 1H, J=14.5, 8.0 Hz), 2.75–2.4 (m, 3H), 2.0–1.7 (m, 3H), 1.5 (s, 10H), 1.26 (s, 3H), 1.21 (s, 3H), 1.08–1.06 (d, 3H, J=7.0 Hz), 0.977–0.963 (d, 3H, J=4.0 Hz), 0.956–0.942 (d, 3H, J=4.1 Hz); $^{13}C$ NMR (63 MHz, $CDCl_3$) 177.5, 170.5, 170.2, 170.1, 165.3, 153.9, 142.2, 139.0, 138.3, 136.1, 130.8, 129.9, 128.7, 128.2, 128.1, 124.5, 122.3, 112.2, 80.0, 76.1, 73.9, 71.1, 66.2, 61.7, 56.1, 54.6, 46.4, 42.7, 42.3, 39.6, 38.4, 36.3, 35.1, 28.2, 24.8, 23.0, 22.9, 22.7, 21.5, 8.6; IR ($CHCl_3$) 3428, 3009, 2966, 2935, 1750, 1714, 1683, 1504, 1486, 1369, 1259, 1193, 1162, 1127, 1067; FAB HRMS [M +H] cacld for ($C_{44}H_{60}ClN_3O_{12}$) 892.3554, found 892.3565.

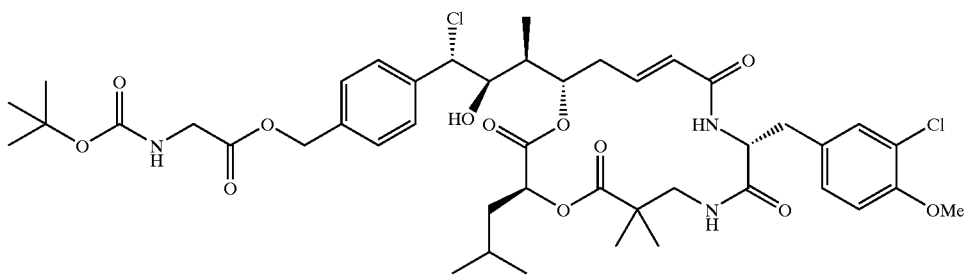

EXAMPLE 44

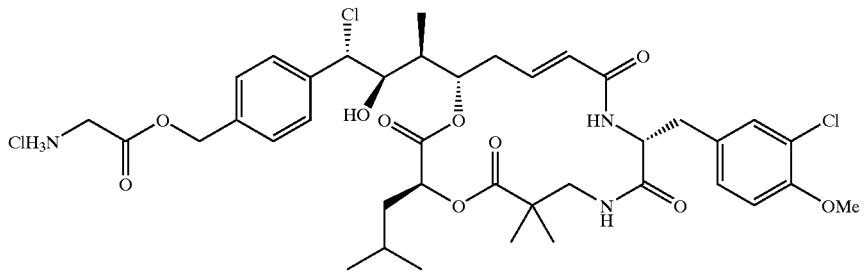

A 4 M solution of hydrogen chloride in 1,4-dioxane (0.08 mL, 0.33 mmol) was added to a solution of the glycinate 25 (0.058 g, 0.065 mmol) in 0.2 mL of $CH_2Cl_2$. The resulting mixture was stirred at room temperature for 3 h, concentrated in vacuo and maintained under vacuum for 3 days to remove the 1,4-dioxane thus giving the desired hydrochloride salt 26 in quantitative yield: $[\alpha]^{20}_D$ +26.2° (c 0.58, MeOH ); $^1$H NMR (500 MHz, $CD_3OD$) δ 7.48–7.42 (q, 4 H, J=11.2 Hz), 7.31–7.3 (d, 1H, J=2.0 Hz), 7.21–7.19 (dd, 1H, J=8.5, 2.0 Hz), 7.01–7.0 (d, 1H, J=8.4 Hz), 6.8–6.7 (m, 1H), 6.0–5.95 (dd, 1H, J=15.2, 1.5 Hz), 5.3 (d, 2H, J=1.3 Hz), 5.16–5.1 (m, 1H), 5.09–5.07 (dd, 1H, J=10.0, 3.6 Hz), 4.84–4.82 (d, 1H, J=9.8 Hz), 4.54–4.51 (dd, 1H, J=11.3, 3.7 Hz), 4.05–4.03 (dd, 1H, J=9.5, 1.8 Hz), 3.9 (s, 2H), 3.86 (s, 3H), 3.5–3.47 (d, 1H, J=13.5 Hz), 3.22–3.18 (dd, 1H, J=14.5, 3.6 Hz), 3.14–3.11 (d, 1H, J=13.5 Hz), 2.8–2.77 (d, 1H, J=14.4 Hz), 2.78–2.75 (m, 2H), 2.55–2.35 (m, 2H), 1.9–1.55 (m, 4H), 1.4–1.3 (m, 1H), 1.24 (s, 3H), 1.2 (s, 3H), 1.04–1.03 (d, 3H, J=7.0 Hz), 1.02–1.0 (t, 6H, J=7.2 Hz); $^{13}$C NMR (75 MHz, $CDCl_3$) δ 178.9, 173.8, 171.9, 168.3, 155.3, 144.2, 141.8, 136.7, 132.3, 131.5, 129.75, 129.7, 129.4, 125.2, 123.3, 113.5, 77.2, 74.7, 72.6, 68.5, 63.5, 57.6, 56.7, 47.6, 44.1, 41.1, 40.4, 37.9, 36.5, 26.3, 23.6, 23.5, 22.2, 9.0; IR (KBr) 3412, 2961, 2935, 1752, 1722, 1669, 1504, 1473, 1279, 1259, 1207, 1151, 1126, 1065 $cm^{-1}$.

EXAMPLE 45

To chlorohydrin 25 (0.14 g, 0.16 mmol), N-(tert-butoxycarbonyl)glycine (0.041 g, 0.24 mmol) and 4-dimethylaminopyridine (DMAP) (0.002 g, 0.016 mmol) in 0.7 mL of $CH_2Cl_2$ was added 1,3-dicyclohexylcarbodiimide (DCC) (0.049 g, 0.24 mmol). The resulting mixture was stirred at room temperature for 1 h, filtered using ethyl acetate and concentrated in vacuo. The resulting residue was purified using column chromatography (silica gel, 50–60–70% EtOAc/hexanes) to give 0.158 g (97%) of the diglycinate 27 as a white solid: $[\alpha]^{20}_D$ +44.0° (c 1.25, $CHCl_3$); $^1$H NMR (300 MHz, $CDCl_3$) δ 7.4–7.2 (m, 7H), 7.13–7.10 (bd, 1H, J=9.8 Hz), 6.91–6.88 (d, 1H, J=8.4 Hz), 5.8–5.77 (d, 1H, J=15.3 Hz), 5.6–5.58 (m, 1H), 5.49–5.46 (d, 1H, J=9.6 Hz), 5.19 (S, 2H), 5.1–4.7 (m, 6H), 3.98–3.97 (d, 2H, J=5.0 Hz), 3.93 (s, 3H), 3.69–3.62 (dd, 1H, J=18.2, 4.0 Hz), 3.5–3.0 (m, 5H), 2.7–2.35 (m, 3H), 2.0–1.7 (m, 3H), 1.49 (s, 9H), 1.44 (s, 9H), 1.28 (s, 3H), 1.22 (s, 3H), 1.1–1.08 (d, 3H, J=7.0 Hz), 1.06–1.04 (d, 3H, J=6.4 Hz), 1.0–0.98 (d, 3H, J=6.2 Hz); $^{13}$C NMR (63 MHz, $CDCl_3$) δ 177.6, 170.4, 169.9, 168.5, 165.0, 155.2, 153.9, 141.6, 138.6, 137.3, 136.3, 130.8, 129.8, 128.2, 128.1, 124.6, 122.3, 112.2, 79.9, 74.7, 71.1, 66.2, 60.0, 56.0, 54.5, 46.5, 42.8, 42.4, 41.8, 39.5, 38.0, 36.5, 35.2, 28.2, 28.15, 24.8, 23.1, 22.8, 22.6, 21.4, 9.9; IR ($CHCl_3$) 3431, 2982, 2966, 2935, 2872, 1756, 1713, 1685, 1504, 1369, 1258, 1193, 1161; FAB HRMS [M–BOC+H] cacld for ($C_{46}H_{63}Cl_2N_4O_{13}$) 949.3769, found 949.3777.

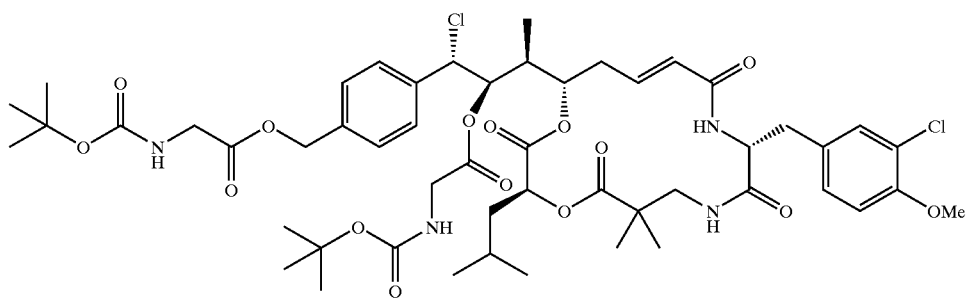

EXAMPLE 46

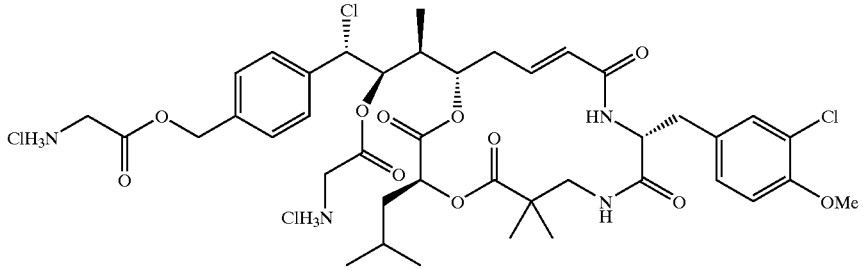

A 4 M solution of hydrogen chloride in 1,4-dioxane (0.1 mL, 0.42 mmol) was added to a solution of the diglycinate 27 (0.044 g, 0.042 mmol) in 0.2 mL of $CH_2Cl_2$. The resulting mixture was stirred at room temperature for 3 h, concentrated in vacuo and maintained under vacuum for 3 days to remove residual 1,4-dioxane thus giving the desired hydrochloride salts 28 in quantitative yield: $[\alpha]^{20}_D$ +33.1° (c 0.865, MeOH); $^1$H NMR (500 MHz, $CD_3OD$) δ 7.77–7.74 (d, 1H), 7.46–7.41 (q, 4H, J=20.3, 8.4 Hz), 7.29–7.28 (d, 1H, J=2.1 Hz), 7.18–7.16 (dd, 1H, J=8.6, 2.1 Hz), 6.99–6.97 (d, 1H, J=8.5 Hz), 6.7–6.6 (m, 1H), 5.95–5.92 (d, 1H, J=15.3 Hz), 5.54–5.52 (dd, 1H, J=9.5, 1.4 Hz), 5.5 (s, 1H), 5.28 (s, 2H), 5.21–5.19 (d, 1H, J=9.4 Hz), 5.12–5.09 (dd, 1H, J=10.5, 3.1 Hz), 4.87–4.85 (d, 1H, J=12.4 Hz), 4.5–4.47 (dd, 1H, J=11.3, 3.7 Hz), 3.9 (s, 2H), 3.84 (s, 3H), 3.82–3.79 (d, 1H, J=17.8 Hz), 3.48–3.45 (d, 1H, J=13.7 Hz), 3.35–3.3 (m, 1H), 3.19–3.15 (dd, 1H, J=14.5, 3.8 Hz), 3.11–3.09 (d, 1H, J=13.8 Hz), 2.77–2.6 (m, 3H), 2.37–2.3 (m, 1H), 1.95–1.75 (m, 3H), 1.22 (s, 3H), 1.17 (s, 3H), 1.08–1.07 (d, 3H, J=7.0 Hz), 1.03–1.02 (d, 3H, J=6.4 Hz), 1.0–0.99 (d, 3H, J=6.2 Hz); $^{13}$C NMR (63 MHz, $CDCl_3$) δ 178.8, 173.8, 171.9, 168.5, 168.2, 167.8, 155.4, 143.5, 139.3, 137.6, 132.2, 131.4, 129.7, 129.5, 129.4, 125.3, 123.3, 113.5, 77.9, 76.2, 72.4, 68.2, 60.8, 57.7, 56.7, 47.5, 44.2, 41.2, 40.5, 39.8, 37.9, 36.5, 26.3, 23.7, 23.4, 22.0, 9.9; IR (KBr) 3417, 3234, 2959, 2873, 2622, 1757, 1724, 1673, 1504, 1473, 1303, 1259, 1221, 1150, 1065 $cm^{-1}$.

EXAMPLE 47

A mixture of the free acid of fragment C' (0.22 g, 1.02 mmol), DMAP (0.032 g, 0.26 mmol) and DCC (0.21 g, 1.02 mmol) was stirred for 30 min at 0° C. in 6.5 mL of $CH_2Cl_2$. The free alcohol 29 (0.35 g, 0.51 mmol) in 6.0 mL of $CH_2Cl_2$ was added dropwise. The mixture was stirred at 0° C. for 10 min and at room temperature for 24 h and finally was heated at reflux for 3 h and cooled back to room temperature. The reaction mixture was concentrated in vacuo and filtered through Celite using EtOAc. The resulting residue was purified using column chromatography (silica gel, 60–70% EtOAc/hexanes) to give 0.38 g (85%) of the ester above as a white solid: $[\alpha]^{20}_D$ +23.2° (c 1.0, $CHCl_3$); $^1$H NMR (300 MHz, $CDCl_3$) δ 7.4–7.2 (m, 6H), 7.12–7.08 (dd, 1H, J=8.4, 2.0 Hz), 6.9–6.87 (d, 1H, J=8.5 Hz), 6.87–6.75 (m, 1H), 6.47–6.42 (d, 1H, J=15.8 Hz), 6.11–6.03 (dd, 1H, J=15.8, 8.8 Hz), 5.82–5.77 (d, 1H, J=14.9 Hz), 5.61–5.58 (d, 1H, J=7.8 Hz), 5.12 (s, 2H), 5.12–4.75 (m, 4H), 3.9 (s, 3H), 3.49–3.42 (dd, 1H, J=13.4, 8.7 Hz), 3.29–3.27 (d, 1H, J=6.5 Hz), 3.2–3.1 (m, 3H), 2.65–2.3 (m, 3H), 1.8–1.6 (m, 3H), 1.47 (s, 9H), 1.45–1.3 (m, 1H), 1.3–1.15 (m, 15H), 0.79–0.75 (t, 6H, J=6.4 Hz); $^{13}$C NMR (75 MHz, $CDCl_3$) δ 177.8, 170.4, 165.1, 153.9, 141.9, 136.7, 135.1, 131.1, 130.8, 129.7, 128.3, 128.2, 126.2, 124.6, 122.4, 112.2, 76.9, 71.3, 66.0, 56.0, 54.4, 48.2, 46.4, 43.7, 42.6, 42.2, 39.4, 36.4, 35.2, 28.3, 24.5, 22.8, 22.6, 21.2, 17.2; IR ($CHCl_3$) 3426, 2968, 2935, 2874, 2841, 1746, 1713, 1684, 1652, 1504, 1486, 1474, 1368, 1318, 1304, 1259, 1244, 1165, 1151, 1067 $cm^{-1}$; FAB HRMS [M–BOC+H] calcd for ($C_{42}H_{57}ClN_3O_9$) 782.3783, found 782.3788.

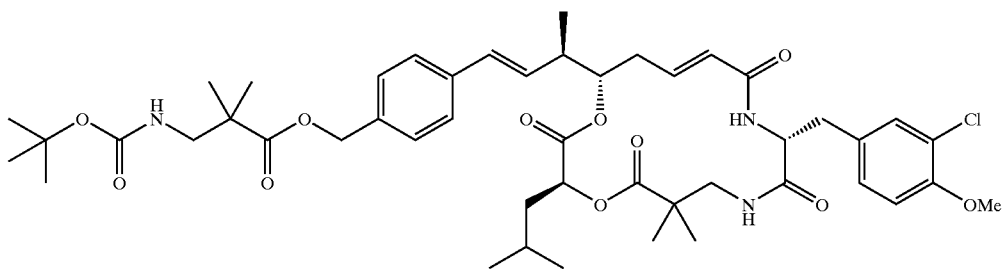

EXAMPLE 48

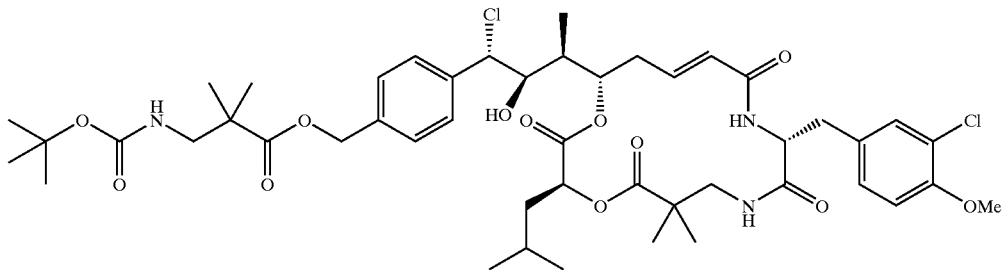

3-Chloroperoxybenzoic acid (0.092 g, 0.54 mmol) was added to a 0° C. solution of the starting styrene (0.45 g, 0.51 mmol) in 9.0 mL of $CH_2Cl_2$. The solution was stirred for 1 h at 0° C. and overnight at room temperature. It was concentrated in vacuo and the resulting epoxides dissolved in 10 mL of $CHCl_3$ and cooled to −60° C.

Freshly distilled TMSCl (0.25 mL, 1.95 mmol) was added to the −60° C. solution and the mixture was stirred for 1 h.

More TMSCl (0.5 mL, 3.9 mmol) was added and stirring continued between −60° C. to −40° C. for an additional 2 h. The solution was allowed to warm up to room temperature and additional TMSCl (0.25 mL, 1.95 mmol) was added. Following 30 min of stirring at room temperature the solution was concentrated and purified by preparative HPLC to separate the resulting chlorohydrins. This purification gave 0.1 g (22%) of the desired chlorohydrin: $[\alpha]^{20}_D$ +47.9° (c 0.75, $CHCl_3$); $^1H$ NMR (300 MHz, $CDCl_3$) δ 7.5–7.2 (m, 6H), 7.13–7.10 (dd, 1H, J=8.4, 1.9 Hz), 6.91–6.88 (d, 1H, J=8.5 Hz), 6.87–6.75 (m, 1H), 5.85–5.8 (d, 1H, J=14.9 Hz), 5.75–5.6 (m, 1H), 5.22–5.1 (m, 3H), 5.0–4.9 (m, 2H), 4.8–4.72 (m, 1H), 4.71–4.68 (d, 1H, J=9.6 Hz), 4.07–4.03 (d, 1H, J=9.5 Hz), 3.9 (s, 3H), 3.45–3.38 (dd, 1H, J=13.4, 8.5 Hz), 3.31–3.26 (d, 1H, J=6.4 Hz), 3.25–3.0 (m, 4.H), 2.8–2.65 (bd, 1H), 2.6–2.35 (m, 2H), 1.9–1.7 (m, 3H), 1.47 (s, 10H), 1.27 (s, 3H), 1.25 (s, 6H), 1.22 (s, 3H), 1.09–1.07 (d, 3H, J=7.0 Hz), 0.98–0.96 (m, 6H); $^{13}C$ NMR (75 MHz, $CDCl_3$) δ 177.5, 170.5, 165.2, 153.9, 142.5, 137.0, 130.8, 129.8, 128.2, 124.5, 122.4, 112.2, 79.1, 76.1, 73.9, 71.1, 65.6, 61.7, 56.1, 54.5, 48.2, 46.4, 43.7, 42.7, 39.6, 38.4, 36.3, 35.2, 28.3, 24.8, 23.0, 22.9, 22.8, 22.7, 21.5, 8.6; IR ($CHCl_3$) 3426, 2967, 2934, 2873, 2841, 1715, 1684, 1605, 1504, 1485, 1474, 1442, 1368, 1305, 1258, 1151 $cm^{-1}$; FAB HRMS [M−BOC+H] calcd for ($C_{42}H_{58}Cl_2N_3O_{10}$) 834.3499, found 834.3487.

EXAMPLE 49

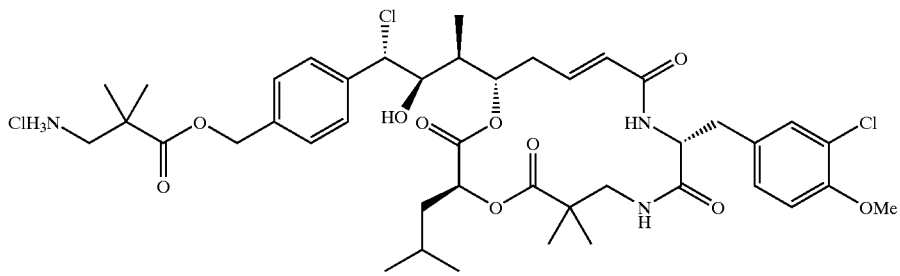

A 4 M solution of hydrogen chloride in 1,4-dioxane (0.11 mL, 0.43 mmol) was added to a solution of the chlorohydrin (0.08 g, 0.086 mmol) in 0.35 mL of $CH_2Cl_2$. The resulting mixture was stirred at room temperature for 3 h, concentrated in vacuo and maintained under vacuum for 3 days to remove the 1,4-dioxane thus giving the desired hydrochloride salt (shown above) (0.075 g) in quantitative yield: $[\alpha]^{20}_D$ +28.0° (c 0.5, $CH_3OH$); $^1H$ NMR (300 MHz, $CD_3OH$) δ 8.52–8.49 (d, 1H, J=7.5 Hz), 7.84–7.81 (d, 2H, J=9.6 Hz), 7.49–7.39 (q, 4H, J=8.3 Hz), 7.32–7.31 (d, 1H, J=1.9 Hz), 7.22–7.19 (dd, 1H, J=8.4, 2.1 Hz), 7.02–7.0 (d, 1H, J=8.4 Hz), 6.8–6.7 (m, 1H), 6.0–5.9 (dd, 1H, J=15.4, 1.0 Hz), 5.22 (s, 2H), 5.2–5.0 (m, 2H), 4.85–4.81 (di 1H, J=9.6 Hz), 4.6–4.5 (m, 1H), 4.06–4.03 (dd, 1H, J=9.6, 1.5 Hz), 3.9 (s, 3H), 3.54–3.46 (dd, 1H, J=13.5, 9.7 Hz), 3.25–3.11 (m, 2H), 3.11 (s, 2H), 2.8–2.7 (m, 2H), 2.6–2.3 (m, 2H), 1.9–1.5 (m, 3H), 1.3 (s, 7H), 1.25 (s, 3H), 1.2 (s, 3H), 1.06–1.03 (d, 3H, J=6.9 Hz), 1.02–1.01 (d, 3H, J=3.2 Hz), 1.0–0.99 (d, 3H, J=3.4 Hz); $^{13}C$ NMR (63 MHz, $CD_3OH$) δ 178.9, 176.5, 173.8, 171.8, 168.3, 155.3, 144.2, 141.6, 137.4, 132.3, 131.5, 129.8, 129.4, 129.3, 125.2, 123.3, 113.5, 77.2, 74.7, 72.6, 67.8, 63.5, 57.6, 56.7, 47.7, 47.6, 44.1, 42.3, 41.1, 40.4, 37.9, 36.5, 26.2, 23.7, 23.4, 22.2, 9.0; IR ($CHCl_3$) 3421, 2964, 2935, 2873, 2841, 1717, 1676, 1528, 1504, 1477, 1464, 1405, 1282, 1259, 1185, 1152, 1067 $cm^{-1}$; FAB HRMS [M−Cl] calcd for ($C_{42}H_{58}Cl_3N_3O_{10}$) 834.3499, found 834.3504.

EXAMPLE 50

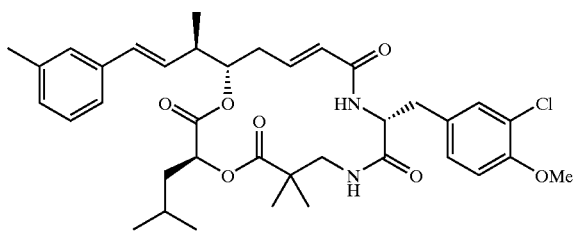

Styrene (shown above) (0.67 g) was prepared from aldehyde 18 (1.0 g, 1.73 mmol) and 3-methylbenzyl triphenylphosphonium chloride (0.886 g, 2.2 mmol) in 58% yield according to the procedure described above for styrene 20: $[\alpha]^{20}_D$ +33.1° (c 1.0, $CH_3OH$ ); $^1H$ NMR (300 MHz, $CDCl_3$) δ 7.24–7.0 (m, 7H), 6.85–6.82 (d, 1H, J=8.4 Hz), 6.82–6.7 (m, 1H), 6.39–6.34 (d, 1H, J=15.8 Hz), 6.03–5.95 (dd, 1H, J=15.8, 8.7 Hz), 5.78–5.73 (d, 1H, J=15.2 Hz), 5.67–5.64 (d, 1H, J=7.8 Hz), 5.1–5.0 (m, 1H), 4.87–4.83 (dd, 1H, J=10.2, 3.5 Hz), 4.8–4.7 (m, 1H), 3.9 (s, 3H), 3.45–3.38 (dd, 1H, J=13.4, 8.6 Hz), 3.2–3.0 (m, 3H), 2.6–2.3 (m, 3H), 2.32 (s, 3H), 1.75–1.25 (m, 3H), 1.22 (s, 3H), 1.15 (s, 3H), 1.13–1.11 (d, 3H, J=6.8 Hz), 0.75–0.72 (t, 6H, J=5.7 Hz); $^{13}C$ NMR (63 MHz, $CDCl_3$) δ 177.9, 170.5, 170.3, 165.1, 154.0, 142.1, 138.0, 136.6, 135.6, 131.8, 130.8, 129.9, 129.6, 128.4, 128.22, 128.17, 126.7, 124.5, 123.3, 122.5, 112.3, 71.4, 56.1, 54.3, 46.4, 42.7, 42.2, 39.4, 36.5, 35.3, 24.5, 22.8, 22.6, 22.56, 21.2, 21.1, 17.2; IR ($CHCl_3$) 3424, 3021, 3017, 2965, 1747, 1711, 1680, 1652, 1528, 1503, 1485, 1259, 1151, 1067 $cm^{-1}$.

EXAMPLE 51

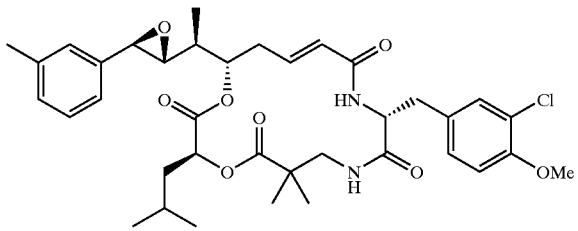

3-Chloroperoxybenzoic acid (0.19 g, 1.1 mmol) was added to the styrene (shown above) (0.667 g, 1.0 mmol) in 5.0 mL of $CH_2Cl_2$. The resulting solution was stirred overnight, concentrated in vacuo to give the β and α epoxides in a 1.8:1 ratio, in favor of the β. Separation of the two epoxides by reverse phase HPLC (70:30) $CH_3CN:H_2O$, gave 0.20 g of the major β epoxide as a white solid: $^1H$ NMR (300 MHz, $CDCl_3$) δ 7.3–7.0 (m, 7H), 6.9–6.87 (d, 1H, J=8.4 Hz), 6.87–6.75 (m, 1H), 5.79–5.74 (d, 1H, J=14.8 Hz), 5.54–5.51 (d, 1H, J=7.8 Hz), 5.28–5.22 (m, 1H), 4.89–4.85 (dd, 1H, J=10.4, 3.5 Hz), 4.82–4.75 (m, 1H), 3.9 (s, 3H), 3.69–3.68 (d, 1H, J=1.6 Hz), 3.51–3.44 (dd, 1H, J=13.4, 8.6 Hz), 3.2–3.1 (m, 2H), 2.98–2.95 (dd, 1H, J=7.6, 1.6 Hz), 2.65–2.32 (m, 3H), 2.32 (s, 3H), 1.85–1.6 (m, 3H), 1.4–1.25 (s, 3H), 1.27 (s, 3H), 1.21 (s, 3H), 1.21–1.18 (d, 3H, J=7.5 Hz), 0.90–0.86 (t, 6H, J=6.13 Hz).

EXAMPLE 52

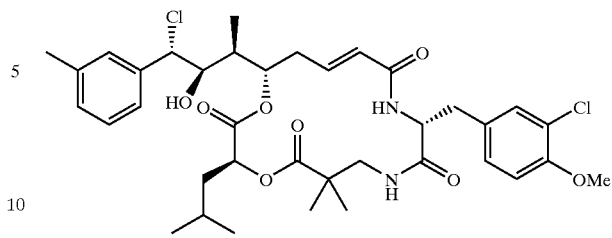

To a solution of the β epoxide (shown above) (0.1 g, 0.147 mmol) in 5.0 mL of $CHCl_3$ at −60° C., was added chlorotrimethylsilane (0.093 mL, 0.74 mmol). The solution was stirred at −60° C. for 30 min and at room temperature for 1.5 h before being concentrated under vacuum. The resulting residue, containing a 50:50 mixture of the syn and anti chlorohydrins, was purified via reverse phase HPLC to yield 0.028 g (27%) of the desired trans isomer: $^1H$ NMR (300 MHz, $CDCl_3$) δ 7.28–7.2 (m, 5H), 7.13–7.1 (dd, 1H, J=8.3, 1.9 Hz), 6.91–6.88 (d, 1H, J=8.5 Hz), 6.88–6.78 (m, 1H), 5.86–5.81 (d, 1H, J=15.0 Hz), 5.73–5.71 (d, 1H, J=7.8 Hz), 5.24–5.17 (t, 1H, J=9.4 Hz), 5.0–4.96 (dd, 1H, J=9.6, 2.9 Hz), 4.81–4.74 (m, 1H), 4.67–4.64 (d, 1H, J=9.7 Hz), 4.06–4.03 (dd, 1H, J=9.6, 1.1 Hz), 3.92 (s, 3H), 3.47–3.39 (dd, 1H, J=13.2, 8.3 Hz), 3.42–3.0 (m, 3H), 2.8–2.4 (m, 2H), 2.4 (s, 3H), 1.9–1.4 (m, 4H), 1.28 (s, 3H), 1.22 (s, 3H), 1.09–1.07 (d, 3H, J=7.0 Hz), 0.98–0.96 (d, 6H, J=6.4 Hz).

EXAMPLE 53

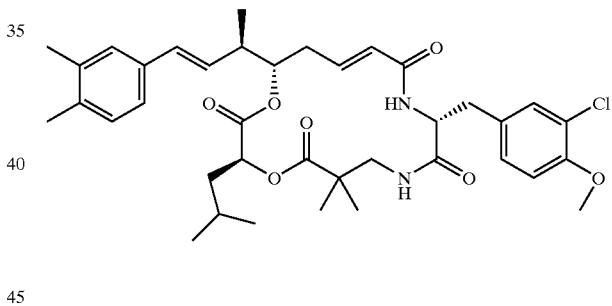

Styrene (shown above) (0.095 g) was prepared from aldehyde 18 (0.2 g, 0.345 mmol) and 3,4-dimethylbenzyl triphenylphosphonium chloride (0.26 g, 0.62 mmol) in 63% yield according to the procedure described above for styrene 20: $[\alpha]^{20}_D$ +27.8° (c 0.576, $CHCl_3$); $^1H$ NMR (300 MHz, $CDCl_3$) δ 7.22–7.18 (d, 1H, J=1.6 Hz), 7.12–7.02 (m, 5H), 6.87–6.81 (d, 1H, J=8.3 Hz), 6.80–6.71 (m, 1H), 6.40–6.30 (d, 1H, J=15.8 Hz), 6.00–5.88 (dd, 1H, J=15.8, 8.8Hz), 5.80–5.70 (d, 1H, J=15.1 Hz), 5.55–5.45 (d, 1H, J=7.7 Hz), 5.10–4.97 (m, 1H), 4.90–4.80 (dd, 1H, J=9.4, 2.8 Hz), 4.80–4.70 (m, 1H), 3.88 (s, 3H), 3.50–3.35 (dd, 1H, J=13.3, 4.8 Hz), 3.20–3.00 (m, 3H), 2.60–2.48 (m, 2H), 2.45–2.30 (m, 1H), 2.23 (s, 3H), 2.24 (s, 3H), 1.80–1.55 (m, 2H), 1.40–1.30 (m, 1H), 1.22 (s, 3H), 1.16 (s, 3H), 1.14–1.10 (d, 3H, J=6.8 Hz), 0.80–0.73 (m, 6H); $^{13}C$ NMR (63 MHz, $CDCl_3$) δ 177.9, 170.5, 170.3, 165.1, 154.0, 142.2, 136.5, 135.9, 134.3, 131.6, 130.8, 129.7, 129.5, 128.8, 128.1, 127.2, 124.4, 123.6, 122.4, 112.2, 71.4, 56.0, 54.2, 46.4, 42.6, 42.1, 39.4, 36.4, 35.2, 24.5, 22.7, 22.6, 22.5, 21.1, 19.6, 19.3, 17.2; IR ($CHCl_3$) 3424, 2965, 2935, 1746, 1711, 1681, 1652, 1527, 1503, 1485, 1259, 1187, 1164, 1151, 1067, 970, 727 $cm^{-1}$; Anal. ($C_{38}H_{49}ClN_2O_7$) C, H, N.

EXAMPLE 54

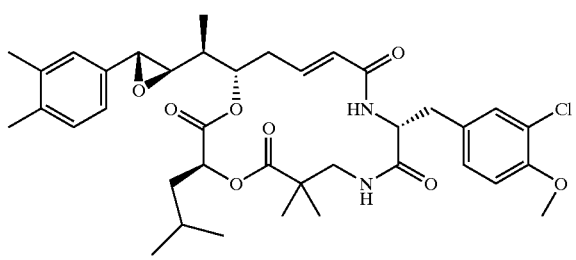

This β epoxide (0.06 g) was prepared from the styrene (shown above) (0.3 g, 0.44 mmol) using 3-chloroperoxybenzoic acid (0.081 g, 0.47 mmol) in 20% yield using the procedure described above: $[\alpha]^{20}_D$ +20.0° (c 1.43, CHCl$_3$); $^1$H NMR (300 MHz, CDCl$_3$) δ 7.26–6.96 (m, 6H), 6.98 (s, 1H), 6.84–6.82 (d, 1H, J=8.5 Hz), 6.79–6.65 (m, 1H), 5.73–5.69 (d, 1H, J=11.9 Hz), 5.68–5.67 (d, 1H, J=4.6 Hz), 5.29–5.15 (m, 1H), 4.83–4.76 (dd, 1H, J=9.7, 2.8 Hz), 4.75–4.58 (m, 1H), 3.86 (s, 3H), 3.61–3.60 (d, 1H, J=1.6 Hz), 3.46–3.38 (dd, 1H, J=13.4, 8.8 Hz), 3.14–2.97 (m, 3H), 2.92–2.89 (dd, 1H, J=7.7, 1.6 Hz), 2.59–2.35 (m, 2H), 2.25 (s, 6H), 1.78–1.58 (m, 3H), 1.28–1.09 (m, 1H), 1.21 (s, 3H), 1.15 (s, 3H), 1.15–1.12 (d, 3H, J=7.8 Hz), 0.85–0.77 (m, 6H); $^{13}$C NMR (63 MHz, CDCl$_3$) δ 177.8, 170.4, 170.3, 164.9, 154.0, 141.7, 137.0, 136.9, 134.0, 130.8, 129.9, 129.5, 128.1, 126.7, 124.6, 123.2, 122.4, 122.3, 75.9, 71.04, 62.8, 59.1, 56.1, 54.3, 46.4, 42.7, 40.7, 39.2, 36.8, 35.2, 24.4, 22.8, 22.6, 21.0, 19.7, 19.4, 13.6; IR (KBr) 3419, 2962, 1752, 1721, 1681, 1654, 1534, 1504, 1473, 1442, 1302, 1282, 1259, 1192, 1126, 1066 cm$^{-1}$; Anal. (C$_{38}$H$_{49}$ClN$_2$O$_8$) C, H, N.

EXAMPLE 55

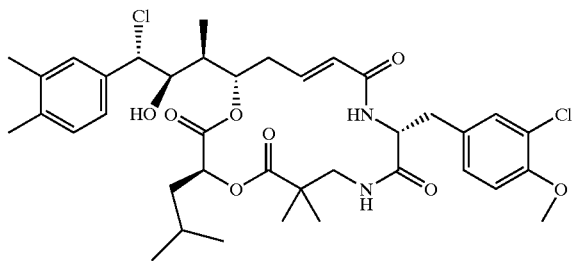

To a solution of the styrene (shown above) (0.492 g, 0.72 mmol) in 2.4 mL CH$_2$Cl$_2$ at 0° C. was added 3-chloroperoxybenzoic acid (0.137 g, 0.79 mmol) and toluene (1.2 mL) and stirring continued at 0° C. for 30 minutes. The ice-bath was removed and the reaction allowed to stir at room temperature for 24 hours. After diluting with 10 mL CH$_2$Cl$_2$, the solution was washed with 10% Na$_2$SO$_5$ (1×10 mL), H$_2$O (1×10 mL), 10% NaHCO$_3$ (1×10 mL) and dried over Na$_2$SO$_4$. Concentration provided a mixture of the b/a crude epoxides in a 2:1 ratio.

The crude epoxides (0.445 g, 0.638 mmol) were dissolved in 10 mL dry CHCl$_3$ cooled to −60° C. and treated with trimethylsilyl chloride (0.2 mL, 1.5 mmol). Stirring was continued for 90 minutes and the solution was concentrated in vacuo. The crude chlorohydrins were purified by reverse-phase HPLC (CH$_3$CN/H$_2$O) to give the product (shown above) (0.115 g) in 21% yield as a white solid: $[\alpha]^{20}_D$ −45.9° (c 0.59, CHCl$_3$); $^1$H NMR (300 MHz, CDCl$_3$) δ 7.26–7.01 (m, 5H), 6.85–6.82 (d, 1H, J=8.4 Hz), 6.80–6.71 (m, 1H), 5.71–5.66 (d, 1H, J=15.1 Hz), 5.50–5.47 (d, 1H, J=7.6 Hz), 5.13–5.08 (t, 1H, J=8.8 Hz), 4.89–4.84 (m, 2H), 4.81–4.71 (m, 1H), 4.09–4.06 (d, 1H, J=9.4 Hz), 3.87 (s, 3H), 3.44–3.37 (dd, 1H, J=13.4, 8.4 Hz), 3.16–3.06 (m, 3H), 2.60–2.54 (m, 2H), 2.26 (s, 6H), 2.26–2.14 (m, 1H), 1.89–1.81 (m, 1H), 1.70–1.62 (m, 2H), 1.58–1.46 (m, 2H) 1.23 (s, 3H), 1.17 (s, 3H), 0.97–0.95 (d, 3H, J=6.6 Hz), 0.93–0.90 (m, 6H); $^{13}$C NMR (63 MHz, CDCl$_3$) δ 177.7, 170.5, 170.1, 165.2, 153.9, 142.3, 137.7, 137.3, 135.1, 130.7, 130.2, 129.8, 128.5, 128.1, 124.6, 124.4, 122.3, 112.2, 75.9, 74.2, 71.2, 68.8, 56.0, 54.4, 46.4, 42.7, 39.6, 38.4, 36.2, 35.2, 24.8, 22.9, 22.8, 22.7, 21.7, 19.8, 19.5, 8.6; IR (KBr) 3421, 2960, 1756, 1721, 1675, 1504, 1258, 1195, 1151, 1126, 1066 cm$^{-1}$; Anal. (C$_{38}$H$_{50}$ClN$_2$O$_8$) C, H, N.

EXAMPLE 56

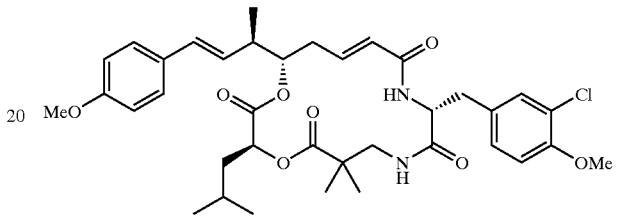

Styrene (shown above) (0.21 g) was prepared from aldehyde 18 (0.5 g, 0.87 mmol) and 4-methoxybenzyl triphenylphosphonium chloride (0.47 g, 1.12 mmol) in 36% yield according to the procedure described above for styrene 20: $[\alpha]^{20}_D$ +31.6° (c 1.03, CHCl$_3$); $^1$H NMR (300 MHz, CDCl$_3$) δ 7.26–7.23 (d, 3H, J=8.4 Hz), 7.20–7.19 (d, 1H, J=1.8 Hz), 7.07–7.03 (dd, 1H, J=8.4, 1.9 Hz), 6.84–6.81 (d, 3H, J=8.5 Hz), 6.80–6.7 (m, 1H), 6.36–6.31 (d, 1H, J=15.8 Hz), 5.89–5.81 (dd, 1H, J=15.8, 8.8 Hz), 5.78–5.73 (d, 1H, J=13.7 Hz), 5.68–5.66 (d, 1H, J=7.9 Hz), 5.05–4.99 (ddd, 1H, J=10.6, 6.6, 1.6 Hz), 4.87–4.82 (dd, 1H, J=9.7, 3.1 Hz), 4.78–4.7 (m, 1H), 3.86 (s, 3H), 3.79 (s, 3H), 3.45–3.37 (dd, 1H, J=13.4, 8.6 Hz), 3.15–3.0 (m, 3H), 2.6–2.25 (m, 3H), 1.7–1.3 (m, 3H), 1.22 (s, 3H), 1.15 (s, 3H), 1.12–1.1 (d, 3H, J=6.8 Hz), 0.76–0.75 (d, 3H, J=2.9 Hz), 0.74–0.73 (d, 3H, J=2.8 Hz); $^{13}$C NMR (63 MHz, CDCl$_3$) δ 177.8, 170.5, 170.4, 165.1, 159.1, 153.9, 142.1, 135.8, 131.0, 130.8, 129.7, 129.5, 128.2, 127.9, 127.2, 124.5, 122.4, 113.9, 112.3, 77.1, 71.4, 56.0, 55.2, 54.4, 46.4, 42.7, 42.1, 39.4, 36.4, 35.3, 24.5, 22.8, 22.6, 21.2, 17.3; IR (CHCl$_3$) 3422, 3003, 2964, 2936, 2873, 2840, 1746, 1712, 1681, 1651, 1607, 1527, 1512, 1504, 1485, 1465, 1301, 1251 cm$^{-1}$; Anal. (C$_{37}$H$_{47}$ClN$_2$O$_8$) C, H, N.

EXAMPLE 57

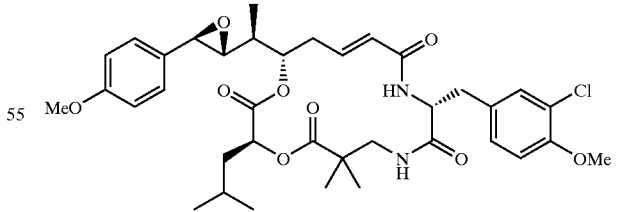

To styrene (shown above) (0.3 g, 0.44 mmol) was added 19 mL of acetone, 9 mL of H$_2$O, 9 mL of CH$_2$Cl$_2$ and solid NaHCO$_3$ (1.2 g, 14.5 mmol) and the mixture was cooled to 0° C. A solution of Oxone (1.08 g, 1.8 mmol) in 9 mL of H$_2$O was prepared and added (2 mL) to the cold styrene mixture. Following 30 min of vigorous stirring at 0° C. an additional 2 mL of Oxone solution was added and again another 2.0 mL was added, following another 30 min, for a total of 6 mL of Oxone solution. The reaction progress was monitored by reverse phase HPLC and was found to be complete after 2.5 hrs of stirring. While still at 0° C., the reaction was quenched with saturated aqueous NaHCO$_3$ (50 mL) and an additional 50 mL of CH$_2$Cl$_2$ was also added. The layers were separated and the organic layer was washed with aq. 10% Na$_2$SO$_3$ (50 mL) followed by saturated aq. NaHCO$_3$ (50 mL) then brine and finally was dried over Na$_2$So$_4$, filtered and concentrated in vacuo. The mixture of b and a epoxides was separated by reverse phase HPLC (45:55) CH$_3$CN:H$_2$O to provide 0.12 g of the b epoxide as a white solid in 39% yield: $[\alpha]^{20}_D$ +25.8° (c 0.66, CHCl$_3$); $^1$H NMR (300 MHz, CDCl$_3$) δ 7.26–7.15 (m, 4H), 7.05–7.03 (d, 1H, J=8.6 Hz), 6.9–6.87 (d, 2H, J=8.6 Hz), 6.85–6.82 (d, 1H, J=8.5 Hz), 6.82–6.7 (m, 1H), 5.74–5.69 (d, 1H, J=15.1 Hz), 5.54–5.52 (d, 1H, J=7.8 Hz), 5.22–5.16 (m, 1H), 4.84–4.7 (m, 2H), 3.87 (s, 3H), 3.81 (s, 3H), 3.63 (s, 1H), 3.46–3.38 (dd, 1H, J=13.5, 8.8 Hz), 3.2–3.0 (m, 3H), 2.91–2.89 (d, 1H, J=7.4 Hz), 2.6–2.38 (m, 2H), 1.8–1.6 (m, 3H), 1.4–1.23 (m, 1H), 1.22 (s, 3H), 1.15 (s, 3H), 1.15–1.12 (d, 3H, J=8.9 Hz), 0.84–0.80 (t, 6H, J=6.0 Hz); $^{13}$C NMR (63 MHz, CDCl$_3$) δ 177.7, 170.5, 170.4, 165.1, 159.8, 153.9, 141.6, 136.8, 130.7, 129.7, 128.6, 128.1, 126.9, 124.6, 122.3, 114.1, 112.2, 75.9, 71.0, 62.8, 58.9, 56.0, 55.2, 54.6, 46.3, 42.7, 40.6, 39.2, 36.8, 35.2, 24.4, 22.8, 22.7, 22.6, 21.1, 13.5; IR (CHCl$_3$) 3423, 3009, 2964, 2936, 2874, 2840, 1751, 1713, 1681, 1653, 1614, 1517, 1504, 1486, 1464, 1442, 1303, 1281, 1257, 1183, 1173, 1152 cm$^{-1}$; Anal. (C$_{37}$H$_{47}$ClN$_2$O$_9$) C, H, N.

EXAMPLE 58

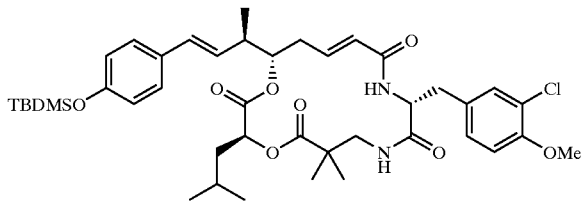

Styrene (shown above) (0.649 g) was prepared from aldehyde 18 (0.911 g, 1.57 mmol) and 4-(tert-butyldimethylsiloxy)benzyl triphenylphosphonium chloride (1.7 g, 3.27 mmol) in 53% yield according to the procedure described above for styrene 20: $[\alpha]^{20}_D$ +30.83° (c 0.52, CHCl$_3$); $^1$H NMR (300 MHz, CDCl$_3$) δ 7.25 (s, 1H), 7.26–7.20 (d, 2H, J=8.5Hz), 7.12 - 7.06 (dd, 1H, J=8.3, 1.6 Hz), 6.92–6.86 (d, 1H, J=8.5 Hz), 6.84–6.78 (d, 2H, J=8.5 Hz), 6.44–6.33 (d, 1H, J=15.9 Hz), 5.95–5.85 (dd, 1H, J=15.8, 8.8 Hz), 5.85–5.77 (d, 1H, J=15.5 Hz), 5.68–5.55 (bd, 1H, J=7.9 Hz), 5.15–5.00 (m, 1H), 4.95–4.80 (dd, 1H, J=10.0, 3.0 Hz), 4.85–4.75 (m, 1H), 3.91 (s, 3H), 3.53–3.43 (dd, 1H, J=13.4, 8.6 Hz), 3.23–3.08 (m, 3H), 2.65–2.50 (m, 2H), 2.50–2.35 (m, 3H), 1.75–1.60 (m, 2H), 1.45–1.36 (m, 1H), 1.27 (s, 3H), 1.20 (s, 3H), 1.16–1.13 (d, 3H, J=6.8 Hz), 1.01 (s, 9H), 0.85–0.74 (m, 6H), 0.22 (s, 6H); $^{13}$C NMR (63 MHz, CDCl$_3$) δ 177.8, 170.5, 170.4, 165.1, 155.2, 153.9, 142.1, 131.1, 130.8, 130.1, 129.7, 128.2, 128.1, 127.1, 124.5, 122.4, 120.2, 112.2, 71.4, 56.0, 54.4, 46.4, 42.7, 42.2, 39.4, 36.5, 35.3, 25.6, 24.5, 22.8, 22.7, 21.2, 18.1, 17.3, –4.5; IR (CHCl$_3$) 3422, 3030, 3008, 2961, 2932, 2899, 2860, 1745, 1712, 1681, 1604, 1527, 1509, 1485, 1442, 1370, 1339, 1303, 1258, 1169, 1151, 1067, 1007, 970, 912, 841, 822, 792 cm$^{-1}$; Anal. (C$_{42}$H$_{59}$ClN$_2$O$_8$Si) C, H, N.

EXAMPLE 59

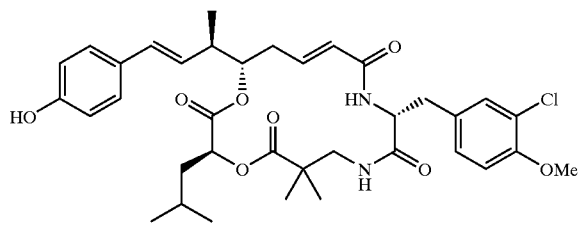

To a –70° C. solution of the silyl protected phenol (0.084 g, 0.107 mmol), in 4 mL of dry THF, was added a 1.0 M THF solution of tetrabutylammonium fluoride (TBAF) (0.11 mL, 0.11 mmol). The light yellow solution was stirred at –70° C. for 30 minutes, then quenched with 2 mL of saturated NH$_4$Cl and extracted with CH$_2$Cl$_2$ (3×25 mL). The combined organic extracts were dried over MgSO$_4$, filtered and concentrated in vacuo. Purification of the crude product by radial PLC (silica gel, 50–100% EtOAc/hexanes) gave the desired alcohol (0.067 g) in 93% yield as a white solid: $[\alpha]^{20}_D$ +30.83° (c 0.52, CHCl$_3$); $^1$H NMR (300 MHz, CDCl$_3$) δ 7.40–7.32 (m, 1H), 7.28–7.20 (m, 3H), 7.13–7.05 (dd, 1H, J=8.3, 1.6 Hz), 6.95–6.75 (m, 5H), 6.57 (s, 1H), 6.42–6.33 (d, 1H, J=15.9 Hz), 5.93–5.83 (dd, 1H, J=15.8, 8.8 Hz), 5.83–5.78 (d, 1H, J=15.5 Hz), 5.75–5.73(bd, 1H, J=7.9 Hz), 5.15–5.00 (m, 1H), 4.93–4.85 (dd, 1H, J=10.0, 3.0 Hz), 4.85–4.75 (m, 1H), 3.90 (s, 3H), 3.54–3.40 (dd, 1H, J=13.4, 8.6 Hz), 3.25–3.02 (m, 3H), 2.65–2.35 (m, 3H), 1.80–1.60 (m, 2H), 1.45–1.36 (m, 1H), 1.27 (s, 3H), 1.20 (s, 3H), 1.17–1.12 (d, 3H, J=6.8 Hz), 0.86–0.74 (d, 6H, J=5.0 Hz); $^{13}$C NMR (63 MHz, CDCl$_3$) δ 177.9, 170.7, 170.6, 156.0, 154.0, 142.6, 137.1, 131.3, 130.8, 129.5, 128.9, 128.1, 127.4, 124.3, 122.5, 115.6, 112.3, 77.2, 71.5, 56.1, 54.5, 46.5, 42.7, 42.1, 39.4, 36.5, 35.3, 24.6, 22.8, 22.7, 21.2, 17.3; IR (CHCl$_3$) 3597, 3421, 3319, 2964, 2935, 2874, 2841, 1746, 1711, 1680, 1652, 1610, 1513, 1504, 1485, 1464, 1259, 1170, 1152, 1067 cm$^{-1}$; Anal. (C$_{36}$H$_{46}$ClN$_2$O$_8$) C, H, N.

EXAMPLE 60

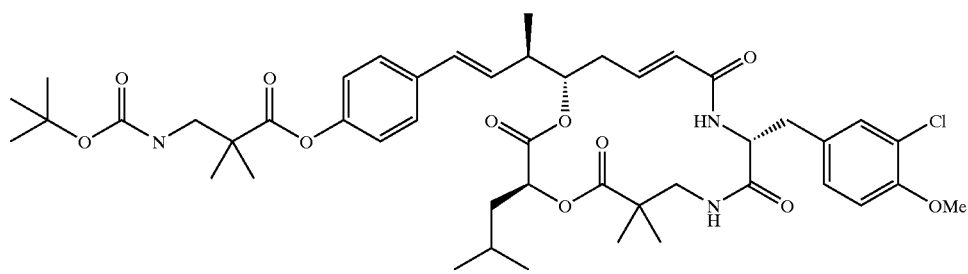

A solution of fragment C' acid (0.040 g, 0.184 mmole) and carbonyldiimidazole (CDI) (0.040 g, 0.25 mmole) in 2 mL of toluene was heated under nitrogen at 45° C. for 45 minutes.

Following the addition of the alcohol (shown above) (0.10 g, 0.15 mmole) in 1 mL of toluene, the reaction was again heated at 45° C. for 4 hrs. Upon cooling to room temperature, the reaction mixture was diluted with EtOAc (100 mL), washed with 0.1 N HCl (1×10 mL), water (1×10 mL), saturated NaHCO$_3$ (1×10 mL) and brine (1×10 mL). The organic layer was dried over MgSO$_4$, filtered and concentrated in vacuo to provide the crude ester as a yellow foam. Purification by radial PLC (silica gel, 50% EtOAc/hexanes) provided the pure ester (0.097) g in 75% yield as a yellow solid: $[\alpha]^{20}_D$ +17.2° (c 0.58, CHCl$_3$); $^1$H NMR (300 MHz, CDCl$_3$) δ 7.40–7.34 (d, 2H, J=8.5 Hz), 7.29–7.22 (m, 3H), 7.13–7.00 (m, 3H), 6.92–6.86 (d, 1H, J=8.8 Hz), 6.86–6.76 (m, 1H), 6.50–6.38 (d, 1H, J=15.9 Hz), 6.10–5.97 (dd, 1H, J=15.8, 8.8 Hz), 5.85–5.75 (d, 1H, J=15.1 Hz), 5.55–5.45 (d, 1H, J=7.9 Hz), 5.15–5.06 (m, 1H), 5.06–4.96 (m, 1H), 4.95–4.85 (m, 1H), 4.83–4.72 (dd, 1H, J=10.0, 3.0 Hz), 3.92 (s, 3H), 3.53–3.35 (m, 3H), 3.22–3.06 (m, 3H), 2.65–2.50 (m, 2H), 2.48–2.35 (m, 1H), 1.80–1.65 (m, 2H), 1.49 (s, 9H), 1.40 (s, 6H), 1.27 (s, 3H), 1.21 (s, 3H), 1.20–1.15 (d, 3H, J=6.9 Hz), 0.86–0.77 (d, 6H, J=6.3 Hz); $^{13}$C NMR (63 MHz, CDCl$_3$) δ 177.8, 170.5, 170.4 165.1, 156.0, 153.9, 150.0, 142.0, 134.5, 130.8, 130.6, 130.4, 129.6, 128.2, 126.9, 124.6, 122.4, 121.5, 112.2, 79.2, 71.3, 56.0, 54.4, 48.2, 46.4, 44.0, 42.7, 42.1, 39.5, 36.5, 35.2, 28.3, 24.9, 24.5, 22.9, 22.8, 22.7, 21.3, 17.2; IR (CHCl$_3$) 3425, 2970, 2934, 2874, 1746, 1711, 1684, 1604, 1505, 1442, 1394, 1368, 1305, 1258, 1166, 1123, 1067, 1015, 971 cm$^{-1}$; Anal. (C$_{41}$H$_{55}$ClN$_3$O$_9$) C, H, N.

EXAMPLE 61 for a total of 6 mL of Oxone solution. The reaction progress was monitored by reverse phase HPLC and was found to be complete after 2.5 hrs of stirring. While still at 0° C., the reaction was quenched with saturated aqueous NaHCO$_3$ (50 mL) and an additional 50 mL of CH$_2$Cl$_2$ was also added. The layers were separated and the organic layer was washed with aq. 10% Na$_2$SO, (50 mL) followed by saturated aq. NaHCO$_3$ (50 mL) then brine and finally was dried over Na$_2$SO$_4$, filtered and concentrated in vacuo to give 0.272 g of the crude epoxides as a yellow foam.

To a solution of the epoxides in 4 mL of CH$_2$Cl$_2$ at −60° C. was added trimethylsilyl chloride (0.2 mL, 1.54 mmol). After 3 hours at −60° C., 5 mL of 0.1 N HCl was added to hydrolyze any trimethylsilyl ether and the mixture warmed to room temperature. The layers were separated and the organic layer was dried over MgSO$_4$, filtered and concentrated in vacuo. The crude chlorohydrins were purified twice by radial PLC (silica gel, 50–60–70–100% EtOAc/hexanes) and finally by reverse-phase HPLC (CH$_3$CN/H$_2$O) to give the product (shown above) (0.090 g, 31%) as a white solid: $[\alpha]^{20}_{D+}$42.7° (c 3.0, CHCl$_3$) ); $^1$H NMR (300 MHz, CDCl$_3$) δ 7.48–7.44 (d, 1H, J=8.4 Hz), 7.31–7.26 (m, 4H), 7.16–7.10 (m, 3H), 6.92–6.89 (d, 1H, J=8.4 Hz), 6.87–6.81 (m, 1H), 5.84–5.79 (d, 1H, J=15.1 Hz), 5.58–5.55 (d, 1H, J=7.8 Hz), 5.24–5.19 (t, 1H, J=8.9 Hz), 5.05–4.95 (m, 2H), 4.79–4.75 (m, 1H), 4.72–4.69 (d, 1H, J=9.5 Hz), 4.04–4.01 (dd, 1H, J=1.3, 9.3 Hz), 3.93 (s, 3H), 3.47–3.40 (m, 3H), 3.25–3.06 (m, 3H), 2.75–2.70 (d, 1H, J=13.9 Hz), 2.55–2.41 (m, 2H), 1.90–1.71 (m, 2H), 1.63 (s, 1H), 1.48 (s, 9H), 1.39 (s, 6H), 1.28 (s, 3H), 1.22 (s, 3H), 1.09–1.06 (d, 3H, J=6.9 Hz), 1.0–0.96 (m, 6H); $^{13}$C NMR (63 MHz, CDCl$_3$) δ 177.6, 170.4, 170.2, 165.2, 153.9, 142.3, 136.1, 130.8, 129.7, 129.1, 128.2, 124.5, 122.4, 121.9, 112.2, 76.1, 74.0, 71.1, 61.5, 56.5, 54.4, 46.4, 44.1, 42.7, 39.6, 38.4, 36.3, 35.2, 28.3, 24.8, 22.9, 22.8, 22.7, 21.5, 8.6; IR (CHCl$_3$) 3417, 2974,

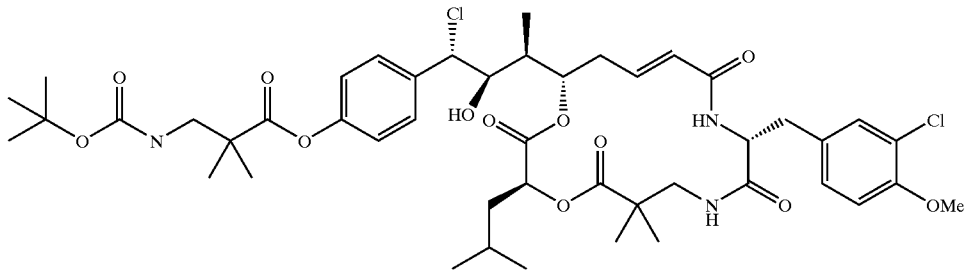

To the styrene (shown above) (0.276 g, 0.32 mmol) was added 12 mL of acetone, 6 mL of H$_2$O, 6 mL of CH$_2$Cl$_2$ and solid NaHCO$_3$ (0.84 g, 10 mmol) and the mixture was cooled to 0° C. A solution of Oxone (0.78 g, 1.27 mmol) in 6 mL of H$_2$O was prepared and added (2 mL) to the cold styrene mixture. Following 30 min of vigorous stirring at 0° C. an additional 2 mL of Oxone solution was added and again another 2.0 mL was added, following another 30 min, 2934, 1755, 1720, 1677, 1505, 1473, 1368, 1320, 1258, 1205, 1167, 1153, 1123, 1066 cm$^{-1}$; FAB HRMS [M−BOC] calcd for (C$_{41}$H$_{56}$Cl$_2$N$_3$O$_{10}$) 820.3343, found 820.3354.

EXAMPLE 62

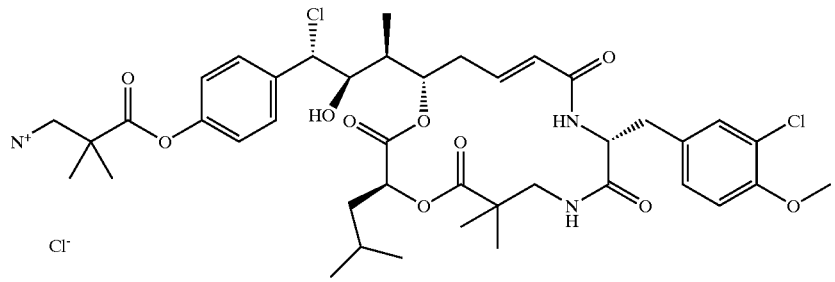

To the BOC protected amine (shown above) (0.070 g, 0.067 mmol) in CH$_2$Cl$_2$ (0.25 mL) was added a 4 M HCl solution (0.1 mL, 0.4 mmol) in 1,4-dioxane. Following 2 hrs of stirring at room temperature the solvents were removed under vacuum and the resulting residue was maintained under high vacuum for 2 days to give the product as a white solid (0.062 g) in 95% yield: [α]$^{20}_D$ +27.68° (c 2.5, CHCl$_3$); $^1$H NMR (300 MHz, CDCl$_3$) δ 7.79–7.76 (d, 1H, J=7.9 Hz), 7.48–7.38 (m, 2H), 7.27–7.26 (d, 1H, J=1.2 Hz), 7.17–7.08 (m, 3H), 6.98–6.95 (d, 1H, J=8.5 Hz), 6.71–6.60 (m, 1H), 5.95–5.90 (d, 1H, J=15.2 Hz), 5.14–5.01 (m, 2H), 4.50–4.46 (dd, 1H, J=3.0, 11.0 Hz), 3.99–3.96 (d, 1H, J=9.1 Hz), 3.82 (s, 3H), 3.49–3.42 (m, 1H), 3.19 (s, 2H), 3.2–3.06 (m, 2H), 2.77–2.68 (m, 2H), 2.49–2.46 (t, 1H, J=6.8 Hz), 2.44–2.31 (q, 1H, J=11.4 Hz), 1.85–1.65 (m, 2H), 1.60–1.50 (m, 1H), 1.46 (s, 6H), 1.20 (s, 3H), 1.16 (s, 3H), 1.08–0.94 (m, 9H); $^{13}$C NMR (63 MHz, CDCl$_3$) δ 178.9, 175.6, 173.8, 171.9, 155.3, 151.8, 144.2, 139.5, 132.2, 131.5, 130.7, 129.4, CHCl$_3$); $^1$H NMR (300 MHz, CDCl$_3$) δ 7.31 (s, 4H), 7.26–7.21 (m, 1H), 7.2–7.19 (d, 1H, J=1.8 Hz), 7.07–7.03 (dd, 1H, J=8.4, 1.7 Hz), 6.85–6.82 (d, 1H, J=8.4 Hz), 6.82–6.7 (m, 1H), 6.43–6.37 (d, 1H, J=15.9 Hz), 6.05–5.97 (dd, 1H, J=15.9, 8.7 Hz), 5.77–5.72 (d, 1H, J=15.0 Hz), 5.58–5.55 (d, 1H, J=7.9 Hz), 5.08–5.02 (dd, 1H, J=9.4, 6.3 Hz), 4.87–4.83 (dd, 1H, J=10.2, 3.1 Hz), 4.8–4.67 (m, 1H), 4.67 (s, 2H), 3.87 (s, 3H), 3.44–3.37 (dd, 1H, J=13.5, 8.5 Hz), 3.2–3.0 (m, 3H), 2.6–2.3 (m, 3H), 1.8–1.6 (m, 3H), 1.4–1.25 (m, 1H), 1.22 (s, 3H), 1.15 (s, 3H), 1.14–1.12 (d, 3H, J=6.8 Hz), 0.76–0.73 (t, 6H, J=5.5 Hz); $^{13}$C NMR (63 MHz, CDCl$_3$) δ 177.7, 170.7, 170.5, 165.4, 153.8, 142.0, 140.5, 135.9, 131.3, 130.7, 130.0, 129.9, 128.1, 127.1, 126.1, 124.5, 122.2, 112.2, 77.0, 71.3, 64.6, 56.0, 54.6, 46.4, 42.7, 42.1, 39.4, 36.4, 35.2, 24.5, 22.8, 22.6, 21.2, 17.2; IR (CHCl$_3$) 3423, 3011, 2965, 2935, 2874, 2841, 1747, 1712, 1681, 1652, 1528, 1503, 1485, 1442, 1371, 1303, 1259, 1151 cm$^{-1}$; Anal. (C$_{37}$H$_{47}$ClN$_2$O$_8$) C, H, N.

EXAMPLE 64

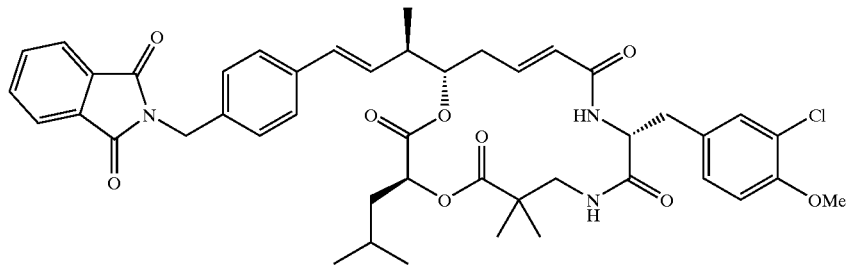

125.2, 123.3, 122.6, 113.5, 77.2, 74.8, 72.6, 63.2, 57.6, 56.7, 50.1, 48.3, 48.0, 47.4, 44.1, 42.7, 41.1, 40.4, 37.8, 36.5, 28.8, 26.2, 23.6, 23.4, 22.2, 9.0; IR (KBr) 3418, 2961, 2934, 1751, 17244, 16,608, 3505, 1474, 1464, 1442, 1303, 1282, 1259, 1203, 1169, 1152, 1126, 1065, 1018; FAB HRMS [M−Cl] calcd for (C$_{41}$H$_{56}$Cl$_2$N$_3$O$_{10}$) 820.3343, found 820.3354.

EXAMPLE 63

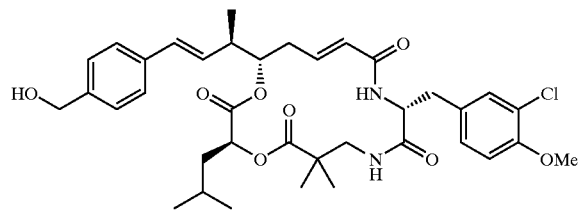

Tetrabutylammonium fluoride (TBAF) (4.0 mL, 4.1 mmol), as a 1.0 M solution in THF, was added dropwise to a −78° C. solution of protected alcohol 20 (3.1 g, 3.69 mmol) in 120 mL of THF. The solution was stirred at −78° C. for 10 min and the dry ice bath was removed allowing it to warm up to room temperature. Following 30 min at room temperature the reaction was quenched with water (80 mL) and ethyl acetate (100 mL). The layers were separated and the aqueous one was extracted with CH$_2$Cl$_2$ (3×50 mL). The combined organic layers were dried over anhydrous Na$_2$SO$_4$, filtered and concentrated in vacuo to yield the free alcohol. Purification by column chromatography (silica gel, 50–70–100% EtOAc/hexanes) yielded 2.51 g (99%) of the pure alcohol 29 as a white solid: [α]$^{20}_D$ +30.0° (c 1.0, To a solution of alcohol 29 (0.13 g, 0.19 mmol) in 2.0 mL of THF, was added triphenyl phosphine (0.065 g, 0.25 mmol), phthalimide (0.037 g, 0.25 mmol) and finally diethyl azodicarboxylate (DEAD) (0.04 mL, 0.25 mmol). The resulting yellow solution was stirred at room temperature for 2 hrs and quenched with H$_2$O (10 mL) and CH$_2$Cl$_2$ (10 mL). The aqueous layer was extracted with CH$_2$Cl$_2$ (2×10 mL) and the combined organic layers were dried over MgSO$_4$, filtered and concentrated in vacuo. The resulting residue was purified by radial PLC (silica gel, 50–60–70% EtOAc/hexanes) to give phthalimide 30 (0.14 g) as a white solid in 90% yield: [α]$^{20}_D$ +19.2° (c 1.0, CHCl$_3$); $^1$H NMR (300 MHz, CDCl$_3$) δ 7.9–7.8 (m, 2H), 7.72–7.69 (m, 2H), 7.39–7.36 (d, 2H, J=8.0 Hz), 7.28–7.26 (d, 2H, J=5.3 Hz), 7.25–7.2 (m, 1H), 7.19–7.18 (d, 1H, J=1.9 Hz), 7.06–7.03 (dd, 1H, J=8.5, 1.9 Hz), 6.85–6.82 (d, 1H, J=8.4 Hz), 6.81–6.7 (m, 1H), 6.39–6.33 (d, 1H, J=15.9 Hz), 6.01–5.93 (dd, 1H, J=15.8, 8.8 Hz), 5.75–5.7 (d, 1H, J=15.4 Hz), 5.47–5.44 (d, 1H, J=7.9 Hz), 5.05–5.0 (dd, 1H, J=9.4, 6.3 Hz), 4.8 (s, 2H), 4.83–4.7 (m, 2H), 3.87 (s, 3H), 3.4–3.36 (dd, 1H, J=13.4, 8.6 Hz), 3.18–3.02 (m, 3H), 2.6–2.25 (m, 3H), 1.65–1.5 (m, 2H), 1.35–1.22 (m, 1H), 1.21 (s, 3H), 1.14 (s, 3H), 1.12–1.09 (d, 3H, J=6.8 Hz), 0.71–0.69 (d, 3H, J=6.4 Hz), 0.65–0.63 (d, 3H, J=6.4 Hz); $^{13}$C NMR (63 MHz, CDCl$_3$) δ 177.8, 170.5, 170.4, 167.8, 165.2, 153.9, 142.0, 136.3, 135.6, 133.9, 131.9, 131.1, 130.7, 130.6, 129.8, 128.9, 128.6, 128.5, 128.1, 126.3, 124.6, 123.2, 122.3, 112.2, 76.9, 71.3, 56.0, 54.5, 46.4, 42.6, 42.1, 41.2, 39.4, 36.4, 35.2, 24.4, 22.8, 22.6, 22.5, 21.1, 17.2; IR (CHCl$_3$) 3421, 2967, 2935, 2873, 2840, 1747, 1716, 1682, 1527, 1503, 1485, 1433, 1395, 1259, 1151.

EXAMPLE 65

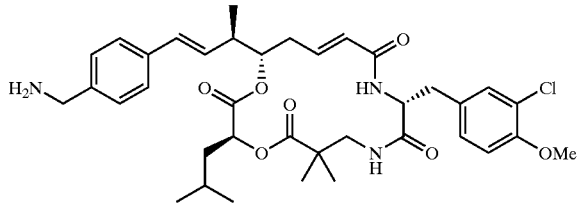

To phthalimide 30 (0.1 g, 0.123 mmol) in 1.8 mL of EtOH, was added n-butylamine (0.04 mL, 0.369 mmol). The solution was heated at 75° C. for 2 days, concentrated in vacuo and purified by radial PLC (silica gel, 10–25% MeOH/CH$_2$Cl$_2$) to provide the free amine 31 (0.048 g) in 57% yield.

EXAMPLE 66

To N-(tert-butoxycarbonyl)sarcosine (0.07 g, 0.37 mmol) in 1.5 mL of DMF was added 1-hydroxybenzotriazole hydrate (HOBT) (0.05 g, 0.37 mmol) and 1-(3-dimethylaminopropyl)-3-ethylcarbodiimide hydrochloride (EDCI) (0.071 g, 0.37 mmol). Following 45 min of stirring at room temperature, amine 31 (0.17 g, 0.25 mmol) in 2.5 mL of DMF was added to the solution dropwise via a double-tipped needle. The resulting mixture was stirred for an additional 3 hrs, quenched with H$_2$O (10 mL) and extracted with CH$_2$Cl$_2$(3×10 mL). The combined organic extracts were dried over MgSO4, filtered and concentrated in vacuo. Purification of the resulting crude product by radial PLC (silica gel, 70–80–100% EtOAc/hexanes) gave the desired amide 32 (0.15 g) in 71% yield as a white solid: [α]$^{20}_D$ +22.4° (c 1.0, CHCl$_3$); $^1$H NMR (300 MHz, CDCl$_3$) δ 7.27–7.1 (m, 6H), 7.04–7.0 (dd, 1H, J=8.5, 1.9 Hz), 6.82–6.79 (d, 1H, J=8.5 Hz), 6.79–6.65 (m, 1H), 6.38–6.32 (d, 1H, J=15.9 Hz), 6.3–6.2 (bs, 1H), 6.01–5.93 (dd, 1H, J=15.9, 8.7 Hz), 5.75–5.70 (d, 1H, J=15.0 Hz), 5.65–5.6 (m, 1H), 5.0–4.99 (dd, 1H, J=9.3, 6.1 Hz), 4.84–4.79 (dd, 1H, J=9.6, 3.6 Hz), 4.74–4.67 (m, 1H), 4.42–4.4 (d, 2H, J=5.7 Hz), 3.87 (s, 2H), 3.84(s, 3H), 3.42–3.34 (dd, 1H, J=13.5, 8.6 Hz), 3.15–3.0 (m, 3H), 2.9 (s, 3H), 2.6–2.25 (m, 3H), 1.8–1.5 (m, 2H), 1.4 (s, 9H), 1.39–1.25 (m, 1H), 1.19 (s, 3H), 1.12 (s, 3H), 1.1–1.08 (d, 3H, J=6.8 Hz), 0.73–0.72 (d, 3H, J=4.4 Hz), 0.71–0.69 (d, 3H, J=4.3 Hz); $^{13}$C NMR (63 MHz, CDCl$_3$) δ 177.7, 170.5, 170.4, 169.2, 165.2, 153.9, 141.9, 137.3, 136.0, 131.1, 130.7, 130.3, 129.8, 128.6, 128.1, 127.7, 126.3, 124.6, 122.3, 112.2, 80.6, 76.9, 71.3, 56.0, 54.5, 53.1, 46.4, 42.8, 42.7, 42.0, 39.4, 36.4, 35.8, 35.2, 28.2, 24.5, 22.8, 22.6, 21.2, 17.1; IR (CHCl$_3$) 3427, 2967, 2935, 2874, 2841, 1747, 1680, 1526, 1504, 1484, 1464, 1442, 1393, 1369, 1302, 1281, 1259, 1151, 1067.

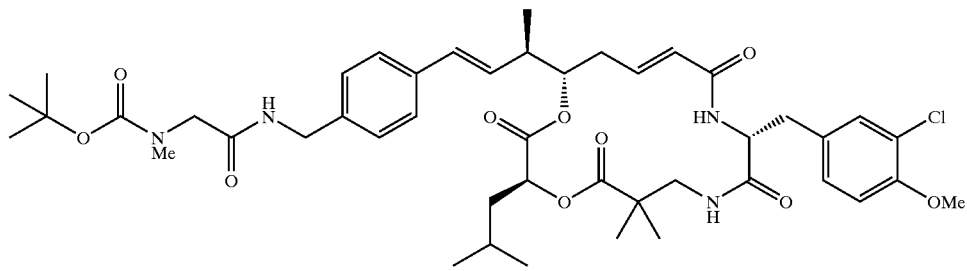

3

EXAMPLE 67

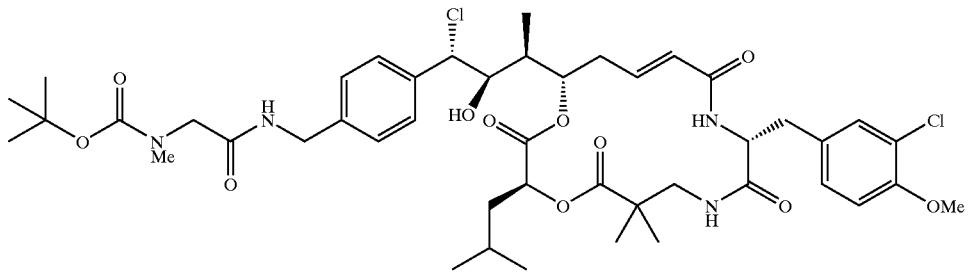

Amide 32 (0.34 g, 0.398 mmol) was epoxidized using mCPBA (0.072 g, 0.42 mmol) in 1.2 mL of $CH_2Cl_2$ according to previously described procedure to give the b and a epoxides in a 2:1 ratio. The resulting crude mixture of epoxides (0.3 g, 0.345 mmol) was dissolved in $CHCl_3$ and cooled to –60° C. TMSCl (0.22 mL, 1.73 mmol) was added and the solution was stirred between –50° C. and –20° C. for 2 hrs. More TMSCl (0.44 mL, 0.173 mmol) was added and the solution was allowed to warm up to room temperature. The solution was concentrated in vacuo and the resulting product was purified twice by column chromatography (70–80% EtOAc/hexanes) and twice by radial PLC (silica gel, 2–5% MeOH/$CH_2Cl_2$) to give the trans chlorohydrin 34 (0.1 g) in 48% yield as a white solid: $[\alpha]^{20}_D$ +46.9° (c 0.85, $CHCl_3$); $^1H$ NMR (300 MHz, $CDCl_3$) δ 7.36–7.34 (d, 2H, J=7.9 Hz), 7.29–7.26 (d, 2H, J=8.3 Hz), 7.21 (s, 2H), 7.08–7.05 (d, 1H, J=8.3 Hz), 6.86–6.83 (d, 1H, J=8.5 Hz), 6.8–6.7 (m, 1H), 6.5–6.2 (bs, 1H), 5.79–5.74 (d, 1H, J=15.2 Hz), 5.64–5.62 (d, 1H, J=7.7 Hz), 5.18–5.12 (t, 1H, J=9.1 Hz), 4.94–4.9 (dd, 1H, J=9.9, 3.5 Hz), 4.8–4.67 (m, 1H), 4.66–4.63 (d, 1H, J=9.6 Hz), 4.47–4.45 (d, 2H, J=5.3 Hz), 4.02–3.98 (d, 1H, J=9.5 Hz), 3.89 (s, 2H), 3.88 (s, 3H), 3.41–3.34 (dd, 1H, J=13.6, 8.5 Hz), 3.2–3.0 (m, 3H), 2.94 (s, 3H), 2.69–2.68 (bdd, 1H, J=14.3, 2.1 Hz), 2.51–2.3 (m, 2H), 1.8–1.6 (m, 3H), 1.42 (s, 10H), 1.22 (s, 3H), 1.17 (s, 3H), 1.03–1.01 (d, 3H, J=6.9 Hz), 0.94–0.9 (t, 6H, J=5.5 Hz); $^{13}C$ NMR (63 MHz, $CDCl_3$) δ 177.6, 170.4, 170.2, 165.2, 153.9, 142.4, 139.1, 130.8, 129.7, 128.3, 128.2, 127.9, 124.4, 122.4, 112.2, 80.7, 76.1, 73.9, 71.2, 61.8, 56.1, 54.4, 53.1, 46.4, 42.7, 39.6, 38.4, 36.3, 35.9, 35.2, 28.2, 24.8, 23.0, 22.9, 22.7, 21.5, 8.5; IR (KBr) 3419, 3317, 2964, 2932, 1755, 1670, 1538, 1504, 1473, 1392, 1368, 1301, 1258, 1151, 1066; FAB HRMS [M+H] calcd for ($C_{45}H_{62}Cl_2N_4O_{11}$) 905.3870, found 905.3876.

EXAMPLE 68

The hydrochloride salt 35 (0.041 g) of BOC protected amine 34 (0.045 g, 0.05 mmol) was prepared in quantitative yield according to the previously described procedure using 4 M HCl in 1,4-dioxane: $^1H$ NMR (300 MHz, MeOD) δ 8.47–8.45 (d, 1H, J=7.7 Hz), 7.79–7.76 (d, 1H, J=8.9 Hz), 7.39–7.36 (d, 2H, J=8.1 Hz), 7.3–7.27 (d, 3H, J=9.0 Hz), 7.17–7.14 (d, 1H, J=8.5 Hz), 6.98–6.95 (d, 1H, J=8.5 Hz), 6.75–6.6 (m, 1H), 5.94–5.89 (d, 1H, J=15.1 Hz), 5.2–5.0 (m, 2H), 4.78–4.75 (d, 1H, J=9.4 Hz), 4.5–4.42 (m, 1H), 4.41 (s, 2H), 4.01–3.98 (d, 1H, J=9.5 Hz), 3.82 (s, 3H), 3.8 (s, 2H), 3.5–3.4 (m, 1H), 3.19–3.13 (dd, 1H, J=14.4, 3.4 Hz), 3.11–3.06 (dd, 1H, J=13.2, 1.9 Hz), 2.8–2.6 (m, 2H), 2.7 (s, 3H), 2.5–2.2 (m, 2H), 1.85–1.45 (m, 3H), 1.3–1.2 (m, 1H), 1.2 (s, 3H), 1.15 (s, 3H), 1.0–0.94 (q, 9H, J=11.3, 6.0 Hz); $^{13}C$ NMR (63 MHz, $CDCl_3$) δ 178.9, 173.7, 171.9, 168.3, 166.3, 155.4, 144.2, 140.5, 139.7, 132.2, 131.5, 129.7, 129.4, 128.8, 125.2, 123.3, 113.5, 77.2, 74.7, 72.6, 63.7, 57.6, 56.6, 50.7, 47.4, 44.1, 43.9, 41.1, 40.4, 37.8, 36.5, 33.7, 26.2, 23.6, 23.4, 22.1, 9.0; IR (KBr) 3410, 3058, 2961, 2933, 1752, 1721, 1675, 1539, 1504, 1463, 1440, 1282, 1259, 1196, 1154, 1127, 1066.

EXAMPLE 69

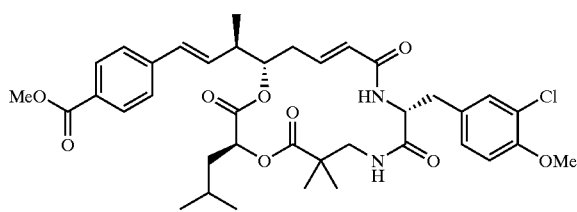

A suspension of sodium hydride (60% suspension) (0.041 g, 1.0 mmol) and 4-carbomethoxybenzyl triphenylphosphonium bromide (0.5 g, 1.0 mmol) in 10 mL of THF was heated at 65° C. for 1 h and cooled back to room temperature. This orange mixture was added dropwise to aldehyde 18 (0.46 g, 0.79 mmol) in THF (10 mL) at –78° C. The resulting solution was warmed up to room temperature, stirred an additional 2 hrs and quenched with sat. $NH_4Cl$ (30 mL) and EtOAc (30 mL). The layers were separated and the aqueous one was further extracted with EtOAc (2×20 mL). The combined organic extracts were washed with brine (30 mL), dried over $MgSO_4$, filtered and concentrated in vacuo. The crude styrene was purified by column chromatography (silica gel, 50–65% EtOAc/hexanes) to give clean styrene (0.129 g) in 23% yield: $[\alpha]^{20}_D$ +29.7° (c 1.15, $CHCl_3$); $^1H$ NMR (300 MHz, $CDCl_3$) δ 8.03–8.0 (d, 2H, J=8.2 Hz), 7.44–7.41 (d, 2H, J=8.3 Hz), 7.3–7.25 (m, 1H), 7.24–7.23 (d, 1H, J=1.6 Hz), 7.11–7.08 (dd, 1H, J=8.3, 1.9 Hz),

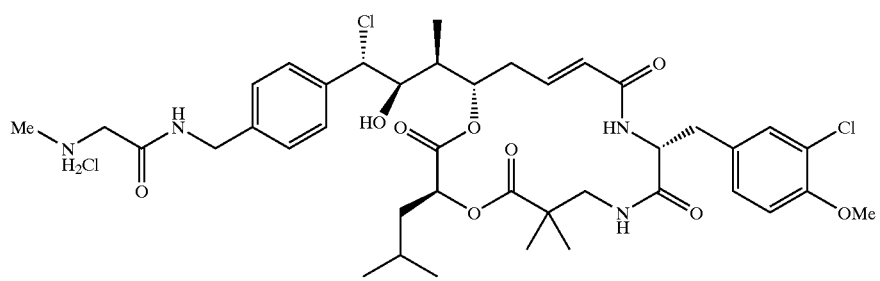

6.89–6.86 (d, 1H, J=8.5 Hz), 6.86–6.8 (m, 1H), 6.52–6.46 (d, 1H, J=15.9 Hz), 6.23–6.15 (dd, 1H, J=15.8, 8.8 Hz), 5.83–5.8 (d, 1H, J=15.3 Hz), 5.64–5.61 (d, 1H, J=7.9 Hz), 5.14–5.09 (dd, 1H, J=9.4, 6.5 Hz), 4.91–4.87 (dd, 1H, J=10.2, 3.6 Hz), 4.85–4.75 (m, 1H), 3.95 (s, 3H), 3.91 (s, 3H), 3.5–3.4 (dd, 1H, J=13.5, 8.7 Hz), 3.2–3.1 (m, 3H), 2.9–2.3 (m, 3H), 1.8–1.6 (m, 3H), 1.4–1.3 (m, 1H), 1.26 (s, 3H), 1.2 (s, 3H), 1.2–1.18 (d, 3H, J=6.9 Hz), 0.8–0.78 (d, 3H, J=5.6 Hz), 0.78–0.76 (d, 3H, J=6.0 Hz); $^{13}$C NMR (63 MHz, CDCl$_3$) δ 177.8, 170.4, 166.7, 165.1, 153.9, 141.8, 141.1, 133.1, 130.8, 129.9, 129.7, 128.9, 128.2, 125.9, 124.6, 122.4, 112.2, 76.8, 71.3, 56.0, 54.4, 52.0, 46.4, 42.7, 42.2, 39.5, 36.5, 35.2, 24.5, 22.8, 22.6, 21.2, 17.1; IR (CHCl$_3$) 3424, 2964, 2936, 2874, 2841, 1748, 1716, 1681, 1608, 1528, 1503, 1485, 1437, 1283, 1259 cm$^{-1}$; Anal. (C$_{38}$H$_{47}$ClN$_2$O$_9$) C, H, N.

EXAMPLE 70

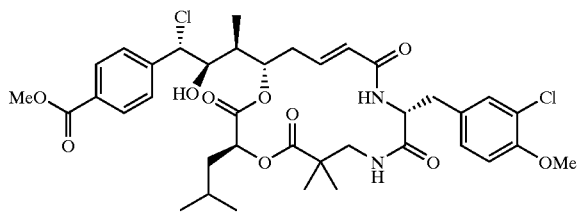

To styrene (shown above) (0.42 g, 0.59 mmol) was added 30 mL of acetone, 15 mL of H$_2$O, 15 mL of CH$_2$Cl$_2$ and solid NaHCO$_3$ (1.7 g, 20.2 mmol) and the mixture was cooled to 0° C. A solution of Oxone (1.4 g, 2.3 mmol) in 12 mL of H$_2$O was prepared and added (2 mL) to the cold styrene mixture. Following 30 min of vigorous stirring at 0° C. an additional 2 mL of Oxone solution was added and the solution was warmed up to room temperature. An additional 2 mL of Oxone solution was added every 2 hrs until the 12 mL was consumed. The reaction was stirred a total of 5 hrs and was quenched with saturated aqueous NaHCO$_3$ (50 mL) and 50 mL of CH$_2$Cl$_2$. The layers were separated and the organic layer was washed with aq. 10% Na$_2$SO$_3$ (50 mL), followed by saturated aq. NaHCO$_3$ (50 mL) then brine and finally was dried over Na$_2$SO$_4$, filtered and concentrated in vacuo. The crude mixture was purified by reverse phase HPLC (45:55) CH$_3$CN:H$_2$O to provide 0.14 g (33% yield) of the b and a epoxides and 0.14 g of a bisepoxidation mixture.

The mixture of b/a epoxides (0.14 g, 0.19 mmol) was dissolved in 3.0 mL of CHCl and cooled to −60° C. Chlorotrimethyl silane (0.1 mL, 0.77 mmol) was added to the −60° C. solution and the mixture was stirred for 1.5 h. More TMSCl (0.1 mL, 0.77 mmol) was added and the solution was allowed to warm up to room temperature. Following 1 h of stirring at room temperature the solution was concentrated and purified by radial PLC (1–2% MeOH/CH$_2$Cl$_2$) to give 0.044 g (30% yield) of the desired chlorohydrin (shown above) as a white solid: [α]$^{20}_D$ +50.0° (c 0.75, CHCl$_3$); $^1$H NMR (300 MHz, CDCl$_3$) δ 8.1–8.08 (d, 2H, J=8.1 Hz), 7.54–7.51 (d, 2H, J=8.2 Hz), 7.3–7.25 (m, 1H), 7.25 (s, 1H), 7.13–7.09 (dd, 1H, J=8.5, 1.5 Hz), 6.91–6.88 (d, 1H, J=8.3 Hz), 6.87–6.78 (m, 1H), 5.86–5.8 (d, 1H, J=15.5 Hz), 5.7–5.6 (m, 1H), 5.24–5.18 (t, 1H, J=9.2 Hz), 4.99–4.95 (dd, 1H, J=10.0, 3.6 Hz), 4.8–4.7 (m, 1H), 4.76–4.73 (d, 1H, J=9.5 Hz), 4.09–4.06 (d, 1H, J=9.6 Hz), 3.97 (s, 3H), 3.93 (s, 3H), 3.45–3.38 (dd, 1H, J=13.6, 8.6 Hz), 3.25–3.0 (m, 3H), 2.75–2.62 (m, 1H), 2.6–2.4 (m, 2H), 1.9–1.6 (m, 3H), 1.5–1.4 (m, 1H), 1.27 (s, 3H), 1.22 (s, 3H), 1.1–1.07 (d, 3H, J=6.95 Hz), 0.98–0.95 (t, 6H, J=5.3 Hz); $^{13}$C NMR (63 MHz, CDCl$_3$) δ 177.5, 170.6, 170.3, 166.3, 165.4, 153.9, 143.8, 142.2, 138.7, 130.7, 130.4, 129.9, 128.1, 128.08, 124.6, 122.3, 112.2, 76.1, 73.8, 71.1, 61.4, 56.0, 54.6, .52.2, 46.4, 42.7, 39.6, 38.4, 36.3, 35.1, 24.8, 23.0, 22.9, 22.7, 21.5, 8.7; IR (CHCl$_1$) 3425, 2962, 2935, 2873, 2842, 1750, 1720, 1680, 1528, 1504, 1484, 1438, 1284, 1259, 1194, 1152, 1114, 1067 cm$^{-1}$; Anal. (C$_{38}$H$_{48}$Cl$_2$N$_2$O$_{10}$) C, H, N.

EXAMPLE 71

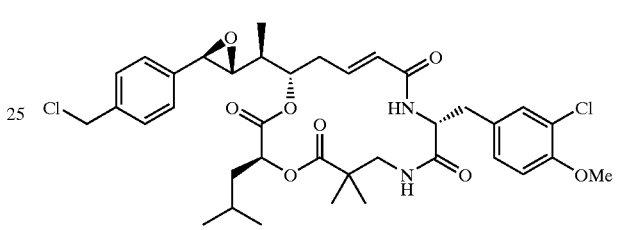

To a 0° C. solution of alcohol 23 (0.32 g, 0.46 mmol) in 8.5 mL of CH$_2$Cl$_2$ was added solid NaHCO, (0.19 g, 2.29 mmol), triphenyl phosphine (0.18 g, 0.69 mmol) and finally N-chlorosuccinimide (0.092 g, 0.69 mmol). The mixture was stirred at 0° C. for 20 min and quenched with sat. aq. NaHCO$_3$ (20 mL). The layers were separated and the aqueous was extracted with CH$_2$Cl$_2$ (3×10 mL). The combined organic layers were washed with brine, dried over Na$_2$SO$_4$, filtered and concentrated in vacuo. The crude yellow solid was purified by radial PLC (silica gel, 20–50% EtOAC/hexanes) to give 0.26 g of the benzyl chloride 36 in a 79% yield as a white solid: [α]$^{20}_D$ +25.6° (c 0.9, CHCl$_3$); $^1$H NMR (300 MHz, CDCl$_3$) δ 7.4–7.38 (d, 2H, J=7.9 Hz), 7.26–7.23 (d, 3H, J=8.3 Hz), 7.19–7.18 (d, 1H, J=1.9 Hz), 7.06–7.03 (dd, 1H, J=8.3, 1.9 Hz), 6.85–6.82 (d, 1H, J=8.4 Hz), 6.8–6.7 (m, 1H), 5.74–5.69 (d, 1H, J=15.4 Hz), 5.49–5.47 (d, 1H, J=7.8 Hz), 5.22–5.17 (m, 1H), 4.85–4.8 (dd, 1H, J=9.7, 3.0 Hz), 4.78–4.7 (m, 1H), 4.6 (s, 2H), 3.9 (s, 3H), 3.69–3.68 (d, 1H, J=1.3 Hz), 3.45–3.38 (dd, 1H, J=13.4, 8.6 Hz), 3.2–3.0 (m, 3H), 2.92–2.89 (dd, 1H, J=7.6, 1.6 Hz), 2.6–2.4 (m, 2H), 1.8–1.6 (m, 3H), 1.4–1.3 (m, 1H), 1.22 (s, 3H), 1.16 (s, 3H), 1.16–1.13 (d, 3H, J=8.6 Hz), 0.86–0.82 (t, 6H, J=6.8 Hz); $^{13}$C NMR (63 MHz, CDCl$_3$) δ 177.8, 175.1, 170.3, 164.9, 154.0, 141.6, 137.7, 137.1, 130.8, 129.5, 128.9, 128.1, 125.9, 124.6, 122.4, 112.3, 77.2, 75.8, 71.1, 63.1, 58.5, 56.1, 54.4, 46.4, 45.7, 42.7, 40.5, 39.3, 36.8, 35.2, 24.5, 22.8, 22.6, 21.2, 13.5; IR (CHCl$_3$) 3416, 3284, 2961, 2933, 2873, 2839, 1752, 1721, 1680, 1658, 1536, 1504, 1473, 1442, 1321, 1302, 1281, 1259, 1192, 1150, 1126, 1066 cm$^{-1}$; Anal. (C$_{37}$H$_{46}$Cl$_2$N$_2$O$_8$) C, H, N.

EXAMPLE 72

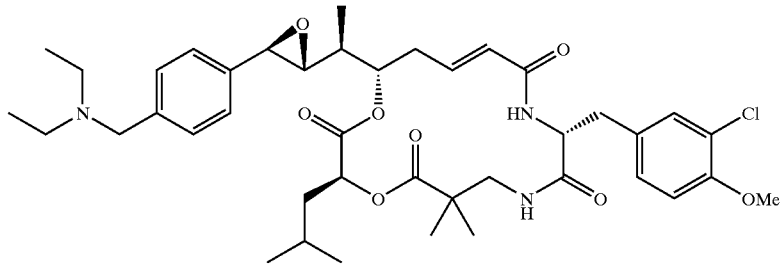

Diethyl amine (0.09 mL, 0.84 mmol) was added to benzyl chloride 36 (0.03 g, 0.042 mmol) in 0.3 mL of THF. The mixture was stirred overnight at room temperature and quenched with sat. aq. $NaHCO_3$ (5 mL). The aqueous layer was extracted with $CH_2Cl_2$ (3×5 mL). The combined organic layers were washed with brine, dried over $Na_2SO_4$, filtered and concentrated in vacuo. The crude yellow solid was purified by radial PLC (silica gel, 50–70–80% EtOAC/hexanes) to give 0.026 g of the amine 37 in a 82% yield as a white solid: $[\alpha]^{20}_D$ +25.9° (c 0.9, $CHCl_3$); $^1H$ NMR (300 MHz, $CDCl_3$) δ 7.35–7.32 (d, 2H, J=7.9 Hz), 7.25–7.12 (m, 4H), 7.06–7.02 (dd, 1H, J=8.4, 1.6 Hz), 6.84–6.82 (d, 1H, J=8.5 Hz), 6.82–6.7 (m, 1H), 5.74–5.69 (d, 1H, J=15.2 Hz), 5.57–5.55 (d, 1H, J=7.8 Hz), 5.22–5.17 (m, 1H), 4.85–4.7 (m, 2H), 3.86 (s, 3H), 3.66 (s, 1H), 3.57 (s, 2H), 3.46–3.38 (dd, 1H, J=13.4, 8.7 Hz), 3.2–3.0 (m, 3H), 2.93–2.91 (d, 1H, J=7.4 Hz), 2.6–2.4 (m, 6H), 1.8–1.6 (m, 3H), 1.4–1.3 (m, 1H), 1.22 (s, 3H), 1.15 (s, 3H), 1.15–1.12 (d, 3H, J=9.2 Hz), 1.07–1.03 (t, 6H, J=7.1 Hz), 0.86–0.82 (t, 6H, J=6.3 Hz); $^{13}C$ NMR (63 MHz, $CDCl_3$) δ 177.9, 170.4, 170.3, 164.9, 154.0, 141.7, 140.1, 135.2, 130.8, 129.6, 129.1, 128.1, 125.4, 124.6, 122.4, 112.3, 77.2, 75.8, 71.1, 62.9, 58.9, 57.1, 56.0, 54.4, 46.6, 46.4, 42.7, 40.6, 39.3, 36.8, 35.2, 24.5, 22.8, 22.6, 21.2, 13.5, 11.5; IR ($CHCl_3$) 3424, 2969, 2936, 2874, 1752, 1711, 1682, 1605, 1527, 1503, 1485, 1303, 1259, 1190, 1151, 1067 $cm^{-1}$; Anal. ($C_{41}H_{56}ClN_3O_8$) C, H, N.

EXAMPLE 73

To a −66° C. solution of epoxide 37 (0.05 g, 0.066 mmol) in 0.8 mL of $CHCl_3$, was added dropwise a 4 M solution of HCl in 1,4-dioxane (0.04 mL, 0.166 mL). The mixture was stirred at ×66° C. for 10 min upon which the dry ice bath was removed allowing the solution to slowly warm up to room temperature. The solvents were removed in vacuo and the resulting salt was placed under high vacuum for 3 days to remove residual dioxane hence yielding 0.054 g of the desired chlorohydrin 38 exclusively in quantitative yield: $[\alpha]^{20}_D$ +29.3° (c 1.0, MeOH ); $^1H$ NMR (300 MHz, MeOD) δ 8.5–8.47 (d, 1H, J=7.5 Hz), 7.79–7.76 (d, 1H, J=8.8 Hz), 7.53 (s, 4H), 7.26–7.25 (d, 1H, J=1.6 Hz), 7.17–7.14 (dd, 1H, J=8.6, 1.6 Hz), 6.97–6.94 (d, 1H, J=8.4 Hz), 6.75–6.6 (m, 1H), 5.96–5.90 (d, 1H, J=15.3 Hz), 5.2–5.0 (m, 2H), 4.85–4.82 (d, 1H, J=8.9 Hz), 4.5–4.4 (m, 1H), 4.33 (S, 2H), 4.02–3.98 (d, 1H, J=9.3 Hz), 3.8 (S, 3H), 3.49–3.42 (dd, 1H, J=13.3, 9.9 Hz), 3.2–3.0 (m, 6H), 2.8–2.6 (m, 2H), 2.5–2.2 (m, 2H), 1.8–1.5 (m, 3H), 1.34–1.3 (m, 7H), 1.2 (s, 3H), 1.15 (s, 3H), 1.01–0.99 (d, 3H, J=7.2 Hz), 0.98–0.94 (t, 6H, J=5.4 Hz); $^{13}C$ NMR (63 MHz, $CDCl_3$) δ 178.9, 173.8, 171.8, 168.3, 155.4, 144.1, 143.4, 132.3, 132.2, 131.5, 131.1, 130.4, 129.4, 125.2, 123.3, 113.5, 77.2, 74.8, 72.6, 63.2, 57.6, 56.7, 56.66, 48.0, 47.5, 44.1, 41.1, 40.4, 37.8, 36.5, 26.2, 23.6, 23.4, 22.2, 9.07, 9.0; IR (KBr) 3414, 2960, 2934, 1751, 1721, 1671, 1521, 1504, 1463, 1443, 1259, 1197, 1155, 1127, 1065 $cm^{-1}$.

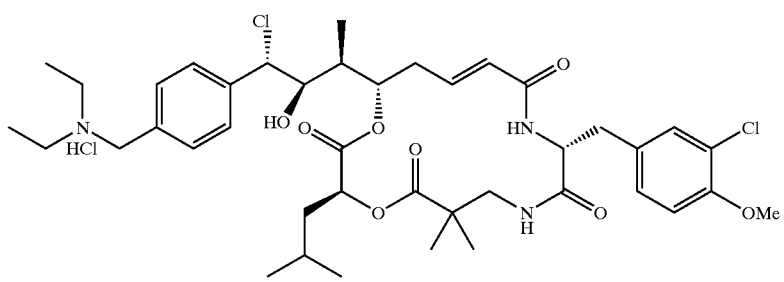

EXAMPLE 74

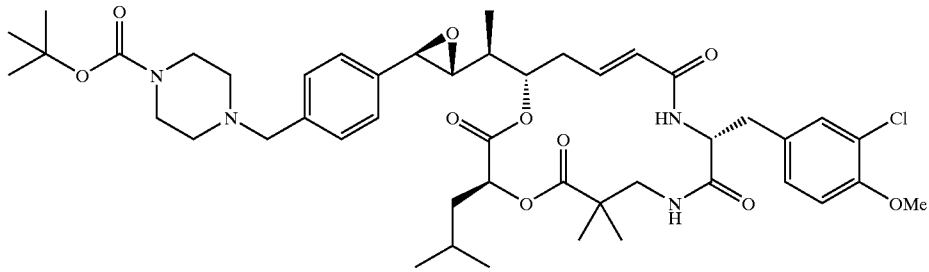

The epoxide (shown above) (0.147 g) was prepared in 81% yield, according to the procedure described above from benzyl chloride 36 (0.15 g, 0.21 mmol) and N-(tert-butoxycarbonyl)piperazine (0.195 g, 1.05 mmol): $[\alpha]^{20}_D$ +25.4° (c 0.65, CHCl$_3$); $^1$H NMR (300 MHz, CDCl$_3$) δ 7.37–7.23 (m, 5H), 7.11–7.08 (d, 1H, J=8.6 Hz), 6.9–6.87 (d, 1H, J=8.5 Hz), 6.86–6.72 (m, 1H), 5.78–5.73 (d, 1H, J=15.2 Hz), 5.53–5.5 (d, 1H, J=7.7 Hz), 5.28–5.23 (m, 1H), 4.88–4.70 (m, 2H), 3.9 (s, 3H), 3.7 (s, 2H), 3.54 (s, 2H), 3.5–3.4 (m, 5H), 3.2–3.05 (m, 3H), 3.0–2.95 (d, 1H, J=7.4 Hz), 2.65–2.4 (m, 6H), 1.85–1.6 (m, 3H), 1.5 (s, 9H), 1.45–1.4 (m, 1H), 1.27 (s, 3H), 1.2 (s, 3H), 1.2–1.18 (d, 3H, J=8.3 Hz), 0.91–0.87 (t, 6H, J=6.1 Hz)); $^{13}$C NMR (63 MHz, CDCl$_3$) δ 177.9, 170.3, 170.26, 164.9, 154.7, 154.0, 141.7, 138.4, 135.6, 130.8, 129.5, 129.3, 128.1, 125.5, 124.6, 122.4, 112.3, 79.5, 77.2, 75.8, 71.1, 62.9, 62.6, 58.8, 56.1, 54.4, 52.8, 46.3, 42.7, 40.6, 39.3, 36.7, 35.2, 28.3, 24.5, 22.8, 22.6, 21.2, 13.4; IR (CHCl$_3$) 3425, 3008, 2965, 2937, 2874, 2817, 1752, 1709, 1683, 1527, 1484, 1463, 1459, 1427, 1367, 1259, 1167, 1150 cm$^{-1}$; FAB HRMS [M–BOC] calcd for (C$_{46}$H$_{64}$ClN$_4$O$_{10}$) 867.4311, found 867.4300.

EXAMPLE 75

To a –66° C. solution of the epoxide (shown above) (0.135 g, 0.156 mmol) in 3.0 mL of CHCl$_3$ was added dropwise trimethylsilyl chloride (0.16 mL, 1.2 mL). The mixture was stirred at –66° C. for 2 hrs and additional TMSCl was added (0.16 mL, 1.2 mL). Following another 1 h at –66° C. the ice bath was removed allowing the solution to slowly warm up to room temperature. The solvents were removed in vacuo and the resulting solid was purified by radial PLC (silica gel, 2–5% MeOH/CH$_2$Cl$_2$) to give 0.13 g of the chlorohydrin (shown above) in 92% yield: $[\alpha]^{20}_D$ +50.0° (c 1.0, CHCl$_3$); $^1$H NMR (300 MHz, CDCl$_3$) δ 7.34 (s, 4H), 7.21–7.2 (d, 2H, J=1.4 Hz), 7.08–7.05 (dd, 1H, J=8.6, 1.6 Hz), 6.86–6.83 (d, 1H, J=8.4 Hz), 6.82–6.7 (m, 1H), 5.8–5.75 (d, 1H, J=15.1 Hz), 5.65–5.62 (d, 1H, J=7.8 Hz), 5.2–5.1 (m, 1H), 5.0–4.7 (m, 2H), 4.66–4.63 (d, 1H, J=9.7 Hz), 4.02–4.0 (d, 1H, J=9.6 Hz), 3.88 (s, 3H), 3.49–3.48 (d, 2H, J=4.2 Hz), 3.45–3.3 (m, 5H), 3.2–3.0 (m, 3H), 2.7–2.3. (m, 7H), 1.8–1.6 (m, 3H), 1.45 (s, 10H), 1.23 (s, 3H), 1.17 (s, 3H), 1.04–1.02 (d, 3H, J=6.9 Hz), 0.93–0.91 (d, 6H, J=6.3 Hz); $^{13}$C NMR (63 MHz, CDCl$_3$) δ 177.5, 170.5, 170.2, 165.2, 154.6, 153.9, 142.3, 139.1, 137.3, 130.8, 129.8, 129.5, 128.1, 127.9, 124.5, 122.3, 112.2, 79.5, 76.0, 73.9, 71.1, 62.4, 61.9, 56.1, 54.5, 52.8, 46.4, 42.7, 39.6, 38.4, 36.4, 35.2, 28.3, 24.7, 23.0, 22.9, 22.7, 21.5, 8.6; IR (CHCl$_3$) 3424, 3007, 2966, 2936, 2872, 2820, 1751, 1712, 1682, 1528, 1504, 1483, 1426, 1367, 1259, 1168, 1150, 1127, 1067, 1006 cm$^{-1}$; Anal. (C$_{46}$H$_{64}$ClN$_4$O$_{10}$) C, H, N.

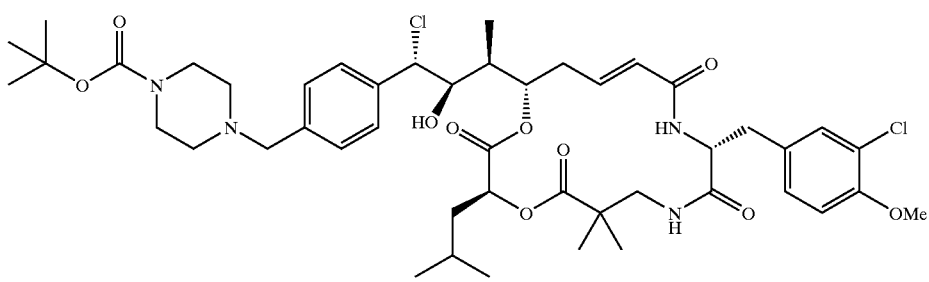

EXAMPLE 76

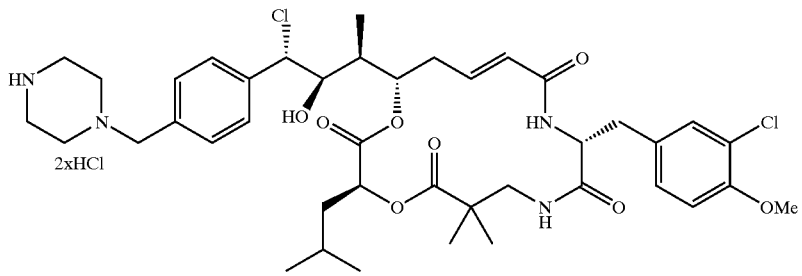

The dihydrochloride salts (0.116 g) of BOC protected piperazine (0.122 g, 0.13 mmol) were prepared in quantitative yield according to the previously described procedure using 4 M HCl in 1,4-dioxane (0.32 ml, 1.3 mmol): $[\alpha]^{20}_D$ +26.3° (c 0.7, MeOH); $^1$H NMR (300 MHz, MeOD) δ 8.47–8.45 (d, 1H, J=7.5 Hz), 7.78–7.75 (d, 1H, J=9.2 Hz), 7.6–7.52 (q, 4H, J=16.9, 7.9 Hz), 7.27–7.26 (d, 1H, J=1.15 Hz), 7.18–7.14 (dd, 1H, J=8.6, 1.8 Hz), 6.98–6.95 (d, 1H, J=8.4 Hz), 6.75–6.6 (m, 1H), 5.95–5.9 (d, 1H, J=15.4 Hz), 5.2–5.0 (m, 2H), 4.85–4.82 (d, 1H, J=9.9 Hz), 4.5–4.4 (m, 1H), 4.4 (s, 2H), 4.0–3.98 (d, 1H, J=9.3 Hz), 3.8 (s, 3H), 3.6–3.4 (m, 9H), 3.32–3.29 (d, 1H, J=11.3 Hz), 3.19–3.13 (dd, 1H, J=14.8, 3.5 Hz), 3.1–3.06 (d, 1H, J=13.7 Hz), 2.8–2.6 (m, 2H), 2.5–2.3 (m, 2H), 1.85–1.5 (m, 3H), 1.3–1.2 (m, 1H), 1.2 (s, 3H), 1.15 (s, 3H), 1.02–0.95 (q, 9H, J=13.4, 6.3 Hz); $^{13}$C NMR (63 MHz, CDCl$_3$) δ 178.8, 173.7, 171.9, 168.3, 155.4, 144.2, 143.7, 132.8, 132.2, 131.5, 130.4, 129.9, 129.4, 125.2, 123.3, 113.5, 77.2, 74.8, 72.6, 63.1, 61.2, 57.6, 56.7, 49.2, 47.5, 44.1, 42.1, 41.1, 40.3, 37.8, 36.5, 26.3, 23.7, 23.4, 22.2, 9.0; IR (KBr) 3415, 2960, 2933, 2455, 1749, 1721, 1671, 1504, 1475, 1442, 1304, 1258, 1197, 1152, 1126, 1065, 1012 cm$^{-1}$; FAB HRMS [M–HCl$_2$] calcd for ($C_{41}H_{57}Cl_2N_4O_8$) 803.3553, found 803.3563.

EXAMPLE 77

Epoxide (shown above) (0.15 g) was prepared in 78% yield, according to the procedure described above from benzyl chloride 36 (0.16 g, 0.22 mmol) and tert-butyl-N-(2-aminoethyl)carbamate (0.35 g, 2.22 mmol): $[\alpha]^{20}_D$ +22.3° (c 1.0, CHCl$_3$); $^1$H NMR (300 MHz, CDCl$_3$) δ 7.41–7.38 (d, 2H, J=7.8 Hz), 7.31 (s, 1H), 7.26–7.24 (d, 3H, J=8.0 Hz), 7.11–7.08 (dd, 1H, J=8.4, 1.7 Hz), 6.88–6.86 (d, 1H, J=8.4 Hz), 6.86–6.72 (m, 1H), 5.88–5.8 (bs, 1H), 5.78–5.73 (d, 1H, J=15.2 Hz), 5.28–5.22 (m, 1H), 5.2–5.08 (bs, 1H), 4.95–4.7 (m, 2H), 3.91 (s, 3H), 3.87 (s, 2H), 3.7 (s, 1H), 3.45–3.38 (dd, 1H, J=13.4, 8.4 Hz), 3.35–3.0 (m, 5H), 2.96–2.93 (dd, 1H, J=7.5, 1.2 Hz), 2.89–2.78 (m, 2H), 2.65–2.4 (m, 2H), 1.85–1.65 (m, 3H), 1.49 (s, 9H), 1.48–1.3 (m, 1H), 1.27 (s, 3H), 1.2 (s, 3H), 1.19–1.17 (d, 3H, 7.1 Hz), 0.91–0.87 (t, 6H, J=6.8 Hz); $^{13}$C NMR (63 MHz, CDCl$_3$) δ 177.7, 170.4, 165.0, 156.0, 153.9, 141.5, 139.9, 135.6, 130.7, 129.7, 128.5, 128.1, 125.6, 124.7, 122.3, 112.2, 77.2, 75.7, 71.0, 63.0, 58.8, 56.0, 54.5, 52.9, 48.5, 46.3, 42.7, 40.5, 39.3, 36.8, 35.2, 28.3, 24.5, 22.83, 22.8, 22.6, 21.2, 13.5; IR (CHCl$_3$) 3425, 3009, 2967, 2936, 2874, 2841, 1751, 1709, 1685, 1504, 1368, 1280, 1259, 1165, 1153, 1067 cm$^{-1}$; Anal. ($C_{44}H_{61}ClN_4O_{10}$) C, H, N.

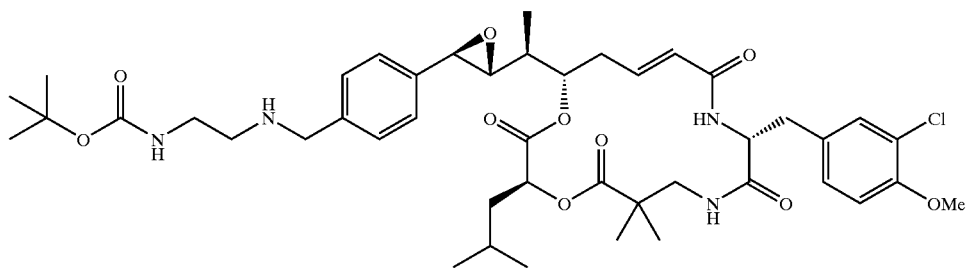

EXAMPLE 78

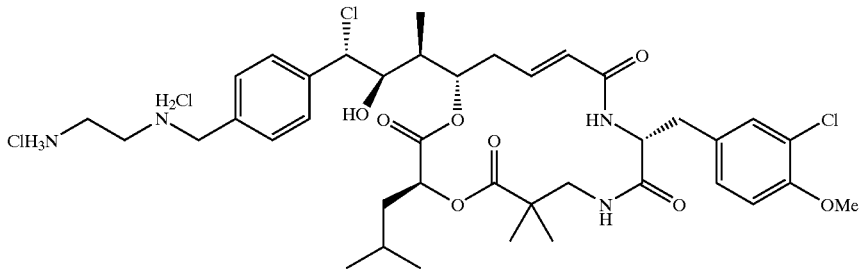

To a −78° C. solution of the epoxide (shown above) (0.065 g, 0.076 mmol) in 0.9 mL of $CH_2Cl_2$ was added dropwise 4 M HCl in 1,4-dioxane (0.09 ml, 0.38 mmol). The solution was stirred at −78° C. for 30 min and then was allowed to slowly warm up to room temperature. It was stirred an additional 2 hrs at room temperature and was concentrated in vacuo to yield the chlorohydrin (shown above) (0.063 g) in quantitative yield: $[\alpha]^{20}_D$ +16.6° (c 1.0, MeOH ); $^1$H NMR (300 MHz, $CDCl_3$) δ 8.54–8.52 (d, 1H, J=7.7 Hz), 7.84–7.81 (dd, 1H, J=8.8, 1.7 Hz), 7.63–7.53 (q, 4H, J=20.0, 8.2 Hz), 7.31–7.3 (d, 1H, J=2.0 Hz), 7.22–7.18 (dd, 1H, J=8.4, 2.0 Hz), 7.02–6.99 (d, 1H, J=8.5 Hz), 6.8–6.7 (m, 1H), 6.0–5.92 (d, 1H, J=15.0 Hz), 5.2–5.0 (m, 2H), 4.9–4.8 (m, 1H), 4.6–4.4 (m, 1H), 4.3 (s, 2H), 4.07–4.03 (dd, 1H, J=9.5, 1.4 Hz), 3.86 (s, 3H), 3.6–3.1 (m, 7H), 2.82–2.7 (m, 2H), 2.6–2.3 (m, 2H), 1.9–1.6 (m, 3H), 1.25 (s, 3H), 1.2 (s, 3H), 1.05–0.99 (m, 9H); $^{13}$C NMR (63 MHz, $CDCl_3$) δ 178.8, 173.8, 171.9, 168.3, 155.3, 144.2, 143.1, 132.2, 131.5, 131.4, 130.3, 129.4, 125.2, 123.2, 113.5, 77.2, 74.7, 72.6, 63.2, 57.6, 56.7, 52.4, 47.5, 45.5, 44.1, 41.1, 40.3, 37.8, 36.9, 36.5, 26.3, 23.7, 23.5, 22.2, 9.0; IR (KBr) 3412, 2961, 2933, 1749, 1721, 1663, 1504, 1462, 1442, 1259, 1199, 1152, 1126, 1065 cm$^{-1}$; FAB HRMS [M-HCl$_2$] calcd for ($C_{39}H_{55}Cl_2N_4O_8$) 777.3397, found 777.3407.

The styrene (shown above) (1.2 g) as a mixture of E:Z isomers was prepared from aldehyde 18 (1.0 g, 1.73 mmol) and 4-(ethyl-2-tert-butyldimethylsiloxy)benzyl triphenylphosphonium bromide (1.23 g, 2.08 mmol) in 86% yield according to the procedure described above for styrene 20.

The mixture of isomers was dissolved in toluene (50 mL) and heated to reflux in the presence of 1,1'-azobis (cyclohexanecarbonitrile) (VAZO) (0.040 g, 0.16 mmol) and thiophenol (0.061 mL, 0.59 mmol) for 3 hours. After concentration the residue was purified by radial PLC (20–75% EtOAc/hexanes) to give the E isomer (0.813 g, 68%) as a white foam: $[\alpha]^{20}_D$ +35.6° (c 0.56, MeOH ); $^1$H NMR (300 MHz, $CDCl_3$) δ 7.26–7.12 (m, 6H), 7.07–7.04 (d, 1H; J=8.5 Hz), 6.85–6.82 (d, 1H, J=8.4 Hz), 6.83–6.70 (m, 1H), 6.40–6.35 (d, 1H, J=15.8 Hz), 6.0–5.92 (dd, 1H, J=15.4, 8.7 Hz), 5.77–5.72 (d, 1H, J=15.2 Hz), 5.46–5.43 (d, 1H, J=7.7 Hz), 5.07–5.02 (m, 1H), 4.86–4.83 (m, 1H), 4.82–4.74 (m, 1H), 3.88 (s, 3H), 3.78–3.74 (t, 2H, J=7.1 Hz), 3.44–3.37 (dd, 1H, J=12.5, 8.6 Hz), 3.15–3.08 (m, 3H), 2.81–2.77 (t, 2H, J=7.1 Hz), 2.57–2.52 (m, 2H), 2.43–2.35 (m, 1H), 1.74–1.56 (m, 2H), 1.38–1.23 (m, 1H), 1.22 (s, 3H), 1.16 (s, 3H), 1.13–1.11 (d, 3H, J=6.8 Hz), 0.88 (s, 9H), 0.84–0.72 (m, 6H), 0.0 (s, 6H); $^{13}$C NMR (75 MHz, $CDCl_3$) δ 177.9, 170.5, 170.3, 165.1, 154.0, 142.2, 138.6, 134.6, 131.5, 130.9, 129.6, 129.4, 128.2, 126.0, 125.3, 124.5, 122.5, 112.3, 92.9, 77.0, 71.4, 64.4, 56.1, 54.3, 46.5, 42.7, 42.2, 39.4, 39.2, 36.5, 35.3, 25.9, 24.5, 22.8, 22.7, 22.6, 21.2, 17.2, −5.44; IR ($CHCl_3$) 3423, 2959, 2931, 2858, 1747, 1712, 1681, 1605, 1527, 1503, 1485, 1442, 1370, 1339, 1303, 1281, 1258, 1194, 1151, 1095, 1067, 1025, 1007, 838 cm$^{-1}$; Anal. ($C_{44}H_{63}ClN_2O_8Si$) C, H, N.

EXAMPLE 79

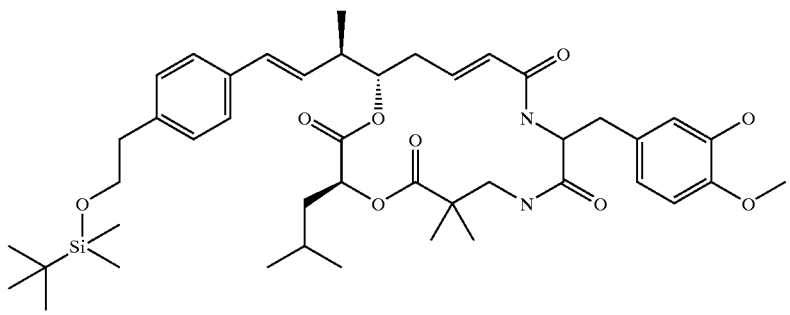

EXAMPLE 80

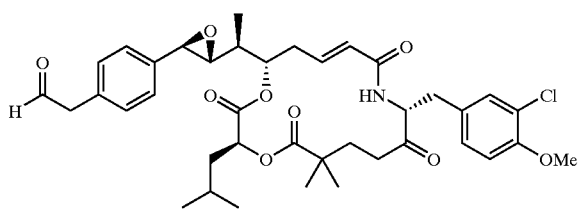

Pyridine (0.06 mL, 0.76 mmol) followed by Dess-Martin reagent (0.161 g, 0.379 mmol) was added to a 0° C. of the free alcohol of the styrene (shown above) (0.135 g, 0.189 mmol) in 4.5 mL of $CH_2Cl_2$. The mixture was stirred for 30 min at 0° C. 20 min at room temperature then was filtered using EtOAc through Celite and was finally concentrated in vacuo. Quick purification of the crude product by radial PLC (silica gel, 80–100% EtOAc/$CH_2Cl_2$) provided the desired aldehyde (0.08 g), in 59% yield as a white solid: $^1H$ NMR (300 MHz, $CDCl_3$) 9.77–9.76 (t, 1H, J=2.0 Hz), 7.3–7.2 (m, 6H), 7.06–7.02 (dd, 1H, J=8.3, 2.0 Hz), 6.85–6.82 (d, 1H, J=8.4 Hz), 6.81–6.7 (m, 1H), 5.74–5.68 (d, 1H, J=15.3 Hz), 5.51–5.48 (d, 1H, J=7.8 Hz), 5.22–5.17 (m, 1H), 4.85–4.81 (dd, 1H, J=10.3, 3.6 Hz), 4.77–4.71 (m, 1H), 3.87 (s, 3H), 3.72–3.71 (d, 2H, J=2.0 Hz), 3.69–3.68 (d, 1H, J=1.5 Hz), 3.45–3.38 (dd, 1H, J=13.5, 8.7 Hz), 3.17–3.0 (m, 3H), 2.92–2.89 (dd, 1H, J=7.6, 1.8 Hz), 2.6–2.4 (m, 2H), 1.8–1.6 (m, 3H), 1.4–1.3 (m, 1H), 1.22 (s, 3H), 1.16 (s, 3H), 1.16–1.13 (d, 3H, J=3 Hz), 0.86–0.82 (t, 6H, J=6.3 Hz).

EXAMPLE 81

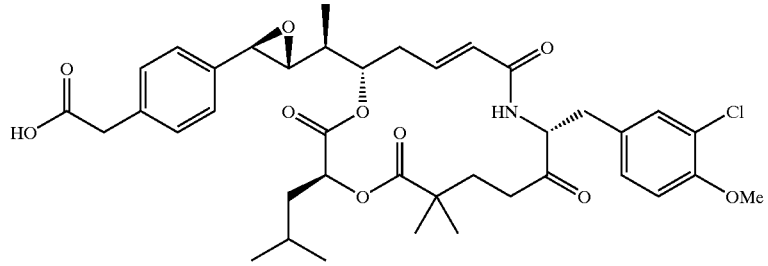

Tetrahydofuran (3.2 mL) and $H_2O$ (3.2 mL) were added to the aldehyde (shown above) (0.08 g, 0.112 mmol) and the mixture was cooled to 0° C. 2-Methyl-2-butene (3.2 mL), followed by $NaClO_2$ (0.081 g, 0.896 mmol) and $NaH_2PO_4H_2O$ (0.139 g, 1.0 mmol) were also added consecutively. The mixture was z allowed to warm to room temperature and was stirred vigorously for 5 hrs. The solution was diluted with 10 mL of $CH_2Cl_2$ and the layers separated. The aqueous layer was extracted with $CH_2Cl_2$ (3×10 mL) and the combined organic extracts were dried over $Na_2SO_4$, filtered and concentrated in vacuo. The crude product was purified twice by radial PLC (silica gel, 5–10–25% MeOH/$CH_2Cl_2$) to give 0.03 g of the carboxylic acid (shown above) in 37% yield as a white solid: $[\alpha]^{20}_D$ +24.5° (c 0.33, MeOH ); $^1H$ NMR (300 MHz, $CD_3OD$) δ 7.75–7.71 (dd, 1H, J=10.3, 1.9 Hz), 7.31–7.2 (m, 5H), 7.16–7.13 (dd, 1H, J=8.4, 1.9 Hz), 6.97–6.95 (d, 1H, J=8.4 Hz), 6.8–6.6 (m, 1H), 5.87–5.81 (d, 1H, J=15.3 Hz), 5.19–5.14 (dd, 1H, J=11.0, 5.0 Hz), 4.9–4.8 (m, 2H), 4.48–4.43 (dd, 1H, J=11.5, 3.5 Hz), 3.8 (s, 3H), 3.77 (s, 1H), 3.53 (s, 2H), 3.5–3.4 (m, 1H), 3.17–3.11 (dd, 1H, J=14.3, 3.5 Hz), 3.05–3.0 (d, 1H, J=13.6 Hz), 2.95–2.92 (dd, 1H, J=7.7, 1.7 Hz), 2.8–2.6 (m, 2H), 2.5–2.3 (m, 1H), 1.8–1.6 (m, 3H), 1.4–1.2 (m, 1H), 1.17 (s, 3H), 1.13 (s, 3H), 1.13–1.1 (d, 3H, J=9.2 Hz), 0.83–0.81 (d, 6H, J=6.3 Hz); $^{13}C$ NMR (126 MHz, $CDCl_3$) δ 178.8, 173.7, 172.0, 168.2, 155.4, 143.4, 138.1, 136.8, 132.2, 131.2, 130.8, 129.3, 126.8, 125.4, 123.3, 113.5, 77.7, 72.4, 64.4, 60.0, 57.5, 56.6, 47.4, 44.1, 41.7, 40.7, 38.6, 36.5, 25.9, 23.4, 23.3, 21.6, 14.0; IR (KBr) 3417, 2961, 2934, 2874, 1750, 1721, 1674, 1561, 1504, 1464, 1441, 1300, 1259, 1194, 1151, 1066 $cm^{-1}$; FAB HRMS [M+H] calcd for ($C_{38}H_{48}ClN_2O_{10}$) 727.2997, found 727.3005.

EXAMPLE 82

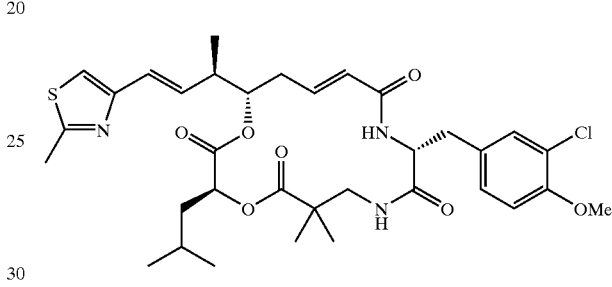

To a mixture of [(2-methyl-4-thiazolyl)methyl] triphenylphosphonium chloride (0.496 g, 1.2 mmol) in 10 mL of THF at −78° C. was added dropwise a 1.6 M solution of n-butyllithium (0.8 mL, 1.2 mmol). The mixture was warmed slowly to room temperature and stirred for an additional 45 min. To aldehyde 18 (0.5 g, 0.865 mmol), in 15 mL of THF and at −78° C., was added dropwise the orange ylide solution via a double tipped needle. The resulting mixture was stirred at −78° C. for 2 h and at room temperature for 1.5 h. Saturated $NH_4Cl$ (30 mL) was added along with ethyl acetate (30 mL), the layers separated and the aqueous one extracted with ethyl acetate (2×20 mL). The combined organic layers were washed with water (2×20 mL) and brine, dried over $MgSO_4$, filtered and concentrated in vacuo. The resulting yellow residue was purified using column chromatography (silica gel, 50–70–80% EtOAc/ hexanes) to give 0.4 g of the desired styrene along with triphenylphosphine oxide. The triphenylphosphine oxide was easily removed by reverse phase HPLC using $CH_3CN:H_2O$ (50:50) to give 0.2 g (34%) of pure thiazole (shown above) as a white solid: [α]²⁰_D +16.7° (c 1.0, CHCl₃); ¹H NMR (300 MHz, CDCl₃) δ 7.3–7.2 (m, 1H), 7.18–7.17 (d, 1H, J=1.7 Hz), 7.06–7.03 (dd, 1H, J=8.5, 1.8 Hz), 6.83 (s, 1H), 6.83–6.8 (d, 1H, J=9.0 Hz), 6.8–6.67 (m, 1H), 6.37–6.35 (m, 2H), 5.85–5.82 (d, 1H, J=7.9 Hz), 5.76–5.71 (d, 1H, J=15.1 Hz), 5.05–5.0 (dd, 1H, J=9.0, 6.0 Hz), 4.86–4.82 (dd, 1H, J=10.2, 3.6 Hz), 4.77–4.68 (m, 1H), 3.85 (s, 3H), 3.44–3.37 (dd, 1H, J=13.4, 8.6 Hz), 3.2–3.0 (m, 3H), 2.68 (s, 3H), 2.6–2.3 (m, 3H), 1.8–1.6 (m, 2H), 1.43–1.3 (m, 1H), 1.2 (s, 3H), 1.14 (s, 3H), 1.12–1.1 (d, 3H, J=6.9 Hz), 0.79–0.78 (d, 3H, J=3.1 Hz), 0.77–0.76 (d, 3H, J=3.1 Hz); ¹³C NMR (63 MHz, CDCl₃) δ 177.8, 170.5, 166.0, 165.2, 153.9, 153.0, 142.1, 136.7, 132.7, 130.8, 129.8, 128.1, 124.6, 124.4, 122.3, 114.1, 112.2, 76.9, 71.4, 56.0, 54.4, 46.4, 42.7, 41.9, 39.3, 36.5, 35.3, 24.5, 22.8, 22.7, 22.6, 21.2, 19.2, 17.1; IR (CHCl₃) 3423, 3027, 3008, 2965, 2935, 2874, 1747, 1712, 1681, 1652, 1604, 1528, 1504, 1485, 1259, 1181, 1152, 1067 cm⁻¹; Anal. ($C_{34}H_{44}ClN_3O_7S$) C, H, N.

EXAMPLE 83

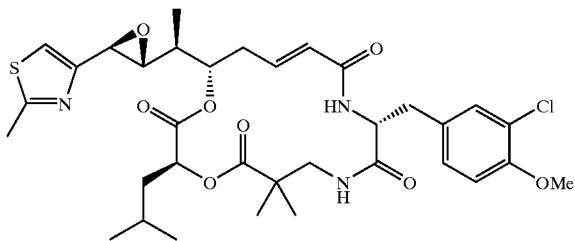

To the styrene(shown above) (0.25 g, 0.37 mmol) was added 15 mL of acetone, 6 mL of H₂O, 6 mL of CH₂Cl₂ and solid NaHCO₃ (1.0 g, 11.9 mmol) and the mixture was cooled to 0° C. A solution of Oxone (0.92 g, 1.5 mmol) in 8 mL of H₂O was prepared and added (2 mL) to the cold styrene mixture. Following 30 min of vigorous stirring at 0° C. an additional 2 mL of Oxone solution was added and again another 2.0 mL was added, following another 30 min, for a total of 6 mL of Oxone solution. The reaction progress was monitored by reverse phase HPLC and was found to be complete after 2.0 hrs of stirring. While still at 0° C., the reaction was quenched with saturated aqueous NaHCO₃ (40 mL) and 40 mL of CH₂Cl₂. The layers were separated and the organic layer was washed with aq. 10% Na₂SO₃ (40 mL), followed by saturated aq. NaHCO₃ (40 mL) then brine and finally was dried over Na₂SO₄, filtered and concentrated in vacuo. The mixture of b and a epoxides (54:46) was separated by reverse phase HPLC (50:50) CH₃CN:H₂O to provide 0.09 g of the b epoxide (shown above) as a white solid in 35% yield: [α]²⁰_D +26.0° (c 1.0, CHCl₃); ¹H NMR (300 MHz, CDCl₃) δ 7.19–7.18 (d, 2H, J=1.8 Hz), 7.1 (s, 1H), 7.06–7.03 (dd, 1H, J=8.5, 1.9 Hz), 6.85–6.82 (d, 1H, J=8.4 Hz), 6.82–6.7 (m, 1H), 5.76–5.71 (d, 1H, J=15.2 Hz), 5.49–5.47 (d, 1H, J=7.8 Hz), 5.23–5.18 (m, 1H), 4.88–4.84 (dd, 1H, J=10.3, 3.6 Hz), 4.8–4.7 (m, 1H), 3.88 (s, 3H), 3.79 (d, 1H, J=0.93 Hz), 3.45–3.38 (dd, 1H, J=13.4, 8.6 Hz), 3.35–3.32 (d, 1H, J=7.2 Hz), 3.2–3.0 (m, 3H), 2.7 (s, 3H), 2.6–2.4 (m, 2H), 1.8–1.6 (m, 3H), 1.4–1.3 (m, 1H), 1.23 (s, 3H), 1.16 (s, 3H), 1.14–1.12 (d, 3H, J=6.8 Hz), 0.89–0.87 (d, 3H, J=6.5 Hz), 0.86–0.84 (d, 3H, J=6.4 Hz); ¹³C NMR (63 MHz, CDCl₃) δ 177.9, 170.33, 170.3, 166.9, 165.0, 154.0, 151.9, 141.8, 130.8, 129.5, 128.2, 124.5, 122.4, 116.4, 112.3, 75.8, 71.1, 61.3, 56.1, 55.2, 54.3, 46.4, 42.7, 40.3, 39.3, 36.6, 35.2, 24.5, 22.85, 22.8, 22.6, 21.2, 19.1, 13.3; IR (CHCl₃) 3425, 3007, 2964, 2936, 2874, 2841, 1751, 1711, 1682, 1604, 1528, 1503, 1485, 1464, 1303, 1259, 1185, 1152, 1067 cm⁻¹; Anal. ($C_{34}H_{44}ClN_3O_8S$) C, H, N.

EXAMPLE 84

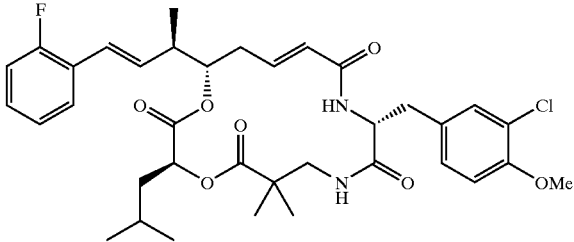

Styrene (shown above) (0.5 g) was prepared from aldehyde 18 (1.3 g, 2.2 mmol) and 2-fluorobenzyltriphenylphosphonium bromide (1.7 g, 3.8 mmol) in 33% yield according to the procedure described above for styrene 20: [α]²⁰_D +17.0° (c 1.16, CHCl₃); ¹H NMR (300 MHz, CDCl₃) δ 7.40–7.34 (m, 1H), 7.23–6.96 (m, 6H), 6.83–6.80 (d, 1H, J=8.4 Hz), 6.78–6.70 (m, 1H), 6.57–6.52 (d, 1H, J=16.0 Hz), 6.10–6.02 (dd, 1H, J=8.8, 16.0 Hz), 5.76–5.71 (d, 1H, J=15.3 Hz), 5.50–5.47 (d, 1H, J=7.8 Hz), 5.05–4.95 (m, 1H), 4.85–4.80 (dd, 1H, J=9.6, 3.1 Hz), 4.75–4.69 (m, 1H), 3.85 (s, 3H), 3.42–3.34 (dd, 1H, J=13.5, 8.7 Hz), 3.13–3.05 (m, 3H), 2.56–2.51 (m, 2H), 2.37–2.33 (m, 1H), 1.68–1.58 (m, 2H), 1.34–1.23 (m, 1H), 1.20 (s, 3H), 1.13 (s, 3H), 1.13–1.11 (d, 3H, J=7.3 Hz), 0.79–0.70 (m, 6H); ¹³C NMR (63 MHz, CDCl₃) δ 177.9, 170.5, 170.4, 165.1, 154.0, 142.0, 137.4, 133.0, 132.9, 130.8, 129.6, 128.8, 128.2, 127.0, 126.9, 124.6, 124.1, 115.9, 115.5, 112.3, 76.9, 71.4, 56.1, 54.4, 46.4, 42.7, 42.6, 39.4, 36.5, 35.3, 24.5, 22.8, 22.7, 22.6, 21.1, 17.2; IR (CHCl₃) 3423, 2965, 2935, 2874, 1747, 1711, 1681, 1605, 1527, 1503, 1487, 1457, 1441, 1370, 1340, 1321, 1280, 1259, 1151, 1093, 1067, 1009, 970 cm⁻¹; Anal. ($C_{36}H_{44}ClFN_2O_7$) C, H, N.

EXAMPLE 85

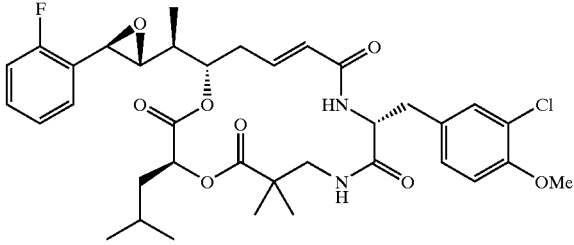

To a solution of the styrene (shown above) (0.26 g, 0.387 mmol) in 1.3 mL CH₂Cl₂ at 0° C., was added 3-chloroperoxybenzoic acid (0.07 g, 0.41 mmol) and toluene (0.65 mL) and stirring continued at 0° C. for 30 minutes. The ice-bath was removed and the reaction allowed to stir at room temperature for 24 hours. After concentration, the residue was purified by reverse-phase HPLC (CH₃CN/H₂O) to give the b-epoxide (shown above) as a white foam (0.058 g, 24% corrected for recovered styrene: [α]²⁰_D +18.98° (c 1.41, CHCl₃); ¹H NMR (300 MHz, CDCl₃) δ 7.30–7.00 (m, 6H), 6.86–6.83 (d, 1H, J=8.5 Hz), 6.80–6.75 (m, 1H), 5.76–5.71 (d, 1H, J=15.1 Hz), 5.47–5.45 (d, 1H, J=7.8 Hz), 5.23–5.20 (m, 1H), 4.86–4.82 (dd, 1H, J=10.3, 3.5 Hz), 4.78–4.70 (m, 1H), 4.01 (s, 1H), 3.88 (s, 3H), 3.45–3.38 (dd, 1H, J=13.4, 8.6 Hz), 3.12–3.08 (m, 3H), 2.91–2.88 (d, 1H, J=7.8 Hz), 2.59–2.53 (m, 2H), 1.80–1.71 (m, 3H), 1.46–1.25 (m, 1H), 1.23 (s, 3H), 1.16 (s, 3H), 1.16–1.14 (d, 3H, J=7.2 Hz), 0.87–0.83 (m, 6H); ¹³C NMR (63 MHz, CDCl₃) δ 178.1, 170.5, 170.3, 165.0, 142.0, 131.0, 129.7, 129.6, 128.3, 126.1, 126.08, 124.65, 124.5, 122.6, 115.5, 115.2, 112.4, 76.0, 71.2, 62.6, 56.2, 54.4, 53.5, 46.5, 42.8, 40.6, 39.4, 36.9, 35.3, 24.7, 22.9, 22.8, 21.3, 13.8; IR (CHCl₃) 3417, 2962, 2948, 1754, 1721, 1681, 1653, 1534, 1504, 1473, 1459, 1441,1303, 1282, 1258,1191, 1148, 1127, 1066 cm⁻¹; FAB HRMS [M+H] for (C₃₆H₄₅ClFN₂O₈) cald 687.2848, found 687.2857.

EXAMPLE 86

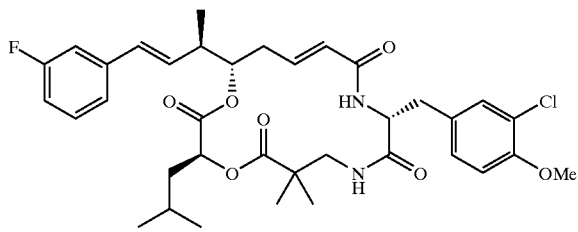

The styrene (shown above) (0.85 g), as an E/Z mixture, was prepared from aldehyde 18 (2.0 g, 3.45 mmol) and 3-fluorobenzyl triphenylphosphonium bromide (1.92 g, 4.25 mmol) in 37% yield according to the procedure described above for styrene 20. The mixture of isomers was dissolved in benzene (25 mL) and heated to reflux in the presence of 1,1'-azobis(cyclohexanecarbonitrile) (VAZO) (0.04 g, 0.16 mmol) and thiophenol (0.06 mL, 0.58 mmol) for 20 hours. After concentration the residue was purified by radial PLC (20–100% EtOAc/hexanes) to give the E isomer (0.652 g, 77%) as a white foam: [α]²⁰_D +30.55° (c 0.98, CHCl₃); ¹H NMR (300 MHz, CDCl₃) δ 7.30–7.01 (m, 8H), 6.95–6.88 (m, 1H), 6.86–6.83 (d, 1H, J=8.5 Hz), 6.81–6.72 (m, 1H), 6.40–6.35 (d, 1H, J=15.9 Hz), 6.07–5.99 (dd, 1H, J=8.8, 15.9 Hz), 5.78–5.73 (d, 1H, J=15.1 Hz), 5.50–5.47 (d, 1H, J=7.9 Hz), 5.08–5.02 (dd, 1H, J=9.7, 6.7 Hz), 4.87–4.82 (dd, 1H, J=9.7, 3.0 Hz), 4.78–4.71 (m, 1H), 3.88 (s, 3H), 3.45–3.37 (dd, 1H, J=13.5, 8.6 Hz), 3.15–3.08 (m, 3H), 2.59–2.52 (m, 2H), 2.43–2.34 (m, 1H), 1.72–1.63 (m, 2H), 1.36–1.26 (m, 1H), 1.22 (s, 3H), 1.16 (s, 3H), 1.15–1.12 (d, 3H, J=6.9 Hz), 0.80–0.73 (m, 6H); ¹³C NMR (63 MHz, CDCl₃) δ 177.8, 170.5, 170.4, 165.1, 165.0, 153.9, 141.9, 137.3, 131.7, 130.8, 130.6, 130.0, 129.6, 128.1, 124.6, 122.4, 114.4, 114.1, 112.6, 112.2, 76.8, 71.3, 56.0, 54.4, 46.4, 42.7, 42.1, 39.5, 36.5, 35.2, 24.5, 22.8, 22.64, 22.6, 21.2, 17.2; IR (CHCl₃) 3423, 3008, 2965, 2936, 2874, 1747, 1712, 1680, 1652, 1585, 1528, 1503, 1486, 1464, 1442, 1320, 1303, 1259, 1193, 1147, 1127, 1067, 973 cm⁻¹; Anal. (C₃₆H₄₄ClFN₂O₇) C, H, N.

EXAMPLE 87

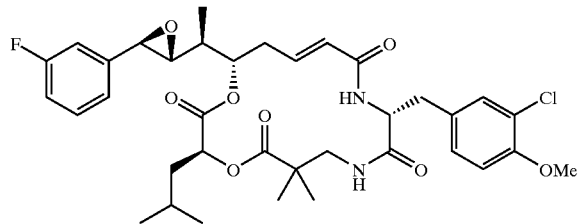

To a solution of the above styrene (0.622 g, 0.927 mmol) in 3.0 mL CH₂Cl₂ at 0° C., was added 3-chloroperoxybenzoic acid (0.170 g, 0.985 mmol) and toluene (1.5 mL) and stirring continued at 0° C. for 30 minutes. The ice-bath was removed and the reaction allowed to stir at room temperature for 22 hours. After concentration, the residue was purified by reverse-phase HPLC (CH₃CN/H₂O) to give the b-epoxide (shown above) as a yellow foam (0.067 g, 11% ): [α]²⁰_D +26.23° (c 1.54, CHCl₃); ¹H NMR (300 MHz, CDCl₃) δ 7.37–6.92 (m, 7H), 6.86–6.83 (d, 1H, J=8.4 Hz), 6.82–6.73 (m, 1H), 5.75–5.70 (d, 1H, J=15.5 Hz), 5.48–5.45 (d, 1H, J=7.8 Hz), 5.22–5.17 (m, 1H), 4.85–4.81 (dd, 1H, J=3.1, 9.8 Hz), 4.76–4.70 (m, 1H), 3.88 (s, 3H), 3.68–3.67 (d, 1H, J=0.89 Hz), 3.46–3.38 (dd, 1H, J=8.6, 13.5 Hz), 3.13–3.07 (m, 3H), 2.90–2.87 (dd, 1H, J=1.5, 7.4 Hz), 2.60–2.37 (m, 2H), 1.82–1.64 (m, 3H), 1.36–1.25 (m, 1H), 1.22 (s, 3H), 1.16 (s, 3H), 1.15–1.12 (d, 3H, J=6.9 Hz), 0.88–0.83 (m, 6H); ¹³C NMR (63 MHz, CDCl₃) δ 177.9, 170.4, 165.0, 154.0, 141.6, 139.5, 130.8, 130.4, 130.2, 129.6, 128.2, 124.7, 122.4, 121.3, 115.6, 115.3, 112.3, 112.2, 75.8, 71.1, 63.2, 58.2, 56.1, 54.5, 46.4, 42.8, 40.4, 39.4, 36.8, 35.3, 24.5, 22.85, 22.82, 22.7, 21.2, 13.4; IR (KBr) 3416, 3034, 2963, 2934, 2874, 1751, 1721, 1680, 1658, 1539, 1504, 1473, 1442, 1304, 1280, 1258, 1192, 1144, 1066 cm⁻¹; Anal. (C₃₆H₄₄ClFN₂O₈) C, H, N.

EXAMPLE 88

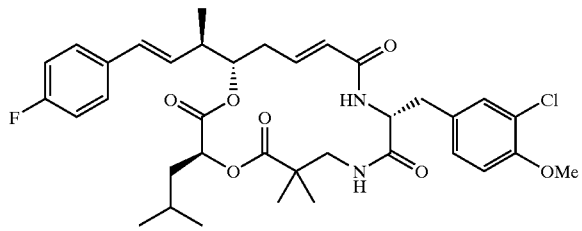

The styrene (shown above) (1.24 g), as an E/Z mixture, was prepared from aldehyde 18 (1.5 g, 2.6 mmol) and 4-fluorobenzyl triphenylphosphonium bromide (1.4 g, 3.1 mmol) in 71% yield according to the procedure described above for styrene 20. The mixture of isomers was dissolved in benzene (40 mL) and heated to reflux in the presence of 1,1'-azobis(cyclohexanecarbonitrile) (VAZO) (0.050 g, 0.20 mmol) and thiophenol (0.076 mL, 0.74 mmol) for 24 hours. After concentration the residue was purified by radial PLC (20–100% EtOAc/hexanes) to give the E isomer (1.06 g) as a white foam containing triphenylphosphine oxide by NMR. A 0.150 g sample was purified by reverse-phase HPLC (60:40) $CH_3CN:H_2O$ to give 0.092 g of pure solid: $[\alpha]^{20}_D$ +27.49° (c 1.05, $CHCl_3$); $^1H$ NMR (300 MHz, $CDCl_3$) δ 7.31–6.96 (m, 7H), 6.85–6.83 (d, 1H, J=8.5 Hz), 6.81–6.74 (m, 1H), 6.39–6.34 (d, 1H, J=15.8 Hz), 5.96–5.88 (dd, 1H, J=8.8, 15.8 Hz), 5.77–5.72 (d, 1H, J=15.2 Hz), 5.49–5.47 (d, 1H, J=7.7 Hz), 5.07–5.02 (m, 1H), 4.86–4.83 (dd, 1H, J=9.2, 2.5 Hz), 4.82–4.73 (m, 1H), 3.87 (s, 3H), 3.45–3.38 (dd, 1H, J=13.4, 8.5 Hz), 3.14–3.08 (m, 3H), 2.57–2.52 (m, 2H), 2.43–2.34 (m, 1H), 1.71–1.58 (m, 2H), 1.36–1.29 (m, 1H), 1.22 (s, 3H), 1.16 (s, 3H), 1.14–1.11 (d, 3H, J=6.9 Hz), 0.78–0.73 (m, 6H); $^{13}C$ NMR (63 MHz, $CDCl_3$) δ 177.8, 170.5, 170.3, 165.1, 160.2, 154.0, 142.0, 137.6, 132.9, 132.8, 130.8, 130.4, 130.0, 129.6, 128.2, 127.6, 127.5, 124.6, 122.4, 115.6, 115.2, 112.2, 71.3, 56.0, 54.4, 46.4, 42.7, 42.1, 39.5, 36.4, 35.2, 24.5, 22.8, 22.6, 21.2, 17.2; IR (KBr) 3421, 3289, 2862, 2933, 1751, 1722, 1678, 1604, 1534, 1509, 1259, 1228, 1149, 1066, 1024, 1011, 971, 815 $cm^{-1}$; Anal. ($C_{36}H_{44}ClFN_2O_7$) C, H, N.

EXAMPLE 89

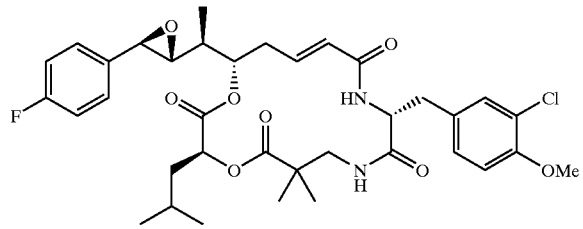

To a solution of the styrene (shown above) (0.906 g, 1.35 mmol) in 4.5 mL $CH_2Cl_2$ at 0° C. was added 3-chloroperoxybenzoic acid (0.25 g, 1.45 mmol) and toluene (2.2 mL) and stirring continued at 0° C. for 30 minutes. The ice-bath was removed and the reaction allowed to stir at room temperature for 23 hours. After diluting with 20 mL of $CH_2Cl_2$ the reaction mixture was washed with 10% $Na_2S_2O_5$ (1×10 mL), water (1×10 mL), saturated $NaHCO_3$ (1×10 mL) and brine (1×10 mL) and finally was dried over $Na_2SO_4$. Filtration and concentration gave 0.814 g of the product as a mixture of the b/a epoxides. A 0.23 g portion was purified by reverse-phase HPLC ($CH_3CN/H_2O$) to give 0.073 g of the b-epoxide (shown above) as a white foam: $[\alpha]^{20}_D$ +25.6° (c 0.626, $CHCl_3$); $^1H$ NMR (300 MHz, $CDCl_3$) δ 7.26–7.03 (m, 7H), 6.85–6.83 (d, 1H, J=8.4 Hz), 6.82–6.72 (m, 1H), 5.74–5.69 (d, 1H, J=15.2 Hz), 5.44–5.42 (d, 1H, J=7.9 Hz), 5.23–5.18 (m, 1H), 4.85–4.81 (dd, 1H, J=9.7, 2.9 Hz), 4.77–4.73 (m, 1H), 3.88 (s, 3H), 3.66 (s, 1H), 3.46–3.39 (dd, 1H, J=13.5, 8.8 Hz), 3.12–3.07 (m, 3H), 2.89–2.87 (dd, 1H, J=1.5, 7.7 Hz), 2.60–2.54 (m, 1H), 2.49–2.41 (m, 1H), 1.81–1.65 (m, 3H), 1.34–1.25 (m, 1H), 1.22 (s, 3H), 1.16 (s, 3H), 1.15–1.13 (d, 3H, J=7.0 Hz), 0.87–0.82 (m, 6H); $^{13}C$ NMR (63 MHz, $CDCl_3$) δ 177.8, 170.3, 164.9, 164.7, 154.0, 141.6, 137.8, 132.4, 130.7, 129.6, 128.1, 127.3, 127.2, 124.6, 122.4, 115.8, 115.5, 112.2, 75.8, 71.0, 63.0, 58.2, 56.0, 54.4, 46.3, 42.7, 40.4, 39.3, 36.7, 35.2, 23.5, 22.8, 22.76, 22.6, 21.1, 13.3; IR ($CHCl_3$) 3426, 3030, 3006, 2964, 2936, 1752, 1711, 1683, 1608, 1514, 1485, 1442, 1303, 1281, 1259, 1188, 1155, 1067, 838 $cm^{-1}$; Anal. ($C_{36}H_{44}ClFN_2O_8$) C, H, N.

EXAMPLE 90

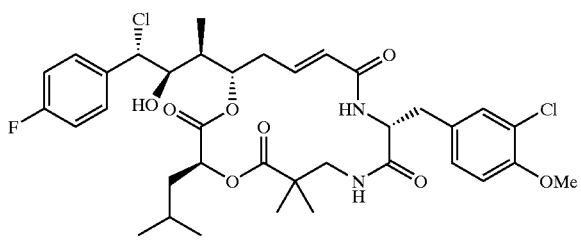

A 4 M solution of HCl in dioxane (0.4 mL, 1.6 mmol) was added dropwise over 5 minutes to a −70° C. solution of b-epoxide (shown above) (0.44 g, 0.64 mmol) in 30 mL $CH_2Cl_2$. Following 2 additional hrs of stirring at −70° C., the solution was concentrated in vacuo. The crude product was purified by radial PLC (silica gel, 30–50–100% EtOAc/$CH_2Cl_2$) followed by reverse phase HPLC (50:50) $CH_3CN:H_2O$ to give 0.152 g (33%) of the desired chlorohydrin (shown above) as a white foam: $[\alpha]^{20}_D$ +60.0° (c 2.62, $CHCl_3$); $^1H$ NMR (300 MHz, $CDCl_3$) δ 7.41–7.05 (m, 7H), 6.87–6.84 (d, 1H, J=8.4 Hz), 6.83–6.77 (m, 1H), 5.80–5.75 (d, 1H, J=15.4 Hz), 5.52–5.49 (d, 1H, J=7.8 Hz), 5.13–5.21 (m, 1H), 4.94–4.90 (dd, 1H, J=9.7,3.2 Hz), 4.75–4.72 (m, 1H), 4.67–4.63 (d, 1H, J=9.5 Hz), 4.00–3.95 (m, 1H), 3.89 (s, 3H), 3.42–3.35 (dd, 1H, J=8.3, 13.5 Hz), 3.20–3.02 (m, 3H), 2.71–2.65 (m, 1H), 2.49–2.37 (m, 2H), 1.82–1.63 (m, 2H), 1.51–1.38 (m, 2H), 1.23 (s, 3H), 1.17 (s, 3H), 1.04–1.02 (d, 3H, J=7.0 Hz). 0.97–0.85 (m, 6H); $^{13}C$ NMR (63 MHz, $CDCl_3$) δ 177.6, 170.5, 170.3, 165.3, 160.7, 153.9, 142.2, 137.5, 134.5, 130.8, 129.8, 129.7, 128.2, 124.6, 122.2, 76.1, 74.0, 71.1, 61.4, 56.1, 54.5, 46.4, 42.7, 39.6, 38.4, 36.3, 35.1, 24.8, 23.0, 22.9, 22.7, 21.5, 8.6; IR ($CHCl_3$) 3423, 2965, 2935, 2873, 1751, 1715, 1679, 1607, 1528, 1504, 1485, 1464, 1442, 1302, 1281, 1193, 1159, 1152, 1127, 1067 $cm^{-1}$; Anal. ($C_{36}H_{45}Cl_2N_2O_8$) C, H, N.

EXAMPLE 91

Cryptophycins-151, -152, -153, -154, 155, -156, -159, 160, -161, -166, -167, -172, -181, -188, 234, 236, 238, 247, 251 and 255.

TABLE 1
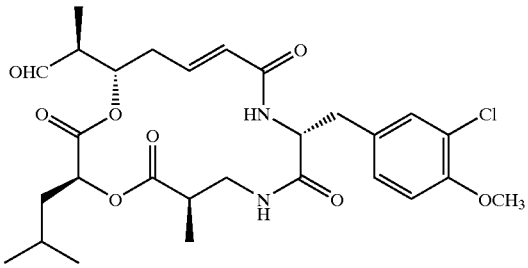
Cryptophycin-108
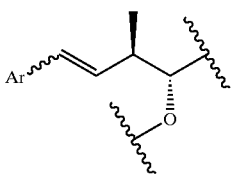
| Cryptophycin # | Ar or alkyl group | yield (E + Z) % | % of trans isomer (approximately) |
|---|---|---|---|
| 151 | 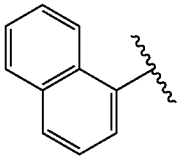 | 72 | 90 |
| 152 | 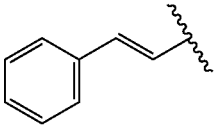 | 80 | 70 |
| 155 | 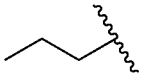 | 60 | <10 |
| 156 | 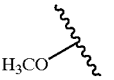 | 51 | 70 |
| 160 | 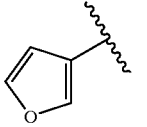 | 61 | 67 |
| 172 | 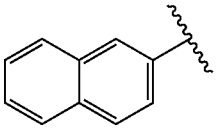 | 78 | 90 |
| 255 | 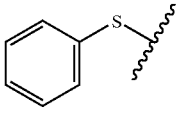 | 85 | 60 |

TABLE 2
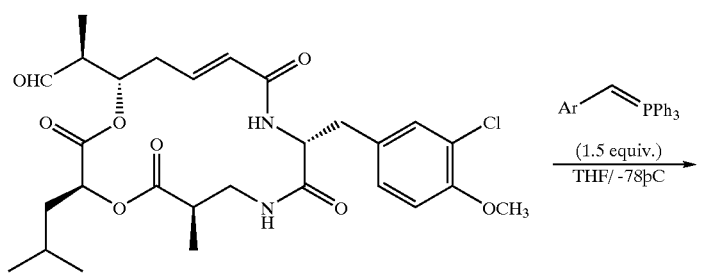
Cryptophycin-108
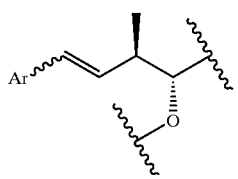
| Cryptophycin # | Ar | yield (E + Z) % | % of E isomer (approximately) |
|---|---|---|---|
| 153 | 3-methoxyphenyl (H₃CO-) | 80 | 90 |
| 154 | 3,5-dimethoxyphenyl | 63 | 90 |
| 159 | 2,4-dimethylphenyl | 75 | 90 |
| 161 | 4-(trifluoromethyl)phenyl | 61 | 80 |
| 166 | 2-methylphenyl | 38 | 90 |
| 167 | 3,5-dimethylphenyl | 48 | 90 |

TABLE 2-continued
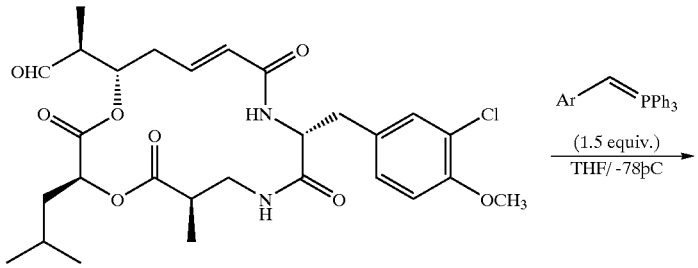
Cryptophycin-108
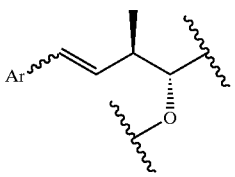
| Cryptophycin # | Ar | yield (E + Z) % | % of E isomer (approximately) |
|---|---|---|---|
| 181 | 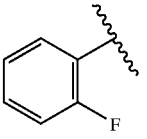 | 73 | 75 |
| 188 | 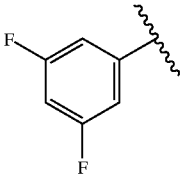 | 85 | 80 |
| 234 | 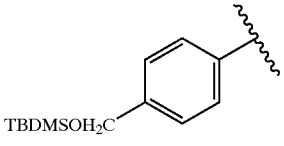 | 81 | 85 |
| 236 | 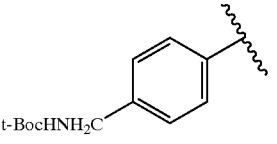 | 59 | 90 |
| 247 | 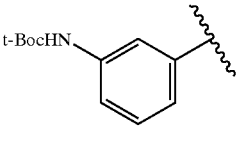 | 51 | >90 |
| 251 | 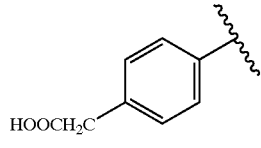 | 43 | >90 |

The typical procedure adapted for the coupling of cryptophycin-108 with a variety of triphenylphosphoranes is described below using the preparation of cryptophycin-152 as an illustrative example.

Cryptophycin-152: Cinnamyltriphenylphosphorane was generated by the treatment of cinnamyl triphenylphosphonium chloride (0.311 gm, 0.750 mmol) in THF (5.7 mL) with butyllithium (300 μL of 2.5 M solution in hexane, 0.750 mmol) at −78° C. and allowing the contents slowly warm up to the room temperature. Cinnamyltriphenylphosphorane from this reaction mixture (1.46 mL, 0.182 mmol) was slowly added to the aldehyde (68.6 mg, 0.122 mmol) in THF (3 mL) at −78 C and continued the stirring for 2 hr. The reaction mixture was brought to the ambient temperature, treated with saturated $NH_4Cl$ (5 mL) followed by water (15 mL) and extracted with ethyl acetate (40 mL). The organic layer was washed with water, dried over $MgSO_4$ and evaporated. The residue was applied to a small ODS column and eluted with 1:1$H_2O$/$CH_3CN$ and 1:3 $H_2O$/$CH_3CN$. The latter fraction was evaporated to obtain a mixture of cryptophycin-152 and its Z isomer (E/Z 7:3, 64.3 mg, 80%).

Using the same experimental procedure the aldehyde (cryptophycin-108) was reacted with 1-naphthylmethyl triphenylphosphorane, 3-methoxybenzyl triphenylphosphorane, 3,5-dimethoxybenzyl triphenylphosphorane, methoxymethyl triphenylphosphorane, 2,4-dimethylbenzyl triphenylphosphorane, 3-furanmethyl triphenylphosphorane, p-trifluoromethylbenzyl triphenylphosphorane, 2-methylbenzyl triphenylphosphorane, 3,5-dimethylbenzyl triphenylphosphorane, 2-naphthylmethyl triphenylphosphorane, 2-fluorobenzyl triphenylphosphorane, 3,5-difluorobenzyl triphenylphosphorane, 4-hydroxymethylbenzyltriphenylphosphorane, 4-(t-Boc-aminomethyl)benzyltriphenylphospho-rane, 3-(N-t-Boc-amino)benzyltriphenylphosphorane and phenylthiomethyltriphenylphos-phonium to obtain cryptophycins-151, -153, -154, -156, -159, -160, -161, -166, -167, -172, -181, -188, -234, -236, -247 and -255 respectively.

Butyllithium was used as a base in the generation of ylides from their corresponding triphenylphosphonium chlorides or bromide salts, except phenyllithium was used in the preparation of methoxymethyltriphenylphosphorane, 3-furanmethyl triphenylphosphorane and 4-hydroxymethylbenzyltriphenylphosphorane.

A similar reaction involving hydroxymehyltriphenylphosphomiumbromide, n-butyllithium and cryptophycin-108 yielded an unexpected analog cryptophycin-155.

A slightly modified procedure was adapted for the preparation of carboxy methyl analog cryptophycin-251. A THF (5 mL) solution of 4-(carboxymethyl)benzyltriphenylphosphoniumbromide (0.289 g, 0.59 mmol) was treated with phenyllithium (1.8 M, 653 μL; 1.18 mmol) at −78° C. for 5 min and transferred the flask to an ice water bath. After 30 min, 0.9 mL of this reaction mixture was added slowly to a flask containing cryptophycin-108 (35 mg) in 3 mL of THF at −78° C. and allowed the contents to stir for 2 h. The reaction mixture was acidified with 1N HCl (1 mL), added water (30 mL) and extracted with ethylacetate (30 mL×2). The organic layer was dried over $MgSO_4$ and evaporated. The residue was subjected to a flash chromatography on ODS silica eluting with 1:1$H_2O$/$CH_3CN$ and 35:65$H_2O$/$CH_3CN$. The later fraction was evaporated and purified on a reversed phase HPLC column (Econosil C18, 10μ, 250×22 mm, 6 mL/min, 35:65$H_2O$/$CH_3CN$) to obtain an impure sample of cryptophycin-251, which was finally purified by another reversed phase chromatography (Econosil C18, 10μ, 250×10 mm, 3 mL/min, 0.5% solution of acetic acid in 2:3$H_2O$/$CH_3CN$) to obtain cryptophycin-251 (10 mg).

The key experimental data involved in the generation of styrene analogs and cytotoxicity data are summarized in tables 1 and 2.

Triphenylphosphonium salts: Cinnamyl triphenylphosphonium chloride, 1-naphthylmethyl triphenylphosphonium chloride, methoxymethyltriphenylphosphonium chloride and 2-methybenzyl triphenylphosphonium bromide are available commercially, where as 3-methoxybenzyl triphenylphosphonium chloride, 3,5-dimethoxybenzyl triphenylphosphonium chloride, 2,4-dimethylbenzyl triphenylphosphonium chloride were prepared by refluxing triphenylphosphine with a slight excess of the corresponding chloride in toluene for 4 h. 4-Trifluomethylbenzyl triphenylphosphonium bromide, 3-furomethyltriphenylphosphonium bromide, 2-naphthylmethyltriphenylphosphonium bromide, 3,5-difluorobenzyl triphenylphosphonium bromide, 4-(t-butyldimethylsilyloxymethyl)benzyltriphenylphosphonium 2t bromide, 4-(N-t-Boc-aminomethyl)benzyltriphenylphosphonium bromide and 3-(N-t-Boc-amino)benzyltriphenyl-phosphonium bromide were prepared by treating the corresponding bromides with triphenylphosphine in toluene at room temperature for 12 h. 4-(Carboxymethyl)benzyltriphenylphosphoniumbromide was prepared by treating the bromide with triphenylphosphine in 5:1 toluene/THF solution at room temperature for 48 h. 3-furonmethylbromide, 2-naphthalenelmethylbromide and 3-(N-t-Boc-amino)benzylbromide were produced respectively from 3-furonmethanol, 2-naphthalenemethanol and 3-(N-t-Boc-amino)benzylalcohol upon treatment with $PBr_3$ in THF at −78° C.$^{ref}$ 3-furonmethanol and 2-naphthalenemethanol are available commercially. 3-(N-t-Boc-amino)benzylalcohol was prepared from a commercial sample of 3-aminobenzylalkohol. 4-(t-butyldimethylsilyloxymethyl)benzylbromide and 4-(N-t-Boc-aminomethyl)benzylbromide were prepared from commercial samples of 4-hydroxymethylbenzoic acid methylester and 4-aminomethylbenzoic acid respectively using the following experimental procedures.

4-(t-butyldimethylsilyloxymethyl)benzylbromide: A mixture of 4-hydroxymethyl-benzoic acid methylester (2 gm) and triethylamine (3.36 mL) in dichloromethane (15 mL) was treated with t-butyldimethylsilyltriflate (4.47 gm) at −78° C. After 30 min the contents were allowed to warm up to the room temperature and continued the stirring for another 30 min. Water (30 mL) and ethylacetate (60 mL) were added to the reaction mixture and the organic layer was washed with 0.3 M $KHSO_4$, water and brine, dried over $MgSO_4$ and filtered. The solvent was evaporated and the residue was subjected to flash chromatography on silica column by eluting with 10% EtOAc/hexane to obtain 4-(t-butyldimethylsilyloxymethyl) benzoic acid methyl ester (3.3 gm, 95% yield).

Lithium/aluminumhydride (0.21 gm) dispersed in diethylether (20 mL) was cooled to −78° C. under argon and treated dropwise with 4-(t-butyldimethylsilyloxymethyl) benzoic acid methyl ester (2.05 gm) in 10 mL of diethylether. After 30 minutes ethylacetate (2 mL) was added to quench the excess hydride, and then was added saturated ammonium chloride (1.5 mL). The precipitate was separated by filtration and washed with ether. The solvent was evaporated to give 4-(t-C, butyldimethylsilyloxymethyl) benzylalcohol (1.71 gm, 93% yield).

4-(t-butyldimethylsilyloxymethyl)benzylalcohol (1.7 gm) was dissolved in THF (15 mL) and treated with phosphoroustribromide (0.609 gm) at −78° C. After 30 min, the reaction was diluted with diethylether (80 mL) and washed with saturated sodium bicarbonate(30 mL), water and brine, dried over $MgSO_4$. The ether layer was evaporated and the residue (2.0 gm) was subjected to flash chromatography on silica using 5% EtOAc/hexane as an eluant to obtain 4-(t-butyldimethylsilyloxymethyl)benzybromide (1.05 gm, 49% yield).

4-(N-t-Boc-aminomethyl)benzyl bromide: To a solution of di-t-butyldicarbonate (2.18 g, 10 mmol) in triethylaminedimethylforamide (1:9, 7.5 mL) was added 4-(aminomethyl) benzoic acid (0.75 g, 5 mmol) at room temp and warmed the reaction mixture at 40–50° C. for 10 min. After the amino/acid was dissolved, the stirring continued at room temp for another hour. The solvent was removed under vacuum and the residue was acidified with dil HCl (pH>2) and immediately extracted with EtOAc and the organic layer was dried over $MgSO_4$. The residue obtained after removal of the solvent was treated with excess of diazomethane (generated from diazald) in ether for 30 min and the excess diazomethane was decomposed by acetic acid. The residue obtained after the removal of solvent was chromatographed over silica column (20 g) using hexanes/EtOAc (9:1) for elution to give methyl 4-(N-t-Boc-aminomethyl)benzoate (1.07 g, 81% yield).

To a cold suspension of $LiAlH_4$ (60 mg, 1.5 mmol) in ether (5 mL) at −78° C. was added dropwise a solution of methyl 4-(N-t-Boc-aminomethyl)benzoate (0.8 g, 3 mmol) in ether (5 mL) and the contents were allowed to warm-up to ambient temp. After 3 h, further amount of $LiAlH_4$ (100 mg) was added and the reaction was continued at room temp for further 10 min. Excess $LiAlH_4$ was destroyed with EtOAc followed by saturated ammonium chloride (1.0 mL), The solid precipitated was filtered and washed with ether. The filtrate was evaporated to give 4-(N-t-Boc-aminomethyl)benzyl alcohol ( 250 mg, 35%).

A solution of 4-(N-t-Boc-aminomethyl)benzyl alcohol (250 mg, 1.1 mmol ) in THF (5 mL) was treated with phosphorustribromide (30 uL, 0.32 mmol) at −78° C. for 2 h. After this period, the reaction was quenched with solid $NaHCO_3$ (50 mg) and filtered to remove the solids and the filtrate was evaporated to give 4-(t-Boc-aminomethyl) benzyl bromide (300 mg, 95%).

The desired E isomers were separated from the corresponding E/Z mixtures by crystallization in ethylacetate/ethylether solutions. In the case of cinnamyl and few other analogs with unimpressive E/Z selectivity, the crude mixture was subjected to isomerization using the following illustrative procedure described for cinnamyl analog, cryptophycin-152.

Isomerization: A mixture of cryptophycin-152 and its cis isomer (E/Z 7:3, 62 mg, 0.10 mmol) was dissolved in benzene (3 mL) and refluxed with thiophenol (10 μL, 0.10 mol) and 1,1'-azobis(cyclohexanecarbonitrile) (12 mg, 0.05 mmol). After 16 h, the mixture was brought to the ambient temp and applied to a small silica column. The column was washed with dichloromethane and the compound was eluted with 1:1 ethylacetate/dichloromethane. The solvent was evaporated to yield cryptophycin-151 (53 mg, 85%), which still contaminated with approximately 5% of its cis isomer.

Cryptophycin-151: EIMS m/z (relative intensity) 688/690 (3.3/1.5), 412/414 (18/6), 277 (100), 233 (18), 195/197 (16/6), 193 (29), 141 (38); high resolution EIMS m/z 688.2900 (calcd for $C_{39}H_{45}ClN_2O_7$ Δ 1.5 mmu). $^1$H NMR data, see table 3; $^{13}$C NMR data, see table 4.

Cryptophycin-152: EIMS m/z (relative intensity) 664/666 (24/7), 412/414 (21/7), 253 (100), 91 (85); high resolution EIMS m/z 664.2939 (calcd for $C_{37}H_{45}ClN_2O_7$, Δ −2.3 mmu). $^1$H NMR data, see table 3; $^{13}$C NMR data, see table 4.

Cryptophycin-153: EIMS m/z (relative intensity) 668/670 (3.7/1.4), 412/414 (32/12), 257 (62), 198 (100), 195/197 (36/11); high resolution EIMS m/z 668.2817 (calcd for $C_{36}H_{45}ClN_2O_8$, Δ 4.7 mmu). $^1$H NMR data, see table 3; $^{13}$C NMR data, see table 4.

Cryptophycin-154: EIMS m/z (relative intensity) 698/700 (2.5/0.8), 412/414 (18/5), 287 (28), 228 (35), 195/197 (18/6), 139 (100); high resolution EIMS m/z 698.2946 (calcd for $C_{37}H_{47}ClN_2O_9$, Δ 2.5 mmu). $^1$H NMR data, see table 3; $^{13}$C NMR data, see table 4.

Cryptophycin-155: EIMS m/z (relative intensity) 604/606 (20/6), 412/414 (24/8), 280/282 (24/8), 195/197 (100/33); high resolution EIMS m/z 604.2894 (calcd for $C_{32}H_{45}ClN_2O_7$, Δ 2.1 mmu). $^1$H NMR ($CDCl_3$) amino or hydroxy acid unit 6 (carbon position, multiplicity; J in Hz) A 5.76 (2, d; 15.5), 6.66 (3, ddd; 15.5, 9.5 and 5.9), 2.32–2.44 (4-$H_2$, m), 4.92 (5, rm), 2.66–2.76 (6, m), 0.98 (6-Me, d; 6.8), 5.21 (7, t; 10.9), 5.46 (8, dt; 10.9 and 7.4), 2.00 (9-$H_2$, m), 1.38 (10-$H_2$, m), 0.91 (10-Me, t; 7.5); B 4.81 (2, m), 5.70 (2-NH, d; 8.5), 3.04 (3, dd; −14.5 and 7.2), 3.14 (3, dd; −14.5 and 5.6), 7.22 (5, d; 2.2), 3.87 (7-OMe, s), 6.84 (8, d; 8.5), 7.08 (9, dd; 8.5 and 2.2); C 2.66–2.76 (2, m), 1.22 (2-Me, d; 7.4), 3.27 (3, dt; 13.5 and 6.8), 3.52 (3, m), 6.93 (3-NH, br t; 6.4); D 4.86 (2, dd; 9.8 and 3.5), 1.49 (3, m), 1.71–1.80 (3/4, m), 0.90 (4-Me, d; 6.0), 0.94 (5, d; 6.5); $^{13}$C NMR ($CDCl_3$) unit δ (carbon position) A 165.5 (1), 125.0 (2), 141.6 (3), 36.5 (4), 77.9 (5), 36.2 (6), 17.7 (6-Me), 130.0 (7), 131.6 (8), 29.6 (9-$H_2$), 22.8 (10-$H_2$), 13.8 (11-$H_3$); B 171.0$^a$ (1), 53.5 (2), 35.1 (3), 129.9 (4), 131.0 (5), 122.4 (6), 153.9 (7), 56.1 (7-$OCH_3$), 112.2 (8), 128.4 (9); C 175.6 (1), 38.3 (2), 14.0 (2-Me), 41.2 (3); D 170.9a(1), 71.6 (2), 39.5 (3), 24.7 (4), 21.4 (4-Me), 23.1 (5) $^a$ signals are interchangeable.

Cryptophycin-156: EIMS m/z (relative intensity) 412/414 (23/6), 381 (11), 280/282 (22/6), 195/197 (100/33); high resolution EIMS m/z 592.2568 (calcd for $C_{30}H_{41}ClN_2O_8$, Δ −1.6 mmu). $^1$H NMR data, see table 3; $^{13}$C NMR data, see table 4.

Cryptophycin-159: EIMS m/z (relative intensity) 666 (3), 412/414 (16/4), 396 (52), 255 (100), 195/197 (30/8), 91 (54); high resolution EIMS m/z 666.3060 (calcd for $C_{37}H_{47}ClN_2O_7$, Δ 1.1 mmu). $^1$H NMR data, see table 3; $^{13}$C NMR data, see table 4.

Cryptophycin-160: EIMS m/z (relative intensity) 628/630 (9/4), 412/414 (63/23), 280 (25), 217 (89), 195/197 (89/30);

high resolution EIMS m/z 628.2532 (calcd for $C_{33}H_{41}ClN_2O_8$, Δ 2.0 mmu). $^1$H NMR data, see table 3; $^{13}$C NMR data, see table 4.

Cryptophycin-161: EIMS m/z (relative intensity) 706/708 (6/2), 412/414 (49/18), 295 (15), 280/282 (25/7), 195/197 (100/34); high resolution EIMS m/z 706.2623 (calcd for $C_{36}H_{42}ClF_3N_2O_7$, Δ 1.0 mmu). $^1$H NMR data, see table 3; $^{13}$C NMR data, see table 4.

Cryptophycin-166: EIMS m/z (relative intensity) 652/654 (1.1/0.4), 412/414 (18/5), 241 (37), 195/197 (64/20); high resolution EIMS m/z 652.2918 (calcd for $C_{36}H_{45}ClN_2O_7$, Δ −0.2 mmu). $^1$H NMR data, see table 3; $^{13}$C NMR data, see table 4.

Cryptophycin-167: EIMS m/z (relative intensity) 666/668 (3.4/1.1), 412/414 (26/9), 280 (11), 255 (67), 195/197 (46/15); high resolution EIMS m/z 666.3058 (calcd for $C_{37}H_{47}ClN_2O_7$, Δ −1.4 mmu). $^1$H NMR data, see table 3; $^{13}$C NMR data, see table 4.

Cryptophycin-172: EIMS m/z (relative intensity) 688/690 (3/2), 412/414 (12/4), 277 (67), 218 (100), 195/197 (29/10), 141 (63); high resolution EIMS m/z 688.:2916 (calcd for $C_{39}H_{45}ClN_2O_7$, Δ −0.1 mmu). $^1$H NMR data, see table 3; $^{13}$C NMR data, see table 4.

Cryptophycin-181: EIMS m/z (relative intensity) 656/658 (9.0/3.3), 412/414 (84/34), 245 (71), 195/197 (47/7); high resolution EIMS m/z 656.2674 (calcd for $C_{35}H_{42}ClFN_2O_7$, Δ −0.9 mmu). $^1$H NMR data, see table 3; $^{13}$C NMR data, see table 4.

Cryptophycin-188: EIMS m/z (relative intensity) 674/676 (20/4), 412/414 (57/20), 280/282 (20/7), 263 (13), 195/197 (89/27); high resolution EIMS m/z 674.2551 (calcd for $C_{35}H_{41}ClF_2N_2O_7$, Δ 1.9 mmu). $^1$H NMR data, see table 3; $^{13}$C NMR data, see table 4.

Cryptophycin-234: The mixture containing cryptophycin-234 and 15% of its z isomer (58.3 mg) was repeatedly crystallized in EtOAc/ethyl ether solutions to obtain cryptophycin-234 (47 mg) and its z isomer (11 mg). $^1$H NMR (CDCl$_3$) amino or hydroxy acid unit δ (carbon position, multiplicity; J in Hz) A 5.77 (2, d; 15.2), 6.68 (3, ddd; 15.2, 9.7 and 5.4), 2.37 (4, dt; 14.2 and 10.5), 2.52 (4, m), 4.99 (5, m), 2.55 (6, m), 1.13 (6-Me, d; 6.8), 5.99 (7, dd; 15.8 and 8.8), 6.40 (8, d; 15.8), 7.25$^a$ (2'/6', d; 8.2), 7.29$^a$ (3'/5', d; 8.2), 4.71 (4'-CH$_2$OTBDMS, brs), 0.08 (6H) and 0.93 (9H) (4'-CH$_2$OTBDMS); B 4.81 (2, m), 5.77 (2-NH, obscured by other signal), 3.03 (3, dd; −14.4 and 7.3), 3.14 (3, dd; −14.4 and 5.4), 7.22 (5, d; 2.0), 3.86 (7-OMe, s), 6.83 (8, d; 8.4), 7.07 (9, dd; 8.4 and 2.0); C 2.71 (2, m), 1.22 (2-Me, d; 7.2), 3.29 (3, m), 3.49 (3, m), 6.98 (3-NH, br t; 5.6); D 4.84 (2, m), 1.36 (3, m), 1.59–1.71 (3/4, m), 0.73 (4-Me, d, 6.4), 0.77 (5, d, 6.2). $^a$ Interchangeable; $^{13}$C NMR (CDCl$_3$) unit δ (carbon position) A 165.5 (1), 125.2 (2), 141.4 (3), 36.4 (4), 77.4 (5), 42.2 (6), 17.3 (6-Me), 129.6 (7), 131.6 (8), 136.4 (1'), 126.0$^a$ (2'/6'), 126.3$^a$ (3'/5'), 140.9 (4'), 64.7 (4'-CH$_2$O—), 25.9 and −5.3 (4'-CH$_2$OTBDMS); B 171.0$^b$ (1), 53.6 (2), 35.1 (3), 129.9 (4), 131.0 (5), 122.4 (6), 153.9 (7), 56.1 (7-OCH$_3$), 112.2 (8), 128.4 (9); C 175.6 (1), 38.3 (2), 14.0 (2-Me), 41.3 (3); D 170.9$^b$(1), 71.5 (2), 39.5 (3), 24.5 (4), 22.7 (4-Me), 21.2 (5). $^a$ and $^b$signals are interchangeable.

Cryptophycin-236: $^1$H NMR (CDCl$_3$) amino or hydroxy acid unit δ (carbon position, multiplicity; J in Hz) A 5.76 (2, d; 15.2), 6.68 (3, ddd; 15.2, 9.6 and 5.6), 2.37 (4, m), 2.51 (4, m), 5.00 (5, m), 2.54 (6, m), 1.13 (6-Me, d; 6.9), 6.00 (7, dd; 15.9 and 8.6), 6.39 (8, d; 15.9), 7.20–7.30 (2'/3'/5'/6', br m), 4.28 (4'-CH$_2$NH-t-Boc, d; 4.9), 4.80 (4'-CH$_2$NH-t-Boc, d; 4.9), 1.46 (4'-CH$_2$NH-t-Boc; s); B 4.80 (2, m), 5.65 (2-NH, d; 8.5), 3.04 (3, dd; −14.4 and 6.9), 3.13 (3, dd; −14.4 and 5.5), 7.22 (5, d; 2.2), 3.87 (7-OMe, s), 6.83 (8, d; 8.4), 7.08 (9, dd; 8.4 and 2.2); C 2.71 (2, m), 1.22 (2-Me, d; 7.3), 3.27 (3, m), 3.51 (3, m), 6.93 (3-NH, br t; 5.6); D 4.84 (2, dd; 9.9 and 3.5), 1.36 (3, m), 1.58–1.70 (3/4, m), 0.74 (4-Me, d, 6.4), 0.78 (5, d, 6.4); $^{13}$C NMR (CDCl$_3$) unit δ (carbon position) A 165.4 (1), 125.2 (2), 141.4 (3), 36.5 (4), * (5), 42.2 (6), 17.3 (6-Me), 130.1 (7), 131.4 (8), 135.9 (1'), 126.4 (2'/6'), 127.8 (3'/5'), 138.4 (4'), 44.4 (4'-CH$_2$NH-t-Boc), 28.4 (4'-CH$_2$NH-t-Boc); B 170.9 (1), 53.5 (2), 35.1 (3), 129.9 (4), 131.1 (5), (6), 154.0 (7), 56.2 (7-OCH$_3$), 112.3 (8), 128.4 (9); C 175.6 (1), 38.3 (2), 14.0 (2-Me), 41.2 (3); D 170.9(1), 71.6 (2), 39.6 (3), 24.5 (4), 22.7 (4-Me), 21.3 (5). * Hidden under solvent signal.

Cryptophycin-238: Cryptophycin-234 (14 mg) in THF (1.5 mL) was treated with tetrabutylammonium fluoride solution (25 μL, 1M in THF) at 0° C. After 1 h, saturated NH$_4$Cl (5 mL) was to the reaction mixture followed by water (15 mL) and extracted with EtOAc (50 mL). The EtoAc layer was dried over MgSO$_4$ and evaporated. The residue was purified on a small silica column using CH$_2$Cl$_2$ and EtOAc as eluants. The latter fraction was evaporated to obtain cryptophycin-238 (11.8 mg) EIMS m/z (relative intensity) 668/670 (3/0.5), 412/414 (38/14), 257 (29), 195/197 (25/10); high resolution EIMS m/z 668.2898 (calcd for $C_{36}H_{45}ClN_2O_8$, Δ −3.4 mmu). $^1$H NMR (CDCl$_3$) amino or hydroxy acid unit δ (carbon position, multiplicity; J in Hz) A 5.76 (2, d; 15.6), 6.68 (3, ddd; 15.6, 9.8 and 5.5), 2.36 (4, dt; 14.4 and 10.4), 2.51 (4, br dd; 14.4 and 5.1), 5.00 (5, m), 2.55 (6, m), 1.13 (6-Me, d; 6.8), 6.01 (7, dd; 15.9 and 8.8), 6.40 (8, d; 15.9), 7.31 (2'/3'/5'/6', br s), 4.47 (4'-CH$_2$OH, brs); B 4.80 (2, m), 5.78 (2-NH, d; 8.4), 3.01 (3, dd; −14.4 and 7.4), 3.13 (3, dd; −14.4 and 5.5), 7.21 (5, d; 2.0), 3.86 (7-OMe, s), 6.83 (8, d; 8.5), 7.07 (9, dd; 8.5 and 2.0); C 2.71 (2, m), 1.21 (2-Me, d; 7.1), 3.28 (3, m), 3.49 (3, m), 6.98 (3-NH, br t; 6.0); D 4.84 (2, dd; 9.9 and 3.2), 1.35 (3, m), 1.58–1.71 (3/4, m), 0.74 (4-Me, d; 6.4), 0.77 (5, d; 6.3); $^{13}$C NMR (CDCl$_3$) unit δ (carbon position) A 165.5 (1), 125.2 (2), 141.4 (3), 36.4 (4), 77.4 (5), 42.2 (6), 17.3 (6-Me), 130.1 (7), 131.4 (8), 136.1 (1'), 126.3$^a$ (2'/6'), 127.2$^a$ (3'/5'), 140.4 (4'), 64.9 (4'-CH$_2$OH); B 171.0$^b$ (1), 53.7 (2), 35.0 (3), 129.9 (4), 131.0 (5), 122.3 (6), 153.9 (7), 56.1 (7-OCH$_3$), 112.2 (8), 128.4 (9); C 175.6 (1), 38.2 (2), 14.0 (2-Me), 41.1 (3); D 170.8$^b$ (1), 71.5 (2), 39.5 (3), 24.5 (4), 22.7 (4-Me), 21.3 (5). $^a$ and $^b$signals are interchangeable.

Cryptophycin-246: Cryptophycin-236 (9 mg, 0.012 mmol) in CH$_2$Cl$_2$ (50 μL) was treated with 4N HCl in dioxane (20 μL, 0.08 mmol) at room temp. After 1 h, the solvent was evaporated and the residue was subjected to flash chromatography on a small C$_{18}$ silica column (Alltech, 500 mg) using methanol/water (1:1) for elution. The first fraction (3 mL) after evaporation of the solvent gave cryptophycin-246 (7 mg, 85%). $^1$H NMR (CD$_3$OD) amino or hydroxy acid unit δ (carbon position, multiplicity; J in Hz) A 5.92 (2, dd; 15.2 and 1.7), 6.69 (3, ddd; 15.2, 11.1 and 3.8), 2.35 (4, m), 2.68 (4, m), 5.06 (5, m), 2.63 (6, m), 1.15 (6-Me, d; 7.4), 6.18 (7, dd; 15.9 and 8.9), 6.50 (8, d; 15.9), 7.40 (2'/6', br d;

8.2), 7.46 (3'/5', br d; 8.2), 4.08 (4'-CH$_2$NH$_2$HCl, s); B 4.51 (2, dd; 11.1 and 3.4), 2.75 (3, m), 3.17 (3, dd; −14.5 and 3.9), 7.27 (5, d; 2.0), 3.83 (7-OMe, s), 6.97 (8, d; 8.5), 7.16 (9, dd; 8.5 and 2.0); C 2.73 (2, m), 1.17 (2-Me, d; 8.0), 3.26 (3, m), 3.56 (3, m); D 4.92 (2, dd; 9.8 and 3.9), 1.35 (3, m), 1.54–1.65 (3/4, m), 0.71 (4-Me, d; 6.4), 0.75 (5, d; 6.4); $^{13}$C NMR (CD$_3$OD) unit δ (carbon position) A 168.4 (1), 125.7 (2), 143.5 (3), 37.7 (4), 78.6 (5), 43.5 (6), 17.5 (6-Me), 133.6 (7), 131.9 (8), 139.5$^a$ (1'), 128.0 (2'/6'), 130.3 (3'/5'), 133.3$^a$ (4'), 44.0 (4'-$\underline{C}$H$_2$NH$_2$HCl); B 174.1 (1), 57.4 (2), 36.3 (3), 132.2 (4), 131.5 (5), 123.3 (6), 155.4 (7), 56.6 (7-OCH$_3$), 113.5 (8), 129.3 (9); C 177.5 (1), 39.0 (2), 15.1 (2-Me), 41.2 (3); D 172.3 (1), 72.8 (2), 41.0 (3), 25.7 (4), 21.7 (4-Me), 23.2 (5). $^a$ signals are interchangeable.

Cryptophycin-250: A solution of cryptophycin-247 (5.1 mg) in dichloromethane (80 μL) was treated with hydrochloric acid (40 μL, 4N in dioxane). After 2 h, the reaction mixture was concentrated, diluted with water and passed through a short ODS column. The column was washed with water (5 mL) followed by CH$_3$CN (3 mL). The latter fraction was evaporated to obtain cryptophycin-250 (5 mg). It was further purified on a reversed phase HPLC (Econosil C$_{18}$, 25 cm×10 mm, 10μ, 35% H$_2$O/CH$_3$CN, 4 mL/min) to obtain a pure sample (4 mg, t$_R$ 18 min). EIMS m/z (relative intensity) 653/655 (15/10), 533 (33), 242 (48), 195/197 (36/13); high resolution EIMS m/z 653.2865 (calcd for C$_{35}$H$_{44}$ClN$_3$O$_7$, Δ 0.3 mmu). $^1$H NMR (CDCl$_3$) amino or hydroxy acid unit δ (carbon position, multiplicity; J in Hz) A 5.78 (2, d; 15.1), 6.68 (3, ddd; 15.1, 9.6 and 5.4), 2.35 (4, dt; 14.4 and 10.7), 2.48 (4, br dd; 14.4 and 5.1), 5.01 (5, m), 2.53 (6, m), 1.12 (6-Me, d; 6.8), 6.01 (7, dd; 15.9 and 8.7), 6.33 (8, d; 15.9), 6.81 m, 6.89 d, 6.94 s and 6.99 m (2'/3'-NH$_3$/4'/6'), 7.15 (5', t; 7.8); B 4.79 (2, m), 5.95 (2-NH), 3.02 (3, dd; -14.4 and 7.3), 3.15 (3, dd; -14.4 and 5.5), 7.22 (5, d; 2.0), 3.86 (7-OMe, s), 6.84 (8, d; 8.4), 7.08 (9, dd; 8.4 and 2.0); C 2.70 (2, m), 1.23 (2-Me, d; 7.1), 3.27 (3, m), 3.51 (3, m), 6.99 (3-NH, m); D 4.87 (2, dd; 9.8 and 3.2), 1.39 (3, m), 1.59–1.73 (3/4, m), 0.76 (4-Me, d, 5.4), 0. 80 (5, d, 5.6); A 165.8 (1), 125.2 (2), 141.5 (3), 36.4 (4), 77.3 (5), 42.0 (6), 17.1 (6-Me), 131.0 (7), 131.3 (8), 138.3 (1'), 116.0 (2'), 121.1 (4'), 130.0 (5'), 118.0 (6'); B 171.2 (1), 54.0 (2), 35.0 (3), 129.8 (4), 131.0 (5), 122.4 (6), 153.9 (7), 56.1 (7-OCH$_3$), 112.3 (8), 128.4 (9); C 175.6 (1), 38.2 (2), 14.2 (2-Me), 41.0 (3); D 170.9 (1), 71.5 (2), 39.6 (3), 24.6 (4), 22.8 (4-Me), 21.4 (5).

Cryptophycin-251: EIMS m/z (relative intensity) 696 (0.7), 652 (M$^+$–CO$_2$; 0.7), 412/414 (4/2), 285 (6), 241 (5), 195/197 (11/3); high resolution EIMS m/z (calcd for C$_{37}$H$_{45}$ClN$_2$O$_9$, Δmmu). $^1$H NMR data, see table 3; $^{13}$C NMR data, see table 4.

Cryptophycin-255: $^1$H NMR (CDCl$_3$) amino or hydroxy acid unit δ (carbon position, multiplicity; J in Hz) A 5.78 (2, d; 15.1), 6.67 (3, ddd; 15.1, 9.5 and 5.9), 2.37 (4, dt; 14.9 and 10.3), 2.45 (4, m), 4.96 (5, m), 2.52 (6, m), 1.09 (6-Me, d; 6.8), 5.74 (7, dd; 15.1 and 8.9), 6.24 (8, d; 15.1), 7.20–7.33 (2'/3'/4'/5'/6', m); B 4.83 (2, m), 5.64 (2-NH, d; 8.8), 3.05 (3, dd; -14.6 and 7.1), 3.14 (3, dd; -14.6 and 5.4), 7.22 (5, d; 2.0), 3.88 (7-OMe, s), 6.85 (8, d; 8.5), 7.08 (9, dd; 8.5 and 2.0); C 2.72 (2, m), 1.23 (2-Me, d; 7.3), 3.29 (3, m), 3.50 (3, m), 6.95 (3-NH, m); D 4.86 (2, dd; 10.0 and 3.4), 1.49 (3, m), 1.63–1.85 (3/4, m), 0.89 (4-Me, d, 6.4), 0.94 (5, d, 6.4).

TABLE 3

500 MHz $^1$H NMR Data for Crytophycins-3, -151, -152, -153, -154, -156, -159, -160, -161, -166, -167, -172, -181, -188 and 251

P = position

| P | 3 | 151 | 152 | 153 | 154 | 156 | 159 | 160 | 161 | 166 | 167 | 172 | 181 | 188 | 251 |
|---|---|---|---|---|---|---|---|---|---|---|---|---|---|---|---|
| A2 | 5.77 d | 5.78 | 5.77 | 5.77 | 5.77 | 5.76 | 5.76 | 5.77 | 5.78 | 5.77 | 5.77 | 5.78 | 5.78 | 5.78 | 5.76 |
| 3 | 6.68 ddd | 6.71 | 6.67 | 6.68 | 6.68 | 6.66 | 6.68 | 6.68 | 6.68 | 6.68 | 6.68 | 6.70 | 6.68 | 6.68 | 6.68 |
| 4R | 2.37 dt | 2.45 | 2.37 | 2.37 | 2.37 | 2.34 | 2.38 | 2.35 | 2.36 | 2.39 | 2.37 | 2.41 | 2.36 | 2.35 | 2.35 |
| 4S | 2.54 brdd | 2.58 | 2.47 | 2.52 | 2.52 | 2.41 | 2.51 | 2.49 | 2.53 | 2.52 | 2.51 | 2.55 | 2.54 | 2.52 | 2.51 |
| 5 | 5.01 ddd | 5.10 | 4.97 | 5.00 | 5.00 | 4.88 | 5.02 | 4.96 | 5.02 | 5.03 | 4.99 | 5.04 | 5.00 | 5.01 | 5.00 |
| 6 | 2.56 m | 2.71 | 2.47 | 2.54 | 2.54 | 2.27 | 2.56 | 2.49 | 2.59 | 2.59 | 2.54 | 2.61 | 2.57 | 2.58 | 2.55 |
| 6-Me | 1.14 d | 1.22 | 1.09 | 1.13 | 1.13 | 1.04 | 1.13 | 1.10 | 1.15 | 1.15 | 1.12 | 1.17 | 1.15 | 1.14 | 1.13 |
| 7 | 6.01 dd | 6.09 | 5.63 dd | 6.00 | 5.99 | 4.53 dd | 5.87 | 5.70 | 6.13 | 5.92 | 5.97 | 6.14 | 6.09 | 6.05 | 6.00 |
| 8 | 6.41 d | 7.19 | 6.23 dd | 6.38 | 6.34 | 6.31 d | 6.59 | 6.26 | 6.45 | 6.63 | 6.34 | 6.57 | 6.58 | 6.34 | 6.39 |
| 9 | | | 6.71 dd | | | | | | | | | | | | |
| 10 | | | 6.49 dd | | | | | | | | | | | | |
| 8/10-Ar-1' | | | | | | | | | | | | 7.67 br s | | | |
| 2' | 7.28 to | 7.41 to | 7.36 br d | 6.85 t | 6.68 d | 2.31 s | 7.37 br s | 7.42 d | 2.33 s | 6.94 br s | | | 6.83 m | 7.30 d | |
| 3' | 7.34 m | 7.58 m | 7.30 m | 3.80 s | 3.79 s | 6.95 brs | | 7.55 d | 7.11 to | 2.29 s | 7.54 m | 7.09 m | | 7.23 d | |
| 4' | 7.23 m | 7.77 d | 7.22 m | 6.78 br d | 6.36 d | 2.31 s | 6.47 br s | | 7.39 m | 6.87 br s | 7.78 m | 7.40 m | 6.68 m | 3.63 s | |
| 5' | 7.28 to | 7.94 d | 7.30 br t | 7.21 t | 3.79 s | 6.95 d | 7.35 br s | 7.55 d | 7.39 m | 2.29 s | 7.78 m | 7.02 m | | 7.23 d | |
| 6' | 7.34 m | 7.41 to | 7.36 br d | 6.92 d | 6.68 d | 7.28 d | | 7.42 d | 7.39 d | 6.94 m | 7.44 br s | 7.19 m | 6.83 m | 7.30 d | |

TABLE 3-continued

500 MHz ¹H NMR Data for Crytophycins-3, -151, -152, -153, -154, -156, -159, -160, -161, -166, -167, -172, -181, -188 and 251

P = position

| P | 3 | 151 | 152 | 153 | 154 | 156 | 159 | 160 | 161 | 166 | 167 | 172 | 181 | 188 | 251 |
|---|---|---|---|---|---|---|---|---|---|---|---|---|---|---|---|
| 7' | | 7.58 d | | | | | | | | | | 7.44 m | | | |
| 8' | | 8.07 d | | | | | | | | | | 7.78 m | | | |
| D2 | 4.84 dd | 4.85 | 4.87 | 4.84 | 4.84 | 4.87 | 4.84 | 4.83 | 4.84 | 4.85 | 4.85 | 4.86 | 4.85 | 4.84 | 4.84 |
| 3 | 1.62 m | 1.64 | 1.72 | 1.65 | 1.66 | 1.75 | 1.68 | 1.67 | 1.65 | 1.69 | 1.66 | 1.67 | 1.66 | 1.67 | 1.36 |
| 3' | 1.36 m | 1.35 | 1.47 | 1.37 | 1.38 | 1.48 | 1.38 | 1.36 | 1.31 | 1.38 | 1.38 | 1.38 | 1.36 | 1.32 | 1.58 to |
| 4 | 1.62 m | 1.64 | 1.72 | 1.65 | 1.66 | 1.75 | 1.68 | 1.67 | 1.65 | 1.69 | 1.66 | 1.64 | 1.66 | 1.67 | 1.70 m |
| 4-Me | 0.77 d | 7.00. | 0.87 | 0.77 | 0.79 | 0.94 | 0.79 | 0.80 | 0.76 | 0.79 | 0.78 | 0.74 | 0.78 | 0.79 | 0.77 |
| 5 | 0.73d | 0.64 | 0.86 | 0.74 | 0.77 | 0.91 | 0.77 | 0.79 | 0.72 | 0.76 | 0.75 | 0.65 | 0.74 | 0.77 | 0.73 |

Spectra recorded in CDCl$_3$; The chemical shifts are for the protons or methyl or methoxyl or hydroxy methyl function positioned on the carbon indicated in the table. The chemical shifts for the protons in units B and C are within ±0.2 ppm and coupling constants within ±0.5 Hz of the corresponding values in cryptophycin-3. J (H,H) in Hz for 151: 3',4'=8.3; 5',6'=8.0; 7',8'=8.1; J (H,H) in Hz for 152: 6,7=8.7; 7,8=15.3; 8,9=10.5; 9,10=15.7; 2',3'=3',4'=4',5'=5',6'=7.4; J (H,H) in Hz for 153: 2',4'=2',6'=2.0; 4',5'=5',6'=7.9; J (H,H) in Hz for 154: 2',4'=4',6'=2.2; δ for 8-OCH$_3$ of the unit A in 156 is 3.51: J (H,H) in Hz for 156: 6,7=9.3; 7,8=12.6; J (H,H) in Hz for 159: 5',6'=8.3; J (H,H) in Hz for 161: 2',3'=4',5'=8.1; J (H,H) in Hz for 251: 2'3'=5',6'=8.2; The observable coupling constants for the rest of the protons in the table are within ±0.5 Hz of the corresponding values in 3.

TABLE 4

125 MHz ¹³C NMR Data for Crytophycins-3, -151, -152, -153, -154, -156, -159, -160, -161, -166, -167, -172, -181, -188 and 251.

P = position

| P | 3 | 151 | 152 | 153 | 154 | 156 | 159 | 160 | 161 | 166 | 167 | 172 | 181 | 188 | 251 |
|---|---|---|---|---|---|---|---|---|---|---|---|---|---|---|---|
| A1 | 165.4 | 165.5 | 165.4 | 165.4 | 165.4 | 165.5 | 165.5 | 165.6 | 165.4 | 165.4 | 165.5 | 165.4 | 165.4 | 165.3 | 165.5 |
| 2 | 125.2 | 125.3 | 125.1 | 125.2 | 125.2 | 125.0 | 125.3 | 125.0 | 125.2 | 125.2 | 125.1 | 125.1 | 125.3 | 125.3 | 125.2 |
| 3 | 141.4 | 141.4 | 141.4 | 141.4 | 141.4 | 141.7 | 141.5 | 141.7 | 141.2 | 141.5 | 141.5 | 141.4 | 141.3 | 141.1 | 141.4 |
| 4 | 36.5 | 36.6 | 36.4 | 36.4 | 36.5 | 36.3 | 36.5 | 36.4 | 36.5 | 36.5 | 36.5 | 36.5 | 36.5 | 36.5 | 35.0 |
| 5 | 77.1 | 77.5 | 77.3 | 77.4 | 77.3 | 77.9 | 77.5 | * | 77.1 | 77.4 | 77.5 | 77.4 | * | 77.1 | 77.2 |
| 6 | 42.3 | 38.3 | 41.9 | 42.2 | 42.2 | 37.7 | 42.3 | 42.2 | 42.3 | 42.3 | 42.3 | 42.3 | 42.7 | 42.1 | 42.2 |
| 6-Me | 17.3 | 17.4 | 17.2 | 17.3 | 17.3 | 18.5 | 17.4 | 17.3 | 17.2 | 17.4 | 17.4 | 17.4 | 17.3 | 17.2 | 17.3 |
| 7 | 130.0 | 133.3 | 134.4 | 130.4 | 130.6 | 103.0 | 129.4 | 129.8 | 130.5 | 130.4 | 129.3 | 130.5 | 127.1 | 133.1 | 130.2 |
| 8 | 130.1 | 128.9 | 132.3 | 131.7 | 132.0 | 148.6 | 130.3 | 121.5 | 133.0 | 131.3 | 132.0 | 131.8 | 132.8 | 130.0 | 131.3 |
| 9 | | | 128.4 | | | | | | | | | | | | |
| 10 | | | 132.0 | | | | | | | | | | | | |
| 8/10-Ar-1' | 136.7 | 134.4 | 137.1 | 138.2 | 138.7 | 55.9† | 134.8 | | 140.2 | 135.8 | 136.6 | 126.0 | ** | ** | 135.9 |
| 2' | 126.1 | 123.6 | 126.2 | 111.7 | 104.4 | | 132.9 | 143.6 | 125.6 | 135.0 | 124.0 | 134.1 | ** | 108.8 d | 126.4 |
| 3' | 128.6 | 125.5 | 128.6 | 159.9 | 161.0 | | 131.1 | 123.8 | 126.3 | 127.5 | 138.1 | 128.2 | 115.8 | ** | 129.6 |
| 4' | 128.4 | 128.0 | 127.5 | 118.8 | 99.7 | | 137.2 | 107.3 | 141.2 | 126.1 | 129.6 | 126.3 | 128.8 | 102.8 t | 132.8 |
| 5' | 128.6 | 123.5 | 128.6 | 129.6 | 161.0 | | 126.8 | 140.1 | 126.3 | 129.5 | 138.1 | 127.8 | 124.2 | ** | 129.6 |
| 6' | 126.1 | 125.8 a | 126.2 | 113.1 | 104.4 | | 125.2 | | 125.6 | 125.4 | 124.0 | 123.3 | 124.2 | 108.8 | 126.4 |
| 7' | | 126.1 a | | | | | | | | | | 125.8 | | | |
| 8' | | 128.6 | | | | | | | | | | 127.6 | | | |
| 9' | | 131.0 | | | | | | | | | | 133.5 | | | |
| 10' | | 133.7 | | | | | | | | | | 132.9 | | | |
| D1 | 170.1 | 171.0 | 170.8 | 170.9 | 170.9 | 170.9 | 170.9 | 170.9 | 170.8 | 170.9 | 171.0 | 170.9 | 170.8 | 170.9 | 170.9 |
| 2 | 71.6 | 71.5 | 71.5 | 71.5 | 71.5 | 71.6 | 71.6 | 71.5 | 71.6 | 71.5 | 71.5 | 71.6 | 71.5 | 71.5 | 71.5 |
| 3 | 39.5 | 39.5 | 39.6 | 39.5 | 39.5 | 39.6 | 39.6 | 39.5 | 39.6 | 39.5 | 39.6 | 39.5 | 39.5 | 39.6 | 39.6 |
| 4 | 24.5 | 24.5 | 24.6 | 24.5 | 24.5 | 24.7 | 24.5 | 24.5 | 24.5 | 24.5 | 24.5 | 24.5 | 24.5 | 24.5 | 24.5 |
| 4-Me | 21.2 | 21.1 | 21.4 | 21.2 | 21.2 | 21.4 | 21.3 | 21.3 | 21.2 | 21.2 | 21.2 | 21.2 | 21.2 | 21.3 | 21.2 |
| 5 | 22.6 | 22.7 | 22.9 | 22.7 | 22.7 | 23.0 | 22.7 | 22.8 | 22.7 | 22.8 | 22.7 | 22.6 | 22.7 | 22.8 | 22.7 |

Spectra recorded in CDCl₃ The chemical shifts for carbons in units B and C are within ±0.5 ppm of the values in cryptophycin-3. * signals submerged under the CDCl₃. signal; ** Signals could not be found. † signal for 8-OCH₃ of the unit A; a signals in a column could be interchangeable. The 3'-OCH₃ carbon of the unit A in cryptophycin-153 was resonated at δ 55.1 and the 3' and 5'-OCH₃ carbons of 154 were resonated at δ 55.3. The 2' and 4'–CH₃ carbon signals of 159 were observed at δ 19.7 and 20.9 respectively . The 2'-CH₃ carbon signal of 166 was observed at δ 19.8. The 3' and 5'-CH₃ carbon signals of 167 were observed at δ 21.2.

The methylene and carboxyl carbons of 4'-CH₂COOH were observed at δ 40.4 and 174.5 respectively.

EXAMPLE 92

Epoxide Analogs

Cryptophycins-157, 158, 164, 165, 168, 169, 170, 171, 173, 177, 178, 179, 180, 182, 183, 200, 242 and 269. Table 5.

* 188 requires 6 equivalents of MCPBA and 36 h for 70% conversion to the epoxides. ** Inseparable mixture.

TABLE 5

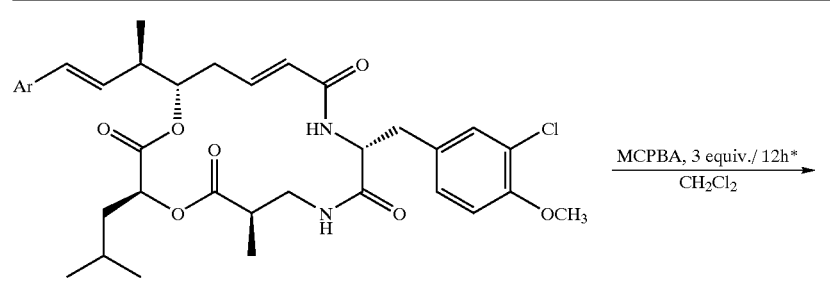

Styrene

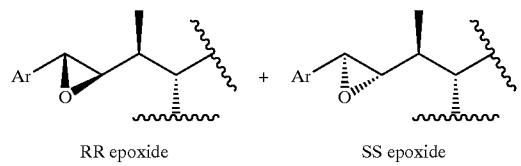

RR epoxide        SS epoxide

80–85% combined yield

| Styrene Cryptophycin # | Ar | Epoxide # | Stereo-chemistry | RR/SS ratio |
|---|---|---|---|---|
| 151 | naphthalen-1-yl | 157<br>158 | RR<br>SS | 2.4:1 |
| 153 | 3-H₃CO-phenyl | 168<br>169 | RR<br>SS | 2.4:1 |
| 159 | 2,4-dimethylphenyl | 170 | RR | 2.8:1 |
| 166 | 2-methylphenyl | 177<br>178 | RR<br>SS | 2.0:1 |

TABLE 5-continued
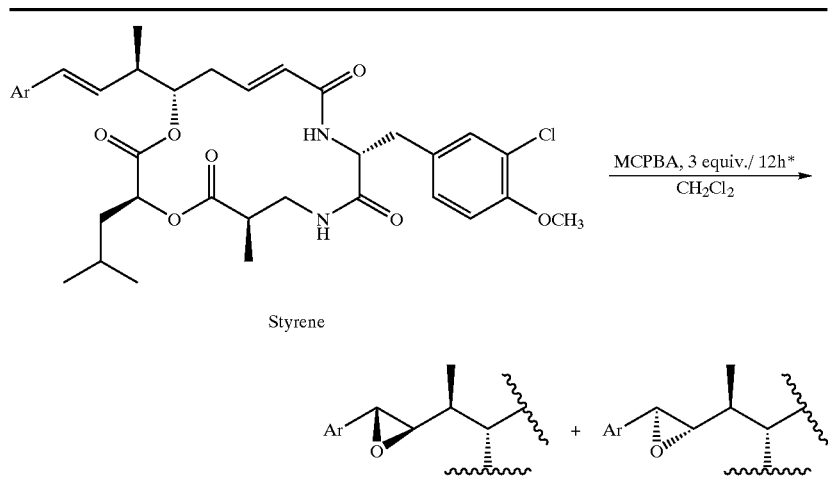
Styrene
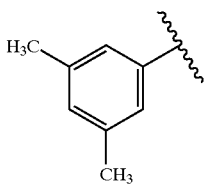 + 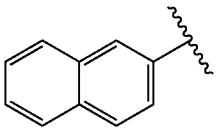
RR epoxide      SS epoxide
80–85% combined yield
| Styrene Cryptophycin # | Ar | Epoxide # | Stereo-chemistry | RR/SS ratio |
|---|---|---|---|---|
| 167 | 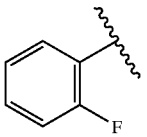 | 179<br>180 | RR<br>SS | 2.7:1 |
| 172 | 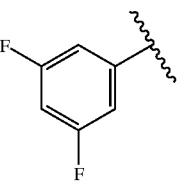 | 173<br>174 | RR<br>SS | 1.5:1 |
| 181 | 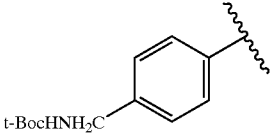 | 182<br>183 | RR<br>SS | 2.0:1 |
| 188 | 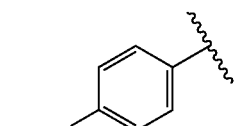 | 200 | RR<br>SS | 1.4:1 |
| 236 |  | 242 | RR<br>SS | 2:1 |
| 238 |  | 269 | RR<br>SS | 2:1** |

TABLE 5-continued

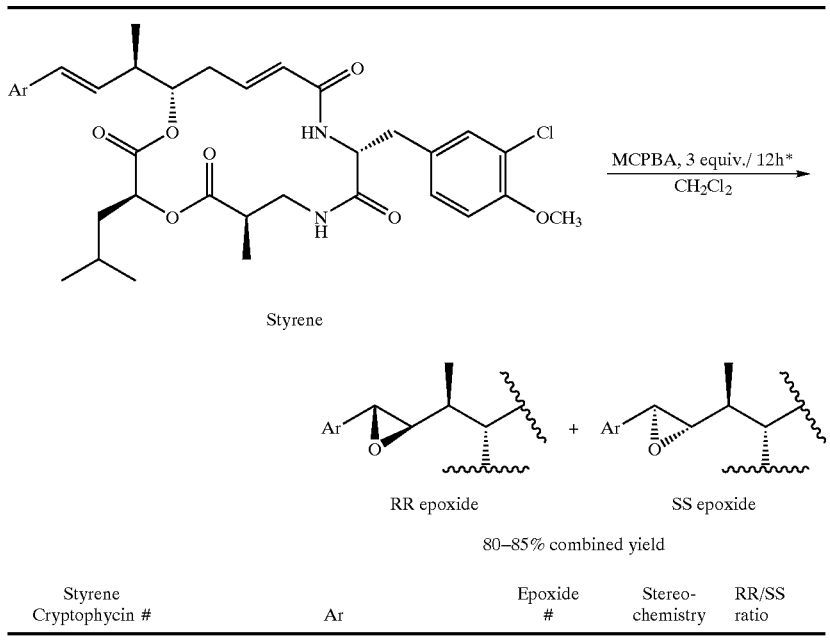

| Styrene Cryptophycin # | Ar | Epoxide # | Stereo-chemistry | RR/SS ratio |
|---|---|---|---|---|

*188 requires 6 equivalents of MCPBA and 36 h for 70% conversion to the epoxides.
**Inseparable mixture.

General procedure for the epoxidation of styrene analogs: A solution of styrene analog (0.1 mmol) and m-chloroperoxybenzoic acid (0.3 mmol) in 3 mL of dichloromethane was allowed to stir at room temperature. After 16 h, the reaction mixture was diluted with dichloromethane (3 mL) and washed with phosphate buffer (0.1M, pH 8, 5 mL) to remove the 3-chlorobenzoic acid generated during the reaction. The organic layer was separated, treated with dimethyl sulfide (20 µL) to quench excess peracid and subjected to the buffer wash for the second time. The dichloromethane layer was separated, dried over $MgSO_4$, evaporated and kept under vacuum for 24 hours. The residue was subjected to HPLC on reversed phase column (Econosil C18, 10µ, 250 mm×22 mm, 35% $H_2O/CH_3CN$, 6 mL/min) to obtain RR and SS -epoxides.

The experimental details and cytotoxicity data are summarized in table 3.

Cryptophycins-157 and -158: Cryptophycin-151 was treated with m-CPBA and the products isolated using reversed phase HPLC to obtain cryptophycins-157 and -158.

Cryptophycin-157: EIMS m/z (relative intensity) 704/706 (1/0.3), 195/197 (14/4), 141 (100), 115 (27); high resolution EIMS m/z 704.2865 (calcd for $C_{39}H_{45}ClN_2O_8$, −0.1 mmu error); $^1H$ NMR data, see table 6; $^{13}C$ NMR data see table 7.

Cryptophycin-158: EIMS m/z (relative intensity) 704/706 (2.2/1.9), 195/197 (25/9), 141 (100); high resolution EIMS m/z 704.2862 (calcd for $C_{39}H_{45}ClN_2O_8$, 0.3 mmu error); $^1H$ NMR data see, table 6; $^{13}C$ NMR data see table 7.

Cryptophycins-164 and -165: A solution of cryptophycin-152 (53 mg, 0.08 mmol) and m-chloroperoxybenzoic acid (15 mg, 0.087 mmol) in 3 mL of dichloromethane was allowed to stir at room temperature for 16 h. The reaction mixture was subjected to the same workup and purification procedure to obtain compounds 164/165A and 164/165B (5 mg each), starting material (10 mg), and other decomposition products. The gross structures were analyzed to be cryptophycins-164 and -165 but the stereochemistry of the epoxide moiety in the compounds could not be assigned.

Cryptophycin-164/165A: $^1H$ NMR ($CDCl_3$) amino or hydroxy acid unit δ (carbon position, multiplicity; J in Hz) A 5.77 (2, d; 15.1), 6.67 (3, ddd; 15.1, 9.7 and 5.4.), 2.37 (4, m), 2.44 (4, m), 4.98 (5, m), 2.48 (6, m), 1.06 (6-Me, d; 6.7), 5.83 (7, dd; 15.6 and 8.5), 5.40 (8, dd; 15.6 and 7.8), 3.32 (9, dd; 7.9 and 2.0), 3.75 (10, d; 2.0), 7.26 (2'/6', m), 7.31–7.37 (3'/4'/5', m); B 4.82 (2, m), 5.75 (2-NH, d; 9.2), 3.04 (3, dd; −14.5 and 7.3), 3.14 (3, dd; −14.5 and 5.5), 7.23 (5, d; 2.2), 3.87 (7-OMe, s), 6.84 (8, d; 8.2), 7.09 (9, dd; 8.2 and 2.2); C 2.73 (2, m), 1.23 (2-Me, d; 7.2), 3.29 (3, m), 3.51 (3, m), 6.97 (3-NH, br t; 6.3); D 4.88 (2, dd; 10.0 and 3.7), 1.52 (3, m), 1.79 (3/4, m), 0.92 (4-Me, d; 6.5), 0.95 (5, d; 6.5). $^{13}C$ NMR ($CDCl_3$) unit δ (carbon position) A 165.4 (1), 125.3 (2), 141.2 (3), 36.5 (4), 77.0 (5), 41.3 (6), 17.0 (6-Me), 136.2 (7), 129.4 (8), 62.5 (9), 60.1 (10), 136.9 (1'), 125.4 (2'/6'), 128.7 (3'/5'), 128.4 (4'); B 171.0 (1), 53.6 (2), 35.0(3), 129.9 (4), 131.0 (5), 122.4 (6), 154.0 (7), 56.1 (7-OMe), 112.3 (8), 128.3 (9); C 175.6 (1), 38.3 (2), 14.1 (2-Me), 41.2 (3); D 170.8 (1), 71.5 (2), 39.6 (3), 24.7 (4), 21.4 (4-Me), 22.9 (5).

Cryptophycin-164/165B: $^1H$ NMR ($CDCl_3$) amino or hydroxy acid unit δ (carbon position, multiplicity; J in Hz) A 5.76 (2, d; 15.3), 6.66 (3, ddd; 15.3, 9.6 and 5.7.), 2.36 (4, m), 2.40 (4, m), 5.00 (5, m), 2.47 (6, m), 1.08 (6-Me, d; 6.8), 5.85 (7, dd; 15.5 and 8.5), 5.43 (8, ddd; 15.5, 7.6 and 0.6), 3.35 (9, dd; 7.6 and 1.9), 3.75 (10, d; 1.9), 7.27 −7.37 (2'/3'/4'/5'/6', m); B 4.82 (2, m), 5.65 (2-NH, d; 8.5), 3.04 (3, dd; −14.4 and 7.2), 3.14 (3, dd; −14.4 and 5.5), 7.22 (5, d; 2.1), 3.87 (7-OMe, s), 6.84 (8, d; 8.5), 7.08 (9, dd; 8.5 and 2.1); C 2.72 (2, m), 1.22 (2-Me, d; 7.2), 3.27 (3, m), 3.52 (3, m), 6.90 (3-NH, br t; 6.3); D 4.87 (2, dd; 9.8 and 3.8), 1.48 (3, m), 1.77 (3, m), 1.73 (4, m), 0.89 (4-Me, d; 6.4), 0.90 (5, d; 6.6). $^{13}C$ NMR ($CDCl_3$) unit δ (carbon position) A 165.4 (1), 125.2 (2), 141.2 (3), 36.4 (4), 41.3 (6), 16.9 (6-Me), 135.9 (7), 129.1 (8), 62.3 (9), 60.4 (10), 136.0 (1'), 125.5 (2'/6'), 128.6 (3'/5'), 128.4 (4'); B 170.9 (1), 53.6 (2), 35.1

(3), 129.8 (4), 131.0 (5), 122.4 (6), 154.0 (7), 56.1 (7-OMe), 112.2 (8), 128.4 (9); C 175.5 (1), 38.3 (2), 14.0 (2-Me), 41.2 (3); D 170.8 (1), 71.4 (2), 39.7 (3), 24.7 (4), 21.5 (4-Me), 22.9 (5).

Cryptophycins-168 and 169: Cryptophycin-153 was treated with m-CPBA and the products isolated using reversed phase HPLC to obtain cryptophycins-168 and -169.

Cryptophycin-168: EIMS m/z (relative intensity) 684/686 (7/2), 412/414 (17/6), 280/282 (12/6), 257 (20), 212/214 (14/4), 195/197 (69/24), 121 (100); high resolution EIMS m/z 684.2789 (calcd for $C_{36}H_{45}ClN_2O_9$, 2.6 mmu error); $^1$H NMR data, see table 6; $^{13}$C NMR data, see table 7.

Cryptophycin-169: $^1$H NMR data, see table 6; $^{13}$C NMR data, see table 7.

Cryptophycins-170 and 171: Cryptophycin-159 was treated with m-CPBA and the products isolated using reversed phase HPLC to obtain cryptophycins-170 and -171.

Cryptophycin-170: EIMS m/z (relative intensity) 682/684 (4/3), 412/414 (11/4), 280/282 (15/4), 255 (25), 195/197 (52/17); high resolution EIMS m/z 682.3043 (calcd for $C_{37}H_{47}ClN_2O_8$, −2.2 mmu error); $^1$H NMR data, see table 6; $^{13}$C NMR data see table 7.

Cryptophycin-171: EIMS m/z (relative intensity) 682/684 (2.0/0.7), 412/414 (7/4), 280/282 (14/4), 255 (19), 195/197 50/17); high resolution EIMS m/z 682.3006 (calcd for $_{37}H_{47}ClN_2O_8$, 1.5 mmu error); $^1$H NMR data, see table 6; $^{13}$C MR data, see table 7.

Cryptophycins-173 and 174: Cryptophycin-171 was treated ith m-CPBA and the products isolated using reversed phase PLC to obtain cryptophycins-173 and -174.

Cryptophycin-173: EIMS m/z (relative intensity) 704/706 (1.3/0.4), 412/414 (5.1/1.9), 277 (6.3), 141 (100); high resolution EIMS m/z 704.2838 (calcd for $C_{39}H_{45}ClN_2O_8$, 2.7 mmu error); $^1$H NMR data, see table 6; $^{13}$C NMR data, see table 7.

Cryptophycin-174: $^1$H NMR data, see table 6; $^{13}$C NMR data, see table 7.

Cryptophycins-177 and 178: Cryptophycin-166 was treated with m-CPBA and the products isolated using reversed phase HPLC to obtain cryptophycins-177 and -178.

Cryptophycin-177: EIMS m/z (relative intensity) 668 (2.7), 412/414 (9/3), 280/282 (11/4), 241 (16), 195/197 (45/17), 105 (100); high resolution EIMS m/z 668.2835 (calcd for $C_{36}H_{45}ClN_2O_8$, 2.9 mmu error); $^1$H NMR data, see table 6; $^{13}$C NMR data, see table 7.

Cryptophycin-178: EIMS m/z (relative intensity) 668/670 (4/1.4), 412/414 (17/6), 280/282 (12/4), 241 (24), 195/197 (59/18), 105 (100); high resolution EIMS m/z 668.2836 (calcd for $C_{36}H_{45}ClN_2O_8$, 2.9 mmu error); $^1$H NMR data, see table 6; $^{13}$C NMR data, see table 7.

Cryptophycins-179 and 180: Cryptophycin-167 was treated with m-CPBA and the products isolated using the same procedure described above, for the epoxidation of cryptophycin-151, to obtain cryptophycins-179 and -180.

Cryptophycin-179: EIMS m/z (relative intensity) 682/684 (25/13), 412/414 (100/43), 280/282 (100/50), 255 (100), 211 (100), 195/197 (100/100), 121 (100); high resolution EIMS m/z 682.2992 (calcd for $C_{37}H_{47}ClN_2O_8$, 2.9 mmu error); $^1$H NMR data, see table 6; $^{13}$C NMR data, see table 7.

Cryptophycin-180: EIMS m/z (relative intensity) 682/684 (4/3), 412/414 (14/7), 280/282 (16/11), 255 (10), 195/197 (58/21), 119 (100); high resolution EIMS m/z 682.3021 (calcd for $C_{37}H_{47}ClN_2O_8$, 0 mmu error); $^1$H NMR data, see table 6; $^{13}$C NMR data, see table 7.

Cryptophycins-182 and 183: Cryptophycin-181 was treated with m-CPBA and the products isolated using reversed phase HPLC to obtain cryptophycins-182 and -183.

Cryptophycin-182: EIMS m/z (relative intensity) 672 (1), 412/414 (11/4), 280/282 (10/4), 245 (12), 195/197 (40/12), 109 (77); high resolution EIMS m/z 672.2590 (calcd for $C_{35}H_{42}ClFN_2O_8$, 2.3 mmu error); $^1$H NMR data, see table 6; $^{13}$C NMR data, see table 7.

Cryptophycin-183: EIMS m/z. (relative intensity) 672/674 (5/2), 412/414 (32/12), 280/282 (13/4), 245 (29), 195/197 (92/30), 109 (100); high resolution EIMS m/z 672.2620 (calcd for $C_{35}H_{42}ClFN_2O_8$, −0.7 mmu error); $^1$H NMR data, see table 6; $^{13}$C NMR data, see table 7.

Cryptophycins-200: Cryptophycin-188 was treated with m-CPBA and the products isolated using the same general procedure, except an additional quantity of peracid (3 equivalents) was added after 12 h and continued the stirring for 36 h to obtain cryptophycins-200 and the SS-epoxide.

Cryptophycin-200: EIMS m/z (relative intensity) 690/692 (42/16), 412/414 (7/1), 263 (19), 195/197 (27); high resolution EIMS m/z 690.2494 (calcd for $C_{35}H_{41}ClF_2N_2O_8$, 2.6 mmu error); $^1$H NMR data, see table 6; $^{13}$C NMR data, see table 7.

Cryptophycin-242: Cryptophycin-236 was treated with m-CPBA and the products isolated using the same general procedure to obtain cryptophycins-242 and its SS--epoxide. Cryptophycin-242 was purified by normal phase HPLC (Econosil Si, 250×10 mm, 10 u, EtOAc ; Hexanes, 1:1, 3 mL/min, $t_R$: 81 min).

Cryptophycin-242: $^1$H NMR (CDCl$_3$) amino or hydroxy acid unit δ (carbon position, multiplicity; J in Hz) A 5.73 (2, d; 15.4), 6.64 (3, ddd; 15.4, 10.2 and 5.0), 2.42 (4, m), 2.57 (4, m), 5.14 (5, m), 1.79 (6, m), 1.12 (6-Me, d; 6.7), 2.93 (7, dd; 8.4 and 1.6), 3.69 (8, d; 1.6), 7.26$^a$ (2'/6', d; 8.2), 7.22$^a$ (3'/5', d; 8.2), 4.28 (4'-CH$_2$NH-t-Boc, d; 5.9), 4.96 (4'-CH$_2$N H-t-Boc, brs ), 1.44 (4'-CH$_2$NH-t-Boc, s); B 4.66 (2, m), 5.66 (2-NH, d; 7.8), 2.92 (3, dd; -14.5 and 7.2), 3.14 (3, dd; −14.5 and 5.0), 7.21 (5, d; 2.0), 3.85 (7-OMe, s), 6.88 (8, d; 8.5), 7.09 (9, dd; 8.5 and 2.0); C 2.68 (2, m), 1.17 (2-Me, d; 7.4), 3.33 (3, m), 3.39 (3, m), 6.95 (3-NH, br t; 6.1); D 4.85 (2, dd; 10.0 and 3.3), 1.37 (3, m), 1.67–1.73 (3/4, m), 0.84 (4-Me, d; 6.7), 0.86 (5, d; 6.7); $^{13}$C NMR (CDCl$_3$) unit δ (carbon position) A 165.7 (1), 125.4 (2), 141.7 (3), 37.2 (4), 76.6 (5), 40.9 (6), 13.7 (6-Me), 63.4 (7), 59.0 (8), 136.4 (1'), 126.2$^b$ (2'/6'), 127.9$^b$ (3'/5'), 140.2 (4'), 44.5 ((4'-CH$_2$NH-t-Boc), 28.5 ((4'-CH$_2$NH-t-Boc); B 171.2 (1), 54.6 (2), 35.5 (3), 130.5 (4), 131.2 (5), 122.5 (6), 154.4 (7), 56.5 (7-OCH$_3$), 112.7 (8), 128.8 (9); C * (1), 38.6 (2), 14.4 (2-Me), 41.1 (3); D 171.2 (1), 71.6 (2), 39.9 (3), 24.9 (4), 23.1 (4-Me), 21.4 (5). $^a$ and $^b$signals with identical superscript are interchangeable.

Cryptophycin-269: Cryptophycin-243 (6 mg) in acetone (1.2 mL) was treated with solid K$_2$CO$_3$ under vigorous stirring in a reaction vial at room temperature. After 12 h, the reaction mixture was filtered and the solvent evaporated. The residue was purified on a short silica column using CH$_2$Cl$_2$ and EtoAc mixtures to obtain cryptophycin-269 (5.1 mg). $^1$H NMR (CDCl$_3$) amino or hydroxy acid unit δ (carbon position, multiplicity; J in Hz) A 5.70 (2, d; 15.4), 6.67 (3, m), 2.42 (4, dt; 14.4 and 10.4), 2.53 (4, m), 5.11–5.19 (5, m), 1.63–1.83 (6, m), 1.14 (6-Me, d; 6.8), 2.92 (7, d; 7.6), 3.69 (8, br s), 7.37$^a$ (2'/6', d; 7.9), 7.24$^a$ (3'/5', d; 7.9), 4.71 (4'-CH$_2$OH, s); B 4.74–4.85 (2, m), 5.76 (2-NH, d; 8.3), 2.98 (3, dd; −14.5 and 7.7), 3.13 (3, dd; −14.5 and 5.3), 7.20 (5, br s), 3.86 (7-OMe, s), 6.82 (8, d; 8.3), 7.05 (9, br d; 8.3); C 2.68 (2, m), 1.14 (2-Me, d; 7.3), 3.32 (3, m)), 3.45 (3, m), 6.98 (3-NH, br m); D 4.74–4.85 (2, m), 1.35 (3, m), 1.63–1.83 (3/4, m), 0.85 (4-Me, d; 6.1), 0.87 (5, d; 6.1).

$^a$ signals with identical superscript are interchangeable.

TABLE 6

¹H NMR Data for Crytophycins-1, -157, -158, -168, -169, -170, -173, -174, -177, -178, -179, -180, -182, -183 and 200.

P = position

| P | 1 | 157 | 158 | 168 | 169 | 170 | 173 | 174 | 177 | 178 | 179 | 180 | 182 | 183 | 200 |
|---|---|---|---|---|---|---|---|---|---|---|---|---|---|---|---|
| A2 | 5.74 d | 5.72 | 5.82 | 5.73 | 5.82 | 5.75 | 5.73 | 5.83 | 5.76 | 5.82 | 5.74 | 5.82 | 5.76 | 5.81 | 5.75 |
| 3 | 6.68 ddd | 6.70 | 6.72 | 6.67 | 6.70 | 6.68 | 6.68 | 6.72 | 6.69 | 6.70 | 6.66 | 6.71 | 6.69 | 6.70 | 6.67 |
| 4R | 2.45 dt | 2.56 | 2.72 m | 2.45 | 2.67 m | 2.49 | 2.46 | 2.70 m | 2.51 | 2.58 m | 2.45 | 2.57 m | 2.55 | 2.57 | 2.42 |
| 4S | 2.55 brdd | 2.63 | 2.62 m | 2.54 | 2.56 m | 2.54 | 2.59 | 2.60 m | 2.54 | 2.69 m | 2.54 | 2.69 m | 2.56 | 2.68 | 2.53 |
| 5 | 5.16 ddd | 5.24 | 5.21 | 5.15 | 5.14 m | 5.17 | 5.18 | 5.17 | 5.18 | 5.15 m | 5.14 | 5.13 m | 5.17 | 5.15 | 5.14 |
| 6 | 1.80 m | 2.04 | 1.93 m | 1.78 | 1.78 | 1.86 | 1.85 | 1.83 | 2.87 | 1.77 | 1.76 | 1.75 | 1.82 | 1.79 | 1.81 |
| 6-Me | 1.14 d | 1.20 | 1.20 | 1.14 | 1.05 | 1.14 | 1.18 | 1.08 | 1.14 | 1.10 | 1.14 | 1.14 | 1.14 | 1.08 | 1.11 |
| 7 | 2.92 d | 2.99 | 2.92 | 2.90 | 2.87 | 2.86 | 3.03 | 3.01 | 2.87 | 2.80 | 2.92 | 2.89 | 2.90 | 2.87 | 2.85 |
| 8 | 3.69 d | 4.41 | 4.26 | 3.66 | 3.58 | 3.85 | 3.85 | 3.77 | 3.88 | 3.74 | 3.61 | 3.53 | 4.01 | 3.88 | 3.66 |
| 9 | | | | | | | | | | | | | | | |
| 10 | | | | | | | | | | | | | | | |
| 8/10-Ar-1' | | | | | | | 7.77 br s | 7.75 br s | | | | | | | |
| 2' | 7.25 m | 7.41 d | 7.42 br d | 6.77 br s | 6.76 br s | 2.38 s | | | 2.42 s | 2.40 s | 6.85 br s | 6.86 br s | | | 6.77 m |
| 3' | 7.34 to | 7.46 t | 7.47 dd | 3.81 s | 3.81 s | 6.99 brs | 7.29 dd | 7.30 d | 7.11 to | 7.15 to | 2.31 s | 2.31 s | 7.05 to | 7.03 to | |
| 4' | 7.39 m | 7.82 d | 7.82 br d | 6.87 d | 6.85 d | 2.30 s | 7.82 d | 7.83 m | 7.24 m | 7.22 m | 6.96 br s | 6.95 br s | 7.33 m | 7.31 m | 6.77 m |
| 5' | 7.39 m | 7.91 d | 7.91 d | 7.27 t | 7.26 t | 7.00 s | 7.84 d | 7.83 m | 7.24 m | 7.22 m | 2.31 s | 2.31 s | 7.33 m | 7.31 m | 6.77 m |
| 6' | 7.25 m | 7.53 td | 7.53 ddd | 6.85 d | 6.85 d | 7.00 s | 7.50 m | 7.46 to | 7.24 m | 7.22 m | 6.85 br s | 6.86 br s | 7.33 m | 7.31 m | 6.77 m |
| 7' | | 7.57 td | 7.57 ddd | | | | 7.50 m | 7.52 m | | | | | | | |
| 8' | | 8.08 d | 8.07 d | | | | 7.84 d | 7.83 m | | | | | | | |
| D 2 | 4.83 dd | 4.81 | 4.91 | 4.82 | 4.91 | 4.83 | 4.81 | 4.92 | 4.84 | 4.90 | 4.82 | 4.92 | 4.84 | 4.91 | 4.84 |
| 3 | 1.36 m | 1.34 | 1.48 | 1.36 | 1.50 | 1.36 | 1.31 | 1.49 | 1.39 | 1.50 | 1.33 | 1.51 | 1.39 | 1.56 | 1.36 |
| 3' | 1.70 m | 1.68 | 1.71 | 1.70 | 1.74 | 1.70 | 1.66 | 1.72 | 1.73 | 1.68 | 1.71 | 1.75 | 1.72 | 1.76 | 1.67 to |
| 4 | 1.70 m | 1.63 | 1.71 | 1.70 | 1.74 | 1.70 | 1.64 | 1.72 | 1.73 | 1.68 | 1.71 | 1.75 | 1.72 | 1.76 | 1.80 m |
| 4-Me | 0.86 d | 0.78 | 0.87 | 0.87 | 0.91 | 0.85 | 0.79 | 0.87 | 0.86 | 0.91 | 0.85 | 0.92 | 0.87 | 0.92 | 0.89 |
| 5 | 0.85 d | 0.74 | 0.85 | 0.85 | 0.89 | 0.84 | 0.75 | 0.87 | 0.85 | 0.89 | 0.84 | 0.89 | 0.85 | 0.90 | 0.87 |

Spectra recorded in CDCl₃; The chemical shifts are for the proton or methyl or methoxyl function positioned on the carbon indicated in the table. The chemical shifts for the protons in units B and C are within ±0.2 ppm and coupling constants within ±0.5 Hz of the values for those in cryptophycin-1. J (H,H) in Hz for 157: 2',3'=3',4'=7.7; 5',6'=6',7'=7',8'=7.9; 5',7'=1.5; 6',8'=1.1; J (H,H) in Hz for 168: 4',5'=5',6'=8.0; J (H,H) in Hz for 173: 3',4'=8.5; 1',3'=1.4; 5',6'=7',8'=8.3; The observable couplings for protons on the aryl segment of 158, 169 and 174 are within ±0.5 Hz of the values of 157, 168 and 173 respectively. The observable coupling constants for the rest of the protons in the table are with in ±0.5 Hz of the values in cryptophycin-1.

TABLE 7

¹³C NMR Data for Crytophycins-157, -157, -158, -168, -169, -170, -173, -174, -177, -178, -179, -180, -182, -183 and 200.

P = position

| P | 157 | 158 | 168 | 169 | 170 | 173 | 174 | 177 | 178 | 179 | 180 | 182 | 183 | 200 |
|---|---|---|---|---|---|---|---|---|---|---|---|---|---|---|
| A1 | 165.3 | 165.5 | 165.3 | 165.5 | 165.3 | 165.3 | 165.4 | 165.4 | 165.5 | 165.3 | 165.5 | 165.3 | 165.4 | 165.3 |
| 2 | 125.3 | 125.2 | 125.3 | 125.2 | 125.3 | 125.3 | 125.3 | 125.3 | 125.3 | 125.2 | 125.2 | 125.2 | 125.3 | 125.4 |
| 3 | 141.0 | 141.4 | 141.0 | 141.4 | 141.0 | 141.0 | 141.4 | 141.1 | 141.4 | 141.2 | 141.5 | 141.2 | 141.3 | 140.8 |
| 4 | 36.6 | 36.8 | 36.7 | 36.7 | 36.6 | 36.8 | 36.8 | 36.5 | 36.8 | 36.8 | 36.7 | 36.7 | 36.7 | 36.7 |
| 5 | 76.1 | * | 76.1 | * | 76.0 | 76.2 | * | 76.0 | * | 76.2 | * | 76.2 | 76.8 | 75.9 |
| 6 | 40.1 | 41.0 | 40.6 | 41.0 | 40.3 | 40.7 | 41.0 | 40.2 | 41.0 | 40.8 | 41.0 | 40.5 | 40.9 | 40.2 |
| 6-Me | 13.1 | 13.8 | 13.6 | 13.5 | 13.3 | 13.6 | 13.5 | 13.1 | 13.8 | 13.7 | 13.6 | 13.7 | 13.3 | 13.3 |

TABLE 7-continued

¹³C NMR Data for Crytophycins-157, -157, -158, -168, -169, -170, -173, -174, -177, -178, -179, -180, -182, -183 and 200.

P = position

| P | 157 | 158 | 168 | 169 | 170 | 173 | 174 | 177 | 178 | 179 | 180 | 182 | 183 | 200 |
|---|---|---|---|---|---|---|---|---|---|---|---|---|---|---|
| 7 | 62.6 | 62.7 | 63.0 | 63.1 | 62.4 | 63.2 | 64.3 | 62.4 | 62.7 | 62.9 | 63.1 | 62.5 | 62.6 | 63.3 |
| 8 | 56.3 | 54.7 | 58.9 | 56.3 | 56.3 | 59.3 | 56.5 | 56.2 | 54.5 | 59.2 | 56.4 | 53.4 | 51.1 | 57.6 |
| 8/10-Ar-1' | 132.6 | 133.0 | 138.4 | 138.8 | 137.8 | 125.3 | 124.9 | 134.9 | 135.3 | 136.3 | 137.0 | 124.3 | ** | 141.1m |
| 2' | 122.4 | 122.4† | 110.9 | 110.5 | 135.8 | 133.5 | 133.3 | 135.9 | 135.6 | 123.4 | 123.1 | 161.2 | ** | 108.4 d |
| 3' | 125.5 | 125.5 | 160.0 | 160.0 | 131.0 | 122.6 | 122.7 | 130.2 | 129.9 | 138.4 | 138.3 | 115.3 | 115.2 | 163.4 dd |
| 4' | 128.5 | 128.3 | 114.0 | 1114.0 | 131.8 | 128.7 | 128.5 | 128.0 | 128.8 | 130.3 | 128.4 | 129.7 | 129.5 | 103.9 t |
| 5' | 129.0 | 128.9 | 129.8 | 129.7 | 124.3 | 127.8 | 127.7ᵃ | 124.2 | 124.0 | 138.4 | 138.3 | 124.5 | 129.5 | 163.4 dd |
| 6' | 126.0 | 126.0 | 118.0 | 117.9 | 127.0 | 126.3ᵃ | 126.2ᵇ | 126.4 | 126.3 | 123.4 | 123.1 | 126.1 | 124.4 | 108.4 |
| 7' | 126.6 | 126.5 | | | | 126.6ᵃ | 126.5ᵇ | | | | | | | |
| 8' | 122.3 | 122.3† | | | | 127.8 | 127.8ᵃ | | | | | | | |
| 9' | 131.4 | 131.2 | | | | 133.2 | 133.2 | | | | | | | |
| 10' | 133.4 | 133.3 | | | | 134.2 | 134.5 | | | | | | | |
| D1 | 170.7 | 170.8 | 170.7 | 170.9 | 170.7 | 170.8 | 170.9 | 170.7 | 170.9 | 170.8 | 171.9 | 170.7 | 170.8 | 170.7 |
| 2 | 71.4 | 71.5 | 71.3 | 71.5 | 71.3 | 71.3 | 71.5 | 71.4 | 71.5 | 71.3 | 71.5 | | 71.5 | 71.3 |
| 3 | 39.4 | 39.3 | 39.4 | 39.3 | 39.4 | 39.4 | 39.3 | 39.5 | 39.3 | 39.4 | 39.3 | 39.4 | 39.3 | 39.5 |
| 4 | 24.5 | 24.6 | 24.5 | 24.7 | 24.5 | 24.5 | 24.7 | 24.6 | 24.7 | 24.5 | 24.7 | 24.6 | 24.7 | 24.6 |
| 4-Me | 22.8 | 23.0 | 21.3 | 21.4 | 21.3 | 21.2 | 21.4 | 21.4 | 21.4 | 21.2 | 21.4 | 21.3 | 21.4 | 21.3 |
| 5 | 21.3 | 21.3 | 22.9 | 23.1 | 22.8 | 22.8 | 23.0 | 22.9 | 23.1 | 22.9 | 23.1 | 22.9 | 23.1 | 22.9 |

Spectra recorded in CDCl₃. The chemical shifts for carbons in units B and C are within ±0.5 ppm of the values in cryptophycin-1. * Signals submerged under the CDCl₃ signal. ** Signals could not be found. †, a and b signals with identical super scripts in a column are interchangeable. The 3'-OCH₃ signal in both 168 and 169 was observed at d 55.3. The 2' and 4'-CH₃ carbon signals of 170 were observed respectively at d 18.9 and 21.0. The 2'-CH₃ carbon of 177 and 178 resonated at d 19.0 and 18.9 respectively. 3' and 5'-CH₃ signals of 179 were observed at d 21.3 and those of 180 were observed at 21.2.

EXAMPLE 93

Chlorohydrin Analogs

Cryptophycins-163, 184, 185, 186, 187, 191, 192, 193, 194, 195, 212, 216, 217, 222, 223, 224, 243, 252, 253, 263, 264, 265, 272 and 273.

TABLE 8

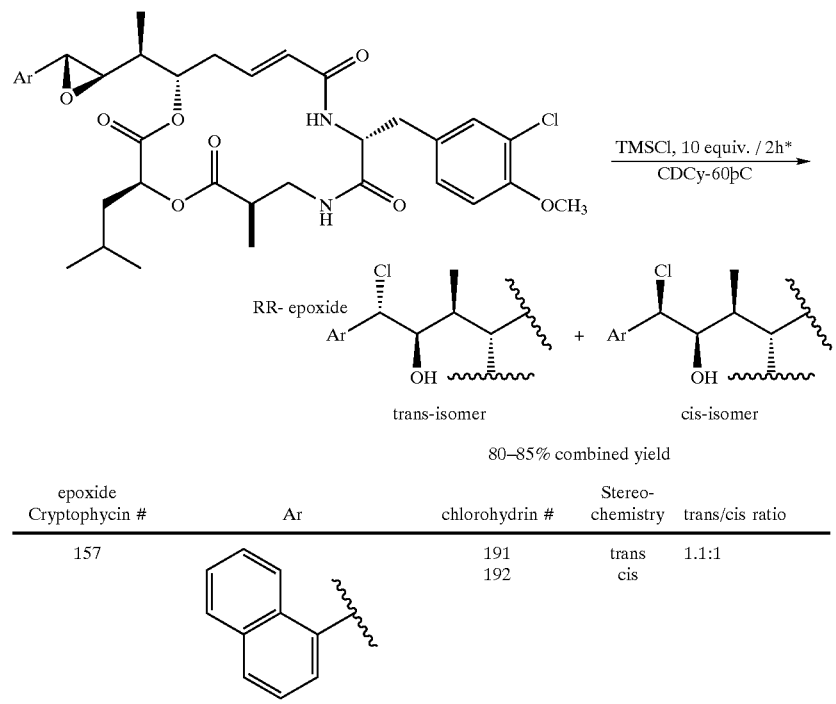

TABLE 8-continued
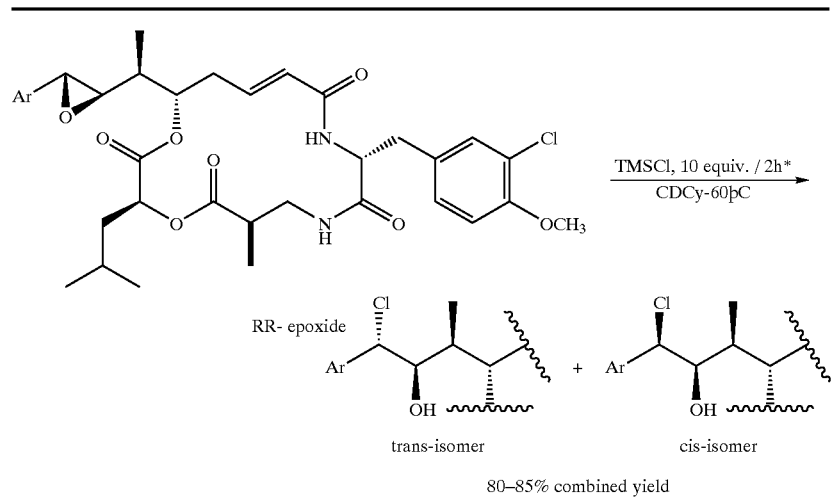
80–85% combined yield
| epoxide Cryptophycin # | Ar | chlorohydrin # | Stereo-chemistry | trans/cis ratio |
|---|---|---|---|---|
| 168 | 3-methoxyphenyl (H₃CO-) | 195 | trans cis | 1:<0.1 |
| 170 | 2,4-dimethylphenyl | 216 217 | trans cis | 1:2.6 |
| 179 | 3,5-dimethylphenyl | 222 | trans cis | <0.1:1 |
| 172 | 2-naphthyl | 193 194 | trans cis | 1:2 |
| 181 | 2-fluorophenyl | 223 | trans cis | 1:<0.1 |

TABLE 8-continued

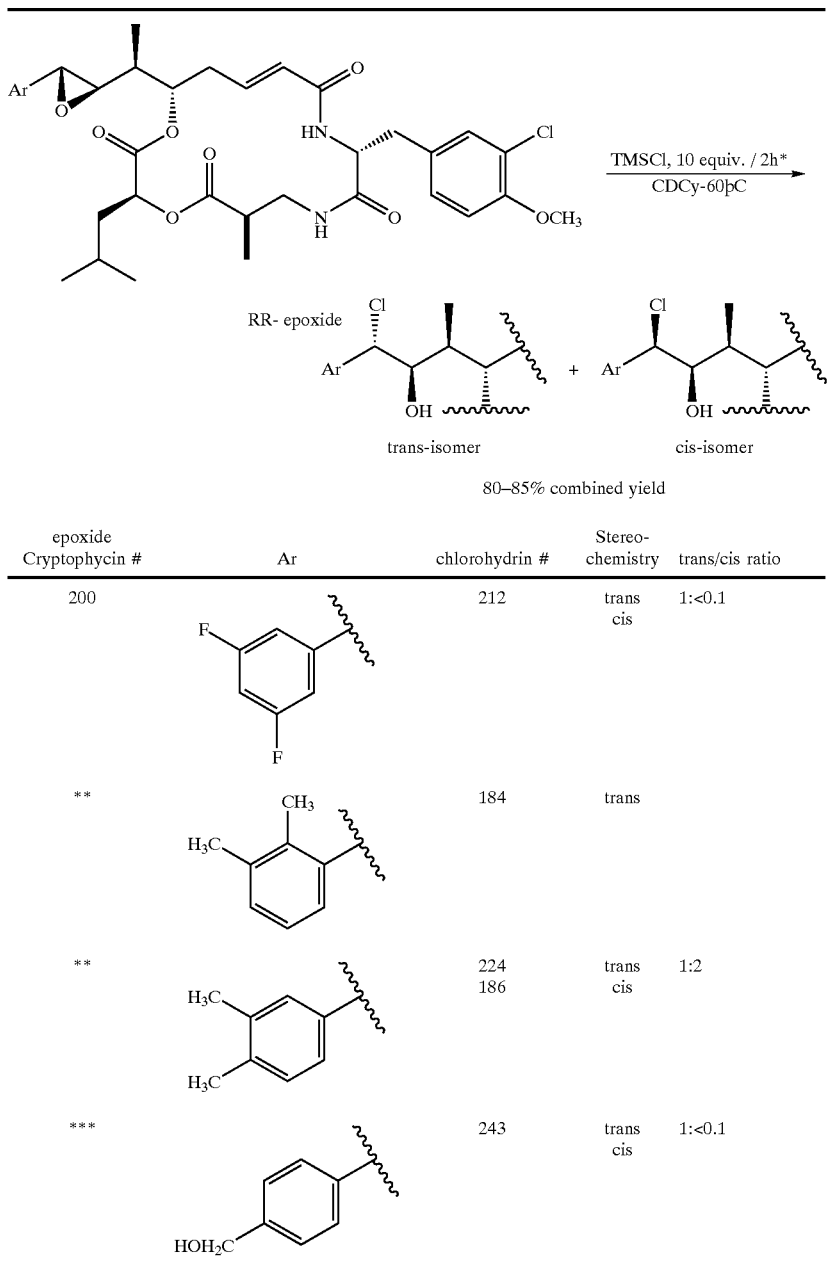

80–85% combined yield

| epoxide Cryptophycin # | Ar | chlorohydrin # | Stereochemistry | trans/cis ratio |
|---|---|---|---|---|
| 200 | 3,5-difluorophenyl | 212 | trans cis | 1:<0.1 |
| ** | 2-methyl-3-methylphenyl (CH₃, H₃C) | 184 | trans | |
| ** | 3,4-dimethylphenyl (H₃C, H₃C) | 224 186 | trans cis | 1:2 |
| *** | 4-(hydroxymethyl)phenyl (HOH₂C) | 243 | trans cis | 1:<0.1 |

*Crytophycin-200 undergo only 30% conversion under these conditions.
**A mixture of RR epoxides of 3,4- and 2,3-dimethylphenyl analogs.
***A mixture of RR and SS epoxides.

Cryptophycin-163: To a solution of cryptophycin-81 (12 mg, 0.018 mmol) in $CH_2Cl_2$ (1.5 mL) at 0° C. was added m-CPBA (5 mg, 0.029 mmol) followed by HCl in acetic acid (1.0 M solution, 25 μL) and the temperature was allowed to rise to rt and continued the stirring for 6 h. Evaporation of the solvent followed by flash chromatography of the residue over C18 silica column (12 cm×1 cm) using $H_2O$ and $CH_3CN$ mixtures yielded a mixture of chlorohydrins (12 mg, 93%). Attempted purification on reversed phase HPLC led to the partial hydrolysis into diols. However, purification by normal phase HPLC (Econosil silica, 250 mm×10 mm, 1:1 EtoAc/hexane) gave cryptophycin-163 ($t_R$ 37.2 min, 3.0 mg). The proton and carbon NMR data was given in the tables 9 and 10 respectively.

Cryptophycins-184, -185, -186, 187 and 224: A mixture of 3,4-dimethylbenzyl triphenyl-phosphonium chloride and 2, 3-dimethylbenzyl triphenylphosphonium chloride (7:3) was converted to 3,4- and 2,3-dimethylbenzyl triphenylphosphoranes and then treated with cryptophycin-108 using the same procedure described earlier for the preparation of cryptophycin-152. An inseparable mixture of four styrene isomers was obtained in 68% combined yield. The mixture (45 mg) in $CH_2Cl_2$ (3 mL) was treated with m-CPBA (25 mg) at rt and kept under stirring for 15 h. The solvent was removed and the residue subjected to HPLC (Econosil C-18, 250×22 mm 7:3$H_2O$/$CH_3CN$, 6 mL/min), and collected two fractions I ($t_R$ 54.0 min, 20 mg) and II ($t_R$ 61.5 min, 12 mg). Fraction I (9 mg) in $CH_2Cl_2$ (2.0 mL) was treated with TMSCl (40 μL) at −78° C. and allowed the temp gradually rise to room temp After 3 h, evaporation of the solvent followed by chromatography on reversed phase HPLC (Econsil $C_{18, 10}$ mn, 250×22 mm, 35:65$H_2O$/$CH_3CN$, 6 mL/min) gave cryptophycin-186 ($t_R$ 57.8 min, 4.7 mg), cryptophycin-224 ($t_R$ 74.5 min, 2.3 mg) and cryptophycin-184 ($t_R$ 78.2 min, 2.6 mg). Using the same procedure, Fraction II was treated with TMSCl and the compounds were separated to obtain cryptophycin-185 ($t_R$ 65.0 min, 0.7 mg) and cryptohycin-187 ($t_R$ 69.2 min, 8.0 mg)

Cryptophycin-184: EIMS m/z (relative intensity) 682/684 (1.1/0.4), 236 (10), 195 (9), 135 (100), 119 (83); high resolution EIMS m/z 682.2999 ($M^+$-HCl, calcd for $C_{37}H_{47}ClN_2O_8$, 2.2 mmu error); The proton and carbon data are given in the tables 9 and 10 respectively.

Cryptophycin-185: EIMS m/z (relative intensity) 682/684 (6/2), 412/414 (14/5), 280/282 (14/5), 255 (10), 195/197 (50/16), 119 (100); high resolution EIMS m/z 682.3015 ($M^+$—HCl, calcd for $C_{37}H_{47}ClN_2O_8$, 0.6 mmu error); The proton and carbon data were given in the tables 9 and 10 respectively.

Cryptophycin-186: EIMS m/z (relative intensity) 682/684 (1.3/0.6), 412/414 (2.5/0.8), 254 (7), 195 (11), 119 (100); high resolution EIMS m/z 682.3015 ($M^+$—HCl, calcd for $C_{37}H_{47}ClN_2O_8$, 0.6 mmu error); The proton and carbon data were given in the tables 9 and 10 respectively.

Cryptophycin-187: EIMS m/z (relative intensity) 682/684 (0.9/0.2), 412/414 (3/1), 255 (3), 254 (7), 195 (11), 135 (100), 119 (94); high resolution EIMS m/z 682.3044 (M+-HCl, calcd for $C_{37}H_{47}ClN_2O_8$, −2.3 mmu error); The proton and carbon data were given in the tables 9 and 10 respectively.

Cryptophycin-224: EIMS m/z (relative intensity) 682/684 (3/1), 412/414 (3/1), 255 (4), 254 (9), 195/197 (28/6), 119 (100); high resolution EIMS m/z 682.3064 ($M^+$—HCl, calcd for $C_{37}H_{47}ClN_2O_8$, −4.3 mmu error); The proton and carbon data were given in the tables 9 and 10 respectively.

Cryptophycins-191, -192, -193, -194, -195, -212, -216, -217, -222 and -223:

General procedure for the preparation of chlorohydrins: A solution of RR-epoxide in chloroform was cooled to −60° C. and treated with excess trimethylsilyl chloride (10 equivalents). After 2 h, the solvent was evaporated and residue was purified on a reversed phase HPLC (Econosil C18, 10μ, 35% $H_2O$/$CH_3CN$, 3 mL/min) to obtain trans and cis chlorohydrins.

The experimental details for the preparation of the cryptophycins-191, 192, -193, -194, -195, -212, -216, -217 -222, -223 and 224, and cytotoxicity are summarized in table 8.

Cryptophycin-195: EIMS m/z (relative intensity) 684/686 (3/2), 412/414 (12/4), 257 (11), 195/197 (46/15); high resolution EIMS m/z 684.2784 ($M^+$-HCl, calcd for $C_{36}H_{45}ClN_2O_9$, Δ 3.0 mmu); $^1H$ NMR data, see table 9; $^{13}C$ NMR data, see table 10.

Cryptophycin-212: EIMS m/z (relative intensity); high resolution EIMS m/z ($M^+$—HCl, calcd for $C_{35}H_{41}ClF_2N_2O_8$, Δmmu); $^1H$ NMR data, see table 9; $^{13}C$ NMR data, see table 10.

Cryptophycin-216: EIMS m/z (relative intensity) 682/684 (6/3), 412/414 (6/2), 255 (4), 195/197 (21/7); high resolution EIMS m/z 682.2990 ($M^+$-HCl, calcd for $C_{37}H_{47}ClN_2O_8$, Δ 3.1 mmu); $^1H$ NMR (CDCl$_3$) amino or hydroxy acid unit δ (carbon position, multiplicity; J in Hz) A 5.79 (2, d; 15.4), 6.70 (3, ddd; 15.4, 9.5 and 5.4), 2.36 (4, m), 2.67 (4, br dd; 14.9 and 4.9), 5.01 (5, m), 2.52 (6, m), 1.07 (6-Me, d; 7.1), 4.07 (7, br d; 9.8), 5.01 (8, d; 9.8), 2.36 (2'-$CH_3$, s), 7.01 (2', br s), 2.31 (4'-$CH_3$, s), 7.06 (5', brd; 8.1), 7.32 (6', d; 8.1); B 4.81 (2, m), 5.71 (2-NH, d; 8.5), 3.02 (3, dd; −14.4 and 7.4), 3.16 (3, dd; −14.4 and 5.6), 7.23 (5, d; 2.0), 3.88 (7-OMe, s), 6.85 (8, d; 8.3), 7.09 (9, dd; 8.3 and 2.0);

C 2.74 (2, m), 1.23 (2-Me, d; 7.1), 3.25 (3, m), 3.53 (3, m), 6.93 (3-NH, br m); D 4.93 (2, dd; 10.2 and 3.2), 1.49 (3, m), 1.68–1.85 (3/4, m), 0.95 (4-Me, d; 6.4), 0.96 (5, d; 6.4).

Cryptophycin-217: EIMS m/z (relative intensity) 682/684 (3/1), 412/414 (6/1), 255 (5), 195/197 (23/7); high resolution EIMS m/z 682.2920 ($M^+$—HCl, calcd for $C_{37}H_{47}ClN_2O_8$, Δ 10.1 mmu); $^1H$ NMR (CDCl$_3$) amino or hydroxy acid unit δ (carbon position, multiplicity; J in Hz) A 5.72 (2, d; 15.4), 6.66 (3, ddd; 15.4, 9.7 and 5.4), 2.17 (4, dt; 13.9 and 10.9), 2.53 (4, br dd; 13.9 and 5.0), 5.08 (5, m), 1.61 (6, m), 0.88 (6-Me, d; 6.8), 4.28 (7, br d; 9.6), 5.13 (8, d; 9.6), 2.38 (2'-$CH_3$, s), 7.03 (2', br s), 2.32 (4'-$CH_3$, s), 7.03 (5', brd; 8.5), 7.17 (6', d; 8.5); B 4.80 (2, m), 5.66 (2-NH, d; 8.1), 3.03 (3, dd; -14.4 and 7.2), 3.14 (3, dd; −14.4 and 5.6), 7.21 (5, d; 1.6), 3.87 (7-OMe, s), 6.83 (8, d; 8.3), 7.08 (9, dd; 8.3 and 1.7); C 2.74 (2, m), 1.24 (2-Me; d; 7.1), 3.29 (3, m), 3.50 (3, m), 6.96 (3-NH, br m); D 4.89 (2, dd; 9.8 and 3.4), 1.52 (3, m), 1.87 (3, m), 1.72 (4, m), 0.94 (4-Me, d; 7.3), 0.97 (5, d; 6.8).

Cryptophycin-222: EIMS m/z (relative intensity) 718/720 (0.4/0.2), 682/684 (13/7), 412/414 (15/5), 280/282 (16/5), 255 (12), 195/197 (59/19), 119 (100); high resolution EIMS m/z 718.2767 (calcd for $C_{37}H_{48}Cl_2N_2O_8$, Δ 2.1 mmu). $^1H$ NMR data, see table 9; $^{13}C$ NMR data, see table 10.

Cryptophycin-223: EIMS m/z (relative intensity) 672/674 (1/0.8), 412/414 (3/1), 195/197 (15/3), 149 (100), 109 (35); high resolution EIMS m/z 708.2373 (calcd for $C_{35}H_{43}FCl_2N_2O_8$, Δ 0.7 mmu). $^1H$ NMR data, see table 9; $^{13}C$ NMR data, see table 10.

Cryptophycins-243:

Epoxidation of cryptophycin-238: Cryptophycin-238 (11.8 mg) was dissolved in dichloromethane (1.5 mL) and treated with MCPBA (9.6 mg). After 15 h, the reaction mixture was diluted with dichloromethane (3 mL) and washed with 0.1 M phosphate buffer at pH 8 (3 mL). The organic layer was treated with dimethylsulfide (10 μL) and repeated the buffer wash. The organic layer was evaporated and the residue (12 mg) was unsuccessfully purified on a reversed phase HPLC 2G (Econosil C18, 25 cm×22 mm, 10μ, 35% $H_2O$/$CH_3CN$, 6 mL/min) to give a mixture of RR and SS epoxides (6.2 mg).

Treatment with TMSCl: The mixture was dissolved in chloroform (1 mL) and treated with TMSCl (15 μL) at −60° C. After 2 h, the solvent was evaporated the residue (7 mg) was subjected to a normal phase HPLC (Econosil Si, 25 cm×10 mm, 10μ, 85% EtOAc/hexane, 4 mL/min). The fraction collected at 30 min was further purified on a reversed phase HPLC (Econosil C18, 25 cm×10 mm, 10μ, 45% $H_2O$/$CH_3CN$, 3 mL/min) to obtain cryptophycin-243 (2.4 mg).

Cryptophycin-243: $^1H$ NMR (CDCl$_3$) amino or hydroxy acid unit δ (carbon position, multiplicity; J in Hz) A 5.76 (2, d; 15.0), 6.67 (3, ddd; 15.0, 9.6 and 5.4), 2.35 (4, dt; 14.4 and 10.4), 2.64 (4, br dd; 14.4 and 5.1), 5.07 (5, m), 2.50 (6, m), 1.04 (6-Me, d; 6.8), 4.02 (7, br d; 9.8), 4.68 (8, d; 9.8), 7.39 (2'/3'/5'/6', br s), 4.70 (4'-C$H_2$OH, brs); B 4.74 (2, m), 5.72 (2-NH, d; 7.8), 2.99 (3, dd; −14.4 and 7.3), 3.14 (3, dd; −14.4 and 5.6), 7.22 (5, d; 2.0), 3.88 (7-OMe, s), 6.84 (8, d; 8.4), 7.08 (9, dd; 8.4 and 2.0); C 2.73 (2, m), 1.21 (2-Me, d; 7.1), 3.23 (3, dt; 13.7 and 7.1), 3.50 (3, dt; 13.7 and 4.5), 6.93 (3-NH, br dd; 7.1 and 4.5); D 4.91 (2, dd; 10.0 and 3.4), 1.47

(3, m), 1.64–1.84 (3/4, m) 0.94 (4-Me, d; 6.4), 0.95 (5, d; 6.3); $^{13}$C NMR (CDCl$_3$) unit δ (carbon position) A 165.6 (1), 125.0 (2), 141.9 (3), 36.3 (4), 76.4 (5), 38.3 (6), 8.7 (6-Me), 74.0 (7), 62.0 (8), 137.7 (1'), 127.4a (2'/6'), 128.2$^a$ (3'/5'), 142.2 (4'), 64.6 (4'-CH$_2$OH); B 171.1$^b$ (1), 53.6 (2), 35.1 (3), 129.9 (4), 131.0 (5), 122.4 (6), 154.0 (7), 56.2 (7-OCH$_3$), 112.3 (8), 128.4 (9); C 175.4 (1), 38.5 (2), 14.1 (2-Me), 41.2 (3); D 170.5$^b$(1), 71.4 (2), 39.7 (3), 24.8 (4), 23.2 (4-Me), 21.6 (5). $^a$ and $^b$ signals with identical superscript are interchangeable.

Cryptophycins-252 and 253:

Epoxidation of cryptophycin-247: Cryptophycin-247 (12 mg) was dissolved in dichloromethane (1 mL) and treated with MCPBA (9.8 mg). After 15 h, the reaction mixture was diluted with dichloromethane (3 mL) and washed with 0.1 M phosphate buffer at pH 8 (3 mL). The organic layer was separated and repeated again the buffer wash after adding dimethylsulfide (15 mL). The organic layer was evaporated and the residue (11.5 mg) was purified on a reversed phase HPLC (Econosil C18, 25 cm×10 mm, 10μ, 35% H$_2$O/CH$_3$CN, 3 mL/min) to give a major RR-epoxide (5 mg) and a minor SS- epoxide (3 mg).

RR-epoxide: $^1$H NMR (CDCl$_3$) amino or hydroxy acid unit δ (carbon position, multiplicity; J in Hz) A 5.74 (2, d; 15.6), 6.67 (3, ddd; 15.6, 9.5 and 5.6), 2.44 (4, dt; 14.7 and 10.5), 2.50–2.58 (4, m), 5.15 (5, m), 1.62–1.81 (6, m), 1.12 (6-Me, d; 6.8), 2.91 (7, dd; 7.3 and 1.5), 3.66 (8, d; 1.5), 7.38 (2', br s), 6.54 (3'-NH, s), 1.51 (3'-NH-t-Boc), 7.21–7.30 (4'/5', m), 6.91 (6', br d; 6.8); B 4.79 (2, m), 5.69 (2-NH, d; 8.5), 3.00 (3, dd; 14.5 and 7.3), 3.13 (3, dd; 14.5 and 5.5), 7.20 (5, d; 2.0), 3.86 (7-OMe, s), 6.83 (8, d; 8.3), 7.06 (9, dd; 8.3 and 2.0); C 2.70 (2, m), 1.22 (2-Me, d; 7.1), 3.30 (3, m), 3.46 (3, m), 6.97 (3-NH, m); D 4.83 (2, dd; 10.0 and 3.4), 1.36 (3, m), 1.62–1.81 (3/4, m), 0.85 (4-Me, d; 5.9), 0.87 (5, d; 5.6).

Deprotection of the amino group and preparation of chlorohydrins:

A solution of RR-epoxide (8.0 mg) in dichloromethane (100 μL) was treated with hydrochloric acid (50 μL, 4N in dioxane). After 30 min, the solvent was evaporated and the residue was purified on a reversed phase HPLC (Econosil C18, 25 cm×10 mm, 10μ, 40% H$_2$O/CH$_3$CN, 3.5 mL/min) to obtain cryptophycin-252 (5 mg, t$_R$ min) and cryptophycin-253 (2 mg, t$_R$ min).

Cryptophycin-252 Cytotoxicity Data: Cell Line (# of folds Potent Than Cryptophycin-1)

KB (1.20) and LoVo (1.25)

Cryptophycin-252: EIMS m/z (relative intensity) 670/672 (7.2/2.2), 669/671 (19.2/7.8), 280/282 (6.8/2.4), 242 (4.7), 195/197 (43/12); high resolution EIMS m/z 669.2856 (M$^+$− 2HCl—H) calcd for C$_{35}$H$_{44}$ClN$_3$O$_8$, −3.9 mmu error); $^1$H NMR (MeOH) amino or hydroxy acid unit δ (carbon position, multiplicity; J in Hz) A 5.93 (2, d; 15.1), 6.61–6.78 (3, m), 2.33 (4, dt; 14.7 and 9.8), 2.69–2.80 (4, m), 5.11 (5, m), 2.46 (6, m), 0.95–1.04 (6-Me, m), 3.99 (7, brd; 9.4), 4.62 (8, d; 9.4), 7.28 (2', br s), 7.17 (4', brd; 8.1), 7.07 (5', t; 8.1), 6.98 (6', d; 8.1); B 4.50 (2, dd; 10.5 and 3.2), 2.69–2.80 (3, m), 3.18 (3, brd; 13.7), 6.61–6.78 (5, 8 and 9, m), 3.86 (7-OMe, s); C 2.69–2.80 (2, m), 1.19 (2-Me, d; 7.3), 3.28 (3, brd; 13.4), 3.58 (3, br d; 13.4); D 5.01 (2, dd; 9.8 and 2.7), 1.53 (3, m), 1.70–1.84 (3/4, m), 0.95–1.04 (4/5-Me, m).

Cryptophycin-253: $^1$H NMR (MeOH) amino or hydroxy acid unit δ (carbon position, multiplicity; J in Hz) A 5.84 (2, dd; 15.3 and 1.6), 6.60–6.74 (3, m), 2.10 (4, dt; 14.9 and 11.2), 2.64 (4, m), 5.05 (5, m), 1.50 (6, m), 0.90 (6-Me, d; 6.8), 4.01 (7, dd; 9.5 and 1.2), 4.75 (8, d; 9.5), 6.60–6.74 (2'/4'/6', m), 7.09 (5', t; 7.8); B 4.48 (2, dd; 11.4 and 3.9), 2.71 (3, dd; 14.4 and 11.4), 3.16 (3, dd; 14.4 and 3.7), 7.26 (5, d; 2.2), 3.86 (7-OMe, s), 6.96 (8, d; 8.4), 7.15 (9, dd; 8.4 and 2.2); C 2.76 (2, m), 1.18 (2-Me, d; 7.3), 3.26 (3, m), 3.58 (3, dd; 13.5 and 3.1); D 4.94 (2, dd; 9.4 and 3.8), 1.58 (3, m), 1.80 (3, m), 1.70 (4, m), 0.97 (4-Me, d; 6.1), 0.98 (5, d; 6.3).

Cryptophycins-263, 264 and 265:

A mixture of cryptophycin-242 and its ss-epoxide (26 mg) was dissolved in CH$_2$Cl$_2$ (5 mL) and treated with TMSCl (1.0 M solution in CH$_2$Cl$_2$, 120 μL) at −78° C. After 3 h, the solvent was evaporated and the residue (27 mg) was subjected to reversed phase HPLC (Econosil C18, 250 mm×22 mm, 10μ, 65:35 CH$_3$CN/H$_2$O, 6 mL/min) to give cryptophycin-264 (6.0 mg, t$_R$ 43 min), and a mixture of cryptophycins-263 and 265 (15.8 mg, t$_R$ 59 min). Cryptophycins-263 and 265 were separated by normal phase HPLC (Econosil silica, 250 mm×10 mm, 10μ, 55:45 EtoAc/hexane, 3 mL/min) to give cryptophycin-265 (7.1 mg, 51 min) and cryptophycin-263 (7.8 mg, 79.0 min).

| | Cytotoxicity data | |
|---|---|---|
| cryptophycin # | cytotoxicity, # of folds potent than crypto-1 KB | LoVo |
| 263 | 1.67 | 0.56 |
| 264 | 0.044 | 0.023 |
| 265 | 0.0033 | 0.021 |

Cryptophycin-263: $^1$H NMR (CDCl$_3$) amino or hydroxy acid unit δ (carbon position, multiplicity; J in Hz) A 5.79 (2, d; 15.6), 6.68 (3, m), 2.37 (4, m), 2.66 (4, br dd; 14.2 and 4.2), 5.10 (5, m), 2.49 (6, m), 1.03 (6-Me, d; 6.8), 4.00 (7, br d; 9.4), 4.64 (8, d; 9.4), 7.35 (2'/6', br d; 7.9), 7.29 (3'/5', brd; 7.9), 4.31 (4'-CH$_2$NH-t-BOC, d; 4.8), 4.92 (4'-CH$_2$N H-t-BOC, brs), 1.45 (4'-CH$_2$NH-t-BOC, s); B 4.79 (2, m), 5.76 (2-NH, d; 8.6), 3.01 (3, dd; −14.4 and 7.3), 3.15 (3, dd; −14.4 and 4.9), 7.23 (5, d; 1.3), 3.87 (7-OMe, s), 6.84 (8, d; 8.4), 7.09 (9, br d; 8.4); C 2.73 (2, m), 1.22 (2-Me, d; 7.2), 3.24 (3, m), 3.53 (3, m), 6.93 (3-NH, br t; 5.5); D 4.92 (2, dd; 9.7 and 3.1), 1.48 (3, *rm), 1.78 (3, m), 1.73 (4, m), 0.93 (4-Me, d; 6.4), 0.94 (5, d; 6.4); $^{13}$C NMR (CDCl$_3$) unit δ (carbon position) A 165.6 (1), 125.3 (2), 141.6 (3), 36.4 (4), 76.5 (5), 38.3 (6), 8.7 (6-Me), 74.1 (7), 61.8 (8), 137.5$^a$ (1'), 128.3 (2'/6'), 128.0 (3'/5' ), 140.3$^a$ (4'), 44.2 (4'-CH$_2$NH-t-BOC), 28.4 & 155.9 (4'-CH$_2$NH-t-BOC); B 171.1$^b$ (1), 53.7 (2), 35.1 (3), 130.0 (4), 131.1 (5), 122.4 (6), 154.0 (7), 56.2 (7-OCH$_3$), 112.3 (8), 128.5 (9); C 175.4 (1), 38.4 (2), 14.1 (2-Me), 41.3 (3); D 170.6$^b$(1), 71.4 (2), 39.8 (3), 24.8 (4), 23.2 (4-Me), 21.6 (5). $^a$ and $^b$ signals with identical superscript are interchangeable.

Cryptophycin-264: $^1$H NMR (CDCl$_3$) amino or hydroxy acid unit δ (carbon position, multiplicity; J in Hz) A 5.71 (2, d; 15.4), 6.63 (3, ddd; 15.4, 9.9 and 5.5), 2.12 (4, m), 2.51 (4, br dd; 14.2 and 5.0), 5.05 (5, m), 1.47 (6, m), 0.92 (6-Me, d; 6.8), 4.06 (7, dd; 9.6 and 1.5), 4.87 (8, d; 9.6), 7.29 (2'/6', br d; 8.4), 7.27 (3'/5', brd; 8.4), 4.33 (4'-CH$_2$NH-t-BOC, brs), 1.47 (4'-CH$_2$NH-t-BOC, s); B 4.80 (2, m), 5.69 (2-NH, brs), 3.01 (3, dd; −14.5 and 7.2), 3.13 (3, dd; −14.5 and 5.4), 7.21 (5, d; 2.0), 3.86 (7-OMe, s), 6.83 (8, d; 8.4), 7.07 (9, dd; 8.4 and 2.0); C 2.73 (2, m), 1.23 (2-Me, d; 7.3), 3.28 (3, m), 3.52 (3, m), 6.93 (3-NH, br t; 5.7); D 4.86 (2, m), 1.50 (3, m), 1.86 (3, m), 1.73 (4, m), 0.95 (4-Me, d; 6.6), 0.98 (5, d; 6.8); $^{1313}$C NMR (CDCl$_3$) unit δ (carbon position) A 165.4 (1), 125.1 (2), 141.4 (3), 36.2 (4), 76.0 (5), 38.3 (6), 8.8 (6-Me), 74.3 (7), 68.4 (8), 136.6a (1'), 128.0 (2'/6'), 127.7 (3'/5'), 140.3a (4'), 44.2 (4'-CH$_2$NH-t-BOC), 28.4 (4'-CH$_2$NH-t-BOC); B170.0$^b$(1), 53.6 (2), 35.0 (3), 129.9 (4), 131.0 (5), 122.4 (6), 153.9 (7), 56.1 (7-OCH$_3$), 112.2 (8), 128.4 (9); C 175.4 (1), 38.5 (2), 14.1 (2-Me), 41.2 (3); D170.4$^b$(1), 71.4 (2), 39.8 (3), 24.8 (4), 23.2 (4-Me), 21.7 (5). $^a$ and $^b$ signals with identical superscript are interchangeable.

Cryptophycin-265: $^1$H NMR (CDCl$_3$) amino or hydroxy acid unit δ (carbon position, multiplicity; J in Hz) A 5.74 (2, d; 15.5), 6.68 (3, ddd; 15.5, 9.9 and 5.3), 2.36 (4, m), 2.54 (4, br dd; 14.2 and 4.9), 5.40 (5, m), 1.87 (6, m), 1.05 (6-Me, d; 7.0), 3.71 (7, br t; 5.8), 5.07 (8, d; 5.3), 7.36 (2'/6', br d; 8.2), 7.28 (3'/5', brd; 8.2), 4.30 (4'-C$\underline{H}_2$NH-t-BOC, brs), 4.91 (4'-CH$_2$N$\underline{H}$-t-BOC, brs), 1.46 (4'-CH$_2$NH-t-$\underline{BOC}$, s); B 4.78 (2, m), S.70 (2-NH, brs), 3.03 (3, dd; -14.5 and 7.1), 3.12 (3, dd; -14.5 and 5.5), 7.21 (5, d; 1.8), 3.87 (7-OMe, s), 6.84 (8, d; 8.4), 7.07 (9, dd; 8.4 and 1.8); C 2.72 (2, m), 1.23 (2-Me, d; 7.1), 3.33 (3, m), 3.48 (3, m), 6.97 (3-NH, br t; 5.7); D 4.83 (2, dd; 9.7 and 4.3), 1.43 (3, m), 1.70 (3, m), 1.63 (4, m), 0.93 (4-Me, d; 6.4), 0.88 (5, d; 6.4); 1$^{313}$C NMR (CDCl$_3$) unit δ (carbon position) A 165.5 (1), 125.0 (2), 142.0 (3), 34.6 (4), 74.4 (5), 39.8 (6), 12.9 (6-Me), 77.5 (7), 66.7 (8), 137.3a ('), 127.9 (2'/6'), 127.8 (3'/5'), 139.9$^a$ (41), 44.2 (4'-$\underline{C}$H$_2$NH-t-BOC), 28.4 (4'-CH$_2$NH-t-BOC); B 171.0$^b$ (1), 53.6 (2), 35.1 (3), 129.9 (4), 131.0 (5), 122.4 (6), 154.0 (7), 56.1 (7-OCH$_3$), 112.3 (8), 128.4 (9); C 175.6 (1), 38.4 (2), 14.1 (2-Me), 41.3 (3); D 170.3$^b$(1), 71.5 (2), 39.4 (3), 24.7 (4), 22.8 (4-Me), 21.6 (5). $^a$ and $^b$ signals with identical superscript are interchangeable.

Cryptophycin-272: Cryptophycin-263 (4.9 mg, 0.006 mmol) in CH$_2$Cl$_2$ (30 μL) was treated with 4N HCl in dioxane (30 μL, 0.012 mmol) at room temperature. After 3 h, the solvent was removed and the residue was kept under vacuum for 2 d to remove last traces of dioxane, to give cryptophycin-272 (4.4 mg, 98%). $^1$H NMR (CD$_3$OD) amino or hydroxy acid unit δ (carbon position, multiplicity; J in Hz) A 5.94 (2, dd; 15.0, 1.8), 6.69 (3, ddd; 15.0, 11.1 and 4.9), 2.36 (4, m), 2.72 (4, m), 5.13 (5, m), 2.48 (6, m), 1.01 (6-Me, d; 7.1), 4.02 (7, dd; 9.4 and 2.0), 4.84 (8, d; 9.4), 7.45 (2'/6', d; 8.4), 7.51 (3'/5', d; 8.4), 4.11 (4'-C$\underline{H}_2$NH$_2$HCl, s); B 4.51 (2, dd; 11.2 and 3.9), 2.74 (3, m), 3.18 (3, dd; -14.5 and 3.9), 7.28 (5, d; 2.2), 3.84 (7-OMe, s), 6.98 (8, d; 8.4), 7.17 (9, dd; 8.4 and 2.3); C 2.77 (2, m), 1.19 (2-Me, d; 7.5), 3.29 (3, m), 3.58 (3, dd; 13.7 and 3.3); D 5.02 (2, dd; 9.5 and 3.8), 1.56 (3, m), 1.78 (3, m), 1.78 (4, m), 0.97 (4-Me, d; 6.6), 0.99 (5, d; 6.6); $^{13}$C NMR (CD$_3$OD) unit δ (carbon position) A 168.4 (1), 125.4 (2), 144.0 (3), 37.7 (4), 77.3 (5), 40.4 (6), 8.1 (6-Me), 74.8 (7), 63.3 (8), 142.5a (1'), 130.0 (2'/6'), 130.3$^a$ (3'/5'), 134.6$^a$ (4'), 44.0 (4'-$\underline{C}$H$_2$NH$_2$HCl); B 174.1 (1), 57.4 (2), 36.3 (3), 132.2 (4), 131.5 (5), 123.3 (6), 155.4 (7), 56.6 (7-OCH$_3$), 113.5 (8), 129.3 (9); C 177.5 (1), 39.1 (2), 15.1 (2-Me), 41.2 (3); D 172.1 (1), 72.8 (2), 41.2 (3), 26.0 (4), 22.1 (4-Me), 23.6 (5). $^a$ signals are interchangeable.

Cryptophycins-273: 3–Chloroperbenzoic acid (128 mg) was added to a solution of cryptophycin-234 (146 mg) in CH$_2$Cl$_2$ (8 mL) at 0° C. The solution was allowed to slowly warm-up to the room temperature and continued the stirring for 12 h. The reaction mixture was diluted with CH$_2$Cl$_2$ (7 mL) and washed with phosphate buffer (2×10 mL, 0.1 M, pH 8). The organic layer was separated and treated with dimethylsulfide (50 mL) to quench excess peracid, and subjected to the buffer wash again. The organic layer was evaporated and the residue was subjected to reversed phase HPLC (250 mm×22 mm, 10μ, 15% H$_2$O/CH$_3$CN, 6 mL/min) to obtain the RR-epoxide (74 mg, 50%).

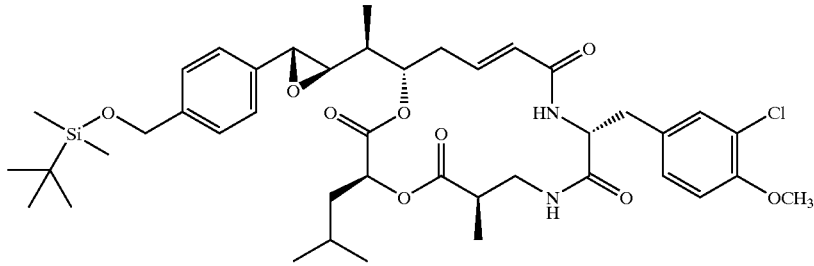

A solution of the epoxide (74 mg) in THF (3 mL) was treated with 115 μL of 1M solution of tetrabutylammonium fluoride in CH$_2$Cl$_2$. After 1.5 h, saturated NH$_4$Cl solution was added to the reaction mixture and extracted with EtOAc (2×30 mL). The organic extract was dried over MgSO$_4$ and evaporated. The residue was purified on a small silica column using 50–100% EtOAc/CH$_2$Cl$_2$ to obtain cryptophycin-269 (62 mg, 98%).

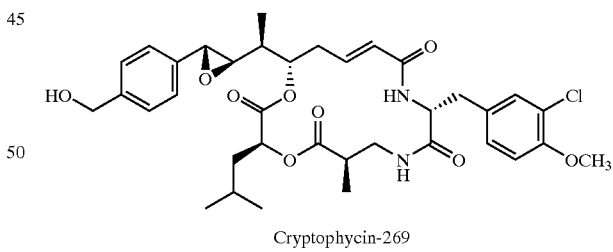

Cryptophycin-269

To a solution of cryptophycin-269 (62 mg), N-(t-BOC) glycine (30 mg) and DMAP (8 mg) in CH$_2$Cl$_2$ (3 mL) was added DCC (160 μL, 1M solution in CH$_2$Cl$_2$ at 0° C. The reaction mixture was stirred at 0° C. for 15 min and at room temperature for 2 h. At the end of this period, the mixture was filtered and concentrated in vacuo. The residue was subjected to a flash chromatography on ODS silica using 75–30% H$_2$O/CH$_3$CN to obtain the N-t-BOC-glycinate ester of cryptophycin-269 (64.4 mg, 85%).

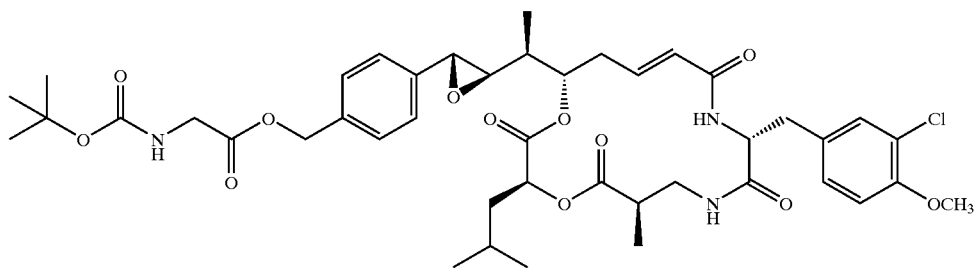

To a solution of glycinate ester (64.4 mg) in chloroform (3 mL) at −60° C. was added 200 μL of 1M solution of TMSCl in CH$_2$Cl$_2$. After 1 h, the solvent was evaporated and the residue was purified on a small silica column using 40–90% EtOAc/hexanes to obtain the trans chlorohydrin of the glycinate(60 mg, 89%).

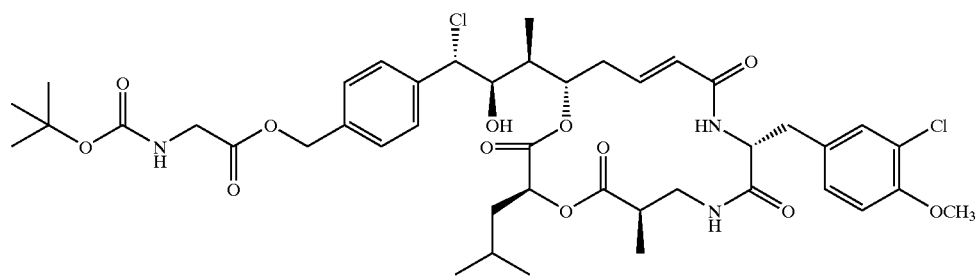

A solution of the chlorohydrin (55 mg) in dichloromethane (0.25 mL) was treated with 4M solution of hydrogen chloride in 1,4-dioxane (0.1 mL). The resulting mixture was stirred at room temperature for 2 h, concentrated in vacuo and dried on the freeze dryer for 48 h. Cryptophycin-273 was obtained as a white solid.

TABLE 9

$^1$H NMR Data for Cryptophycins-8, 163, 184, 185, 186, 187, 191, 192, 193, 194, 195, 212, 222, 223 and 224.
P = position

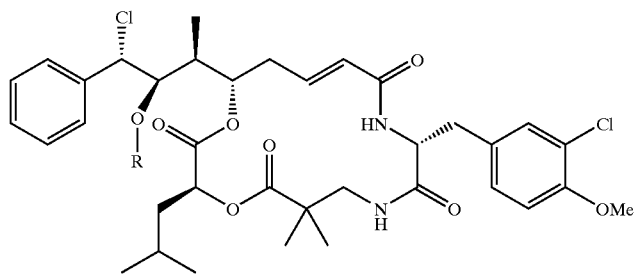

| P | 8 | 163 | 184 | 185 | 186 | 187 | 191 | 192 | 193 | 194 | 195 | 212 | 222 | 223 | 224 |
|---|---|-----|-----|-----|-----|-----|-----|-----|-----|-----|-----|-----|-----|-----|-----|
| A 2 | 5.79 d | 5.80 | 5.79 | 5.74 | 5.71 | 5.75 | 5.80 | 5.68 | 5.80 | 5.67 | 5.79 | 5.80 | 5.71 | 5.80 | 5.79 |

TABLE 9-continued

¹H NMR Data for Cryptophycins-8, 163, 184, 185, 186, 187, 191, 192, 193, 194, 195, 212, 222, 223 and 224.
P = position

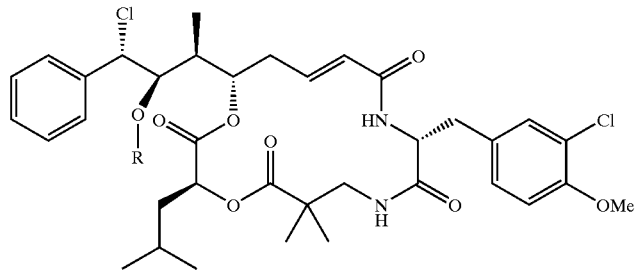

| P | 8 | 163 | 184 | 185 | 186 | 187 | 191 | 192 | 193 | 194 | 195 | 212 | 222 | 223 | 224 |
|---|---|-----|-----|-----|-----|-----|-----|-----|-----|-----|-----|-----|-----|-----|-----|
| 3 | 6.69 ddd | 6.70 | 6.70 | 6.68 | 6.64 | 6.69 | 6.70 | 6.63 | 6.70 | 6.62 | 6.69 | 6.68 | 6.65 | 6.69 | 6.69 |
| 4R | 2.37 m | 2.35 m | 2.38 m | 2.36 m | 2.15 m | 2.37 m | 2.40 | 2.10 | 2.40 | 2.09 | 2.37 | 2.40 | 2.17 | 2.39 | 2.37 |
| 4S | 2.67 m | 2.75 m | 2.70 m | 2.55 m | 2.53 m | 2.59 m | 2.70 | 2.47 | 2.69 | 2.51 | 2.68 | 2.64 | 2.54 | 2.60 | 2.68 |
| 5 | 5.10 ddd | 5.00 | 5.12 | 5.32 m | 5.06 m | 5.40 m | 5.14 | 5.07 | 5.13 brt | 5.07 | 5.11 | 5.10 | 5.07 | 5.11 | 5.11 |
| 6 | 2.50 m | 2.85 | 2.54 | 1.91 | 1.50 m | 1.83 m | 2.65 | 1.64 | 2.55 | 1.57 | 2.49 | 2.47 | 1.51 | 2.48 | 2.50 |
| 6-Me | 1.05 d | 1.13 | 1.09 | 1.09 | 0.93 | 1.06 | 1.18 | 0.95 | 1.09 | 0.90 | 1.04 | 1.03 | 0.93 | 1.04 | 1.04 |
| 7 | 4.00 brdt | 4.41 | 4.09 | 3.84 | 4.07 | 3.74 | 4.35 | 4.48 | 4.12 | 4.20 | 3.99 | 3.95 | 4.07 | 4.16 | 3.98 |
| 8 | 4.65 d | 4.80 | 5.12 | 5.46 | 4.83 | 5.02 | 5.66 | 5.72 | 4.84 | 5.06 | 4.61 | 4.59 | 4.81 | 5.03 | 4.60 |
| 9 | | | | | | | | | | | | | | | |
| 10 | | | | | | | | | | | | | | | |
| 8/10-Ar-1' | | | | | | | | | 7.84 m | 7.76 brs | | | | | |
| 2' | 7.36 to | 7.25 d | 2.30 s | 2.28 | 7.06 d | 7.15 br s | 7.72 brs | 7.56 | | | 6.97 brd | 6.94 m | 6.90 br s | | 7.15 br s |
| 3' | 7.40 m | 6.88 d | 2.31 s | 2.30 | 2.27 d | 2.24 s | 7.50 brm | 7.49 | 7.52 m | 7.42 dd | 7.30 t | | 2.32 | 7.06 to | 2.26 |
| 4' | 7.40 m | 3.81 s | 7.13 to | 7.13 to | 2.27 d | 2.26 s | 7.88 d | 7.88 | 7.89 d | 7.88 d | 6.88 dd | 6.80 tt | 6.99 br s | 7.46 m | 2.26 |
| 5' | 7.40 m | 6.88 d | 7.17 m | 7.16 m | 7.13 d | 7.11 br s | 7.90 d | 7.92 | 7.84 m | 7.85 m | 3.81 s | | 2.32 | 7.46 m | 7.12 to |
| 6' | 7.40 m | 7.25 d | 7.17 m | 7.16 m | 7.03 dd | 7.11 br s | 7.54 t | 7.52 to | 7.52 m | 7.51 to | 6.93 t | 6.94 m | 6.90 bs | 7.46 m | 7.15 m |
| 7' | | | | | | | 7.59 t | 7.63 m | 7.52 m | 7.56 m | | | | | |
| 8' | | | | | | | 8.13 brs | 8.13 brs | 7.84 m | 7.85 m | | | | | |
| D 2 | 4.92 dd | 4.93 | 4.93 | 4.81 m | 4.86 | 4.81 | 4.93 | 4.86 | 4.93 dd | 4.84 dd | 4.92 | 4.91 | 4.87 dd | 4.92 dd | 4.93 m |
| 3 | 1.45 m | 1.41 | 1.50 | 1.43 | 1.53 | 1.42 | 1.47 | 1.51 | 1.46 | 1.46 | 1.45 | 1.43 | 1.54 | 1.50 | 1.46 m |
| 3' | 1.78 m | 1.78 | 1.79 | 1.68 | 1.85 | 1.69 | 1.74 | 1.86 | 1.70 to | 1.84 | 1.70 to | 1.66 to | 1.85 | 1.74 to | 1.72 to |
| 4 | 1.76 m | 1.78 | 1.79 | 1.63 | 1.85 | 1.59 | 1.74 | 1.64 | 1.81 m | 1.58 | 1.82 m | 1.82 m | 1.70 | 1.84 m | 1.82 m |
| 4-Me | 0.94 d | 0.95 | 0.95 | 0.91 | 0.97 | 0.91 | 0.93 brs | 0.93 | 0.95 | 0.97 | 0.93 | 0.94 | 0.97 | 0.95 | 0.98 |
| 5 | 0.93 d | 0.92 | 0.95 | 0.87 | 0.94 | 0.86 | 0.93 brs | 0.90 | 0.93 | 0.96 | 0.93 | 0.92 | 0.94 | 0.93 | 0.98 |

Spectra recorded in CDCl₃; The chemical shifts are for the protons or methyl or methoxyl function positioned on the carbons indicated in the table. The chemical shifts for the protons on units B and C are within ±0.2 ppm and coupling constants ±0.5 Hz of the values for those in cryptophycin-8. J (H,H) in Hz for 163: 2',3'=5',6'=8.7; J (H,H) in Hz for 186: 2',6'=2.0; 5',6'=7.7; J (H,H) in Hz for 193 and 194: 3',4'=8.5; J (H,H) in Hz for 195: 2', 3'=3',4'=7.9; 2',6'=4'6'=2.4; The observable coupling constants for the rest of the protons in the table are with in ±0.5 Hz of the values for those in cryptophycin-8. J (HH) and J (H,F) in Hz for 212: 3'-F,4-H=4-H,5-F=8.7; 2',4'=4',6'=2.3.

TABLE 10

125 MHz $^{13}$C NMR Data for Cryptophycins-8, -163, -184, -185, -186, 187, 191, 192, 194, 195, 222, 223 and 224.

P = position

| P | 8 | 163 | 184 | 185 | 186 | 187 | 191[†] | 192[†] | 194 | 195 | 212 | 222 | 223 | 224 |
|---|---|---|---|---|---|---|---|---|---|---|---|---|---|---|
| A1 | 165.5 | 165.4 | 165.5 | 165.4 | 165.4 | 165.5 | 165.5 | 165.4 | 165.4 | 165.5 | 165.5 | 165.4 | 165.5 | 165.5 |
| 2 | 125.1 | 125.3 | 125.2 | 124.9 | 125.0 | 125.0 | 125.1 | 125.4 | 125.1 | 125.1 | 125.4 | 125.1 | 125.3 | 125.2 |
| 3 | 141.6 | 141.1 | 141.7 | 142.0 | 141.6 | 142.1 | 141.7 | 141.6 | 141.5 | 141.7 | 141.3 | 141.6 | 141.4 | 141.6 |
| 4 | 36.3 | 36.9 | 36.5 | 34.9 | 36.2 | 34.6 | 36.5 | 36.2 | 36.1 | 36.4 | 36.3 | 36.1 | 36.4 | 36.4 |
| 5 | 76.3 | 75.8 | 76.4 | 74.7 | 76.2 | 74.3 | 76.4 | 76.3 | 76.1 | 76.3 | 76.3 | 76.2 | 76.4 | ** |
| 6 | 38.2 | 39.5 | 38.3 | 39.9 | 38.3 | 39.6 | 38.3 | 38.3 | 38.3 | 38.3 | 38.5 | 38.4 | 38.5 | 38.4 |
| 6-Me | 8.7 | 9.6 | 8.7 | 13.3 | 8.7 | 12.9 | 8.8 | 9.2 | 8.7 | 8.7 | 8.7 | 8.7 | 8.6 | 8.7 |
| 7 | 74.0 | 65.1 | 74.1 | 76.4 | 74.3 | 77.7 | 74.0 | 73.9 | 74.3 | 74.0 | 74.0 | 74.3 | 73.1 | 74.0 |
| 8 | 61.9 | 62.3 | 57.5 | 63.6 | 69.0 | 67.3 | 57.2 | 62.8 | 67.1 | 61.9 | 60.7 | 69.1 | 55.3 | 62.0 |
| 9 | | | | | | | | | | | | | | |
| 10 | | | | | | | | | | | | | | |
| 8/ 10-Ar-1' | 138.3 | 131.2 | 135.9 | 133.6 | 135.0 | 135.5 | * | * | 126.9 | 139.7 | 142.7 | 137.4 | 130.7 | 135.5 |
| 2' | 128.0 | 128.8 | 137.7 | 137.5 | 128.6 | 128.7 | * | * | * | 114.1 a | 111.2 d | 125.1 | 160.6 | 129.1 |
| 3' | 129.1 | 114.1 | 137.7 | 136.1 | 137.4 | 137.3 | 125.2 | 125.0 | 124.0 | 160.0 | 163.0 dd | 138.7 | 116.1 | 137.5 |
| 4' | 129.2 | 160.1 | 130.5 | 130.4 | 137.9 | 137.5 | 129.2 | 127.1 | 129.3 | 114.2 a | 104.5 t | 130.9 | 129.3 | 138.0 |
| 5' | 129.1 | 114.1 | 126.4 | 126.1 | 130.3 | 130.1 | 129.2 | 129.4 | 127.8 | 130.2 | 163.0 | 138.7 | 124.8 | 130.3 |
| 6' | 128.0 | 128.8 | 124.5 | 125.7 | 124.7 | 124.9 | 127.0 | 126.3 | 127.0 | 120.0 | 111.2 d | 125.1 | 130.7 | 125.3 |
| 7' | | | | | | | 126.2 | 126.3 | 127.1 | | | | | |
| 8' | | | | | | | * | * | 128.0 | | | | | |
| 9' | | | | | | | * | 130.5 | * | | | | | |
| 10' | | | | | | | 134.5 | * | 134.7 | | | | | |
| D1 | 170.6 | 170.2 | 170.6 | 170.2 | 170.4 | 170.3 | 170.6 | 170.4 | 170.9 | 170.6 | 170.7 | 170.4 | 170.7 | 170.6 |
| 2 | 71.3 | 71.3 | 71.3 | 71.5 | 71.4 | 71.5 | 71.3 | 71.4 | 71.4 | 71.3 | 71.3 | 71.4 | 71.4 | 71.4 |
| 3 | 39.7 | 39.6 | 39.7 | 39.3 | 39.7 | 39.4 | 39.6 | 39.7 | 39.7 | 39.7 | 39.9 | 39.7 | 39.6 | 39.7 |
| 4 | 24.7 | 24.8 | 24.7 | 24.6 | 24.8 | 24.7 | 24.0 | 24.8 | 24.8 | 24.7 | 24.7 | 24.8 | 24.7 | 24.7 |
| 4-Me | 23.1 | 23.3 | 23.2 | 22.8 | 23.1 | 22.7 | 23.1 | 23.1 | 23.1 | 23.0 | 23.0 | 23.1 | 23.1 | 23.1 |
| 5 | 21.5 | 21.5 | 21.5 | 21.6 | 21.7 | 21.6 | 21.5 | 21.7 | 21.7 | 21.4 | 21.5 | 21.8 | 21.4 | 21.5 |

Spectra recorded in CDCl3. The chemical shifts for carbons in units B and C are within ±0.5 ppm of the values in cryptophycin-8. * Signals could not be found due to the smaller size of the sample. † Assignments are tentative. ** Merged with solvent signals. The 4-OMe carbon of 163 and also that of 195 was resonated at δ 55.3. The 2'-Me and 3'-Me carbons of 185 appeared at δ 15.0 and 20.9 respectively. The 3'-Me and 4'-Me carbons of 186 were observed at δ 19.6 and 19.9 respectively. The same carbons were observed respectively at δ 19.5 and 19.8 in 187 and at δ 19.5 and 19.8 in 224. The 3' and 5'-Me carbons of 223 were observed at 21.3.

EXAMPLE 94

The general group R in 2' (below) is comprised of an ether substituent and several acyl substituents, as depicted in Table 1 (also below). The novel cryptophycin analogs were prepared in moderate to high yield via esterification techniques. See, Mulzer, J., Trost B. M. Fleming, I., Ed. *Comprehensive organic Synthesis*; 6:323–380, (Pergamon press: Oxford, 1991); Benz, G. Trost, B. M., Fleming, I., Ed., *Comprehensive Organic Synthesis*, 6:381–417, (Pergamon press: Oxford, 1991). Amine hydrochloride salts were prepared in high yield from the corresponding t-butyl carbamates upon treatment with hydrochloric acid while di-sodium salt 7' was derived from 6' following hydrochloric acid induced t-butyl ester cleavage and sodium hydroxide treatment. Pyridinium salt 9' was prepared from 1' following the method of Nicolaou. Nicolauo, et. al. *Angew. Chem.Int. Ed. Engl.*, 333:1583+ (1994).

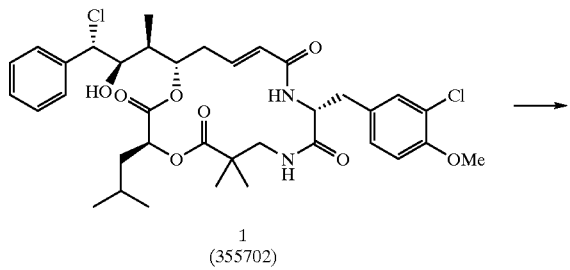

1
(355702)

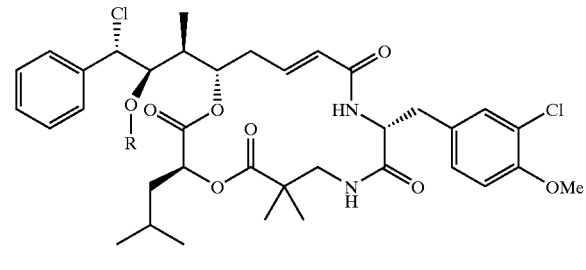

2

1'        2'
(as used in description of synthesis methods below)

TABLE 1

R groups of general structure 2' (above).

| Compound | R |
|---|---|
| 3' | acetyl (methyl ketone) |
| 4' | -C(O)CH₂CH₂CO₂t-Bu |
| 5' | -C(O)CH₂CH₂CO₂H |
| 6' | -C(O)CH₂-(2-OP(O)(Ot-Bu)₂-phenyl) |
| 7' | -C(O)CH₂-(2-OP(O)(ONa)₂-phenyl) |
| 8' | -C(O)CH₂-(2-pyridyl) · HCl |
| 9' | 2-(N-Me-N-OAc-amino)pyridyl |
| 10' | -C(O)CH(NHCO₂t-Bu)CH₂-(3-Cl-4-OMe-phenyl) |
| 11' | -C(O)CH(NH₂)CH₂-(3-Cl-4-OMe-phenyl) · HCl |

TABLE 1-continued

R groups of general structure 2' (above).

| Compound | R |
|---|---|
| 12' | -C(O)CH(NHCO₂t-Bu)CH₂-phenyl |
| 13' | -C(O)CH(NH₂)CH₂-phenyl · HCl |
| 14' | -C(O)CH(NHCO₂t-Bu)CH₂-(1-CO₂t-Bu-imidazol-4-yl) |
| 15' | -C(O)CH(NH₂)CH₂-(imidazol-4-yl) · HCl |
| 16' | -C(O)-(1-CO₂t-Bu-pyrrolidin-2-yl) |
| 17' | -C(O)-(pyrrolidin-2-yl) · HCl |
| 18' | -C(O)CH₂NHCO₂t-Bu |
| 19' | -C(O)CH₂NH₂ · HCl |

TABLE 1-continued

R groups of general structure 2' (above).

| Compound | R |
|---|---|
| 20' | (structure: ketone-CH2-CH2-NHCO2t-Bu) |
| 21' | (structure: ketone-CH2-CH2-NH2 · HCl) |
| 22' | (structure: ketone-(CH2)3-NHCO2t-Bu) |
| 25' | (structure: ketone-(CH2)3-NH2 · HCl) |
| 26' | (structure: ketone-CH(CH3)-NHCO2t-Bu, wedge) |
| 28' | (structure: ketone-CH(CH3)-NH2 · HCl, wedge) |
| 29' | (structure: ketone-CH(CH3)-NHCO2t-Bu, dash) |
| 30' | (structure: ketone-CH(CH3)-NH2 · HCl, dash) |
| 31' | (structure: ketone-CH(NHCO2t-Bu)-(CH2)4-NHCO2t-Bu) |
| 32' | (structure: ketone-CH(NH2·HCl)-(CH2)4-NH2·HCl) |
| 33' | (structure: ketone-CH(NHCO2t-Bu)-(CH2)4-NHCO2t-Bu, dashed) |
| 34' | (structure: ketone-CH(NH2·HCl)-(CH2)4-NH2·HCl, dashed) |
| 35' | (structure: ketone-CH(NHCO2t-Bu)-CH2-CH2-CO2t-Bu) |
| 36' | (structure: ketone-CH(NH2·HCl)-CH2-CH2-CO2H) |
| 37' | (structure: ketone-CH(NHCO2t-Bu)-CH2-CO2t-Bu) |
| 38' | (structure: ketone-CH(NH2·HCl)-CH2-CO2H) |
| 39' | (structure: ketone-CH(NHCO2t-Bu)-CH2-CO2t-Bu, dashed) |
| 40' | (structure: ketone-CH(NH2·HCl)-CH2-CO2H, dashed) |
| 41' | (structure: ketone-CH2-CH2-CH(CO2t-Bu)(NHCO2t-Bu)) |
| 42' | (structure: ketone-CH2-CH2-CH(CO2H)(NH2·HCl)) |

TABLE 1-continued

R groups of general structure 2' (above).

| Compound | R |
|---|---|
| 43' | ![structure with C=O, NHCO₂t-Bu (two branches)] |
| 44' | ![structure with C=O, NH₂·HCl (two branches)] |
| 45' | ![structure with C=O, NHCO₂t-Bu, OH] |
| 46' | ![structure with C=O, NH₂·HCl, OH] |
| 47' | ![structure with C=O, NH, C=O, NH₂·HCl] |
| 48' | ![structure with C=O, O-CH₂CH₂-O-CH₂CH₂-O-CH₃] |

The preparation of the conjugates depicted in Table 1 follows several protocols typically involving activated ester methodology followed by chromatography and acid induced deblocking where necessary. Thus, treatment of 1' with acetic anhydride in the presence of triethylamine and 4-dimethylamino pyridine provides 3' in 89% yield after flash chromatography. Similarly, 5' can be prepared from 1' via the agency of succinic anhydride followed by reverse phase HPLC purification.[7] Alternatively, 5' is prepared in high yield upon acid treatment of mono-t-butyl ester 4'. Exposure of a pyridine solution of 1' to commercially available nicotinoyl chloride hydrochloride in the presence of triethylamine and 4-dimethylamino pyridine followed by chromatography and hydrogen chloride treatment gives rise to 8' in high yield. Pyridinium salt 9' is prepared in 47% yield according to the method of Nicolaou (ibid) whereby 1' is treated with commercially available 2-fluoro-1-methylpyridinium p-toluenesulfonate followed by reverse phase HPLC purification with concomitant anion exchange (acetate for p-toluenesulfonate) and lyophilization. Remaining esters are all prepared in moderate to high yields from 1' and commercially available (except in the case of 4', 6, 10', 43', and 45') N-t-boc protected amino acids with activation via the agency 1,3-dicyclohexylcarbodiimide in the presence of 4-dimethylamino pyridine. Hydrochloride salts are prepared in high yield upon treatment with a 4.0 M solution of hydrogen chloride in dioxane and removal of solvent in vacuo. Di-sodium salt 7' is derived from 6' following hydrochloric acid induced t-butyl ester cleavage and sodium hydroxide treatment. The requisite acid 24' for the preparation of 5' is synthesized in 63% yield by way of a 5 step sequence featuring the method of Johns for installing the phosphate functionality. Perich, J. W.; Johns R. B. et al. Synthesis 1988: 142.

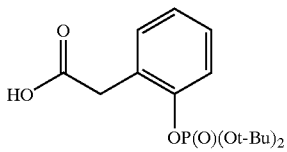

(379402)

Several of the novel conjugates have been assayed for in vitro cytotoxicity in the Gc3 tumor cell model, as described herein supra. These results are shown in Table 2 below:

TABLE 2

In vitro cytotoxicity data for cryptophycin derivatives.

| Compound | Gc3 IC$_{50}$ (nM) |
|---|---|
| 1' | 0.065 |
| 3' | 83 |
| 5' | 31 |
| 7' | 3.7 |
| 8' | 116 |
| 9' | 2.2 |
| 11' | 6.8 |
| 13' | 7.0 |
| 15' | 60 |
| 17' | 3.6 |
| 19' | 0.10 |
| 21' | 21 |
| 25' | 230 |
| 28' | 2.6 |
| 30' | 30 |
| 32' | 7.2 |
| 34' | 6.5 |
| 36' | 2.8 |
| 38' | 1.6 |
| 40' | 2.0 |
| 42' | 15 |
| 44' | 28 |
| 46' | 50 |
| 47' | 2.5 |
| 48' | 10 |

Stability studies were conducted at aqueous pHs ranging from 4–8 and percent product remaining intact was determined.

The conversion of t-butyl carbamates to the corresponding salts could be effected with any strong acid, namely, mineral acids comprised of hydrogen halides, hydrogen sulfates, hydrogen phosphates, hydrogen nitrates, hydrogen perchlorates, or strong organic acids such as trifluoroacetic, p-toluenesulfonic, and methanesulfonic. The same acids could be used to produce salts of type 8' from the corresponding free base. A variety of counterions (cations) could comprise salts of type 7' including any of the alkali and alkaline earth metals. A variety of counterions (anions) could comprise salts of type 9', namely, any conjugate base of an acid (organic or mineral).

Preparation of Cryptophycin 55 Acetate (3') (LSN 362376)

To a solution of 1' (93 mg, 0.13 mmol) in 659 µl of methylene chloride at 0° C. was added triethylamine (55 µl, 0.40 mmol), 4-dimethylamino pyridine (1.6 mg, 0.013 mmol), and acetic anhydride (19 µl, 0.20 mmol). After stirring at 0° C. for 1 h the reaction was quenched with 19 µl of methanol, concentrated to 0.5 volume, and applied directly to a flash chromatography column (19 g of flash silica gel). Elution with ethyl acetate-hexanes (3:1) provided 88 mg (89%) of the title compound as a white foam: 500 MHz $^1$H NMR (CDCl$_3$) δ 7.38–7.31 (m, 5H), 7.24 (d, 1H, J=2.1 Hz), 7.22–7.18 (m, 1H), 7.10 (dd, 1H, J=8.5, 2.1 Hz), 6.88 (d, 1H, J=8.5 Hz), 6.75 (ddd, 1H, J=15, 13, 4.6 Hz), 5.78 (dd, 1H, J=15, 1.0 Hz), 5.55 (d, 1H, J=7.9 Hz), 5.46 (dd, 1H, J=9.8, 1.2 Hz), 4.95 (dd, 1H, J=11, 2.9 Hz), 4.89 (ddd, 1H, J=9.9, 9.9, 1.7 Hz), 4.81 (d, 1H, J=9.8 Hz), 4.79–4.74 (m, 1H), 3.91 (s, 3H), 3.39 (dd, 1H, J=13, 8.1 Hz), 3.22 (dd, 1H, J=13, 4.1 Hz), 3.16 (dd, 1H, J=14, 5.1 Hz), 3.07 (dd, 1H, J=14, 7.6 Hz), 2.65–2.55 (m, 2H), 2.47–2.39 (m, 1H), 1.95 (ddd, 1H, J=14, 13, 4.6 Hz), 1.86–1.77 (m, 1H), 1.73–1.66 (m, 1H), 1.68 (s, 3H), 1.27 (s, 3H), 1.19 (s, 3H), 1.09 (d, 3H, J=7.1 Hz), 1.03 (d, 3H, J=6.7 Hz), 0.97 (d, 3H, J=6.6 Hz)

Preparation of Cryptophycin 55 Succinate/tert-butyl Ester (4') (LSN 384665)

To a solution of 1'# (133 mg, 0.188 mmol), succinic acid mono-tert-butyl ester[10] (66 mg, 0.377 mmol) and 4-dimethylamino pyridine (2.3 mg, 0.019 mmol) in 850 µl of anhydrous methylene chloride at room temperature was added a solution of 1,3-dicyclohexylcarbodiimide (78 mg, 0.377 mmol) in 92 µl of methylene chloride. After stirring at room temperature for 1 h the reaction was treated with 150 mg of celite and diluted with 1 ml of ethyl acetate-hexanes (3:1) and filtered through a plug of celite, washing with ethyl acetate-hexanes (3:1). The filtrate and washings were concentrated in vacuo to an off-white oil. Chromatography (25 g of flash silica gel), eluting with ethyl acetate-hexanes (2:1) provided 157 mg (97%) of the title compound as a white foam: 500 MHz $^1$H NMR (CDCl$_3$) δ 7.38–7.30 (m, 5H), 7.24 (d, 1H, J=2.0 Hz), 7.22–7.18 (m, 1H), 7.09 (dd, 1H, J=8.5, 2.0 Hz), 6.88 (d, 1H, J=8.5 Hz), 6.74 (ddd, 1H, J=15, 10, 4.6 Hz), 5.76 (d, 1H, J=15 Hz), 5.51 (d, 1H, J=8.0 Hz), 5.47 (d, 1H, J=9.6 Hz), 4.97 (dd, 1H, J=11, 3.1 Hz), 4.90 (t, 1H, J=9.3 Hz), 4.83 (d, 1H, J=9.6 Hz), 4.79–4.73 (m, 1H), 3.91 (s, 3H), 3.39 (dd, 1H, J=13, 8.0 Hz), 3.22 (dd, 1H, J=13, 4.0 Hz), 3.16 (dd, 1H, J=14, 5.1 Hz), 3.08 (dd, 1H, J=14, 7.6 Hz), 2.63–2.55 (m, 2H), 2.44–2.37 (m, 1H), 2.32–2.21 (m, 2H), 2.19–2.06 (m, 2H), 1.99–1.92 (m, 1H), 1.85–1.68 (m, 2H), 1.42 (s, 9H), 1.27 (s, 3H), 1.19 (s, 3H), 1.08 (d, 3H, J=7.0 Hz), 1.03 (d, 3H, J=6.6 Hz), 0.98 (d, 3H, J=6.5 Hz).

Preparation of Cryptophycin 55 Succinate (5') (LSN 377092) From Cryptophycin 55 Succinate tert-Butyl Ester To a solution of 4' (127 mg, 0.147 mmol) in 491 µl of methylene chloride at room temperature was added a 4.0 M solution of hydrogen chloride in 1,4-dioxane (184 µl, 0.737 mmol). The solution was allowed to stir at room temperature for 5 h. Concentration in vacuo provided 119 mg (100%) of the title compound as a white foam.

Preparation of Cryptophycin 55 Succinate (5') (LSN 377092) From Succinic Anhydride To a solution of 1' (27 mg, 0.038 mmol) and succinic anhydride (5.7 mg, 0.057 mmol) in 383 µl of methylene chloride at room temperature was added triethylamine (16 µl, 0.115 mmol) and 4-dimethylamino pyridine (4.7 mg, 0.038 mmol). After stirring for 19 h, another 5.7 mg (0.057 mmol) of succinic anhydride and 4.7 mg (0.038 mmol) of 4-dimethylamino pyridine were added followed by stirring an additional 29 h. The reaction was treated with 0.5 ml of 1 N aqueous hydrochloric acid and washed with methylene chloride (3×0.5 ml). The combined organic extracts were dried (Na$_2$SO$_4$), filtered, and concentrated in vacuo to white foam. Reverse phase HPLC[7] purification provided 10 mg (32%) of the title compound as a white foam: 500 MHz $^1$H NMR (CDCl$_3$) δ 7.36–7.31 (m, 6H), 7.22 (br s, 1H), 7.08 (d, 1H, J=8.4 Hz), 7.02 (br s, 1H), 6.87 (d, 1H, J=8.4 Hz), 6.61 (m, 1H), 5.94–5.87 (m, 2H), 5.51 (d, 1H, J=9.8 Hz), 4.95 (dd, 1H, J=10, 2.8 Hz), 4.87–4.76 (m, 3H), 3.90 (s, 3H), 3.39 (dd, 1H, J=16, 5.6 Hz), 3.28 (dd, 1H, J=16, 8.2 Hz), 3.17 (dd, 1H, J=16, 5.6 Hz), 3.05 (dd, 1H, J=16, 8.2 Hz), 2.68–2.62 (m, 1H), 2.60–2.46 (m, 2H), 2.45–2.28 (m, 3H), 2.01–1.93 (m, 2H), 1.88–1.70 (m, 2H), 1.26 (s, 3H), 1.18 (s, 3H), 1.12 (d, 3H, J=7.0 Hz), 1.04 (d, 3H, J=6.6 Hz), 1.00 (d, 3H, J=6.5 Hz).

Preparation of Cryptophycin 55 (2'-di-t-Butylphosphatyl)phenylacetate (6') (LSN 379407)

To a solution of 1' (0.102 mmol), 24' (46 mg, 0.134 mmol), and 4-dimethylamino pyridine (12 mg, 0.102 mmol) in 250 µl of anhydrous methylene chloride at room temperature was added a solution of 1,3-dicyclohexylcarbodiimide (27 mg, 0.134 mmol) in 50 µl of methylene chloride. After stirring at room temperature for 6 h the reaction was diluted with 1 ml of ethyl acetate-hexanes (3:1) and filtered through a plug of celite, washing with ethyl acetate-hexanes (3:1). The filtrate and washings were concentrated in vacuo to a purple foam. Chromatography (15 g of flash silica gel), eluting with ethyl acetate-hexanes (4:1) provided 86 mg (82%) of the title compound as a white foam: 500 MHz $^1$H NMR (CDCl$_3$) δ 7.35 (d, 1H, J=8.3 Hz), 7.30–7.19 (m, 8H), 7.11 (dd, 1H, J=8.4, 2.0 Hz), 7.02 (t, 1H, J=7.5 Hz), 6.87 (d, 1H, J=8.4 Hz), 6.84 (d, 1H, J=7.5 Hz), 6.73 (ddd, 1H, J=15, 13, 4.7 Hz), 5.92 (d, 1H, J=7.9 Hz), 5.79 (dd, 1H, J=15, 1.0 Hz), 5.43 (dd, 1H, J=9.4, 1.8 Hz), 4.98 (dd, 1H, J=12, 3.1 Hz), 4.81 (ddd, 1H, J=9.9, 9.9, 1.8 Hz), 4.75 (d, 1H, J=9.4 Hz), 4.73–4.67 (m, 1H), 3.90 (s, 3H), 3.49 (d, 1H, J=16 Hz), 3.44–3.38 (m, 1H), 3.38 (d, 1H, J=16 Hz), 3.27–3.17 (m, 2H), 3.10 (dd, 1H, J=14, 8.2 Hz), 2.55–2.46 (m, 2H), 2.37–2.27 (m, 1H), 1.95 (ddd, 1H, J=14, 12, 4.5 Hz), 1.83–1.70 (m, 2H), 1.49 (s, 18H), 1.27 (s, 3H), 1.20 (s, 3H), 1.03 (d, 3H, J=6.5 Hz), 0.97 (d, 3H, J=6.4 Hz), 0.92 (d, 3H, J=7.0 Hz).

Preparation of 2'-(di-t-Butylphosphatyl)phenylacetic Acid (24') (LSN 379402)

To a solution of 2'-hydroxyphenethyl alcohol (1.05 g, 7.60 mmol) in 15.2 ml of N,N-dimethylformamide at 0° C. was added imidazole (621 mg, 9.11 mmol) and tert-butyldimethylsilyl chloride (1.26 g, 8.34 mmol). After stirring at 0° C. for 40 min and at room temperature for 45 min, another 155 mg (2.28 mmol) of imidazole and 229 mg (1.52 mmol) of tert-butyldimethylsilyl chloride were added. The reaction was allowed to stir for an additional 15 min at which time 150 ml of tert-butyl methy ether was added. The mixture was washed with cold 1N aqueous hydrochloric acid (1×15 ml) followed by water (1×15 ml). The organic layer was dried (Na$_2$SO$_4$), filtered, and concentrated in vacuo to a yellow oil. Chromatography (70 g of flash silica gel), eluting with hexanes-ethyl acetate (5:1) provided 1.81 g (94%) of the primary silyl ether as a faintly off-white oil. To a solution of the silyl ether (506 mg, 2.00 mmol) and di-tert-butyl diethylphosphoramidite (600 µl of 93%, 2.00 mmol) in 2 ml of tetrahydrofuran at room temperature was added 1-H-tetrazole (421 mg, 6.01 mmol). After stirring for 45 min the reaction mixture was cooled to −10° C. and rapidly treated with a solution of m-chloroperbenzoic acid (450 mg of 99%, 2.61 mmol) in 3.6 ml of methylene chloride. The cloudy white reaction was allowed to warm to room temperature and stir for 15 min. The reaction was quenched with 4 ml of 10% aqueous sodium bisulfite, stirred vigorously for 10 min, diluted with 15 ml of tert-butyl methy ether, and washed with 10% aqueous sodium bisulfite (2×10 ml) followed by 0.5 N aqueous sodium hydroxide (2×10 ml). The organic layer was dried ($Na_2SO_4$), filtered, and concentrated in vacuo to a colorless oil (941 mg) which was used directly in the next step. The crude phosphate was dissolved in 10 ml of tetrahydrofuran, cooled to 0° C., and treated with a 1 M solution of tetra-n-butylammonium fluoride in tetrahydrofuran (2.4 ml, 2.4 mmol). After stirring at 0° C. for 20 min and at room temperature for 1.5 h, the reaction was diluted 60 ml of tert-butyl methy ether and washed with water (1×10 ml) followed by brine (1×10 ml). The organic layer was dried ($Na_2SO_4$), filtered, and concentrated in vacuo to a yellow oil. Chromatography (50 g of flash silica gel), eluting with ethyl acetate-hexanes (3:1) provided 525 mg (79%) of the 1° alcohol as an off-white oil. To a solution of the alcohol (123 mg, 0.372 mmol) in acetonitrile-carbon tetrachloride (1:1, 1.49 ml) at room temperature was added water (1.1 ml) followed by sodium periodate (239 mg, 1.12 mmol) and ruthenium(III)chloride hydrate (1.8 mg, 0.0082 mmol). The brown mixture was allowed to stir rapidly at room temperature for 55 min. Upon concentration in vacuo and chromatography (8 g of flash silica gel, eluting with 10% methanol-ethyl acetate) 109 mg (85%) of the title compound was obtained as a purple oil: 500 MHz $^1$H NMR (CDCl$_3$) δ 7.49 (d, 1H, J=7.53 Hz), 7.30–7.15 (m, 3H), 3.77 (s, 2H), 1.51 (s, 18H).

Preparation of Cryptophycin 55 (2'-phosphatyl) phenylacetate di-sodium Salt (7') (LSN 374122)

To a solution of 6' (84 mg, 0.081 mmol) in 400 µl of methylene chloride at room temperature was added a 4.0 M solution of hydrogen chloride in 1,4-dioxane (81 µl, 0.33 mmol). The faint yellow solution was allowed to stir at room temperature for 2 h. After concentration in vacuo to an off-white foam, the crude dihydrogen phosphate was dissolved in 614 µl of tetrahydrofuran and treated with a 5.00 N aqueous solution of sodium hydroxide (33 µl, 0.163 mmol). After stirring for 10 min the mixture was concentrated in vacuo to a tan foam. The crude salt was taken up in 1 ml of hot acetonitrile and 0.1 ml of hot water. The insolubles were filtered off and the filtrate was concentrated in vacuo to provide 69 mg (87%) of the title compound as a white solid: 500 MHz $^1$H NMR (MeOH-d$_4$) δ 7.58 (d, 1H, J=8.2 Hz), 7.38–7.32 (m, 2H), 10 7.32–7.28 (m, 3H), 7.28 (d, 1H, J=2.1 Hz), 7.17 (dd, 1H, J=8.5, 2.1 Hz), 7.09 (ddd, 1H, J=7.8, 7.8, 1.7 Hz), 6.98 (d, 1H, J=8.5 Hz), 6.79–6.70 (m, 2H), 6.67 (d, 1H, J=7.4 Hz), 5.91 (dd, 1H, J=15, 1.7 Hz), 5.45 (dd, 1H, J=9.4, 1.6 Hz), 5.06 (dd, 1H, J=10, 2.7 Hz), 5.01 (d, 1H, J=9.4 Hz), 4.89–4.80 (m, 1H), 4.47 (dd, 1H, J=11, 3.8 Hz), 3.84 (s, 3H), 3.67 (d, 1H, J=16 Hz), 3.45 (d, 1H, J=14 Hz), 3.42 (d, 1H, J=16 Hz), 3.18 (dd, 1H, J=14, 3.8 Hz), 3.12 (d, 1H, J=14 Hz), 2.77 (dd, 1H, J=14, 11 Hz), 2.67–2.60 (m, 1H), 2.56–2.48 (m, 1H), 2.31–2.22 (m, 1H), 1.96–1.88 (m, 1H), 1.85–1.77 (m, 2H), 1.22 (s, 3H), 1.20 (s, 3H), 1.03 (d, 3H, J=6.2 Hz), 0.98 (d, 3H, J=6.1 Hz), 0.93 (d, 3H, J=7.1 Hz).

Preparation of Cryptophycin 55 Nicotinoate Hydrochloride Salt (8') (LSN 368265)

To a solution of 1' (50 mg, 0.071 mmol) in 354 µl of pyridine at room temperature was added nicotinoyl chloride hydrochloride (15 mg, 0.085 mmol) followed by triethylamine (23 µl, 0.170 mmol). After stirring for 1.5 h, 4-dimethylamino pyridine (8.6 mg, 0.071 mmol) was added. After stirring 5 h, additional triethylamine (23 µl, 0.170 mmol), 4-dimethylamino pyridine (8.6 mg, 0.071 mmol), and nicotinoyl chloride hydrochloride (15 mg, 0.085 mmol) was added along with a 50 µl pyridine rinse. After stirring 18 h the reaction was treated with 0.5 ml of saturated aqueous sodium bicarbonate and washed with methylene chloride (4×1 ml). The combined organic extracts were dried ($Na_2SO_4$), filtered, and concentrated in vacuo to a light brown oil. Chromatography (14 g of flash silica gel), eluting with ethyl acetate-hexanes. (10:1) provided 49 mg (85%) of the free base as a white foam. The nicotinoate was dissolved in 1 ml of methylene chloride and treated with a 1.0 M solution of hydrogen chloride in diethyl ether (90 µl, 0.090 mmol). The clear, colorless solution was allowed to stand at room temperature for 5 min. Removal of the solvent in vacuo produced 51 mg of the title compound as a white foam: 500 MHz $^1$H NMR (CDCl$_3$) δ 8.94 (s, 1H), 8.78 (br s, 1H), 8.29 (d, 1H, J=7.0 Hz), 7.57 (br s, 1H), 7.38 (d, 2H, J=7.1 Hz), 7.30–7.16 (m, 5H), 7.10 (dd, 1H, J=8.4, 1.7 Hz), 6.88 (d, 1H, J=8.4 Hz), 6.71 (m, 1H), 5.80 (d, 1H, J=15 Hz), 5.74 (d, 1H, J=9.6 Hz), 5.56 (br s, 1H), 5.00 (d, 1H, J=9.6 Hz), 4.95 (t, 1H, J=8.9 Hz), 4.84 .(d, 1H, J=9.8 Hz), 4.77–4.72 (m, 1H), 3.91 (s, 3H), 3.39 (dd, 1H, J=13, 8.2 Hz), 3.23–3.14 (m, 2H), 3.06 (dd, 1H, J=14, 7.6 Hz), 2.81–2.74 (m, 1H), 2.62–2.45 (m, 2H), 1.93 (ddd, 1H, J=14, 12, 4.8 Hz), 1.78–1.70 (m, 1H), 1.66–1.59 (m, 1H), 1.25 (s, 3H), 1.20 (d, 3H, J=7.0 Hz), 1.19 (s, 3H), 0.98 (d, 3H, J=6.7 Hz), 0.84 (d, 3H, J=6.5 Hz).

Preparation of Cryptophycin 55 N-Methylpyridinium Acetate Salt (9') (LSN 366550)

To a solution of 1' (53 mg, 0.075 mmol) in 751 µl of methylene chloride at 0° C. was added triethylamine (13 µl, 0.090 mmol) followed by 2-fluoro-1-methylpyridinium p-toluenesulfonate (23 mg, 0.083 mmol). The heterogeneous reaction mixture was warmed to room temperature and stirred for 3.5 h at which time another 11 mg (0.039 mmol) of 2-fluoro-1-methylpyridinium p-toluenesulfonate was added. After stirring for 14.5 h another 11 mg (0.039 mmol) of 2-fluoro-1-methylpyridinium p-toluenesulfonate was added followed by another 11 mg (0.039) of 2-fluoro-1-methylpyridinium p-toluenesulfonate and 13 µl (0.090) of triethylamine after 2.5 h. After stirring an additional 1 h the reaction was concentrated in vacuo to an orange foam. Purification by reverse phase HPLC[8] with concomitant anion exchange (acetate for p-toluenesulfonate) followed by lyophilization yielded 30 mg (47%) of the title compound as a white solid: 500 MHz $^1$H NMR (DMSO-d$_6$) δ 8.65–8.58 (m, 2H), 8.36 (t, 1H, J=7.8 Hz), 7.68 (d, 1H, J=8.9 Hz), 7.60 (d, 1H, J=6.6 Hz), 7.48 (t, 1H, J=6.6 Hz), 7.35–7.21 (m, 6H), 7.19 (dd, 1H, J=8.5, 1.9 Hz), 7.05 (d, 1H, J=8.5 Hz), 6.49 (ddd, 1H, J=16, 13, 4.0 Hz), 5.91 (d, 1H, J=16 Hz), 5.72 (d, 1H, J=8.0 Hz), 5.66 (dd, 1H, J=8.0, 1.9 Hz), 5.32–5.27 (m, 1H), 4.73 (dd, 1H, J=9.7, 4.3 Hz), 4.24 (ddd, 1H, J=11, 9.8, 3.7 Hz), 3.93 (s, 3H), 3.81 (s, 3H), 3.32 (dd, 1H, J=13, 9.3 Hz), 3.05–2.97 (m, 2H), 2.77–2.57 (m, 3H), 2.54–2.47 (m, 1H), 1.76 (s, 3H), 1.68–1.62 (m, 1H), 1.55–1.46 (m, 1H), 1.37–1.30 (m, 1H), 1.15 (d, 3H, J=7.0 Hz), 1.13 (s, 3H), 1.00 (s, 3H), 0.88 (d, 3H, J=6.7 Hz), 0.73 (d, 3H, J=6.5 Hz).

Preparation of Cryptophycin 55 N-t-Boc-3-(3-Chloro-4-methoxyphenyl)-(D)-alaninate (10') (LSN 382049)

To a solution of 1' (23 mg, 0.033 mmol), N-t-Boc-3-(3-chloro-4-methoxyphenyl)-(D)-alanine[4c] (16 mg, 0.049 mmol), and 4-dimethylamino pyridine (few crystals) in 143 µl of anhydrous methylene chloride at room temperature was added a solution of 1,3-dicyclohexylcarbodiimide (10 mg, 0.049 mmol) in 20 µl of methylene chloride. After stirring for 2 h, the cloudy white reaction mixture was diluted with ethyl acetate-hexanes (2:1, 1 ml), stirred for 10 min, and filtered through a plug of celite, washing with ethyl acetate-:hexanes (2:1). The filtrate and washings were concentrated in vacuo to a colorless oil. Chromatography (14 g of flash silica gel, 2:1 ethyl acetate-hexanes) afforded 29 mg (88%) of the title compound as a white foam: 500 MHz $^1$H NMR (CDCl$_3$) δ 7.42–7.27 (m, 5H), 7.24 (d, 1H, J=2.0 Hz), 7.25–7.18 (m, 1H), 7.09 (dd, 1H, J=8.4, 1.9 Hz), 6.91–6.86 (m, 2H), 6.84–6.70 (m, 3H), 5.75 (d, 1H, J=15 Hz), 5.53 (d, 1H, J=9.6 Hz), 5.47 (d, 1H, J=7.6 Hz), 5.00 (dd, 1H, J=10, 2.9 Hz), 4.90–4.80 (m, 2H), 4.78–4.71 (m, 1H), 4.63 (d, 1H, J=8.3 Hz), 4.19–4.12 (m, 1H), 3.91 (s, 3H), 3.88 (s, 3H), 3.40 (dd, 1H, J=13, 8.1 Hz), 3.25–3.12 (m, 2H), 3.07 (dd, 1H, J=14, 7.6 Hz), 2.67–2.57 (m, 2H), 2.39–2.27 (m, 2H), 2.15 (dd, 1H, J=14, 8.0 Hz), 2.01 (ddd, 1H, J=14, 12, 4.2 Hz), 1.87–1.76 (m, 2H), 1.39 (s, 9H), 1.27 (s, 3H), 1.20 (s, 3H), 1.09–1.04 (m, 6H), 1.01 (d, 3H, J=6.3 Hz).

Preparation of Cryptophycin 55 3-(3-Chloro-4-methoxyphenyl)-(D)-alaninate Hydrochloride Salt (11') (LSN 382048)

To a solution of 10' (27 mg, 0.027 mmol) in 265 µl of methylene chloride at room temperature was added a 4.0 M solution of hydrogen chloride in 1,4-dioxane (33 µl, 0.133 mmol). After stirring for 3 h, the clear, colorless reaction mixture was concentrated in vacuo to provide 26 mg (96%, corrected for 5 wt % dioxane) of the title compound as a white foam: 500 MHz $^1$H NMR (MeOH-d$_4$) δ 7.79 (d, 1H, J=7.3 Hz), 7.49–7.45 (m, 2H), 7.43–7.48 (m, 3H), 7.31 (d, 1H, J=2.0 Hz), 7.20 (dd, 1H, J=8.4, 2.1 Hz), 7.13 (d, 1H, J=2.2 Hz), 7.07–6.95 (m, 3H), 6.71 (ddd, 1H, 15, 13, 3.8 Hz), 5.98 (dd, 1H, J=15, 1.8 Hz), 5.69 (d, 1H, J=10 Hz), 5.22 (d, 1H, J=10 Hz), 5.18 (dd, 1H, J=10, 2.5 Hz), 4.89–4.80 (m, 1H), 4.53 (dd, 1H, J=11, 3.7 Hz), 4.16 (dd, 1H, J=10, 4.4 Hz), 3.88 (s, 3H), 3.87 (s, 3H), 3.51 (dd, 1H, J=13, 9.9 Hz), 3.20 (dd, 1H, J=14, 3.7 Hz), 3.14 (dd, 1H, J=13, 2.3 Hz), 2.82–2.75 (m, 3H), 2.45 (dd, 1H, J=15, 4.5 Hz), 2.42–2.34 (m, 1H), 2.08–2.00 (m, 1H), 1.97–1.86 (m, 3H), 1.27 (s, 3H), 1.21 (s, 3H), 1.16 (d, 3H, J=7.1 Hz), 1.10 (d, 3H, J=6.1 Hz), 1.06 (d, 3H, J=6.0 Hz).

Preparation of Cryptophycin 55 N-t-Boc-(L)-phenylalaninate (12') (LSN 382235)

To a solution of 1' (29 mg, 0.041 mmol), N-t-Boc-L)-phenylalanine (16 mg, 0.062 mmol), and 4-dimethylamino pyridine (0.5 mg, 0.0041 mmol) in 165 µl of anhydrous methylene chloride at room temperature was added a solution of 1,3-dicyclohexylcarbodiimide (13 mg, 0.062 mmol) in 42 µl of methylene chloride. After stirring for 40 min, the cloudy white reaction mixture was diluted with ethyl acetate-hexanes (2:1, 0.5 ml), stirred for 10 min, and filtered through a µlug of celite, washing with ethyl acetate:hexanes (2:1). The filtrate and washings were concentrated in vacuo to a colorless oil. Chromatography (12 g of flash silica gel, 2:1/ethyl acetate-hexanes) afforded 20 mg (50%) of the title compound as a white foam: 500 MHz $^1$H NMR (MeOH-d$_4$) δ 7.40–7.47 (m, 2H), 7.26–7.37 (m, 6H), 7.12–7.22 (m, 4H), 7.00 (d, 1H, J=8.4 Hz), 6.78–6.71 (m, 1H), 5.94 (d, 1H, J=15 Hz), 5.48 (d, 1H, J=9.5 Hz), 5.15–5.10 (m, 1H), 5.06 (d, 1H, J=9.5 Hz), 4.68 (t, 1H, J=9.7 Hz), 4.52 (dd, 1H, J=11, 3.7 Hz), 4.14–4.10 (m, 1H), 3.87 (s, 3H), 3.49 (d, 1H, J=13 Hz), 3.20 (dd, 1H, J=14, 3.7 Hz), 3.14 (d, 1H, J=13 Hz), 2.77 (dd, 1H, J=14, 11 Hz), 2.67 (dd, 1H, J=14, 6.2 Hz), 2.62–2.57 (m, 2H), 2.51 (dd, 1H, J=14, 9.1 Hz), 2.31–2.23 (m, 1H), 2.00–1.92 (m, 1H), 1.91–1.82 (m, 2H), 1.38 (s, 9H), 1.26 (s, 3H), 1.24 (s, 3H), 1.08 (d, 3H, J=5.9 Hz), 1.03 (d, 3H, J=5.8 Hz), 0.87 (d, 3H, J=7.0 Hz).

Preparation of Cryptophycin 55 (L)-Phenylalaninate Hydrochloride Salt (13') (LSN 382236)

To a solution of 12' (18 mg, 0.019 mmol) in 189 µl of methylene chloride at room temperature was added a 4.0 M solution of hydrogen chloride in 1,4-dioxane (24 µl, 0.094 mmol). After stirring for 4 h, the clear, colorless reaction mixture was concentrated in vacuo to provide 15 mg (88%, corrected for 2 wt % dioxane) of the title compound as a white foam: 500 MHz $^1$H NMR (MeOH-d$_4$) δ 7.79 (d, 1H, J=7.6 Hz), 7.48–7.23 (m, 11H), 7.20 (dd, 1H, J=8.6, 1.6 Hz), 6.75–6.68 (m, 1H), 5.97 (d, 1H, J=16 Hz), 5.55 (d, 1H, J=9.2 Hz), 5.15–5.11 (m, 2H), 4.71 (t, 1H, J=10 Hz), 4.55–4.51 (m, 1H), 3.87 (s, 3H), 3.21 (dd, 1H, J=14, 3.8 Hz), 3.17–3.10 (m, 2H), 2.94 (dd, 1H, J=15, 8.1 Hz), 2.78 (dd, 1H, J=14, 12 Hz), 2.69–2.63 (m, 2H), 2.34–2.27 (m, 1H), 1.98–1.92 (m, 1H), 1.89–1.82 (m, 2H), 1.25 (s, 3H), 1.22 (s, 3H), 1.06 (d, 3H, J=6.2 Hz), 1.03 (d, 3H, J=6.1 Hz), 0.89 (d, 3H, J=7.0 Hz).

Preparation of Cryptophycin 55 (L)-Histidinate Dihydrochloride Salt (15') (LSN 384046)

To a solution of 1' (19 mg, 0.027 mmol), N,N'-di-t-Boc-(L)-histidine benzene complex (18 mg, 0.040 mmol), and 4-dimethylamino pyridine (0.3 mg, 0.0027 mmol) in 100 al of anhydrous methylene chloride at room temperature was added a solution of 1,3-dicyclohexylcarbodiimide (8.3 mg, 0.040 mmol) in 35 µl of methylene chloride. After stirring for 60 min, another 18 mg of N,N'-di-t-Boc-(L)-histidine benzene complex (0.040 mmol) and 8.3 mg of 1,3-dicyclohexylcarbodiimide (0.040 mmol) was added. The cloudy white reaction mixture was stirred another 4 h, diluted with ethyl acetate-hexanes (3:1, 0.5 ml), stirred for 10 min, and filtered through a plug of celite, washing with ethyl acetate:hexanes (3:1). The filtrate and washings were concentrated in vacuo to a colorless oil. Chromatography (13 g of flash silica gel, 3:1/ethyl acetate-hexanes) afforded 17 mg (61%) of the N,N'-di-t-Boc compound (14') as a white foam. To a solution of 14 (17 mg, 0.016 mmol) in 160 µl of methylene chloride at room temperature was added a 4.0 M solution of hydrogen chloride in 1,4-dioxane (24 µl, 0.098 mmol). After stirring for 5 h, the cloudy white reaction mixture was concentrated in vacuo to provide 15.7 mg (100%, corrected for 4 wt % dioxane) of the title compound as a white foam: 500 MHz $^1$H NMR (MeOH-d4) δ 8.91 (s, 1H), 7.77 (d, 1H, J=9.5 Hz), 7.51–7.37 (m, 6H), 7.31 (d, 1H, J=2.1 Hz), 7.20 (dd, 1H, J=8.4, 2.1 Hz), 6.66–6.58 (m, 1H), 5.99 (d, 1H, J=15 Hz), 5.57 (d, 1H, J=9.6 Hz), 5.20 (d, 1H, J=9.6 Hz), 5.15 (dd, 1H, J=10, 3.0 Hz), 4.58 (t, 1H, J=11 Hz), 4.53 (dd, 1H, 11, 3.8 Hz), 4.14 (t, 1H, J=6.4 Hz), 3.87 (s, 3H), 3.55–3.47 (m, 1H), 3.27–3.12 (m, 3H), 2.81–2.68 (m, 3H), 2.40–2.31 (m, 1H), 1.98–1.81 (m, 3H), 1.25 (s, 3H), 1.21 (s, 3H), 1.10–1.04 (m, 6H), 1.04 (d, 3H, J=6.1 Hz).

Preparation of Cryptophycin 55 N-t-Boc-(L)-prolinate (16') (LSN 382926)

To a solution of 1' (19 mg, 0.027 mmol), N-t-Boc-(L)-proline (8.7 mg, 0.040 mmol), and 4-dimethylamino pyridine (0.3 mg, 0.0027 mmol) in 100 µl of anhydrous methylene chloride at room temperature was added a solution of 1,3-dicyclohexylcarbodiimide (8.3 mg, 0.040 mmol) in 35 µl of methylene chloride. After stirring for 45 min, the cloudy white reaction mixture was diluted with ethyl acetate-hexanes (3:1, 0.5 ml), stirred for 10 min, and filtered through a plug of celite, washing with ethyl acetate:hexanes (3:1). The filtrate and washings were concentrated in vacuo to a colorless oil. Chromatography (15 g of flash silica gel, 3:1/ethyl acetate-hexanes) afforded 11 mg (46%) of the title compound as a white foam: 500 MHz $^1$H NMR (CDCl$_3$) δ 7.39–7.30 (m, 5H), 7.24 (d, 1H, J=2.0 Hz), 7.21–7.18 (m, 1H), 7.09 (dd, 1H, J=8.4, 2.0 Hz), 6.87 (d, 1H, J=8.4 Hz), 6.80–6.68 (m, 1H), 5.77 (d, 1H, J=15 Hz), 5.61 (br s, 1H), 5.56 (t, 1H, J=9.5 Hz), 5.04–4.68 (m, 4H), 4.19–4.15 (m, 1H), 3.90 (s, 3H), 3.41–3.34 (m, 2H), 3.27–3.02 (m, 4H), 2.64–2.50 (m, 2H), 2.35–2.25 (m, 1H), 2.10–2.00 (m, 1H), 1.90–1.72 (m, 3H), 1.70–1.50 (m, 3H), 1.44 (s, 9H), 1.28 (s, 3H), 1.20 (s, 3H), 1.08–0.90 (m, 9H).

Preparation of Cryptophycin 55 (L)-Prolinate Hydrochloride Salt (17') (LSN 382927)

To a solution of 16' (11 mg, 0.012 mmol) in 122 µl of methylene chloride at room temperature was added a 4.0 M solution of hydrogen chloride in 1,4-dioxane (15 µl, 0.061 mmol). After stirring for 5 h, the clear, colorless reaction mixture was concentrated in vacuo to provide 10 mg (100%) of the title compound as a white solid: 500 MHz $^1$H NMR (MeOH-d$_4$) δ 7.77 (dd, 1H, J=9.4, 2.3 Hz), 7.48–7.42 (m, 2H), 7.39–7.35 (m, 3H), 7.31 (d, 1H, J=2.2 Hz), 7.20 (dd, 1H, J=8.4, 2.2 Hz), 7.01 (d, 1H, J=8.4 Hz), 6.68 (ddd, 1H, J=15, 13, 3.8 Hz), 5.98 (dd, 1H, J=15, 1.4 Hz), 5.52 (d, 1H, J=9.8 Hz), 5.18 (d, 1H, J=9.8 Hz), 5.18–5.14 (m, 1H), 4.78 (t, 1H, J=10 Hz), 4.52 (dd, 1H, J=11, 3.9 Hz), 3.99 .(t, 1H, J=7.3 Hz), 3.87 (s, 3H), 3.48 (dd, 1H, J=14, 9.7 Hz), 3.28–3.12 (m, 4H), 2.82–2.73 (m, 3H), 2.42–2.34 (m, 2H), 2.09–1.79 (m, 6H), 1.24 (s, 3H), 1.88 (s, 3H), 1.16 (d, 3H, J=7.0 Hz), 1.07 (d, 3H, J=6.3 Hz), 1.04 (d, 3H, J=6.2 Hz).

Preparation of Cryptophycin 55 N-t-Boc-glycinate (18') (LSN 379403)

To a solution of 1' ( 118 mg, 0.167 mmol), N-t-Boc-glycine (44 mg, 0.251 mmol), and 4-dimethylamino pyridine (2.0 mg, 0.0167 mmol) in 490 µl of anhydrous methylene chloride at room temperature was added a solution of 1,3-dicyclohexylcarbodiimide (52 mg, 0.251 mmol) in 67 µl of methylene chloride. After stirring for 50 min, the cloudy white reaction mixture was diluted with ethyl acetate-hexanes (3:1, 1 ml), stirred for 10 min, and filtered through a plug of celite, washing with ethyl acetate-hexanes (3:1). The filtrate and washings were concentrated in vacuo to a colorless oil. Chromatography (19 g of flash silica gel, 3:1/ethyl acetate-hexanes) afforded 138 mg (96%) of the title compound as a white foam: 500 MHz $^1$H NMR (CDCl$_3$) δ 7.34 (s, 5H), 7.24 (d, 1H, J=2.0 Hz), 7.23–7.19 (m, 1H), 7.10 (dd, 1H, J=8.4, 2.0 Hz), 6.88 (d, 1H, J=8.4 Hz), 6.79–6.70 (m, 1H), 5.77 (d, 1H, J=13 Hz), 5.50 (d, 1H, J=8.0 Hz), 5.47 (d, 1H, J=9.8 Hz), 4.97 (dd, 1H, J=11, 2.7 Hz), 4.89 (t, 1H, J=10 Hz), 4.83 (d, 1H, J=9.8 Hz), 4.79–4.72 (m, 1H), 4.68 (br s, 1H), 3.91 (s, 3H), 3.66 (dd, 1H, J=18, 5.3 Hz), 3.42–3.35 (m, 2H), 3.21 (dd, 1H, J=13, 4.0 Hz), 3.17 (dd, 1H, J=15, 5.1 Hz), 3.08 (dd, 1H, J=15, 7.6 Hz), 2.66–2.57 (m, 2H), 2.47–2.38 (m, 1H), 1.95 (ddd, 1H, J=14, 12, 4.7 Hz), 1.85–1.77 (m, 1H), 1.75–1.67 (m, 1H), 1.43 (s, 9H), 1.27 (s, 3H), 1.20 (s, 3H), 1.08 (d, 3H, J=7.0 Hz), 1.03 (d, 3H, J=6.7 Hz), 0.98 (d, 3H, J=6.5 Hz).

Preparation of Cryptophycin 55 Glycinate Hydrochloride Salt (19') (LSN 368422)

To a solution of 18' (122 mg, 0.141 mmol) in 471 µl of methylene chloride at room temperature was added a 4.0 M solution of hydrogen chloride in 1,4-dioxane (178 µl, 0.707 mmol). After stirring for 1 h 20 min, the clear, colorless reaction mixture was concentrated in vacuo to provide 120 mg (99%, corrected for 7 wt % dioxane) of the title compound as a white foam: 500 MHz $^1$H NMR (MeOH-d$_4$) δ 7.81 (dd, 1H, J=8.5, 2.2 Hz), 7.46–7.41 (m, 2H), 7.40–7.36 (m, 3H), 7.31 (d, 1H, J=2.1 Hz), 7.20 (dd, 1H, J=8.4, 2.1 Hz), 7.01 (d, 1H, J=8.4 Hz), 6.70 (ddd, 1H, J=15, 13, 3.7 Hz), 5.97 (dd, 1H, J=15, 1.7 Hz), 5.55 (d, 1H, J=9.9 Hz), 5.18 (d, 1H, J=9.9 Hz), 5.14 (dd, 1H, J=10, 2.8 Hz), 4.84 (t, 1H, J=10 Hz), 4.52 (dd, 1H, J=11, 3.7 Hz), 3.87 (s, 3H), 3.78 (d, 1H, J=18 Hz), 3.50 (dd, 1H, J=13, 9.8 Hz), 3.23 (d, 1H, J=18 Hz), 3.20 (dd, 1H, J=14, 3.6 Hz), 3.13 (dd, 1H, J=13, 2.4 Hz), 2.80–2.69 (m, 3H), 2.41–2.32 (m, 1H), 1.99–1.92 (m, 1H), 1.91–1.81 (m, 2H), 1.25 (s, 3H), 1.20 (s, 3H), 1.12 (d, 3H, J=7.0 Hz), 1.06 (d, 3H, J=6.2 Hz), 1.04 (d, 3H, 6.2 Hz).

Preparation of Cryptophycin 55 N-t-Boc-β-alaninate (20') (LSN 379404)

To a solution of 1' (102 mg, 0.145 mmol), N-t-Boc-β-alanine (41 mg, 0.217 mmol), and 4-dimethylamino pyridine (18 mg, 0.145 mmol) in 400 µl of anhydrous methylene chloride at room temperature was added a solution of 1,3-dicyclohexylcarbodiimide (45 mg, 0.217 mmol) in 82 µl of methylene chloride. After stirring for 3.5 h, the cloudy white reaction mixture was diluted with ethyl acetate-hexanes (3:1, 1 ml), stirred for 10 min, and filtered through a plug of celite, washing with ethylacetate-hexanes (3:1). The filtrate and washings were concentrated in vacuo to a colorless oil. Chromatography (21 g of flash silica gel, 2:1 then 4:1/ethyl acetate-hexanes) afforded 121 mg (95%) of the title compound as a white foam: 500 MHz $^1$H NMR (CDCl$_3$) δ 7.44–7.39 (m, 2H), 7.37–7.31 (m, 3H), 7.32 (d, 1H, J=2.1 Hz), 7.20 (dd, 1H, J=8.4, 2.1 Hz), 7.01 (d, 1H, J=8.4 Hz), 6.72 (ddd, 1H, J=15, 13, 3.7 Hz), 5.96 (dd, 1H, J=15, 1.6 Hz), 5.51 (d, 1H, J=9.8 Hz), 5.11–5.06 (m, 1H), 5.08 (d, 1H, J=9.8 Hz), 4.90–4.83 (m, 1H), 4.50 (dd, 1H, J=11, 3.6 Hz), 3.86 (s, 3H), 3.52–3.46 (m, 1H), 3.20 (dd, 1H, J=14, 3.6 Hz), 3.13 (br d, 1H, J=14 Hz), 3.05–2.92 (m, 2H), 2.79–2.63 (m, 3H), 2.45–2.37 (m, 1H), 2.24 (dt, 1H, J=16, 7.0 Hz), 2.08–1.99 (m, 1H), 1.96–1.79 (m, 3H), 1.43 (s, 9H), 1.25 (s, 3H), 1.21 (s, 3H), 1.12 (d, 3H, J=7.0 Hz), 1.06 (d, 3H, J=6.2 Hz), 1.02 (d, 3H, J=6.1 Hz).

Preparation of Cryptophycin 55 β-Alaninate Hydrochloride Salt (21') (LSN 377718)

To a solution of 20' (119 mg, 0.136 mmol) in 452 µl of methylene chloride at room temperature was added a 4.0 M solution of hydrogen chloride in 1,4-dioxane (170 µl, 0.679 mmol). After stirring for 2 h 15 min, the cloudy, white reaction mixture was concentrated in vacuo to provide 110 mg (96%, corrected for 4 wt % dioxane) of the title compound as a white foam: 500 MHz $^1$H NMR (MeOH-d$_4$) δ 7.80 (dd, 1H, J=9.7, 2.3 Hz), 7.45–7.40 (m, 2H), 7.39–7.32 (m, 3H), 7.20 (dd, 1H, J=8.4, 2.1 Hz), 7.01 (d, 1H, J=8.4 Hz), 6.68 (ddd, 1H, J=15, 13, 3.8 Hz), 5.98 (dd, 1H, J=15, 1.7 Hz), 5.48 (dd, 1H, J=9.4 1.0 Hz), 5.15–5.11 (m, 1H), 5.13 (d, 1H, J=9.4 Hz), 4.82 (t, 1H, J=10 Hz), 4.51 (dd, 1H, J=11, 3.7 Hz), 3.90 (s, 3H), 3.50 (dd, 1H, J=14, 9.8 Hz), 3.20 (dd, 1H, J=14, 3.7 Hz), 3.14 (dd, 1H, J=14, 2.4 Hz), 2.85 (t, 2H, J=7.0 Hz), 2.80–2.65 (m, 5H), 2.54 (dt, 1H, J=17, 7.4

Hz), 2.42–2.33 (m, 1H), 2.22 (dt, 1H, J=17, 6.7 Hz), 1.90–1.81 (m, 3H), 1.25 (s, 3H), 1.20 (s, 3H), 1.13 (d, 3H, J=7.1 Hz), 1.08 (d, 3H, J=6.3 Hz), 1.04 (d, 3H, J=6.2 Hz).

Preparation of Cryptophycin 55 N-t-boc-γ-Aminobutyrate (22') (LSN 379401)

To a solution of 1' (48 mg, 0.068 mmol), N-t-Boc-4-aminobutyric acid (18 mg, 0.088 mmol), and 4-dimethylamino pyridine (8 mg, 0.068 mmol) in 150 μl of anhydrous methylene chloride at room temperature was added a solution of 1,3-dicyclohexylcarbodiimide (18 mg, 0.088 mmol) in 50 μl of methylene chloride. After stirring for 45 min, the cloudy white reaction mixture was diluted with ethyl acetate-hexanes (3:1, 0.5 ml), stirred for 5 min, and filtered through a plug of celite, washing with ethyl acetate-hexanes (3:1). The filtrate and washings were concentrated in vacuo to a colorless oil. Chromatography (15 g of flash silica gel, 3:1/ethyl acetate-hexanes) afforded 55 mg (90%) of the title compound as a white foam: 500 MHz $^1$H NMR (CDCl$_3$) δ 7.38–7.32 (m, 5H), 7.24 (d, 1H, J=1.9 Hz), 7.22–7.19 (m, 1H), 7.10 (dd, 1H, J=8.4, 1.9 Hz), 6.88 (d, 1H, J=8.4 Hz), 6.75 (ddd, 1H, J=15, 13, 3.9 Hz), 5.78 (d, 1H, J=15 Hz), 5.60–5.55 (m, 1H), 5.49 (dd, 1H, J=9.8, 1.4 Hz), 4.96 (dd, 1H, J=11, 3.0 Hz), 4.89 (t, 1H, J=9.2 Hz), 4.81 (d, 1H, J=9.8 Hz), 4.78–4.70 (m, 1H), 4.44 (br s, 1H), 3.91 (s, 3H), 3.40 (dd, 1H, J=14, 8.1 Hz), 3.22 (dd, 1H, J=14, 4.1 Hz), 3.22–3.15 (m, 1H), 3.08 (dd, 1H, J=14, 7.8 Hz), 2.89–2.82 (m, 2H), 2.67–2.56 (m, 2H), 2.47–2.38 (m, 1H), 2.11–2.04 (m, 1H), 2.00–1.77 (m, 3H), 1.75–1.67 (m, 1H), 1.45 (s, 9H), 1.50–1.40 (m, 2H), 1.27 (s, 3H), 1.20 (s, 3H), 1.09 (d, 3H, J=7.0 Hz), 1.04 (d, 3H, J=6.6 Hz), 0.98 (d, 3H, J=6.6 Hz).

Preparation of Cryptophycin 55 γ-Aminobutyrate Hydrochloride Salt (25') (LSN 368513)

To a solution of 22' (53 mg, 0.059 mmol) in 297 μl of methylene chloride at room temperature was added a 1.0 M solution of hydrogen chloride in diethyl ether (297 μl, 0.297 mmol). The starting material precipitated as a white paste which was redissolved with an additional 150 μl of methylene chloride. After stirring for 4 h, another 59 μl (0.059 mmol) of hydrogen chloride solution was added. Stirring was continued for another 14 h and the reaction mixture was concentrated in vacuo to provide 49 mg (100%) of the title compound as a white foam: 500 MHz $^1$H NMR (DMSO-d$_6$) δ 8.49 (d, 1H, J=8.0 Hz), 7.72 (br s, 3H), 7.44–7.33 (m, 5H), 7.32 (d, 1H, J=1.9 Hz), 7.29 (dd, 1H, J=9.4, 2.6 Hz), 7.20 (dd, 1H, J=8.5, 1.9 Hz), 7.06 (d, 1H, J=8.5 Hz), 6.48 (ddd, 1H, J=15, 13, 3.9 Hz), 5.87 (d, 1H, J=15 Hz), 5.37 (d, 1H, J=9.7 Hz), 5.33 (d, 1H, J=9.7 Hz), 5.04–5.01 (m, 1H), 4.73 (t, 1H, J=11 Hz), 4.25 (ddd, 1H, J=12, 9.8, 3.5 Hz), 3.82 (s, 3H), 3.40–3.30 (m, 1H), 3.07–3.01 (m, 2H), 2.72 (dd, 1H, J=14, 12 Hz), 2.65–2.47 (m, 4H), 2.38–2.28 (m, 1H), 2.21 (dt, 1H, J=17, 7.5 Hz), 1.97 (dt, 1H, J=17, 7.5 Hz), 1.80–1.70 (m, 3H), 1.54–1.46 (m, 2H), 1.17 (s, 3H), 1.03 (s, 3H), 1.01 (d, 3H, J=7.0 Hz), 0.99 (d, 3H, J=5.8 Hz), 0.95 (d, 3H, J=5.8 Hz).

Preparation of Cryptophycin 55 N-t-Boc-(L)-alaninate (26') (LSN 379405)

To a solution of 1' (103 mg, 0.146 mmol), N-t-Boc-(L)-alanine (41 mg, 0.219 mmol), and 4-dimethylamino pyridine (18 mg, 0.146 mmol) in 400 μl of anhydrous methylene chloride at room temperature was added a solution of 1,3-dicyclohexylcarbodiimide (45 mg, 0.219 mmol) in 87 μl of methylene chloride. After stirring for 5 h 50 min, the cloudy white reaction mixture was treated with another 5.5 mg (0.029 mmol) of N-t-Boc-(L)-alanine, 6.0 mg (0.029 mmol) of 1,3-dicyclohexylcarbodiimide, and a few crystals of 4-dimethylamino pyridine. After stirring an additional 1 h, the reaction was diluted with ethyl acetate-hexanes (3:1, 1 ml), stirred for 10 min, and filtered through a plug of celite, washing with ethyl acetate:hexanes (3:1). The filtrate and washings were concentrated in vacuo to a colorless oil. Chromatography (22 g of flash silica gel, 1.5:1 then 2:1 then 4:1/ethyl acetate-hexanes) afforded 96 mg (75%) of the title compound as a white foam: 500 MHz $^1$H NMR (CDCl$_3$) δ 7.35–7.30 (m, 5H), 7.26–7.21 (m, 2H), 7.10 (dd, 1H, J=8.4, 1.9 Hz), 6.88 (d, 1H, J=8.4 Hz), 6.76 (ddd, 1H, J=15, 13, 4.2 Hz), 5.77 (d, 1H, J=15 Hz), 5.52 (d, 1H, 7.6 Hz), 5.44 (d, 1H, J=9.7 Hz), 4.98 (dd, 1H, J=11, 2.5 Hz), 4.85–4.81 (m, 2H), 4.75 (q, 1H, J=6.8 Hz), 4.56 (d, 1H, J=7.8 Hz), 4.01–3.96 (m, 1H), 3.91 (s, 3H), 3.41 (dd, 1H, J=13, 8.3 Hz), 3.20 (dd, 1H, J=13, 4.0 Hz), 3.16 (dd, 1H, J=15, 5.9 Hz), 3.08 (dd, 1H, J=15, 7.6 Hz), 2.65–2.57 (m, 2H), 2.40–2.31 (m, 1H), 2.02–1.96 (m, 1H), 1.87–1.73 (m, 2H), 1.43 (s, 9H), 1.27 (s, 3H), 1.20 (s, 3H), 1.11–1.02 (m, 9H), 0.99 (d, 3H, J=6.3 Hz).

Preparation of Cryptophycin 55 (L)-Alaninate Hydrochloride Salt (2B') (LSN 377719)

To a solution of 26' (95 mg, 0.108 mmol) in 361 μl of methylene chloride at room temperature was added a 4.0 M solution of hydrogen chloride in 1,4-dioxane (135 μl, 0.542 mmol). After stirring for 2.5 h, the cloudy, white reaction mixture was concentrated in vacuo to provide 90 mg (96%, corrected for 6 wt % dioxane) of the title compound as a white foam: 500 MHz $^1$H NMR (MeOH-d$_4$) δ 8.54 (d, 1H, 7.6 Hz), 7.81 (br d, 1H, J=9.7 Hz), 7.46–7.44 (m, 2H), 7.39–7.37 (m, 3H), 7.32 (d, 1H, J=2.0 Hz), 7.20 (dd, 1H, J=8.4, 2.0 Hz), 7.01 (d, 1H, J=2.0 Hz), 6.69 (ddd, 1H, J=15, 11, 3.7 Hz), 5.99 (d, 1H, 15 Hz), 5.55 (d, 1H, J=9.8 Hz), 5.20 (d, 1H, J=9.8 Hz), 5.15 (dd, 1H, J=11, 2.7 Hz), 4.78 (t, 1H, J=11 Hz), 4.53–4.50 (m, 1H), 3.87 (s, 3H), 3.65 (q, 1H, J=7.3 Hz), 3.50 (dd, 1H, J=13, 9.8 Hz), 3.20 (dd, 1H, J=14, 3.5 Hz), 3.14 (br d, 1H, J=13 Hz), 2.81–2.71 (m, 3H), 2.41–2.34 (m, 1H), 1.98–1.93 (m, 1H), 1.88–1.82 (m, 2H), 1.41 (d, 3H, J=7.3 Hz), 1.25 (s, 3H), 1.20 (s, 3H), 1.13 (d, 3H, J=7.0 Hz), 1.06 (d, 3H, J=6.2 Hz), 1.04 (d, 3H, 6.0 Hz).

Preparation of Cryptophycin 55 N-t-boc-(D)-Alaninate (29') (LSN 382426)

To a solution of 1' (25 mg, 0.035 mmol), N-t-Boc-(D)-alanine (10 mg, 0.053 mmol), and 4-dimethylamino pyridine (0.4 mg, 0.0035 mmol) in 130 μl of anhydrous methylene chloride at room temperature was added a solution of 1,3-dicyclohexylcarbodiimide (11 mg, 0.053 mmol) in 47 μl of methylene chloride. After stirring for 5.5 h, the cloudy white reaction mixture was diluted with ethyl acetate-hexanes (3:1, 0.5 ml), stirred for 10 min, and filtered through a plug of celite, washing with ethyl acetate:hexanes (3:1). The filtrate and washings were concentrated in vacuo to a colorless oil. Chromatography (15 g of flash silica gel, 2:1/ethyl acetate-hexanes) afforded 26 mg (83%) of the title compound as a white foam: 500 MHz $^1$H NMR (CDCl$_3$) δ 7.49–7.29 (m, 5H), 7.24 (d, 1H, J=2.0 Hz), 7.22–7.18 (m, 1H), 7.09 (dd, 1H, 8.4, 2.0 Hz), 6.87 (d, 1H, J=8.4 Hz), 6.76 (ddd, 1H, J=15, 13, 4.4, Hz), 5.77 (d, 1H, 15 Hz), 5.56 (d, 1H, J=9.9 Hz), 5.48 (d, 1H, J=7.7 Hz), 5.01 (dd, 1H, J=10, 2.6 Hz), 4.91 (t, 1H, J=9.4 Hz), 4.84 (d, 1H, J=9.9 Hz), 4.81–4.73 (m, 2H), 3.99–3.93 (m, 1H), 3.91 (s, 3H), 3.39 (dd, 1H, J=13, 8.0 Hz), 3.22 (dd, 1H, J=13, 3.6 Hz), 3.17 (dd, 1H, J=14, 5.0 Hz), 3.08 (dd, 1H, J=14 Hz), 2.68–2.58 (m, 2H), 2.42–2.35 (m, 1H), 2.04–1.94 (m, 1H), 1.87–1.50 (m, 2H), 1.42 (s, 9H), 1.27 (s, 3H), 1.20 (s, 3H), 1.09 (d, 3H, J=7.1 Hz), 1.04 (d, 3H, J=6.4 Hz), 0.99 (d, 3H, J=6.3 Hz), 0.65 (d, 3H, J=6.8 Hz).

Preparation of Cryptophycin 55 (D)-alaninate Hydrochloride Salt (30') (LSN 382425)

To a solution of 29' (24 mg, 0.027 mmol) in 274 µl of methylene chloride at room temperature was added a 4.0 M solution of hydrogen chloride in 1,4-dioxane (34 µl, 0.137 mmol). After stirring for 3.5 h, the clear, colorless reaction mixture was concentrated in vacuo to provide 24 mg (100%, corrected for 8 wt % dioxane) of the title compound as a white foam: 500 MHz $^1$H NMR (MeOH-d$_4$) δ 7.79 (d, 1H, J=9.5 Hz), 7.47–7.40 (m, 2H), 7.40–7.36 (m, 3H), 7.31 (d, 1H, J=2.0 Hz), 7.20 (dd, 1H, J=8.4, 2.0 Hz), 7.01 (d, 1H, J=8.4 Hz), 6.71 (ddd, 1H, J=15, 13, 3.7 Hz), 5.98 (dd, 1H, J=15, 1.6 Hz), 5.65 (d, 1H, J=10 Hz), 5.20 (d, 1H, J=10 Hz), 5.17 (dd, 1H, J=11, 2.5 Hz), 4.88–4.78 (m, 1H), 4.53 (dd, 1H, J=11, 3.7 Hz), 3.95 (q, 1H, J=7.2 Hz), 3.87 (s, 3H), 3.51 (dd, 1H, J=13, 9.8 Hz), 3.20 (dd, 1H, J=14, 3.6 Hz), 3.14 (dd, 1H, J=13, 2.3 Hz), 2.81–2.74 (m, 3H), 2.41–2.34 (m, 1H), 2.07–1.99 (m, 1H), 1.96–1.84 (m 2H), 1.26 (s, 3H), 1.21 (s, 3H), 1.15 (d, 3H, J=7.1 Hz), 1.09 (d, 3H, J=6.0 Hz), 1.05 (d, 3H, J=6.0 Hz), 0.80 (d, 3H, J=7.4 Hz).

Preparation of Cryptophycin 55 Nα-Nε-di-t-Boc-(L)-lysinate (31') (LSN 379406)

To a solution of 1' (105 mg, 0.149 mmol), Nα-Nε-di-t-Boc-(L)-lysine (67 mg, 0.193 mmol), and 4-dimethylamino pyridine (18 mg, 0.149 mmol) in 400 µl of anhydrous methylene chloride at room temperature was added a solution of 1,3-dicyclohexylcarbodiimide (40 mg, 0.193 mmol) in 96 µl of methylene chloride. After stirring for 4 h, the cloudy white reaction mixture was treated with another 10 mg (0.030 mmol) of Nα-Nε-di-t-Boc-(L)-lysine and 6.1 mg (0.030 mmol) of 1,3-dicyclohexylcarbodiimide as a soln in 100 µl of methylene chloride. After stirring an additional 1 h, the cloudy white reaction mixture was diluted with ethyl acetate-hexanes (3:1, 1 ml), stirred for 10 min, and filtered through a plug of celite, washing with ethyl acetate:hexanes (3:1). The filtrate and washings were concentrated in vacuo to a white foam which was resubmitted to the above conditions using 34 mg (0.097 mmol) of Nα-Nε-di-t-Boc-(L)-lysine, 20 mg (0.097 mmol) of 1,3-dicyclohexylcarbodiimide, and 9.1 mg (0.075 mmol) of 4-dimethylamino pyridine. After stirring for 1.5 h, the reaction was processed as above to provide a crude white foam. Chromatography (21 g of flash silica gel, 1:1 then 4:1/ethyl acetate-hexanes) afforded 112 mg (73%) of the title compound as a white foam: 500 MHz $^1$H NMR (MeOH -d$_4$) δ 7.42–7.37 (m, 2H), 7.36–7.29 (m, 3H), 7.27 (br s, 1H), 7.16 (br d, 1H, J=8.5 Hz), 6.97 (d, 1H, J=8.5 Hz), 6.72 (ddd, 1H, J=15, 13, 3.5 Hz), 5.92 (d, 1H, J=15 Hz), 5.50 (d, 1H, J=11 Hz), 5.11–5.04 (m, 2H), 4.84 (t, 1H, J=10 Hz), 4.48 (dd, 1H, J=11, 3.6 Hz), 3.84 (s, 3H), 3.75 (br s, 1H), 3.50–3.43 (m, 1H), 3.17 (dd, 1H, J=14, 3.6 Hz), 3.11 (d, 1H, J=14 Hz), 2.97–2.91 (in, 2H), 2.76–2.58 (m, 3H), 2.36–2.27 (m, 1H), 1.98–1.80 (m, 3H), 1.48–1.38 (m, 2H), 1.43 (s, 9H), 1.40 (s, 9H), 1.35–1.25 (m, 2H), 1.23 (s, 3H), 1.20 (s, 3H), 1.15–1.09 (m, 2H), 1.07 (d, 3H, J=6.8 Hz), 1.06 (d, 3H, J=6.0 Hz), 1.01 (d, 3H, J=6.1 Hz).

Preparation of Cryptophycin 55 (L)-Lysinate di-Hydrochloride Salt (32') (LSN 377562)

To a solution of 31' (107 mg, 0.103 mmol) in 345 µl of methylene chloride at room temperature was added a 4.0 M solution of hydrogen chloride in 1,4-dioxane (155 µl, 0.621 mmol). After stirring for 4 h, the cloudy white reaction mixture was filtered. The collected white solid was washed with methylene chloride (2×1 ml) and dried in vacuo at room temperature to provide 87 mg (93%) of the title compound: 500 MHz $^1$H NMR (MeOH-d$_4$) δ 8.61 (d, 1H, J=7.7 Hz), 7.81 (d, 1H, J=7.7 Hz), 7.47–7.44 (m, 2H), 7.40–7.38 (m, 3H), 7.31 (d, 1H, J=2.2 Hz), 7.20 (dd, 1H, J=8.4, 2.2 Hz), 7.00 (d, 1H, J=8.4 Hz), 6.63 (ddd, 1H, J=15, 13, 4.0 Hz), 6.00 (dd, 1H, J=15, 1.6 Hz), 5.55 (d, 1H, J=9.8 Hz), 5.20 (d, 1H, J=9.8 Hz), 5.15 (dd, 1H, J=10, 2.9 Hz), 4.68 (t, 1H, J=11 Hz), 4.55–4.49 (m, 1H), 3.87 (s, 3H), 3.79 (t, 1H, J=5.6 Hz), 3.52 (dd, 1H, J=14, 9.9 Hz), 3.20 (dd, 1H, J=14, 3.6 Hz), 3.13 (dd, 1H, J=13, 2.4 Hz), 3.06–2.98 (m, 1H), 2.94–2.87 (m, 1H), 2.85–2.74 (m, 3H), 2.45–2.38 (m, 1H), 1.98–1.76 (m, 5H), 1.71–1.64 (m, 2H), 1.39–1.30 (m, 2H), 1.25 (s, 3H), 1.18 (d, 3H, J=8.2 Hz), 1.17 (s, 3H), 1.08 (d, 3H, J=6.2 Hz), 1.05 (d, 3H, J=6.1 Hz).

Preparation of Cryptophycin 55 Nα-Nε-di-t-boc-(D)-Lysinate (33') (LSN 382504)

To a solution of 1' (24 mg, 0.035 mmol), Nα-Nε-di-t-Boc-(D)-lysine 247 mg, 0.069 mmol), and 4-dimethylamino pyridine (0.4 mg, 0.0035 mmol) in 140 µl of anhydrous methylene chloride at room temperature was added a solution of 1,3-dicyclohexylcarbodiimide (14 mg, 0.069 mmol) in 30 µl of methylene chloride. After stirring for 70 min, the cloudy white reaction mixture was diluted with ethyl acetate-hexanes (3:1, 0.5 ml), stirred for 10 min, and filtered through a plug of celite, washing with ethyl acetate:hexanes (3:1). The filtrate and washings were concentrated in vacuo to an off-white oil. Chromatography (15 g of flash silica gel, 2:1/ethyl acetate-hexanes) afforded 30 mg (87%) of the title compound as a white foam: 500 MHz $^1$H NMR (MeOH-d$_4$) δ 7.46–7.40 (m, 2H), 7.39–7.31 (m, 3H), 7.31 (d, 1H, J=1.8 Hz), 7.20 (dd, 1H, J=8.4, 1.8 Hz), 7.01 (d, 1H, J=8.4 Hz), 6.75 (ddd, 1H, J=16, 11, 3.7 Hz), 5.93 (d, 1H, J=16 Hz), 5.59 (d, 1H, J=10 Hz), 5.13–5.09 (m, 2H), 4.92 (t, 1H, J=9.8 Hz), 4.52 (dd, 1H, J=11, 3.6 Hz), 3.87 (s, 3H)., 3.79–3.75 (m, 1H), 3.48 (d, 1H, J=13 Hz), 3.21 (dd, 1H, J=14, 3.7 Hz), 3.12 (d, 1H, J=13 Hz), 2.97–2.91 (m, 2H), 2.80–2.62 (m, 3H), 2.41–2.32 (m, 1H), 1.98–1.82 (m, 3H), 1.48–1.38 (m, 2H), 1.46 (s, 9H), 1.42 (s, 9H), 1.35–1.20 (m, 2H), 1.25 (s, 3H), 1.21 (s, 3H), 1.15–0.09 (m, 2H), 1.14 (d, 3H, J=7.0 Hz), 1.07 (d, 3H, J=6.0 Hz), 1.03 (d, 3H, J=6.0 Hz).

Preparation of Cryptophycin 55 (D)-Lysinate di-Hydrochloride Salt (34') (LSN 377503)

To a solution of 33' (28 mg, 0.027 mmol) in 181 µl of methylene chloride at room temperature was added a 4.0 M solution of hydrogen chloride in 1,4-dioxane (41 µl, 0.162 mmol). After stirring for 5.5 h, the cloudy white reaction mixture was concentrated in vacuo to provide 25 mg (96%, corrected for 4.5 wt % dioxane) of the title compound as a white solid: 500 MHz $^1$H NMR (MeOH-d$_4$) δ 8.47 (d, 1H, J=7.6 Hz), 7.76 (dd, 1H, J=9.6, 2.1 Hz), 7.47–7.36 (m, 5H), 7.28 (d, 1H, J=2.1 Hz), 7.17 (dd, 1H, J=8.4, 2.1 Hz), 6.98 (d, 1H, J=8.4 Hz), 6.68 (ddd, 1H, J=15, 11, 3.7 Hz), 5.95 (dd, 1H, J=15, 1.1 Hz), 5.67 (d, 1H, J=10 Hz), 5.21 (d, 1H, J=10 Hz), 5.14 (dd, 1H, J=10, 2.5 Hz), 4.83–4.77 (m, 1H), 4.52–4.49 (m, 1H), 3.92 (t, 1H, J=6.1 Hz), 3.84 (s, 3H), 3.47 (dd, 1H, J=14, 9.8 Hz), 3.18 (dd, 1H, J=14, 3.6 Hz), 3.12 (dd, 1H, J=14, 2.2 Hz), 2.83 (t, 2H, J=7.6 Hz), 2.78–2.70 (m, 3H), 2.38–2.30 (m, 1H), 2.02–1.82 (m, 3H), 1.52–1.43 (m, 2H), 1.23 (s, 3H), 1.22–1.00 (m, 4H), 1.18 (s, 3H), 1.13 (d, 3H, J=8.2 Hz), 1.06 (d, 3H, J=6.2 Hz), 1.02 (d, 3H, J=6.1 Hz).

Preparation of Cryptophycin 55 N-t-boc-γ-t-Butyl Ester-(L)-glutamate (35') (LSN 382366)

To a solution of 1' (27 mg, 0.038 mmol), N-t-Boc-(L)-glutamic acid γ-t-butyl ester (17 mg, 0.057 mmol), and 4-dimethylamino pyridine (0.5 mg, 0.0038 mmol) in 150 μl of anhydrous methylene chloride at room temperature was added a solution of 1,3-dicyclohexylcarbodiimide (12 mg, 0.057 mmol) in 41 μl of methylene chloride. After stirring for 60 min, the cloudy white reaction mixture diluted with ethyl acetate-hexanes (2:1, 2 ml), stirred for 10 min, and filtered through a plug of celite, washing with ethyl acetate-:hexanes (2:1). The filtrate and washings were concentrated in vacuo to an off-white oil. Chromatography (15 g of flash silica gel, 1:1 ethyl acetate-hexanes) afforded 28 mg (74%) of the title compound as a white foam: 500 MHz $^1$H NMR (CDCl$_3$) δ 7.39–7.29 (m, 5H), 7.24 (d, 1H, J=1.9 Hz), 7.22–7.18 (m, 1H), 7.10 (dd, 1H, J=8.5, 1.9 Hz), 6.87 (d, 1H, J=8.5 Hz), 6.76 (ddd, 1H, J=15, 13, 4.5 Hz), 5.78 (d, 1H, J=15 Hz), 5.65 (d, 1H, J=7.6 Hz), 5.43 (d, 1H, J=9.7 Hz), 4.99 (dd, 1H, J=10, 2.7 Hz), 4.90–4.80 (m, 1H), 4.83 (d, 1H, J=9.7 Hz), 4.69–4.61 (m, 1H), 4.55 (d, 1H, J=8.4 Hz), 4.01–3.96 (m, 1H), 3.90 (s, 3H), 3.40 (dd, 1H, J=13, 8.0 Hz), 3.24 (dd, 1H, J=13, 4.1 Hz), 3.18 (dd, 1H, J=15, 5.0 Hz), 3.11 (dd, 1H, J=15, 7.9 Hz), 2.65–2.57 (m, 2H), 2.39–2.30 (m, 1H), 2.14–2.09 (m, 2H), 2.00–1.92 (m, 1H), 1.87–1.73 (m, 3H), 1.60–1.50 (m, 1H), 1.44 (s, 18H), 1.27 (s, 3H), 1.21 (s, 3H), 1.08 (d, 3H, J=7.0 Hz), 1.05 (d, 3H, J=6.4 Hz), 1.00 (d, 3H, J=6.3 Hz).

Preparation of Cryptophycin 55 (L)-α-glutamate Hydrochloride Salt (36') (LSN 382367)

To a solution of 35' (23 mg, 0.023 mmol) in 232 al of methylene chloride at room temperature was added a 4.0 M solution of hydrogen chloride in 1,4-dioxane (29 μl, 0.116 mmol). After stirring for 8.5 h, the clear, colorless reaction mixture was concentrated in vacuo to provide 20 mg (97%, corrected for 3 wt % dioxane) of the title compound as a white foam: 500 MHz $^1$H NMR (MeOH-d$_4$) δ 7.79 (d, 1H, J=7.6 Hz), 7.50–7.36 (m, 5H), 7.31 (d, 1H, J=2.0 Hz), 7.20 (dd, 1H, J=8.6, 2.0 Hz), 7.01 (d, 1H, J=8.6 Hz), 6.75–6.65 (m, 1H), 5.98 (d, 1H, 15 Hz), 5.57 (d, 1H, J=9.7 Hz), 5.20 (d, 1H, J=9.7 Hz), 5.15 (dd, 1H, J=11, 3.0 Hz), 4.90–4.80 (m, 1H), 4.52 (dd, 1H, J=11, 3.7 Hz), 3.87 (s, 3H), 3.80–3.66 (m, 1H), 3.49 (dd, 1H, J=13, 10 Hz), 3.21 (dd, 1H, J=14, 3.6 Hz), 3.15 (dd, 1H, J=14, 2.3 Hz), 2.82–2.72 (m, 3H), 2.41–2.30 (m, 3H), 2.05–1.81 (m, 5H), 1.25 (s, 3H), 1.20 (s, 3H), 1.15 (d, 3H, J=7.1 Hz), 1.07 (d, 3H, J=6.2 Hz), 1.05 (d, 3H, J=6.1 Hz).

Preparation of Cryptophycin 55 N-t-boc-β-t-Butyl Ester-(L)-aspartate (37') (LSN 382501) and Cryptophycin 55 N-t-Boc-β-t-Butyl Ester-(D)-aspartate (39') (LSN 387040)

To a solution of 1' (176 mg, 0.249 mmol), N-t-Boc-(L)-aspartic acid β-t-butyl ester (144 mg, 0.499 mmol), and 4-dimethylamino pyridine (2.0 mg, 0.066 mmol) in 1.0 ml of anhydrous methylene chloride at room temperature was added a solution of 1,3-dicyclohexylcarbodiimide (103 mg, 0.499 mmol) in 200 μl of methylene chloride. After stirring for 45 min, the cloudy white reaction mixture was treated with 88 mg of celite and diluted with ethyl acetate-hexanes (3:1, 2 ml), stirred for 10 min, and filtered through a plug of celite, washing with ethyl acetate:hexanes (3:1). The filtrate and washings were concentrated in vacuo to an off-white oil. Chromatography (30 g of flash silica gel, 2:1 ethyl acetate-hexanes) afforded pure 37' (lower Rf) along with mixed fractions. The mixed fractions were chromatographed (25 g of flash silica gel, 1:1 then 2:1 then 3:1 ethyl acetate-hexanes) affording more pure 37' along with pure 39' (higher Rf). All fractions containing pure 37' were combined to yield 149 mg (61%) as a white foam while all fractions containing pure 39' were combined to yield 56 mg (23%) as a white foam. 500 MHz $^1$H NMR (CDCl$_3$) data for 37': δ 7.39–7.30 (m, 5H), 7.24 (d, 1H, J=2.0 Hz), 7.24–7.18 (m, 1H), 7.09 (dd, 1H, J=8.4, 2.0 Hz), 6.88 (d, 1H, J=8.4 Hz), 6.76 (ddd, 1H, J=15, 13, 4.3 Hz), 5.75 (d, 1H, 15 Hz), 5.50 (d, 1H, J=7.9 Hz), 5.46 (d, 1H, J=9.2 Hz), 5.01–4.98 (m, 2H), 4.93 (t, 1H, J=9.9 Hz), 4.85 (d, 1H, J=9.2 Hz), 4.78–4.71 (m, 1H), 4.17–4.10 (m, 1H), 3.91 (s, 3H), 3.41 (dd, 1H, J=13, 8.2 Hz), 3.22 (dd, 1H, J=13, 3.9 Hz), 3.17 (dd, 1H, J=14, 5.1 Hz), 3.09 (dd, 1H, J=14, 7.7 Hz), 2.61–2.50 (m, 4H), 2.36–2.28 (m, 1H), 2.02–1.97 (m, 1H), 1.83–1.76 (m, 2H), 1.45 (s, 9H), 1.41 (s, 9H), 1.28 (s, 3H), 1.20 (s, 3H), 1.06–1.01 (m, 6H), 0.99 (d, 3H, J=6.2 Hz). 500 MHz $^1$H NMR (CDCl$_3$) data for 39': δ 7.39–7.30 (m, 5H), 7.24 (d, 1H, J=2.0 Hz), 7.24–7.18 (m, 1H), 7.09 (dd, 1H, J=8.4, 2.0 Hz), 6.88 (d, 1H, J=8.4 Hz), 6.73 (ddd, 1H, J=15, 13, 4.3 Hz), 5.74 (d, 1H, 15 Hz), 5.47 (d, 1H, J=7.9 Hz), 5.42 (d, 1H, J=9.1 Hz), 5.29 (d, 1H, J=9.0 Hz), 4.98 (dd, 1H, J=10, 3.0 Hz), 4.92 (t, 1H, J=9.6 Hz), 4.85 (d, 1H, J=9.1 Hz), 4.77–4.71 (m, 1H), 4.18–4.12 (m, 1H), 3.91 (s, 3H), 3.39 (dd, 1H, J=13, 8.1 Hz), 3.21 (dd, 1H, J=13, 4.0 Hz), 3.16 (dd, 1H, J=14, 5.2 Hz), 3.07 (dd, 1H, J=14, 7.6 Hz), 2.63–2.52 (m, 2H), 2.45 (dd, 1H, J=17, 5.8 Hz), 2.36–2.26 (m, 1H), 2.22 (dd, 1H, J=17, 4.5 Hz), 1.99–1.90 (m, 1H), 1.86–1.69 (m, 2H), 1.47 (s, 9H), 1.43 (s, 9H), 1.25 (s, 3H), 1.19 (s, 3H), 1.11 (d, 3H, J=7.0 Hz), 1.03 (d, 3H, J=6.5 Hz), 0.99 (d, 3H, J=6.4 Hz).

Preparation of Cryptophycin 55 (L)-Aspartate Hydrochloride Salt (38') (LSN 382502)

To a solution of 37' (146 mg, 0.149 mmol) in 498 μl of methylene chloride at room temperature was added a 4.0 M solution of hydrogen chloride in 1,4-dioxane (374 μl, 1.49 mmol). After stirring for 19 h, the clear, colorless reaction mixture was concentrated in vacuo to provide 131 mg (100%, corrected for 2 wt % dioxane) of the title compound as a white foam: 500 MHz $^1$H NMR (MeOH-d$_4$) δ 7.79 (d, 1H, J=7.6 Hz), 7.45–7.36 (m, 5H), 7.31 (d, 1H, J=2.0 Hz), 7.20 (dd, 1H, J=8.6, 2.0 Hz), 7.01 (d, 1H, J=8.6 Hz), 6.75 (ddd, 1H, J=15, 13, 3.7 Hz), 5.96 (dd, 1H, 15, 1.8 Hz), 5.54 (d, 1H, J=10 Hz), 5.17 (d, 1H, J=10 Hz), 5.14 (dd, 1H, J=11, 2.1 Hz), 4.89 (t, 1H, J=11 Hz), 4.52 (dd, 1H, J=11, 3.7 Hz), 3.87 (s, 3H), 3.55 (t, 1H, J=4.4 Hz), 3.52–3.47 (m, 1H), 3.21 (dd, 1H, J=14, 3.6 Hz), 3.13 (d, 1H, J=14 Hz), 2.99 (dd, 1H, J=18, 5.0 Hz), 2.83 (dd, 1H, J=18, 3.9 Hz), 2.81–2.68 (m, 3H), 2.35–2.28 (m, 1H), 2.02–1.84 (m, 3H), 1.26 (s, 3H), 1.21 (s, 3H), 1.08–1.02 (m, 9H).

Preparation of Cryptophycin 55 (D)-Aspartate Hydrochloride Salt (40') (LSN 387039)

To a solution of 39' (53 mg, 0.054 mmol) in 271 μl of methylene chloride at room temperature was added a 4.0 M solution of hydrogen chloride in 1,4-dioxane (136 μl, 0.542 mmol). After stirring for 14 h, the clear, colorless reaction mixture was concentrated in vacuo to provide 47 mg (94%, corrected for 6 wt % dioxane) of the title compound as a white foam: 500 MHz $^1$H NMR (MeOH-d$_4$) δ 7.79 (d, 1H, J=7.6 Hz), 7.45–7.36 (m, 5H), 7.31 (d, 1H, J=2.0 Hz), 7.20 (dd, 1H, J=8.6, 2.0 Hz), 7.01 (d, 1H, J=8.6 Hz), 6.71 (ddd, 1H, J=15, 13, 3.7 Hz), 5.96 (dd, 1H, 15, 1.8 Hz), 5.63 (d, 1H, J=10 Hz), 5.19 (d, 1H, J=10 Hz), 5.15 (dd, 1H, J=11, 2.1 Hz), 4.86–4.80 (m, 1H), 4.55–4.50 (m, 1H), 4.24 (dd, 1H, J=8.4, 4.0 Hz), 3.87 (s, 3H), 3.50 (dd, 1H, J=13, 9.7 Hz), 3.21 (dd, 1H, J=14, 3.6 Hz), 3.14 (dd, 1H, J=13, 2.5 Hz), 2.80–2.70 (m, 3H), 2.40–2.32 (m, 1H), 2.21 (dd, 1H, J=18, 4.0 Hz), 2.09–1.97 (m, 2H), 1.92–1.84 (m, 2H), 1.26 (s, 3H), 1.21 (s, 3H), 1.15 (d, 3H, J=7.1 Hz), 1.08 (d, 3H, J=6.1 Hz), 1.04 (d, 3H, J=6.0 Hz).

Preparation of Cryptophycin 55 N-t-boc-α-t-Butyl Ester-(L)-glutamate (41') (LSN 382572)

To a solution of 1' (23 mg, 0.033 mmol), N-t-Boc-(L)-glutamic acid α-t-butyl ester (15 mg, 0.049 mmol), and 4-dimethylamino pyridine (0.4 mg, 0.0033 mmol) in 120 µl of anhydrous methylene chloride at room temperature was added a solution of 1,3-dicyclohexylcarbodiimide (10 mg, 0.049 mmol) in 40 µl of methylene chloride. After stirring for 45 min, the cloudy white reaction mixture diluted with ethyl acetate-hexanes (3:1, 0.5 ml), stirred for 10 min, and filtered through a plug of celite, washing with ethyl acetate-:hexanes (3:1). The filtrate and washings were concentrated in vacuo to an off-white oil. Chromatography (15 g of flash silica gel, 2:1 ethyl acetate-hexanes) afforded 24 mg (75%) of the title compound as a white foam: 500 MHz $^1$H NMR (CDCl$_3$) δ 7.39–7.30 (m, 5H), 7.24 (d, 1H, J=2.1 Hz), 7.20–7.16 (m, 1H), 7.09 (dd, 1H, J=8.4, 2.1 Hz), 6.87 (d, 1H, J=8.4 Hz), 6.74 (ddd, 1H, J=15, 13, 4.6 Hz), 5.78 (d, 1H, J=15 Hz), 5.55 (br d, 1H, J=6.4 Hz), 5.46 (dd, 1H, J=9.6, 1.0 Hz), 4.96 (dd, 1H, J=11, 3.0 Hz), 4.91–4.80 (m, 2H), 4.83 (d, 1H, J=9.6 Hz), 4.72 (br s, 1H), 3.99 (br s, 1H), 3.91 (s, 3H), 3.39 (dd, 1H, J=13, 7.9 Hz), 3.24 (dd, 1H, J=13, 3.9 Hz), 3.18 (dd, 1H, J=14, 4.5 Hz), 3.09 (dd, 1H, J=14, 7.8 Hz), 2.63–2.55 (m, 2H), 2.44–2.37 (m, 1H), 2.10–1.92 (m, 3H), 1.85–1.78 (m, 1H), 1.76–1.61 (m, 3H), 1.46 (s, 9H), 1.45 (s, 9H), 1.27 (s, 3H), 1.20 (s, 3H), 1.08 (d, 3H, J=7.0 Hz), 1.04 (d, 3H, J=6.6 Hz), 0.98 (d, 3H, J=6.4 Hz).

Preparation of Cryptophycin 55 (L)-γ-Glutamate Hydrochloride Salt (42') (LSN 382514)

To a solution of 41' (21 mg, 0.021 mmol) in 212 µl of methylene chloride at room temperature was added a 4.0 M solution of hydrogen chloride in 1,4-dioxane (53 µl, 0.212 mmol). After stirring for 23.5 h, the reaction mixture was diluted with methanol and passed through a small plug of celite. Concentration in vacuo to provide 20 mg (100%, corrected for 6 wt % dioxane) of the title compound as a white foam: 500 MHz $^1$H NMR (MeOH-d$_4$) δ 7.79 (d, 1H, J=7.6 Hz), 7.50–7.29 (m, 6H), 7.20 (dd, 1H, J=8.4, 2.0 Hz), 7.01 (d, 1H, J=8.4 Hz), 6.66 (ddd, 1H, J=15, 13, 3.7 Hz), 5.97 (dd, 1H, 15, 1.5 Hz), 5.52 (dd, 1H, J=10, 0.8 Hz), 5.14 (dd, 1H, J=11, 3.0 Hz), 5.10 (d, 1H, J=10 Hz), 4.90–4.80 (m, 1H), 4.51 (dd, 1H, J=11, 3.7 Hz), 3.90–3.80 (m, 1H), 3.87 (s, 3H), 3.50 (dd, 1H, J=13, 10 Hz), 3.19 (dd, 1H, J=14, 3.7 Hz), 3.13 (dd, 1H, J=14, 2.3 Hz), 2.81–2.67 (m, 3H), 2.41–2.32 (m, 2H), 2.15–2.06 (m, 1H), 1.97–1.79 (m, 5H), 1.25 (s, 3H), 1.19 (s, 3H), 1.13 (d, 3H, J=7.1 Hz), 1.08 (d, 3H, J=5.9 Hz), 1.04 (d, 3H, J=5.8 Hz).

Preparation of Cryptophycin 55 N,N'-di-t-boc-(S)-2, 3-Diaminopropionate (43') (LSN 382765)

To a solution of 1' (21 mg, 0.030 mmol), N,N'-di-t-Boc-(S)-2,3-diaminopropionic acid (18 mg, 0.060 mmol), and 4-dimethylamino pyridine (0.3 mg, 0.0030 mmol) in 110 µl of anhydrous methylene chloride at room temperature was added a solution of 1,3-dicyclohexylcarbodiimide (12 mg, 0.060 mmol) in 39 µl of methylene chloride. After stirring for 70 min, the cloudy white reaction mixture diluted with ethyl acetate-hexanes (3:1, 0.5 ml), stirred for 10 min, and filtered through a plug of celite, washing with ethyl acetate-:hexanes (3:1). The filtrate and washings were concentrated in vacuo to an off-white oil. Chromatography (15 g of flash silica gel, 2:1 ethyl acetate-hexanes) afforded 24 mg (80%) of the title compound as a white foam: 500 MHz $^1$H NMR (MeOH-d$_4$) δ 7.49–7.40 (m, 2H), 7.38–7.30 (m, 4H), 7.19 (dd, 1H, J=8.5, 1.9 Hz), 7.00 (d, 1H, J=8.5 Hz), 6.74 (ddd, 1H, J=16, 11, 3.5 Hz), 5.95 (d, 1H, J=16 Hz), 5.49 (d, 1H, J=10 Hz), 5.16–5.08 (m, 2H), 4.90–4.80 (m, 1H), 4.51 (dd, 1H, J=11, 3.7 Hz), 4.06–4.10 (m, 1H), 3.87 (s, 3H), 3.48 (d, 1H, J=13 Hz), 3.19 (dd, 1H, J=14, 3.7 Hz), 3.14 (d, 1H, J=13 Hz), 3.03 (dd, 1H, J=14, 4.2 Hz), 2.94–2.87 (m, 1H), 2.80–2.59 (m, 3H), 2.39–2.30 (m, 1H), 1.98–1.81 (m, 3H), 1.43 (s, 18H), 1.25 (s, 3H), 1.21 (s, 3H), 1.10 (d, 3H, J=7.0 Hz), 1.07 (d, 3H, J=6.0 Hz), 1.03 (d, 3H, J=5.8 Hz).

Preparation of Cryptophycin 55 (S)-2,3-Diaminopropionate Dihydrochloride Salt (44') (LSN 382764)

To a solution of 43' (21 mg, 0.021 mmol) in 211 µl of methylene chloride at room temperature was added a 4.0 M solution of hydrogen chloride in 1,4-dioxane (42 µl, 0.169 mmol). After stirring for 5 h, the reaction mixture was concentrated in vacuo to provide 18.5 mg (100%, corrected for 3 wt % dioxane) of the title compound as a white solid: 500 MHz $^1$H NMR (MeOH-d$_4$) δ 7.50–7.39 (m, 5H), 7.31 (d, 1H, J=2.0 Hz), 7.20 (dd, 1H, J=8.4, 2.0 Hz), 7.01 (d, 1H, J=8.4 Hz), 6.68 (ddd, 1H, J=15, 11, 3.8 Hz), 5.99 (dd, 1H, 15, 1.7 Hz), 5.56 (d, 1H, J=9.6 Hz), 5.24 (d, 1H, J=9.6 Hz) 5.16 (dd, 1H, J=10, 3.1 Hz), 4.90–4.80 (m, 1H), 4.51 (dd, 1H, J=11, 3.8 Hz), 4.04–4.00 (m, 1H), 3.87 (s, 3H), 3.50–3.45 (m, 1H), 3.26 (dd, 1H, J=14, 4.0 Hz), 3.22–3.12 (m, 3H), 2.81–2.75 (m, 3H), 2.42–2.32 (m, 1H), 1.98–1.78 (m, 3H), 1.25 (s, 3H), 1.19 (s, 3H), 1.22–1.16 (m, 3H), 1.07 (d, 3H, J=6.4 Hz), 1.04 (d, 3H, J=6.3 Hz).

Preparation of Cryptophycin 55 N-t-boc-(L)-Serinate (45') (LSN 384340)

To a solution of 1' (38 mg, 0.053 mmol), N-t-Boc-O-tert-butyldimethylsilyl(L)-serine[11] (51 mg, 0.160 mmol), and 4-dimethylamino pyridine (0.6 mg, 0.0053 mmol) in 200 µl of anhydrous methylene chloride at room temperature was added a solution of 1,3-dicyclohexylcarbodiimide (33 mg, 0.160 mmol) in 69 µl of methylene chloride. After stirring for 4 h, the cloudy white reaction mixture was diluted with ethyl acetate-hexanes (2:1, 1 ml), stirred for 10 min, and filtered through a plug of celite, washing with ethyl acetate-:hexanes (2:1). The filtrate and washings were concentrated in vacuo to a colorless oil which was used directly in the next step. To a solution of the crude silyl ether (54 mg, 0.054 mmol) in 268 µl of tetrahydrofuran at room temperature was added 268 µl of a stock solution of hydrogen fluoride-pyridine (prepared from 0.5 g of HF.pyridine (Aldrich), 4 ml of tetrahydrofuran, and 1 ml of pyridine). After stirring for 4 h, another 67 µl of stock HF.pyridine solution was added. After stirring for 30 min, the reaction was treated with 0.6 ml of saturated aqueous sodium bicarbonate and washed with ethyl acetate (1 ml×3). The combined organics were dried (Na$_2$SO$_4$), filtered, and concentrated in vacuo to a faint yellow foam. Chromatography (16 g of flash SiO$_2$ eluting with 3:1 then 6:1 ethyl acetate-hexanes) provided 26 mg (44%) of the title compound as a white foam: 500 MHz $^1$H NMR (MeOH-d$_4$) δ 7.79 (dd, 1H, J=9.5, 2.4 Hz), 7.45–7.38 (m, 2H), 7.37–7.29 (m, 3H), 7.29 (d, 1H, J=2.0 Hz), 7.18 (dd, 1H, J=8.4, 2.0 Hz), 6.99 (d, 1H, J=8.4 Hz), 6.72 (ddd, 1H, J=15, 13, 3.7 Hz), 5.95 (dd, 1H, J=15, 1.6 Hz), 5.53 (d, 1H, J=9.5 Hz), 5.12–5.08 (m, 2H), 4.94 (t, 1H, J=10 Hz), 4.52 (dd, 1H, J=12, 3.6 Hz), 3.92 (t, 1H, J=4.6 Hz), 3.85 (s, 3H), 3.52–3.46 (m, 3H), 3.20 (dd, 1H, J=14, 3.5 Hz), 3.14 (dd, 1H, J=13, 3.0 Hz), 2.75 (dd, 1H, J=14, 11 Hz), 2.73–2.66 (m, 1H), 2.65–2.59 (m, 1H), 2.38–2.29 (m, 1H), 2.00–1.82 (m, 3H), 1.43 (s, 9H), 1.25 (s, 3H), 1.22 (s, 3H), 1.10–1.06 (m, 6H), 1.03 (d, 3H, 6.0 Hz).

Preparation of Cryptophycin 55 (L)-Serinate Hydrochloride Salt (46') (LSN 384339)

To a solution of 45' (26 mg, 0.029 mmol) in 291 μl of methylene chloride at room temperature was added a 4.0 M solution of hydrogen chloride in 1,4-dioxane (36 μl, 0.146 mmol). After stirring for 2.5 h, the clear, colorless reaction mixture was concentrated in vacuo to provide 23 mg (94%, corrected for 2 wt % dioxane) of the title compound as a white foam: 500 MHz $^1$H NMR (MeOH-$d_4$) δ 7.48–7.40 (m, 2H), 7.39–7.31 (m, 3H), 7.31 (d, 1H, J=2.2 Hz), 7.20 (dd, 1H, J=8.5, 2.0 Hz), 7.01 (d, 1H, J=8.5 Hz), 6.70 (ddd, 1H, J=15, 13, 3.7 Hz), 5.95 (dd, 1H, 15, 1.8 Hz), 5.59 (d, 1H, J=10 Hz), 5.20 (d, 1H, J=10 Hz), 5.14 (dd, 1H, J=11, 2.1 Hz), 4.94 (t, 1H, J=10 Hz), 4.52 (dd, 1H, J=3.5 Hz), 3.96 (dd, 1H, J=11, 3.9 Hz), 3.83 (dd, 1H, J=11, 2.8 Hz), 3.66 (t, 1H, J=3.2 Hz), 3.50 (d, 1H, J=14 Hz), 3.20 (dd, 1H, J=14, 3.5 Hz), 3.13 (d, 1H, J=14 Hz), 2.80–2.71 (m, 3H), 2.38–2.28 (m, 1H), 2.01–1.82 (m, 3H), 1.26 (s, 3H), 1.21 (s, 3H), 1.13 (d, 3H, J=7.0 Hz), 1.07 (d, 3H, J=6.1 Hz), 1.05 (d, 3H, J=6.1 Hz).

Preparation of Cryptophycin 55 Glycidylglycinate Hydrochloride Salt (47') (LSN 387750)

To a solution of 1' (18 mg, 0.026 mmol), N-t-Boc-glycidylglycine (12 mg, 0.051 mmol), and 4-dimethylamino pyridine (0.3 mg, 0.0026 mmol) in 128 μl of anhydrous methylene chloride and 28 μl of N,N-dimethylformamide at room temperature was added a solution of 1,3-dicyclohexylcarbodiimide (11 mg, 0.151 mmol) in 28 μl of methylene chloride. After stirring for 3 h, another 24 mg (0.102 mmol) of N-t-Boc-glycidylglycine and 22 mg (0.102 mmol) of 1,3-dicyclohexylcarbodiimide in 30 μl of N,N-dimethylformamide was added. After stirring for 1.5 h, the cloudy white reaction mixture diluted with ethyl acetate-hexanes (3:1, 0.5 ml), stirred for 10 min, and filtered through a plug of celite, washing with ethyl acetate:hexanes (3:1). The filtrate and washings were concentrated in vacuo to a colorless oil. Chromatography (12 g of flash silica gel, 1% methanol in ethyl acetate) afforded 12 mg of a white foam which was used as is in the next experiment. To a solution of the N-Boc glycidylglycinate (12 mg, 0.013 mmol) from above in 130 μl of methylene chloride at room temperature was added a 4.0 M solution of hydrogen chloride in 1,4-dioxane (16 μl, 0.065 mmol). After stirring for 3.5 h, the reaction mixture was concentrated in vacuo to provide 11 mg (100%) of the title compound as a white foam: 500 MHz $^1$H NMR (MeOH-$d_4$) δ 7.45–7.29 (m, 5H), 7.31 (d, 1H, J=2.1 Hz), 7.20 (dd, 1H, J=8.4, 2.1 Hz), 7.01 (d, 1H, J=8.4 Hz), 6.72 (ddd, 1H, J=15, 11, 3.8 Hz), 5.96 (dd, 1H, 15, 1.4 Hz), 5.49 (dd, 1H, J=10, 0.8 Hz), 5.14–5.09 (m, 2H), 4.90–4.80 (m, 1H), 4.51 (dd, 1H, J=11, 3.9 Hz), 3.91–3.84 (m, 1H), 3.87 (s, 3H), 3.70–3.65 (m, 2H), 3.50 (d, 1H, J=14 Hz), 3.38 (d, 1H, J=18 Hz), 3.19 (dd, 1H, J=14, 3.6 Hz), 3.12 (d, 1H, J=14 Hz), 2.82–2.63 (m, 3H), 2.40–2.30 (m, 1H), 1.97–1.80 (m, 3H), 1.25 (s, 3H), 1.20 (s, 3H), 1.12 (d, 3H, J=7.0 Hz), 1.06 (d, 3H, J=6.0 Hz), 1.03 (d, 3H, J=5.9 Hz).

Preparation of Cryptophycin 55 3,6,9-Tioxadecanoate (48') (LSN 387414)

To a solution of 1' (18 mg, 0.026 mmol), 3,6,9-trioxadecanoic acid (7.8 μl, 0.051 mmol), and 4-dimethylamino pyridine (0.3 mg, 0.0026 mmol) in 100 μl of anhydrous methylene chloride at room temperature was added a solution of 1,3-dicyclohexylcarbodiimide (11 mg, 0.051 mmol) in 28 μl of methylene chloride. After stirring for 30 min, the cloudy white reaction mixture diluted with ethyl acetate-hexanes (3:1, 0.5 ml), stirred for 10 min, and filtered through a plug of celite, washing with ethyl acetate-:hexanes (3:1). The filtrate and washings were concentrated in vacuo to an off-white oil. Chromatography (12 g of flash silica gel, 2% methanol in ethyl acetate) afforded 19 mg (86%) of the title compound as a white foam: 500 MHz, $^1$H NMR (CDCl$_3$) δ 7.49–7.29 (m, 5H), 7.24 (d, 1H, J=1.8 Hz), 7.22–7.19 (m, 1H), 7.10 (dd, 1H, J=8.4, 1.8 Hz), 6.87 (d, 1H, J=8.4 Hz), 6.74 (ddd, 1H, J=15, 10, 4.5 Hz), 5.32–5.28 (m, 2H), 5.56 (d, 1H, J=9.7 Hz), 4.98–4.90 (m, 2H), 4.83 (d, 1H, J=9.7 Hz), 4.77–4.71 (m, 1H), 3.90 (s, 3H), 3.83 (d, 1H, J=17 Hz), 3.65–3.55 (m, 7H), 3.42–3.33 (m, 6H), 3.24–3.18 (m, 2H), 3.03 (dd, 1H, J=15, 8.1 Hz), 2.69–2.61 (m, 1H), 2.61–2.56 (m, 1H), 2.54–2.46 (m, 1H), 2.00–1.93 (m, 1H), 1.85–1.77 (m, 1H), 1.72–1.66 (m, 1H), 1.26 (s, 3H), 1.19 (s, 3H), 1.09 (d, 3H, J=7.0 Hz), 1.02 (d, 3H, J=6.6 Hz), 0.97 (d, 3H, J=6.5 Hz).

We claim:

1. A compound of Formula I

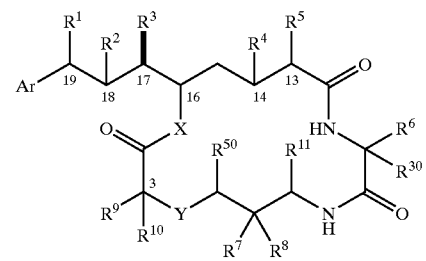

wherein

Ar is selected from the group consisting of phenyl, any simple unsubstituted or substituted aromatic, heteroaromatic group, $C_1$–$C_{12}$ alkyl, $C_2$–$C_{12}$ alkenyl, $C_2$–$C_{12}$ alkynyl, $NR^{51}R^{52}$, $OR^{53}$, and Formula Ar'

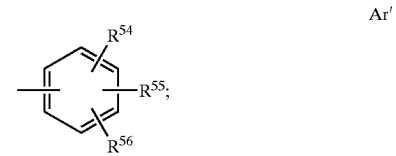

$R^1$ is selected from the group consisting of halogen and OH;

$R^2$ is halogen or $OR^{31}$, provided that one, but not both, of $R^1$ and $R^2$ is halogen;

$R^3$ is a lower alkyl group;

$R^4$ is H or OH;

$R^5$ is H or OH; or $R^4$ and $R^5$ may be taken together to form a second bond between $C_{13}$ and $C_{14}$;

$R^6$ is selected from the group consisting of benzyl, hydroxybenzyl, alkoxybenzyl, halohydroxybenzyl, dihalohydroxybenzyl, haloalkoxybenzyl, or dihaloalkoxybenzyl group;

$R^7$ is H or a lower alkyl group;

$R^8$ is H or a lower alkyl group;

$R^9$ is H or a lower alkyl group;

$R^{10}$ is H or a lower alkyl group;

$R^{11}$ is hydrogen;
$R^{30}$ is hydrogen;
$R^{31}$ is $R^{32}$;
$R^{32}$ is selected from the group consisting of amino acid, carbohydrate, amino sugar, (saccharide)$_q$, and C(O)$R^{33}$;
$R^{33}$ is $R^{37}R^{38}$;
$R^{37}$ is ($C_1$–$C_6$)alkyl linker;
$R^{38}$ is COOR$^{39}$,

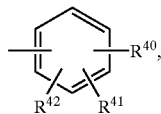

NH$_2$, and amino acid;
$R^{39}$ is H or ($C_1$–$C_6$)alkyl;
$R^{40}$, $R^{41}$, and $R^{42}$ are each independently selected from the group consisting of hydrogen, OR$^{43}$, halo, NH$_2$, NO$_2$, OPO(OR$^{46}$)$_2$, OR$^{44}$phenyl, and $R^{45}$;
$R^{43}$ is $C_1$–$C_6$ alkyl;
$R^{44}$ is $C_1$–$C_6$ alkylene;
$R^{45}$ is selected from the group consisting of an aromatic group and a substituted aromatic group;
$R^{46}$ is selected from the group consisting of H, Na, and —C(CH$_3$)$_3$;
$R^{50}$ is hydrogen or

$R^{51}$ is selected from the group consisting of hydrogen and $C_1$–$C_3$ alkyl;
$R^{52}$ is selected from the group consisting of hydrogen and $C_1$–$C_3$ alkyl;
$R^{53}$ is selected from the group consisting of $C_1$–$C_{12}$ alkyl;
$R^{54}$ is selected from the group consisting of hydrogen, $C_1$–$C_6$ alkyl, simple aromatic, phenyl, COOR$^{57}$, PO$_3$H, SO$_3$H, SO$_2$R$^{58}$, NR$^{59}$R$^{60}$, NHOR$^{61}$, NHCH$_2$R$^{61'}$, CN, NO$_2$, halogen, OR$^{62}$, and SR$^{63}$;
$R^{55}$ is selected from the group consisting of hydrogen, $C_1$–$C_6$ alkyl, simple aromatic, phenyl, COOR$^{57}$, PO$_3$H, SO$_3$H, SO$_2$R$^{58}$, NR$^{59}$R$^{60}$, NHOR$^{61}$, NHCH$_2$R$^{61'}$, CN, NO$_2$, halogen, OR$^{62}$, and SR$^{63}$;
$R^{56}$ is selected from the group consisting of hydrogen, $C_1$–$C_6$ alkyl, simple aromatic, phenyl, COOR$^{57}$, PO$_3$H, SO$_3$H, SO$_2$R$^{58}$, NR$^{59}$R$^{60}$, NHOR$^{61}$, NHCH$_2$R$^{61'}$, CN, NO$_2$, halogen, OR$^{62}$, and SR$^{63}$;
$R^{57}$ is selected from the group consisting of hydrogen and $C_1$–$C_{12}$ alkyl;
$R^{58}$ is selected from the group consisting of hydrogen and $C_1$–$C_{12}$ alkyl;
$R^{59}$ is selected from the group consisting of hydrogen, ($C_1$–$C_6$) alkyl and fluorenylmethoxycarbonyl (FMOC);
$R^{60}$ is selected from the group consisting of hydrogen and ($C_1$–$C_6$) alkyl;
$R^{61}$ is selected from the group consisting of hydrogen, OR$^{64}$, CH$_2$NHR$^{65}$, NHR$^{65}$ and fluorenylmethoxycarbonyl (FMOC);
$R^{61}$ is selected from the group consisting of hydrogen, OR$^{64}$, CH$_2$NHR65, NHR$^{65}$ and fluorenylmethoxycarbonyl (FMOC);
$R^{62}$ is selected from hydrogen and $C_1$–$C_6$ alkyl;
$R^{63}$ is selected from hydrogen and $C_1$–$C_6$ alkyl;
$R^{64}$ is selected from the group consisting of hydrogen, ($C_1$–$C_6$) alkyl, and CH$_2$NR$^{66}$R$^{67}$;
$R^{65}$ is selected from the group consisting of hydrogen, $C_1$–$C_6$ alkyl, NH$_2$, and fluorenylmethoxycarbonyl (FMOC);
$R^{66}$ is selected from the group consisting of hydrogen, $C_1$–$C_6$ alkyl and fluorenylmethoxycarbonyl (FMOC);
$R^{67}$ is selected from the group consisting of hydrogen, $C_1$–$C_6$ alkyl;
q is 2, 3, or 4;
X is O, NH or alkylamino; and
Y is C, O, NH, S, SO, SO$_2$ or alkylamino;
or a pharmaceutically acceptable salt or solvate thereof.

2. A compound of claim 1 wherein Y is O.
3. A compound of claim 2 wherein X is O.
4. A compound of claim 3 wherein $R^9$ is isobutyl and $R^{10}$ is hydrogen.
5. A compound of claim 3 wherein $R^{50}$ is

6. A compound of claim 1 wherein Y is NH.
7. A compound of claim 6 wherein $R^{50}$ is

8. A compound of claim 7 wherein X is O.
9. A compound of claim 8 wherein $R^9$ is isobutyl and $R^{10}$ is hydrogen.
10. A compound of claim 5 wherein Ar is phenyl.
11. A compound of claim 10 wherein $R^7$ and $R^8$ are each methyl.
12. A compound of claim 11 wherein $R^2$ is a glycinate.
13. The compound of claim 12 of the Formula

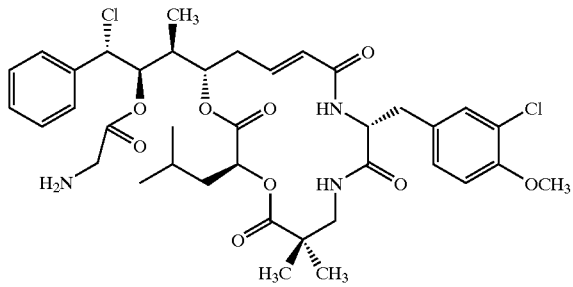

wherein the compound is Cryptophycin 55 glycinate, or a pharmaceutically acceptable salt thereof.
14. The compound of claim 13 wherein the compound is the hydrochloride salt of Cryptophycin 55 glycinate.
15. A compound of claim 10 wherein $R^7$ is hydrogen.
16. A compound of claim 15 wherein $R^2$ is a glycinate.
17. A compound selected from the group consisting of Cryptophycin 55 acetate, Cryptophycin 55 succinate, Cryptophycin 55 (2'-di-t-butylphosphatyl) phenylacetate, Cryptophycin 55 (2'-phosphatyl) phenylacetate, Cryptophycin 55 nicotinoate, Cryptophycin 55 N-methylpyridinium, Cryptophycin 55 N-t-Boc-3-(3-chloro-4-methoxyphenyl)-(D)-alaninate, Cryptophycin 55 3-(3-chloro-4-methoxyphenyl)-(D)-alaninate, Cryptophycin 55 N-t-Boc-glycinate, Cryptophycin 55 N-t-Boc-β-alaninate, Cryptophycin 55 N-t-Boc-γ-aminobutyrate, Cryptophycin 55 N-t-Boc-(L)-alaninate, Cryptophycin 55 N-t-Boc-(D)-alaninate, and Cryptophycin 55 Nα-Nε-di-t-Boc-(L)-lysinate; or a pharmaceutically acceptable salt thereof.

18. A compound selected from the group consisting of Cryptophycin 129, Cryptophycin 138, Cryptophycin 145, Cryptophycin 140, Cryptophycin 141; or a pharmaceutically acceptable salt thereof.

19. A compound selected from the group consisting of Cryptophycin 152, Cryptophycin 255, Cryptophycin 153, Cryptophycin 154, Cryptophycin 161, Cryptophycin 234, Cryptophycin 236, Cryptophycin 247, Cryptophycin 251, and Cryptophycin 238; or a pharmaceutically acceptable salt thereof.

20. A compound selected from the group consisting of Cryptophycin 55 succinate tert-butyl ester, Cryptophycin 55 (2'-di-t-butylphosphatyl) phenylacetate, Cryptophycin 55 (2'-phosphatyl) phenylacetate, Cryptophycin 55 nicotinoate, Cryptophycin 55 N-methylpyridinium, Cryptophycin 55 N-t-Boc-3-(3-chloro-4-methoxyphenyl)-(D)-alaninate, Cryptophycin 55 N-t-Boc-(L)-phenylalaninate, Cryptophycin 55 (L)-phenylalaninate, Cryptophycin 55 (L)-histidinate, Cryptophycin 55 N-t-Boc-(L)-prolinate, Cryptophycin 55 (L)-prolinate, Cryptophycin 55 N-t-Boc glycinate, Cryptophycin 55 glycinate, Cryptophycin 55 N-t-Boc-β-alaninate, Cryptophycin 55 β-alaninate, Cryptophycin 55 N-t-Boc-γ-aminobutyrate, Cryptophycin 55 γ-aminobutyrate, Cryptophycin 55 N-t-Boc-(L)-alaninate, Cryptophycin 55 (L)-alaninate, Cryptophycin 55 N-t-Boc-(D)-alaninate, Cryptophycin 55 (D)-alaninate, Cryptophycin 55 Nα-Nε-di-t-boc-(L)-Lysinate, Cryptophycin 55 (L)-lysinate, Cryptophycin 55 Nα-Nε-di-t-Boc-(D)-lysinate, Cryptophycin 55 (D)-lysinate, Cryptophycin 55 N-t-Boc-γ-t-butyl ester-(L)-glutamate, Cryptophycin 55 (L)-α-glutamate, Cryptophycin 55 N-t-Boc-β-t-butyl ester-aspartate, Cryptophycin 55 (D)-aspartate, Cryptophycin 55 N-t-Boc-α-t-butyl ester-(L)-glutamate, Cryptophycin 55 (L)-γ-glutamate, Cryptophycin 55 N,N'-di-t-Boc-(S)-2,3-diaminopropionate, Cryptophycin 55 (S)-2,3-diaminopropionate, Cryptophycin 55 N-t-Boc-(L)-serinate, Cryptophycin 55 (L)-serinate, and Cryptophycin 55 succinate; or a pharmaceutically acceptable salt thereof.

21. A method for treating a susceptible neoplasm in a mammal comprising administering an effective amount of a compound of claim 1 to a patient in need thereof.

* * * * *

UNITED STATES PATENT AND TRADEMARK OFFICE
CERTIFICATE OF CORRECTION

PATENT NO. : 6,680,311 B1
DATED : January 20, 2004
INVENTOR(S) : Al-Awar et al.

Page 1 of 1

It is certified that error appears in the above-identified patent and that said Letters Patent is hereby corrected as shown below:

Title page,
Item [56], References Cited, U.S. PATENT DOCUMENTS, "6,180,679 B1*" should read -- 6,180,679 B1 --

Column 210,
Line 45, "$NR^{51}R^{52}, OR^{53}$, and Formula Ar' 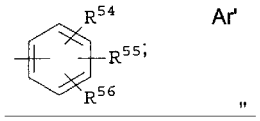 "

should read -- $NR^{51}R^{52}, OR^{53}$, and Formula Ar'

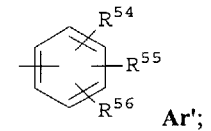 Ar';

Column 211,
Line 65, "R61 is selected" should read -- R61' is selected --

Column 213,
Line 5, "N-t-Boc-y-aminobutyrate," should read -- N-t-Boc-γ-aminobutyrate, --
Line 7, "55 Na-NE-di-t-Boc" should read -- 55Nα-Nϵ-di-5-Boc --

Signed and Sealed this

Fourteenth Day of September, 2004

JON W. DUDAS
*Director of the United States Patent and Trademark Office*